US009243055B2

(12) United States Patent
Wang-Johanning

(10) Patent No.: US 9,243,055 B2
(45) Date of Patent: Jan. 26, 2016

(54) HERV-K ANTIGENS, ANTIBODIES, AND METHODS

(71) Applicant: Board of Regents, The University of Texas System, Austin, TX (US)

(72) Inventor: Feng Wang-Johanning, Bastrop, TX (US)

(73) Assignee: Board of Regents, The University of Texas System, Austin, TX (US)

(*) Notice: Subject to any disclaimer, the term of this patent is extended or adjusted under 35 U.S.C. 154(b) by 9 days.

(21) Appl. No.: 13/846,612

(22) Filed: Mar. 18, 2013

(65) Prior Publication Data

US 2014/0099324 A1 Apr. 10, 2014

Related U.S. Application Data

(63) Continuation of application No. 12/475,009, filed on May 29, 2009, now abandoned, which is a continuation-in-part of application No. 11/752,235, filed on May 22, 2007, now abandoned.

(60) Provisional application No. 60/747,850, filed on May 22, 2006.

(51) Int. Cl.
*C07K 16/10* (2006.01)
*A61K 39/00* (2006.01)
*A61K 47/48* (2006.01)
*C07K 16/30* (2006.01)
*G01N 33/574* (2006.01)

(52) U.S. Cl.
CPC ......... *C07K 16/1036* (2013.01); *A61K 39/0011* (2013.01); *A61K 47/48523* (2013.01); *A61K 47/48584* (2013.01); *A61K 47/48623* (2013.01); *A61K 47/48638* (2013.01); *C07K 16/3015* (2013.01); *C07K 16/3053* (2013.01); *C07K 16/3069* (2013.01); *G01N 33/57407* (2013.01); *G01N 33/57415* (2013.01); *G01N 33/57434* (2013.01); *G01N 33/57449* (2013.01); *G01N 33/57484* (2013.01); *G01N 33/57492* (2013.01); *A61K 2039/505* (2013.01); *C07K 2316/95* (2013.01); *C07K 2317/21* (2013.01); *C07K 2317/24* (2013.01); *C07K 2317/565* (2013.01); *C07K 2317/622* (2013.01); *C07K 2317/73* (2013.01); *C07K 2317/732* (2013.01); *C07K 2317/734* (2013.01); *C07K 2317/77* (2013.01); *C07K 2319/55* (2013.01); *C12N 2740/10011* (2013.01)

(58) Field of Classification Search
None
See application file for complete search history.

(56) References Cited

U.S. PATENT DOCUMENTS

| 4,542,225 | A | 9/1985 | Blattler et al. |
|---|---|---|---|
| 5,858,723 | A | 1/1999 | Mueller-Lantzsch et al. |
| 6,656,480 | B2 | 12/2003 | Retter et al. |
| 6,670,466 | B1 | 12/2003 | Garry et al. |
| 6,800,469 | B1 | 10/2004 | Conrad et al. |
| 7,115,367 | B1 | 10/2006 | Seifarth et al. |
| 7,183,384 | B2 | 2/2007 | Sun et al. |
| 7,510,862 | B2 | 3/2009 | Wolff et al. |
| 2003/0162263 | A1 | 8/2003 | Dupuis et al. |
| 2004/0096457 | A1 | 5/2004 | Huber et al. |
| 2004/0242851 | A1 | 12/2004 | Zhu et al. |
| 2006/0275747 | A1 | 12/2006 | Hardy et al. |
| 2007/0037147 | A1 | 2/2007 | Garcia et al. |
| 2008/0171061 | A1 | 7/2008 | Nixon et al. |
| 2008/0261216 | A1 | 10/2008 | Markovitz et al. |
| 2009/0130129 | A1 | 5/2009 | Mayer et al. |

FOREIGN PATENT DOCUMENTS

| WO | WO 94/11514 | 5/1994 |
|---|---|---|
| WO | WO 03/050258 | 6/2003 |
| WO | WO 2006/103562 | 10/2006 |
| WO | WO 2007/109583 | 9/2007 |

OTHER PUBLICATIONS

Wang-Johanning et al, (Cancer Research, Jul. 15, 2008, vol. 68, p. 5869-5877).*
Adams, et al., "Monoclonal antibody therapy of cancer," *Nature Biotechnology*, 2005, 23:1147-1157.
Dewannieux, et al., "Identification of a functional envelope protein from the HERV-K family of human endogenous retroviruses," *J. Virology*, 2005, 79:15573-15577.
Herve, et al., "Autoantibodies to human endogenous retrovirus-K are frequently detected in health and disease and react with multiple epitopes," *Clinical & Experimental Immunology*, 2002, 128:75-82.
Ishida, et al., "Identification of HERV-K gag antigen in prostate cancer by SEREX using autologous patient serum and its immunogenicity," *Cancer Immunity*, 2008, 13:8-15.
Notification of Transmittal of the International Search Report and the Written Opinion of the International Searching Authority, or the Declaration, issued in International Application No. PCT/US07/69497, dated May 22, 2007.
Office Communication issued in U.S. Appl. No. 12/475,009, dated Oct. 18, 2012.
Office Communication issued in U.S. Appl. No. 12/475,009, dated Jan. 31, 2012.
Office Communication issued in U.S. Appl. No. 12/475,009, dated Oct. 26, 2010.
Office Communication issued in U.S. Appl. No. 11/752,235, dated Dec. 1, 2008.

(Continued)

*Primary Examiner* — Agnieszka Boesen
(74) *Attorney, Agent, or Firm* — Parker Highlander PLLC

(57) ABSTRACT

Methods and compositions for cancer diagnostics and therapy are provided. More particular, methods and compositions for detecting, preventing, and treating HERV-K⁺ cancers are provided. One example of a method may involve a method for preventing or inhibiting cancer cell proliferation by administering to a subject a cancer cell proliferation blocking or reducing amount of a HERV-K env protein binding antibody.

6 Claims, 97 Drawing Sheets
(86 of 97 Drawing Sheet(s) Filed in Color)

(56) References Cited

OTHER PUBLICATIONS

Office Communication issued in U.S. Appl. No. 11/752,235, dated Aug. 28, 2008.
Owens, et al., "The genetic engineering of monoclonal antibodies," *J. Immunological Methods*, 1994, 168:149-165.
Schiavetti, et al., "A human endogenous retroviral sequence encoding an antigen recognized on melanoma by cytolytic T lymphocytes," *Cancer Res.*, 2002, 62:5510-5516.
Wang-Johanning, et al., "Detecting the expression of human endogenous retrovirus E envelope transcripts in human prostate adenocarcinoma," *Cancer*, 2003, 98:187-197.
Wang-Johanning, et al., "Expression of HERV-K envelope transcripts in human breast cancer," *Clin. Cancer Res.*, 2001, 7:1553-1560.
Wang-Johanning, et al., "Expression of multiple human endogenous retrovirus surface envelope proteins in ovarian cancer," *Intl. J. Cancer*, 2007, 120:81-90.
Wang-Johanning, et al., "Human endogenous retrovirus-K triggers an antigen-specific immune response in breast cancer patients," *Cancer Res.*, 2008, 68:5869-5877.
Wang-Johanning, et al., "Quantitation of HERV-K env gen expression and splicing in human breast cancer," *Oncogene*, 2003, 22:1528-1535.

\* cited by examiner

DCIS　　　　　　IDC　　　Normal epithelial cells

FIGURE 1B
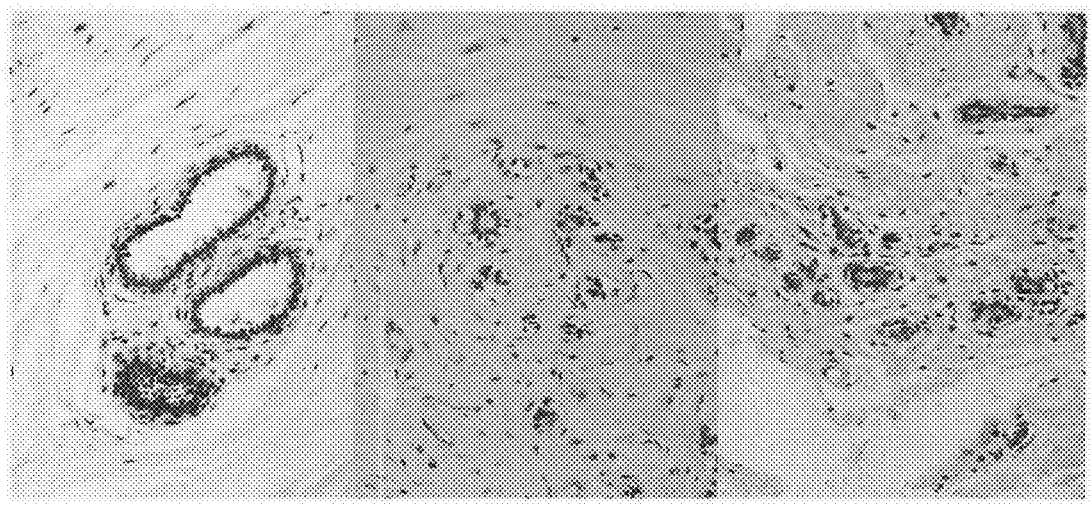
Case #1      Case #4      Case #16
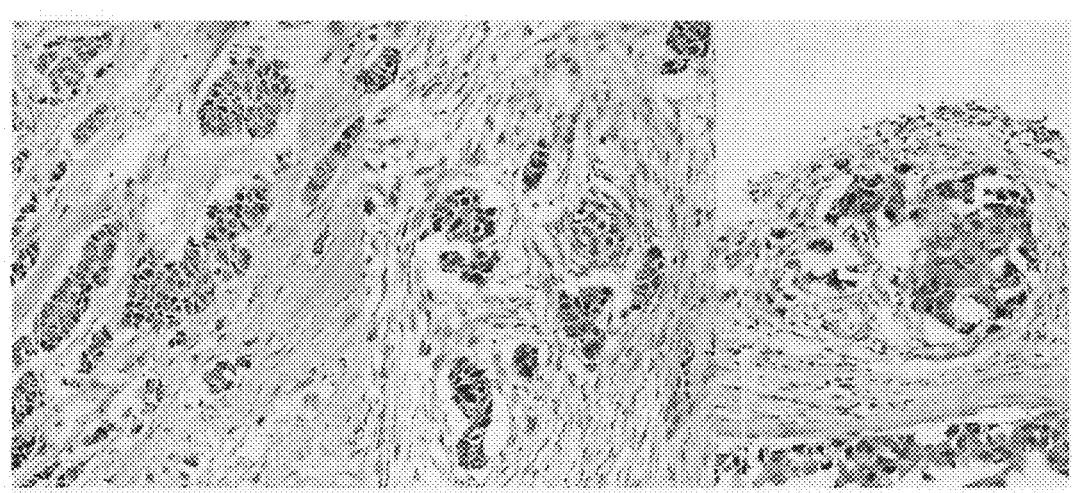
Case #8      Case #17      Case #11

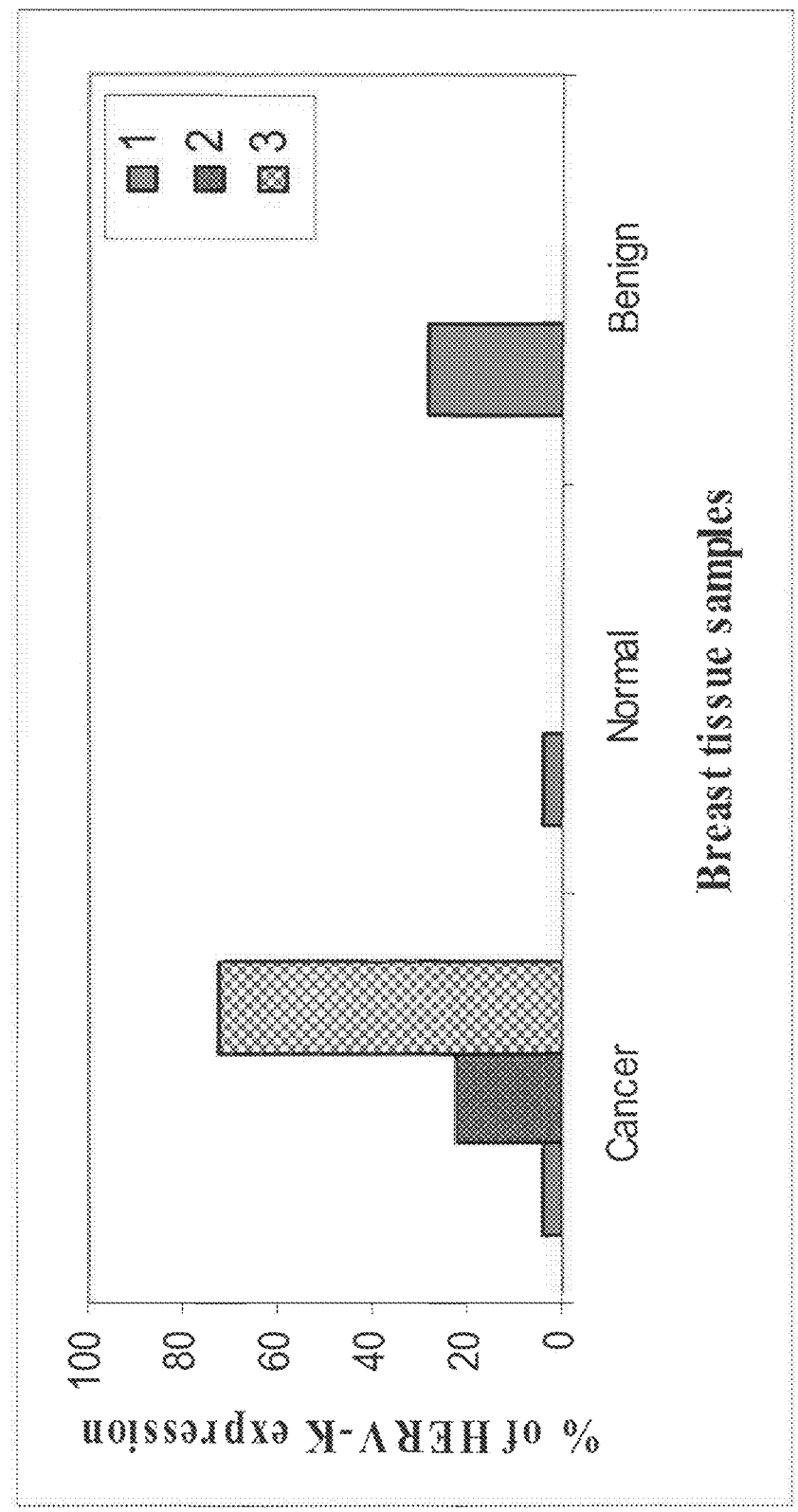

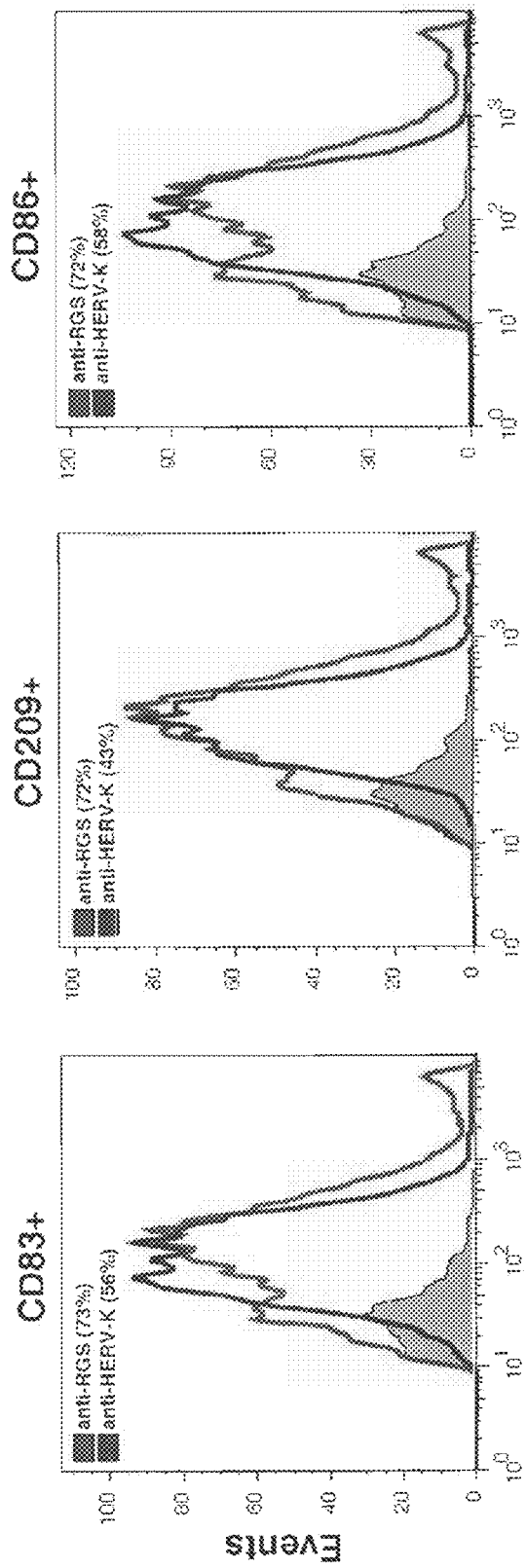

FIGURE 8A.
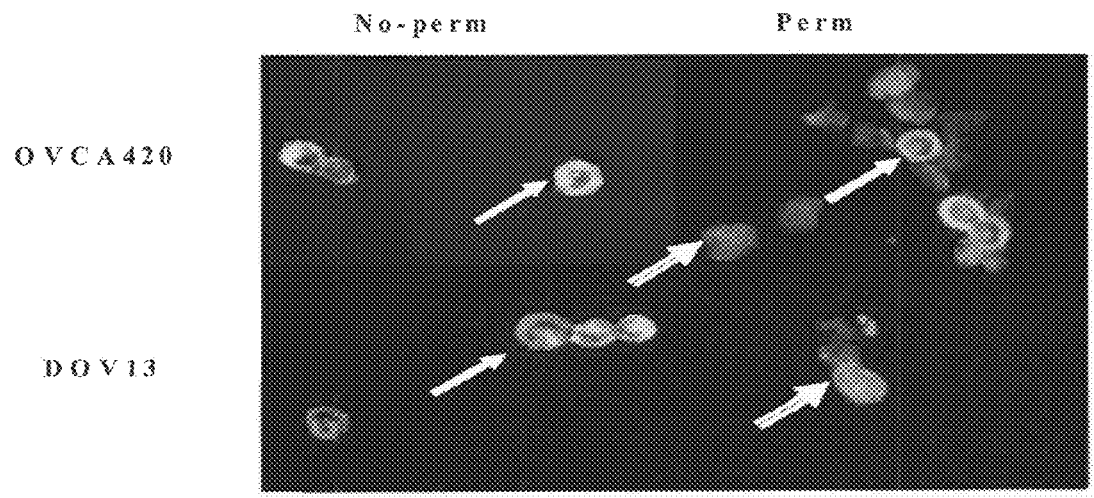
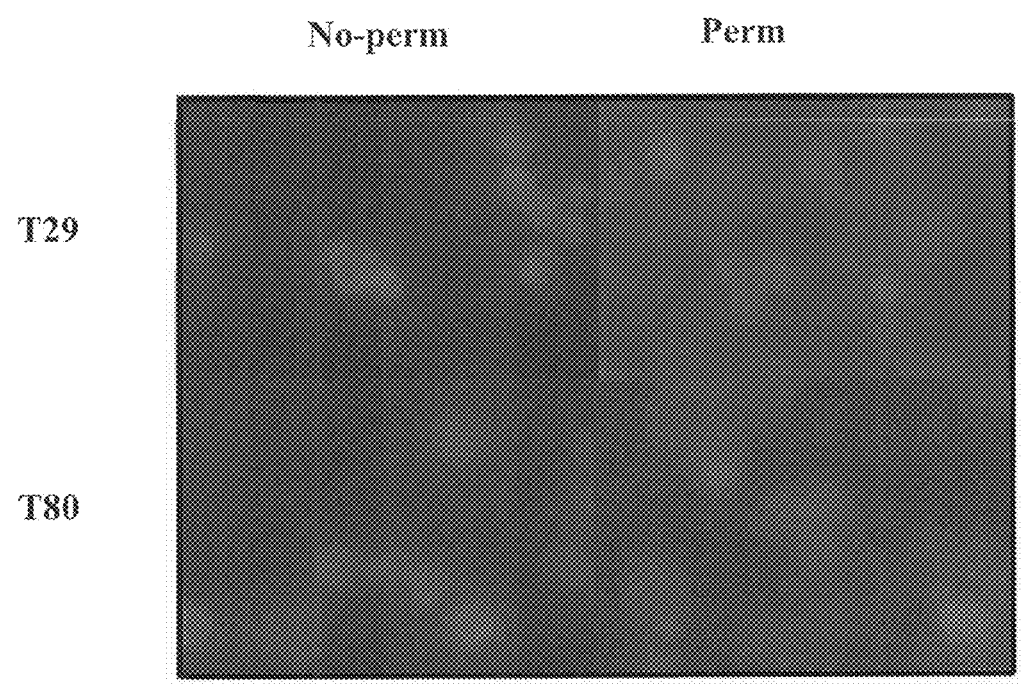

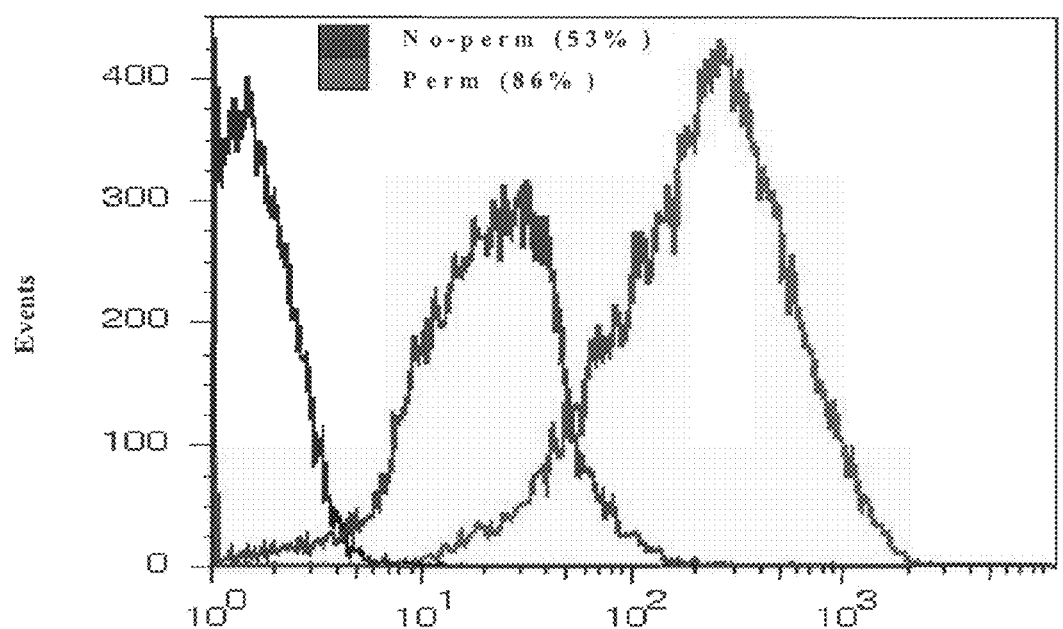

FIGURE 15.

A. DNA sequence

GGCCCAGGCGGCCATGGCCCAGGTCCAGCTGCAGGAGTCAGGAGGAGGCTGGTGCAGCCTGGAGGATCCCTGAAAC
TCTCCTGTGCAGCCTCAGGATTCGATTTTAGTAGATACTGGATGAGTTGGGTCCGCCAGGCTCCAGGAAAGGCTAGA
ATGGATTGGAGAAATTAATCCAGATAGCATATACGCCATCTAAAGGATAATCATCTCCAGA
GACAACGCCAAAAATACGTACTGCAAATGAGCAAAGTGAGATTGAGACACAGCCTTATTACTGTGCAAGA
CGAGGGTACTACGGTAGTAGTACTGGTTCCTTGCTACCACCAAGGCCACCACGGTCACGTCTCCTCAGGTGGAG
GCGGTTCAGGCGGCGGAGGTGCGGCGTGGGCGGAGGTGCCGGATCCGACATCGAGCTCACTCAGTCTCCAGCAATCATGTCT
GCATCTCTAGGAGAACGGGTCACCATGACCTGCAGTGTAAGTTCCAGTACTGTAGTTCCAGCA
GAAGCCAGGATCCTCCCCAAACTGGATTTATAGCACATCCAACCTGGCTTCTGGAGTCCCAGCTCGCTTCAGTGGC
AGTGGGTCTGGGACCTCTTACTCTCTCACAATCAGCAGCATGGAGGCTGAAGATGCCACTTATTACTGCCACCAGT
ATCATCGTTCCCCACCGTTCGGCTCGGGGACAAAGTTGGAAATCAAACGG<u>CGGCCGCA</u>

B. Protein Sequence

Met A Q V Q L Q E S G G G L V Q P G G S L K L S C A A S G F D F S R Y W Met S W V R Q A P G K G L E W I G E I N P D S
S T I N Y T P S L K D K F I I S R D N A K N T L Y L Q Met S K V R S E D T A L Y Y C A R R G Y Y G S S Y W F A Y W G Q
G T T V T V S S G G G G S G G G G S A G G G G S D I E L T Q S P A I Met S A S L G E R V T Met T C T A S S S V S S S Y L H
W Y Q Q K P G S S P K L W I Y S T S N L A S G V P A R F S G S G S G T S Y S L T I S S Met E A E D A A T Y Y C H Q Y H R
S P P T F G S G T K L E I K R A A A E Stop Non-perm    Perm FIGURE 16E
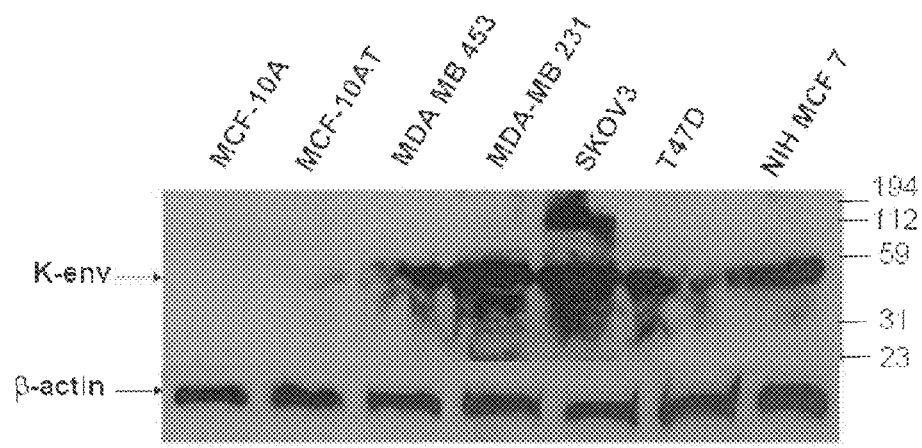
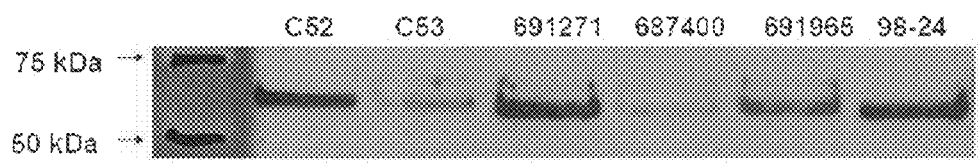
FIGURE 16F
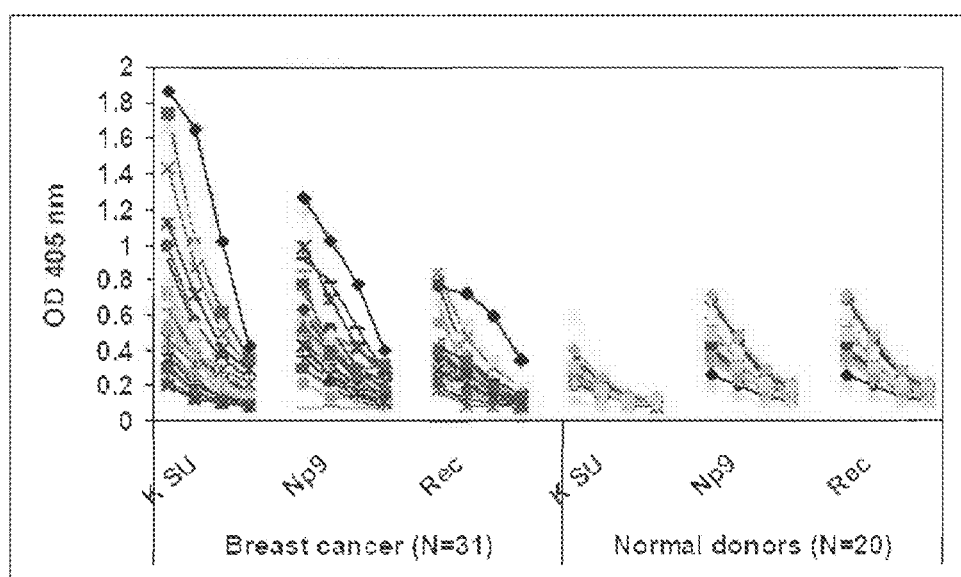

FIGURE 17C
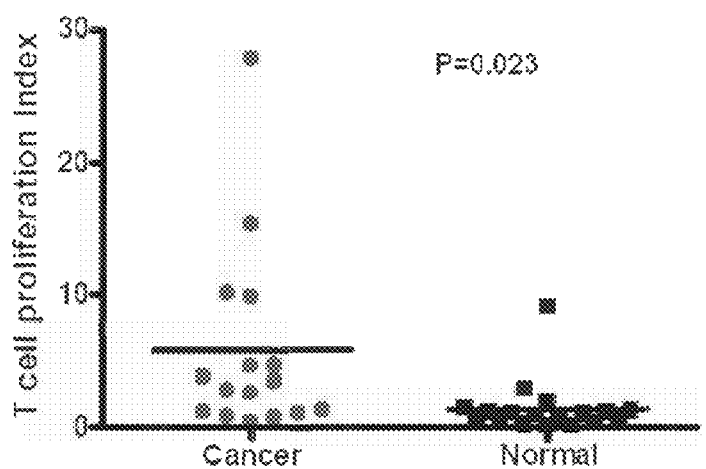
FIGURE 18A
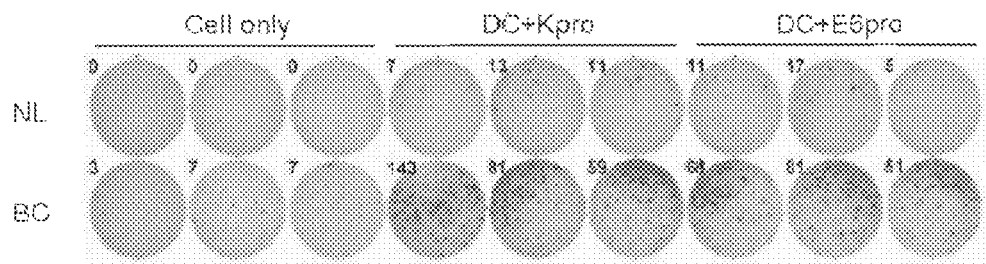
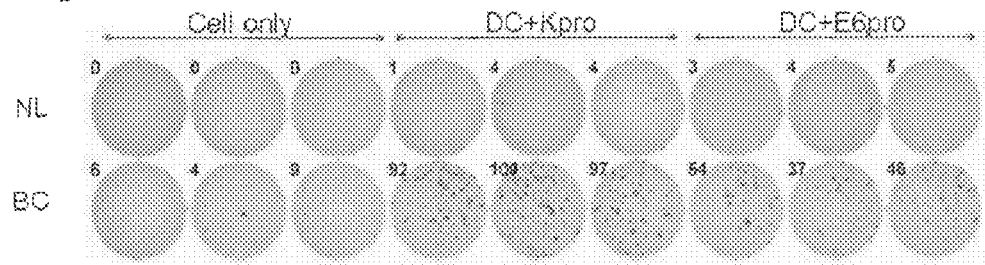

FIGURE 32A
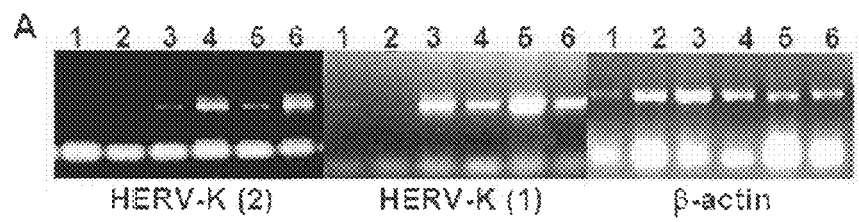
FIGURE 32B
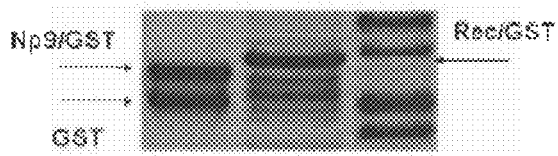
FIGURE 33
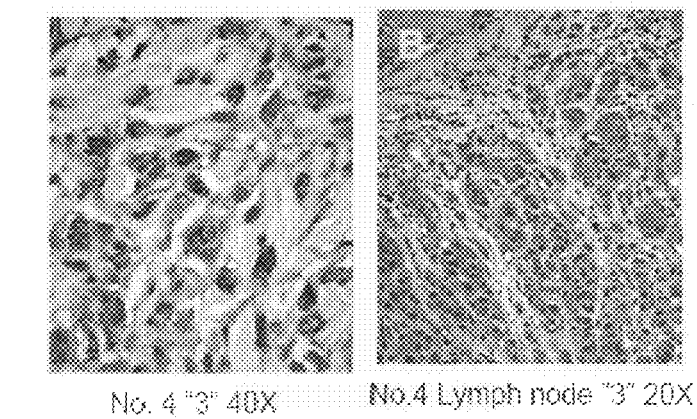
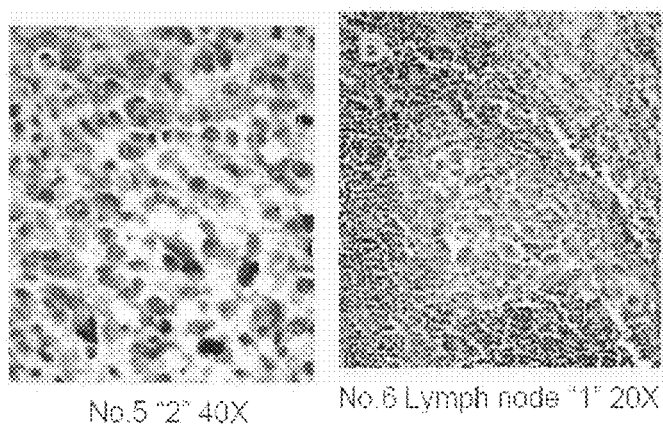

Figure 53
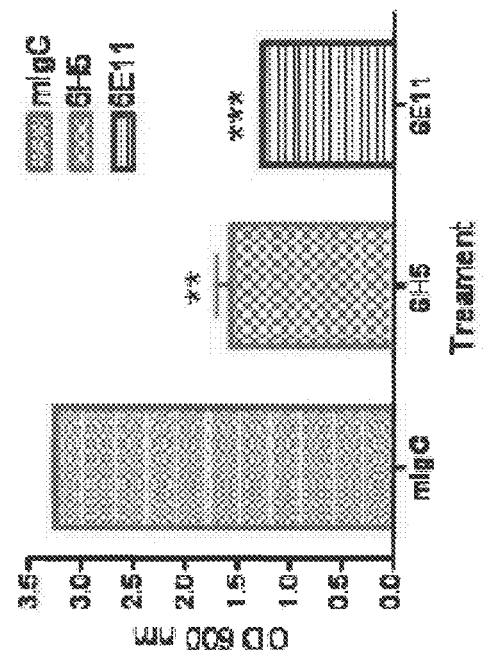
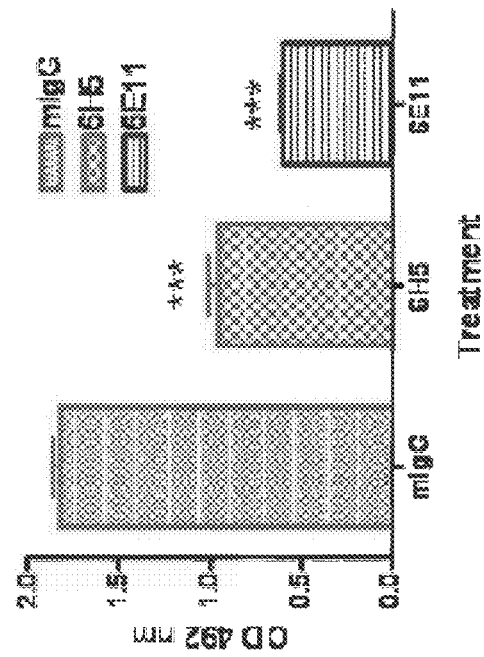

Figure 68

```
  1 GAGGTGCAGCTGGTGGAGTCTGGGGGAGGCTTGGTCCAGCCTGGGGGGTCCCTGAGACTC   60
    GluValGlnLeuValGluSerGlyGlyGlyLeuValGlnProGlyGlySerLeuArgLeu
 61 TCCTGTGCAGCCTCT ATGAGCTGGGTCCGCCAGGCT  120
    SerCysAlaAlaSer MetSerTrpValArgGlnAla
                    muCDR-H1
121 CCAGGAAAGGGCTGGAGTGGGTGGCAAC                    TACTAT        180
    ProGlyLysGlyLeuGluTrpValAlaAsn                  TyrTyr
                                  muCDR-H2
181 GTGGACTCTGTGAAGGGCCGATTCACCATCTCCAGAGACAACGCCAAGAACTCACTGTAT  240
    ValAspSerValLysGlyArgPheThrIleSerArgAspAsnAlaLysAsnSerLeuTyr
241 CTGCAAATGAACAGCCTGAGAGCCGAGGACACGGCTGTGTATTACTGT              300
    LeuGlnMetAsnSerLeuArgAlaGluAspThrAlaValTyrTyrCys
301                             TGGGCCAAGGCCACCACGGTCACCGTCTCC    360
                                TrpGlyGlnGlyThrThrValThrValSer
     muCDR-H3
361 TCAGGTGGAGGCGGTTCAGGCGGAGGTGGCTCTGGCGGTGGCGGATCGGATATCGAGCTC  420
    SerGlyGlyGlyGlySerGlyGlyGlyGlySerGlyGlyGlyGlySerAspIleGluLeu
421 ACTCAGTCTCCAGAAATGTCATGACGCAGTCTCCAGCCTCCCTGTCTGTGTCTCCAGGG   480
    ThrGlnSerProGluMetSerMetThrGlnSerProAlaSerLeuSerValSerProGly
481 GAAAGAGCCACCCTCTCCTGCAGGGCCAGTTTA                TTAGCCTGG     540
    GluArgAlaThrLeuSerCysArgAlaSerLeu                LeuAlaTrp
     muCDR-L1
541 TACCAGCAGAAACCTGGCCAGGCTCCCAGGCTCCTCATCTATGCAG  CACCAGGGCC     600
    TyrGlnGlnLysProGlyGlnAlaProArgLeuLeuIleTyrAla   HisGlnGlyAla
                                             muCDR-L2
601 ACTGGTATCCCAGCAGGTTCAGTGGCAGTGGGTCTGGGACAGAGTTCACTCTCACCATC   660
    ThrGlyIleProAlaArgPheSerGlySerGlySerGlyThrGluPheThrLeuThrIle
661 AGCAGCCTGCAGTCTGAAGATTTCAGTTTATTACTGTCAGTATCGTTCGCA           720
    SerSerLeuGlnSerGluAspPheSerPheTyrTyrCysGlnHis
721 CCCGGTTCGGCCAAGGGACCAAGCTGGAAATCAAACGG 759
    ProGlyPheGlyGlnGlyThrLysLeuGluIleLysArg
```

Figure 69

HERV-K ANTIGENS, ANTIBODIES, AND METHODS

CROSS-REFERENCE TO RELATED APPLICATION

This application is a continuation of U.S. application Ser. No. 12/475,009, filed May 29, 2009, which is a continuation-in-part application of U.S. application Ser. No. 11/752,235, filed May 22, 2007, which claims priority to U.S. Provisional Application No. 60/747,850, filed May 22, 2006. The entire text of each of the above referenced disclosures is specifically incorporated herein by reference.

STATEMENT REGARDING FEDERALLY SPONSORED RESEARCH OR DEVELOPMENT

This disclosure was developed at least in part using funding from the Department of Defense, Grant No. DAMD1700-1-0123 and the Susan G. Komen Breast Cancer Foundation (BCTR0402892). The U.S. government may have certain rights in the invention.

SEQUENCE LISTING

This disclosure includes a sequence listing submitted as a text file pursuant to 37 C.F.R. §1.52(e)(v) named sequence listing.txt, created on Sep. 4, 2007, with a size of 4,866 bytes, which is incorporated herein by reference. The attached sequence descriptions and Sequence Listing comply with the rules governing nucleotide and/or amino acid sequence disclosures in patent applications as set forth in 37 C.F.R. §§1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. §1.822.

BACKGROUND

Human endogenous retroviruses (HERVs) and elements containing long terminal repeat-like sequences may comprise up to 8% of the human genome. HERVs entered the human genome after fortuitous germ line integration of exogenous retroviruses and were subsequently fixed in the general population. They may have been preserved to ensure genome plasticity and this can provide the host with new functions, such as protection from exogenous viruses and fusiogenic activity (e.g., membrane fusion, exocytosis, or endocytosis). HERVs contain over 200 distinct groups and subgroups. The accumulation of mutations has led to a loss of infectivity of HERVs, and in general they are largely noninfectious retroviral remnants. However, open reading frames (ORFs) have been observed for ERV3, HERV-E 4-1, and HERV-K, but their significance is unknown.

The most biologically active HERVs are members of the HERV-K superfamily which is characterized by the presence of primer binding sites for lysine tRNA. Only HERV-K appears to have the full complement of open reading frames typical of replication competent mammalian retroviruses. The K family contains a central open reading frame (cORF) and is comparable to HIV-1 Rev protein. HERV-K was originally identified by its homology to the mouse mammary tumor virus (MMTV), and is transcriptionally active in several human cancer tissues, including breast cancer tissues, as well as tumor cell lines, such as the human breast cancer cell line T47D and the teratocarcinoma cell line GH.

HERV-K env mRNA is frequently expressed in human breast cancer and HERV-E mRNA is expressed in prostate cancer. Additionally, mRNA from multiple HERV families is transcribed only in ovarian cancer cell lines and tissues. For example, the expression of HERV-K env mRNA was greater in ovarian epithelial tumors than it was in normal ovarian tissues (N=254).

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine screening procedures) and aggressive treatment, which may include one or more of a variety of treatments such as surgery, radiotherapy, chemotherapy, and hormone therapy. The course of treatment for a particular breast cancer is often selected based on a variety of prognostic parameters, including an analysis of specific-tumor markers. See, e.g., Porter-Jordan & Lippman, Breast Cancer 8:73-100, 1994. However, the use of established markers often leads to a result that is difficult to interpret, and the high mortality observed in breast cancer patients indicates that improvements are needed in the treatment, diagnosis, and prevention of the disease.

Ovarian cancer is another leading cause of cancer deaths among women and has the highest mortality of any of the gynecologic cancers. Symptoms usually do not become apparent until the tumor compresses or invades adjacent structures, or ascites develops, or metastases become clinically evident. As a result, two thirds of women with ovarian cancer have advanced (Stage III or IV) disease at the time of diagnosis.

Potential screening tests for ovarian cancer include the bimanual pelvic examination, the Papanicolaou (Pap) smear, tumor markers, and ultrasound imaging. The pelvic examination, which can detect a variety of gynecologic disorders, is of unknown sensitivity in detecting ovarian cancer. Although pelvic examinations can occasionally detect ovarian cancer, small, early-stage ovarian tumors are often not detected by palpation due to the deep anatomic location of the ovary. Thus, ovarian cancers detected by pelvic examination are generally advanced and associated with poor survival. The pelvic examination may also produce false positives when benign adnexal masses (e.g., functional cysts) are found. The Pap smear may occasionally reveal malignant ovarian cells, but it is not considered to be a valid screening test for ovarian carcinoma. Ultrasound imaging has also been evaluated as a screening test for ovarian cancer, since it is able to estimate ovarian size, detect masses as small as 1 cm, and distinguish solid lesions from cysts.

Serum tumor markers are often elevated in women with ovarian cancer. Examples of these markers include carcinoembryonic antigen, ovarian cystadenocarcinoma antigen, lipid-associated sialic acid, NB/70K, TAG 72.3, CAI 15-3, and CA-125, respectively. Evidence is limited on whether tumor markers become elevated early enough in the natural history of occult ovarian cancer to provide adequate sensitivity for screening, and tumor markers may have limited specificity.

Tumor-associated antigens recognized by the immune system are a very attractive target for human cancer diagnostics and therapy. However, few immunotherapy approaches have been used for the treatment and prevention of cancers. One problem limiting the success of cancer vaccines is that the immune system generally does not recognize cancer cells as being foreign, which is a requirement for initiating an immune response. Cancer immunotherapy, however, is limited due in part to the limited number of tumor-associated antigens identified to date.

SUMMARY

The present disclosure, according to specific example embodiments, generally relates to HERV-K$^+$ cancers.

The present disclosure is based in part on the observation that HERV-K surface env protein has antigenic and immunogenic properties. HERV-K env protein may not be expressed, or expressed at low-levels, in normal or benign tissues. This may lead to the production of T cells that are not autoreactive. Thus, the present disclosure uses HERV-K env proteins as unrecognized tumor associated antigens in HERV-K$^+$ cancers.

The involvement of the HERV-K env protein in host immune functions thus makes it of potential use in HERV-K$^+$ cancer diagnosis and treatment. Accordingly, the present disclosure provides methods of preventing or inhibiting HERV-K$^+$ cancers, such as breast and ovarian cancers, cell proliferation, and diagnosing or staging cancers. The present disclosure also provides HERV-K env protein-specific antibodies; and related methods of using these materials to detect the presence of HERV-K env proteins or nucleic acids.

The present disclosure also advantageously provides for screening assays and kits, such as methods of screening for compounds that inhibit or prevent HERV-K$^+$ cancer proliferation The present disclosure also provides HERV-K$^+$ cancer specific antigen that may be used for, among other things, in vitro expansion of HERV-K$^+$ cancer-specific CD8$^+$ cytotoxic T lymphocytes (CTLs) for autologous transfer. Such antigens also may be used to generate anti-HERV-K antibodies and to detect the presence of anti-HERV-K antibodies in HERV-K$^+$ cancer patients.

The present disclosure also provides autologous dendritic cells (DCs) pulsed with HERV-K env protein, peptides, and cRNAs. Such DCs enable autologous professional antigen presenting cells to process and present one or more HERV-K epitopes in association with host human leukocyte antigen (HLA) molecules. HERV-K env antigens are capable of breaking tumor patient immune tolerance, and the IVS cells subsequently generated are capable of killing HERV-K$^+$ target cells.

The present disclosure also provides HERV-K env protein for use as, among other things, a diagnostic marker for endometrioid, serous, mixed mullerian tumors (MMT), poorly differentiated, and transitional carcinoma. Expression of HERV-K env SU protein was significantly increased in low malignant potential serous tumors and endometrioid tumors, compared with normal ovaries.

The present disclosure also provides antibodies against HERV-K env SU protein, HERV-K gag protein, HERV-K spliced envelope protein, HERV-E surface protein, or ERV3 env protein.

The features and advantages of the present disclosure will be readily apparent to those skilled in the art upon a reading of the description of the embodiments that follows.

FIGURES

The patent or application file contains at least one drawing executed in color. Copies of this patent or patent application publication with color drawing(s) will be provided by the Office upon request and payment of the necessary fee.

Some specific example embodiments of the disclosure may be understood by referring, in part, to the following description and the accompanying drawings.

FIG. 1A is an illustration of HERV-K env protein expression in tumor epithelial cells obtained from a patient with infiltrating ductal carcinoma. Detection of HERV-K env protein expression in tumor epithelial cells obtained from a patient with infiltrating ductal carcinoma. Serial breast tissue sections obtained from a breast cancer patient were assessed by immunohistochemistry using antibody specific against HERV-K env protein. The expression of HERV-K env protein was detected only in tumor epithelial cells, including ductal carcinoma in situ (DCIS) and invasive ductal carcinoma (IDC), and not in uninvolved normal epithelial cells (C).

FIG. 1B is an illustration of examples of immunostaining with anti-HERV-K env antibody in a multiple-tissue microarray. Case #1, normal mammary lobule from a 43-year-old female; case #4, normal mammary lobule from a 50-year-old female; case #16, mammary gland tissue from a 61-year-old female; case #8, IDC (grade II) from a 45-year-old female; case #17, IDC (grade II; 49 year-old female); Case #11, intraductal carcinoma (grade II) from a 52-year-old female.

FIG. 1C is a graph of HERV-K env protein expression in two microarrays of 126 breast tissue samples. "1" indicates low expression, "2" indicates intermediate expression, and "3" indicates strong expression of HERV-K env protein. The levels of expression were associated with tissue type (cancer, benign, and normal) (P<0.001; Fisher's exact test).

FIG. 1D is a summary of HERV-K env protein expression in three arrays of 182 breast tissue samples (0 indicates no expression; 1 indicates low expression; 2 indicates intermediate expression; 3 indicates strong expression). The expression levels were associated with tissue type (cancer, benign, and normal) (P<0.001; Chi-square test). Two of the seven benign breast biopsies (ductal epithelial hyperplasia) were weakly HERV-K positive (low expression). More than 50% of breast cancer biopsies had intermediate or strongly positive staining for HERV-K.

FIG. 2A is a graph of ELISA detection of antibodies against anti-HERV-K env surface protein (K-SU), gag protein (K-gag), and spliced env protein (K-spliced) in the sera from cancer patients and normal female control subjects. Sera were diluted 1:200. The ELISA plate was read at a wavelength of 405 nm, with a cutoff of 0.5 absorbance units.

FIG. 2B is a graph of ELISA detection of IgG antibody against HERV-K env surface protein in plasma from cancer patients and normal female control subjects. Plasma was diluted 1:100. Only IgG antibodies from plasma binding HERV-K env surface protein were detected by this assay. The level of anti-HERV-K IgG antibodies in plasma from cancer patients (N=14) was higher (P<0.001) than the level in plasma from normal control subjects (N=12).

FIG. 3A are graphs of phenotyping of immature and mature human DCs by flow cytometry. Immature DCs were exposed to TNF-α overnight for maturation, with or without prior pulsing with HERV-K proteins. Mature DCs not stained with antibody were used as negative control cells and DCs stained with single antibody were used as compensation controls (data not shown). The percentage of CD86+/CD83+ DCs, CD209+/CD83+ DCs, and CD209+/CD86+ DCs obtained from immature DCs (immature), mature DCs without (mature) or with HERV-K (HERV-K pulsed) prior pulsing with are shown.

FIG. 3B are graphs of determination of surface expression of HERV-K env protein on HERV-K-pulsed mature DCs. The percentage of surface expression of HERV-K on DCs was determined by flow cytometry using anti-RGS mAb (anti-RGS; as a positive control) or anti-HERV-K specific antibody (anti-HERV-K).

FIG. 3C is an illustration of the expression of HERV-K env protein on human breast cancer cells by flow cytometry and fluorescence microscopy. The cells were permeabilized (permeabilized) for detection of cytoplasmic expression, or not (non permeabilized) for detection of surface expression. Cells stained with anti-IgG-FITC were used as negative controls (data not shown). The same cells used for flow cytometry were subjected to fluorescence microscopy (micrographs are shown in insets). Surface and cytoplasmic expression of HERV-K in MCF-7, but not in MCF-10AT cells is shown.

FIG. 4A is an illustration of T-cell proliferation results from PBMCs obtained from control subjects (N=7). The T cell proliferation was compared between PBMCs and CD3+ T cells obtained from the same donors. Results are shown for PBMCs or CD3+ T cells without protein stimulation ('Cells only'); cells stimulated with HERV-K env protein ('HERV-K'); cells stimulated with HERV-E env protein ('HERV-E'); cells stimulated with the superantigen *Staphylococcus* enterotoxin A ('SEA'). The data are presented as corrected mean counts per minute per $1\times10^5$ PBMCs or CD3+ T cells. All assays were done in triplicate.

FIG. 4B is a graph of proliferation results from IVS cells. Each donor was tested for proliferation of PBMCs stimulated with unpulsed DCs and IVS cells stimulated with HERV-K pulsed DCs. The proliferation index data obtained from IVS/PBMC were compared between the cancer patients and control subjects. The proliferation was higher in IVS obtained from cancer patients than in IVS obtained from control subjects (P=0.025).

FIG. 4C is a graph of antigen-specific granzyme B producing cells, as assessed by ELISPOT analysis. Granzyme B spots obtained from IVS or PBMCs were compared between cancer patients and control subjects. The granzyme B spots were higher in IVS obtained from cancer patients than in IVS obtained from control subjects (P=0.003).

FIG. 4D is a graph of HERV-K-specific lysis of target cells. Determination of HERV-K-specific lysis of target cells. Cytotoxic T cell assay of 3-week IVS cells obtained from two cancer patients. Target cells were K562 cells used to assess natural killer activity, autologous DCs pulsed with HERV-K env protein (DC+K) or with control protein (DC+Mock), MCF-7 breast cancer cells, or autologous B-LCL cells pulsed with HERV-K (B-LCL+K) or with control protein (B-LCL+Mock). The ratio of effector cells to target cells was 20:1.

FIG. 5A is a graph of cytokine secretion by IVS cells obtained from breast cancer patients and normal control subjects showing the mean values of IL-2 secretion from cancer patients (82 pg/ml) and normal subjects (22 pg/ml). The mean values of IL-2 secretion from cancer patients (82 pg/ml) and normal subjects (22 pg/ml) are shown. IL-2 secretion was higher (P=0.029) in IVS cells from cancer patients (Cancer; N=13) than in IVS from normal female donors (Normal; N=17).

Figure 6A:
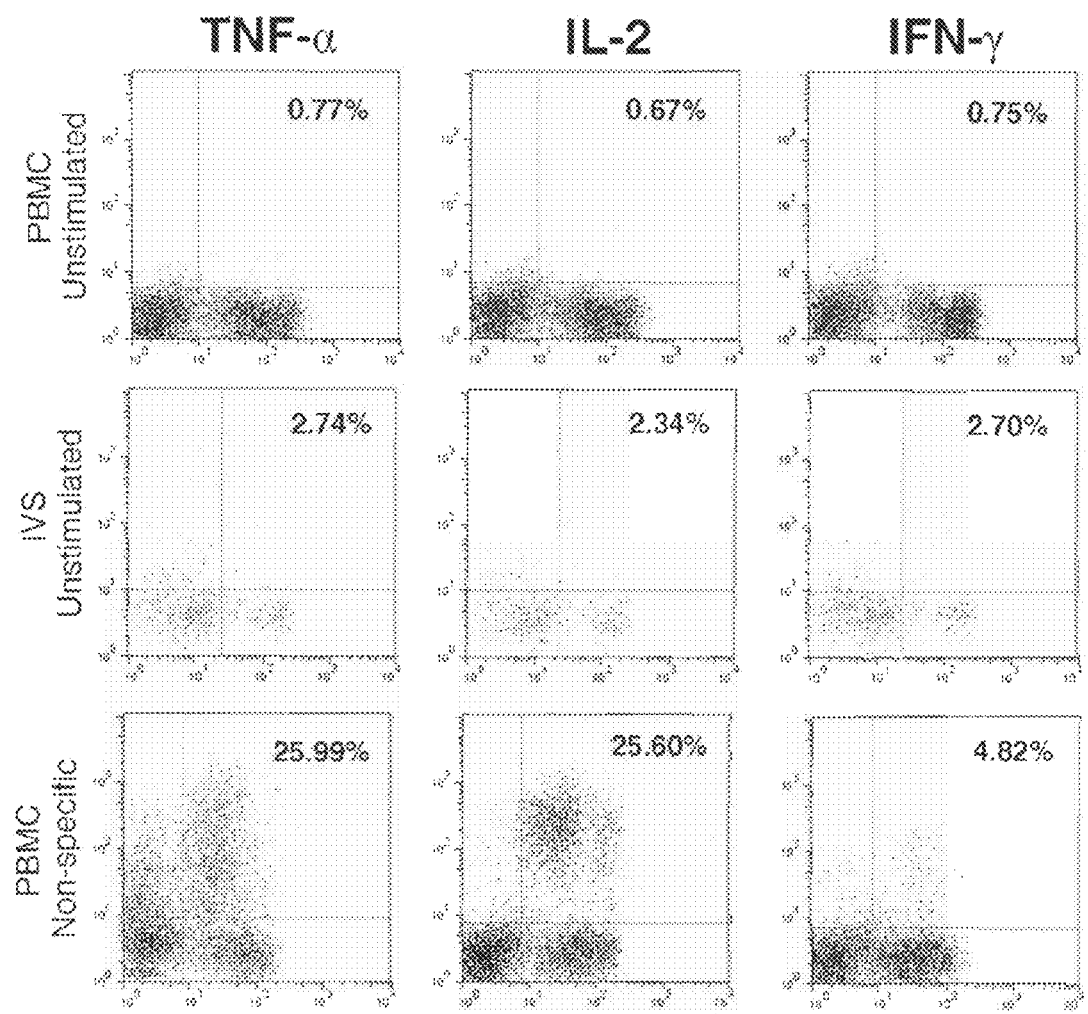

FIG. 6A are graphs of intracellular TNF-α, IL-2 and IFN-γ production by PBMCs and HERV-K-specific IVS cells, as assessed by intracellular cytokine staining. PBMCs, or IVS cells obtained by stimulating PBMCs from the same donor with HERV-K pulsed DCs, were either not activated as negative controls (Unactivated), nonspecifically activated with a leukocyte activation cocktail as positive controls (Non-specific), or activated with HERV-K plus brefeldin A (HERV-K-activated). Increased HERV-K-activated cytokine production was observed in the IVS cells only (CD3+ T cells).

Figure 6B:
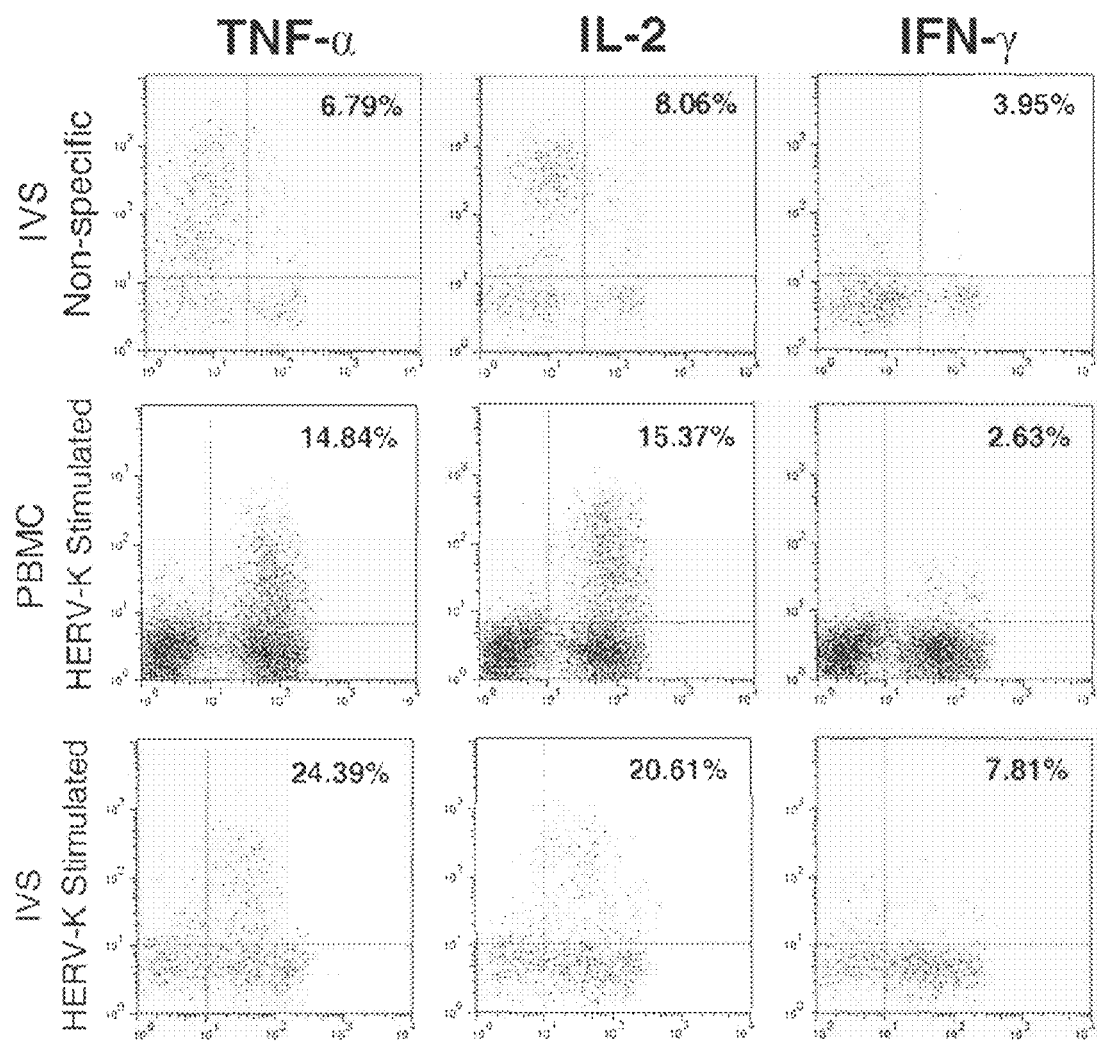

FIG. 6B are graphs of intracellular TNF-α, IL-2 and IFN-γ production by PBMCs and HERV-K-specific IVS cells, as assessed by intracellular cytokine staining. PBMCs, or IVS cells obtained by stimulating PBMCs from the same donor with HERV-K pulsed DCs, were either not activated as negative controls (Unactivated), nonspecifically activated with a leukocyte activation cocktail as positive controls (Non-specific), or activated with HERV-K plus brefeldin A (HERV-K-activated). Increased HERV-K-activated cytokine production was observed in the IVS cells only (CD3+ T cells).

Figure 6C:
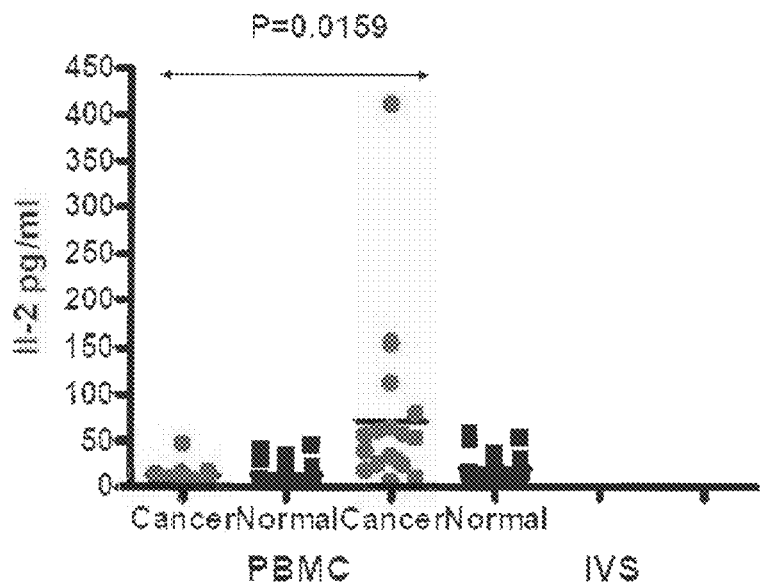

FIG. 6C is a graph of the results of a cytokine bead array, used to determine HERV-K-specific cytokine production after 1 week IVS. IL-2 secretion was significantly elevated in 1 week IVS from BC patients, in comparison to PBMC obtained from BC patients (N=17; p=0.0159; Student's t-test). In contrast, no significant change was observed in 1 week IVS from normal controls, in comparison to PBMC obtained from normal controls (N=15).

Figure 6D:
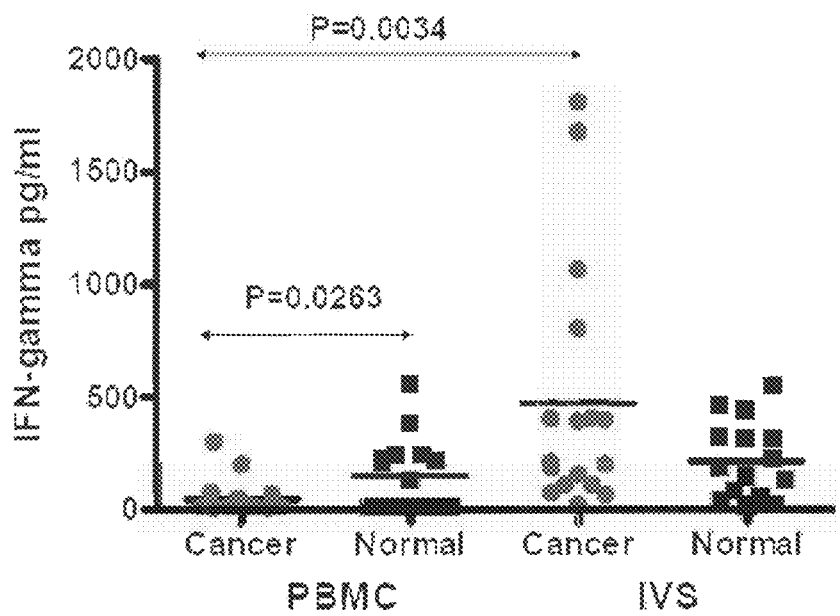

FIG. 6D is a graph of the results of a cytokine bead array, used to determine HERV-K-specific cytokine production after 1 week IVS. Similar to IL-2, IFN-γ secretion was significantly elevated in 1 week IVS from BC patients, in comparison to PBMC obtained from BC patients (N=17; p=0.0034; Student's t-test). As with IL-2 normal control subjects, no significant difference in IFN-γ secretion was observed between 1 week IVS and PBMC obtained from normal controls (N=15). IFN-γ secretion was significantly lower (p=0.0263) in PBMC obtained from BC patients than in PBMC from normal controls, which suggests that BC patients may be immunosuppressed.

Figure 7A:
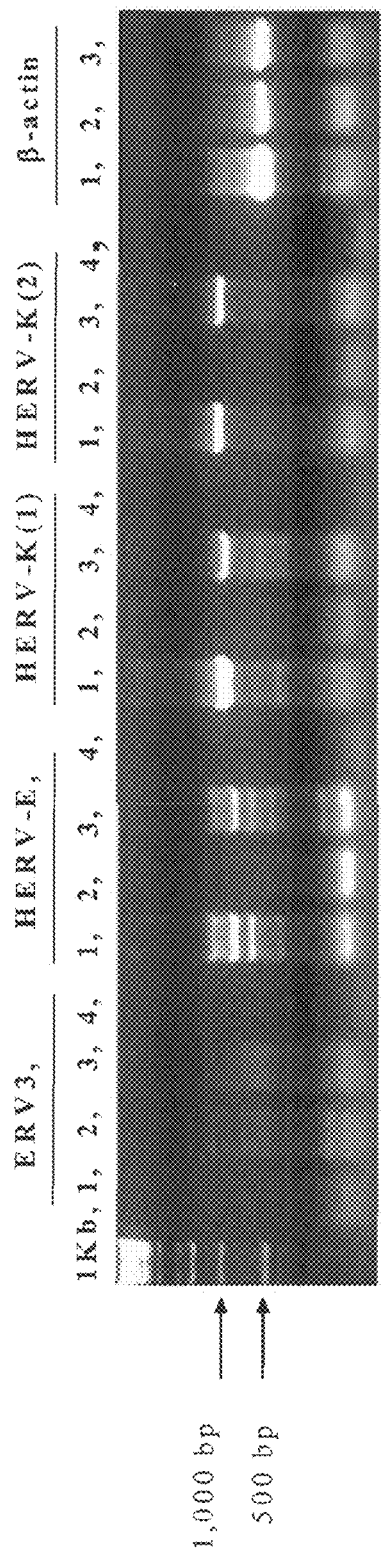

FIG. 7A is an illustration of expression of HERV env RNAs in ovarian cell lines and tissues by RT-PCR for ERV3, HERV-E, HERV-K type 1, HERV-K type 2, and β-actin primers in OVCAR3 ovarian cancer cells, NOE 114 normal ovarian epithelial cells, and SKOV3 ovarian cancer cell. Cell lines: From left to right, each set of lanes for a given amplified gene represents the RT-PCR expression pattern using ERV3, HERV-E, HERV-K type 1 (HERV-K (1)), HERV-K type 2

(HERV-K (2)), and β-actin primers in OVCAR3 ovarian cancer cells (lane 1), NOE 114 normal ovarian epithelial cells (lane 2) and SKOV3 ovarian cancer cell (lane 3). 4. The final lane in each set is a no-template control (lane 4).

Figure 7B:
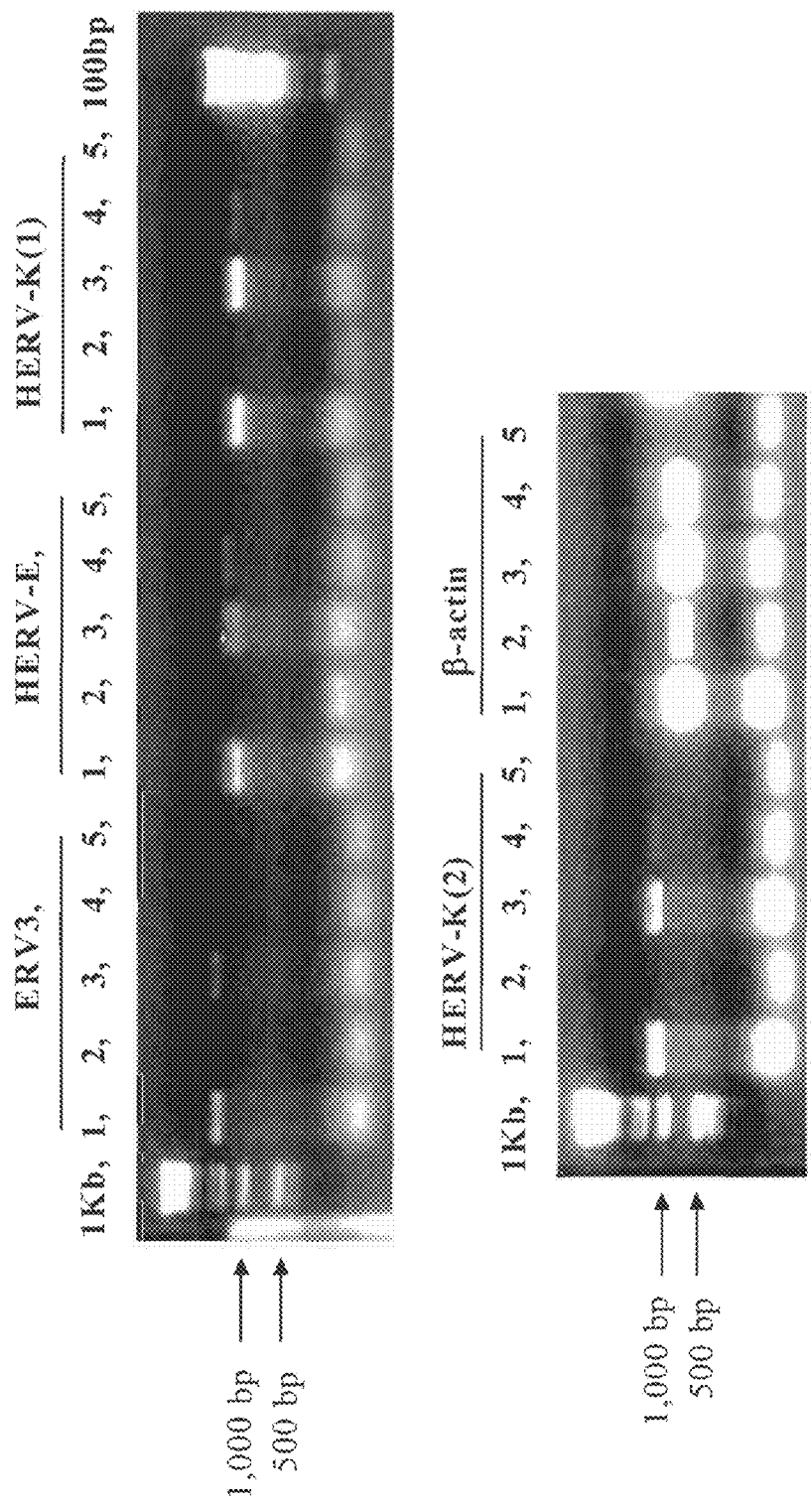

FIG. 7B are illustrations of expression of HERV env RNAs in ovarian cell lines and tissues by RT-PCR for ERV3, HERV-E, HERV-K type 1, and HERV-K type 2 env mRNA in matched tumor/normal tissues. Expression of various HERV env mRNAs was evaluated in two cancer tissues (lanes 1 and 3) with their matched uninvolved normal ovarian tissues (lanes 2 and 4) obtained from the same patients. The final lane in each set is a no-template control (lane 5).

Figure 7C:
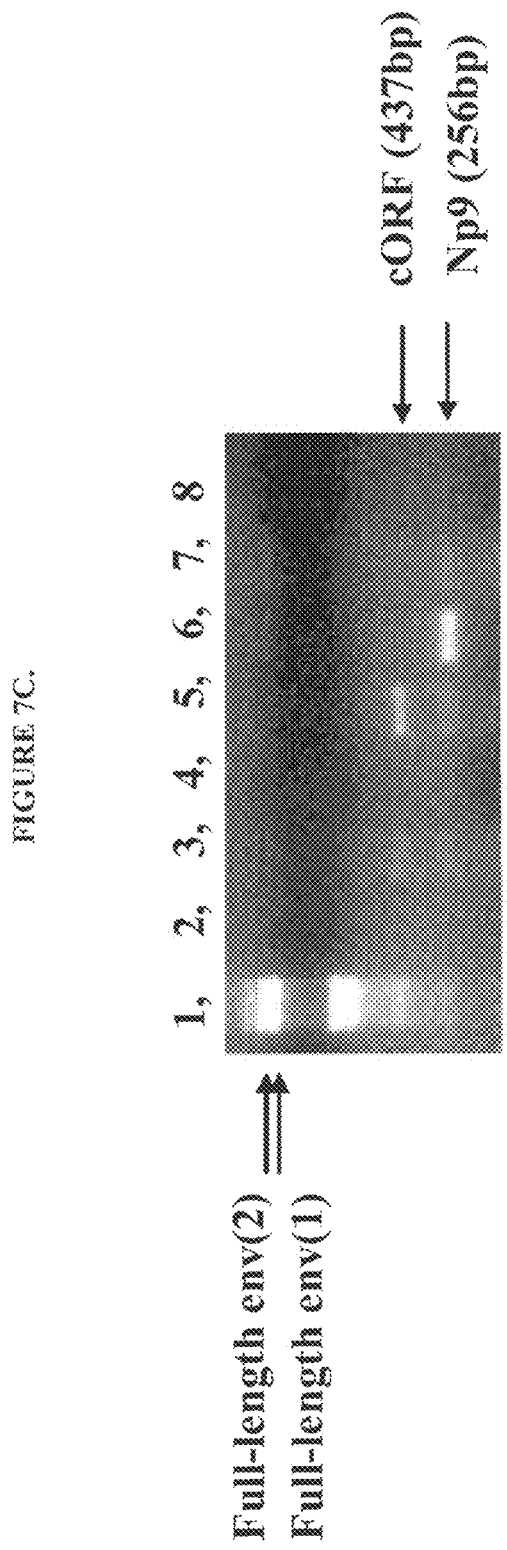

FIG. 7C is an illustration of expression of HERV env RNAs in ovarian cell lines and tissues by RT-PCR for spliced HERV-K transcripts. Lanes 1-7: each lane represents a different ovarian cancer specimen. The final lane is a no-template control (lane 8). Full-length (2) and Full-length (1) represent unspliced full-length HERV-K type-2 and type-1 transcripts, respectively.

Figure 7D:
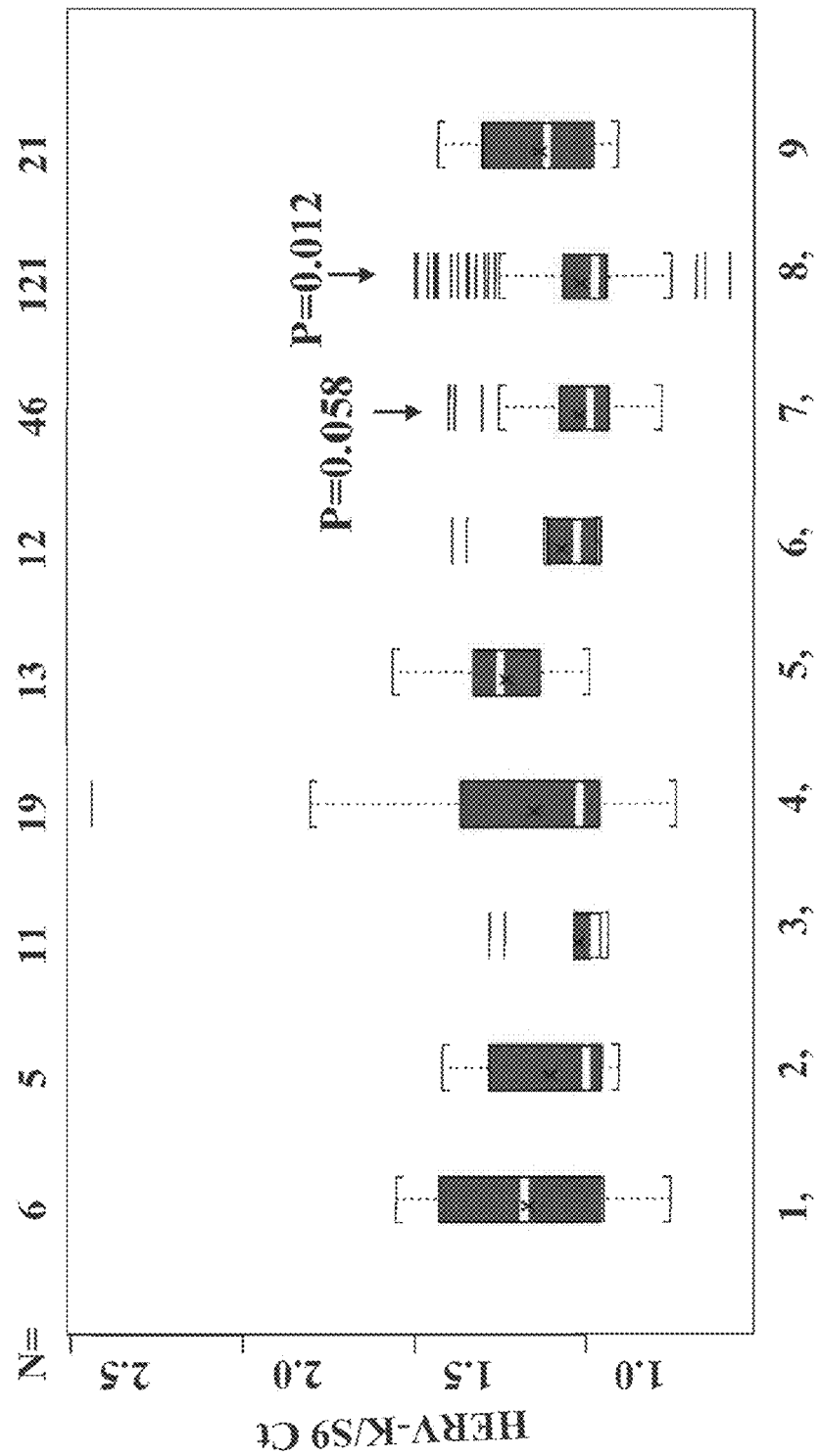

FIG. 7D is a graph quantifying HERV-K env mRNA in various ovarian tissues. The amount of HERV-K in unknown samples was quantitated using cycle threshold ($C_T$) values of HERV-K env mRNA obtained from each specimen by real-time RT-PCR, normalized on the basis of the $C_T$ of *Homo sapiens* ribosomal protein S9. The ratio of HERV-K mRNA $C_T$ in ovarian tumor tissues to the average $C_T$ in normal ovarian control tissues was calculated. The boxplot gives the upper extreme value (the line on the top), upper quartile (the top of box), median (the white band inside the box), mean (the 'X' symbol), lower quartile (the bottom of box), and lower extreme (the line on the bottom) for each box. Boxplots not only show the location and spread of data but indicate skewness as well. For this case, the bulb-peak distance has a smaller average value and variation than the it-peak distance. From left to right: 1. Benign epithelial tumor; N=6; 2. Epithelial tumor with low potential, N=5; 3. Mixed epithelial tumor, N=11; 4. Normal ovarian controls, N=19; 5. Placenta (as a control), N=13; 6. Uninvolved ovarian tissues, N=12; 7. Epithelial tumor with metastasis, N=46; 8. Epithelial tumor without metastasis, N=121; and 9. Sex cord and stromal tumor (including germ cell tumor), N=21. HERV-K env expression was significantly greater (lower $C_T$) in tissues from epithelial tumor without metastasis (p=0.012), and epithelial tumor with metastasis (p=0.058), relative to expression in normal and benign ovarian control tissues.

FIG. 8A are illustrations of surface expression of HERV-K env protein on ovarian cancer cells. Surface and cytoplasmic expression of HERV-K env protein was detected in ovarian cancer cell lines (OVCA 420 and DOV13), but not in normal ovarian epithelial cells (T29 and T80) without permeabilization (No-perm) and permeabilized with 0.1% Triton X-100 (Perm). Surface and cytoplasmic expression of HERV-K env protein was detected in DOV13 cells by FACS analysis. Cells stained with FITC-IgG Ab served as a negative control.

FIG. 8B is a graph of expression of HERV proteins in various ovarian tissues.

Figure 8C:
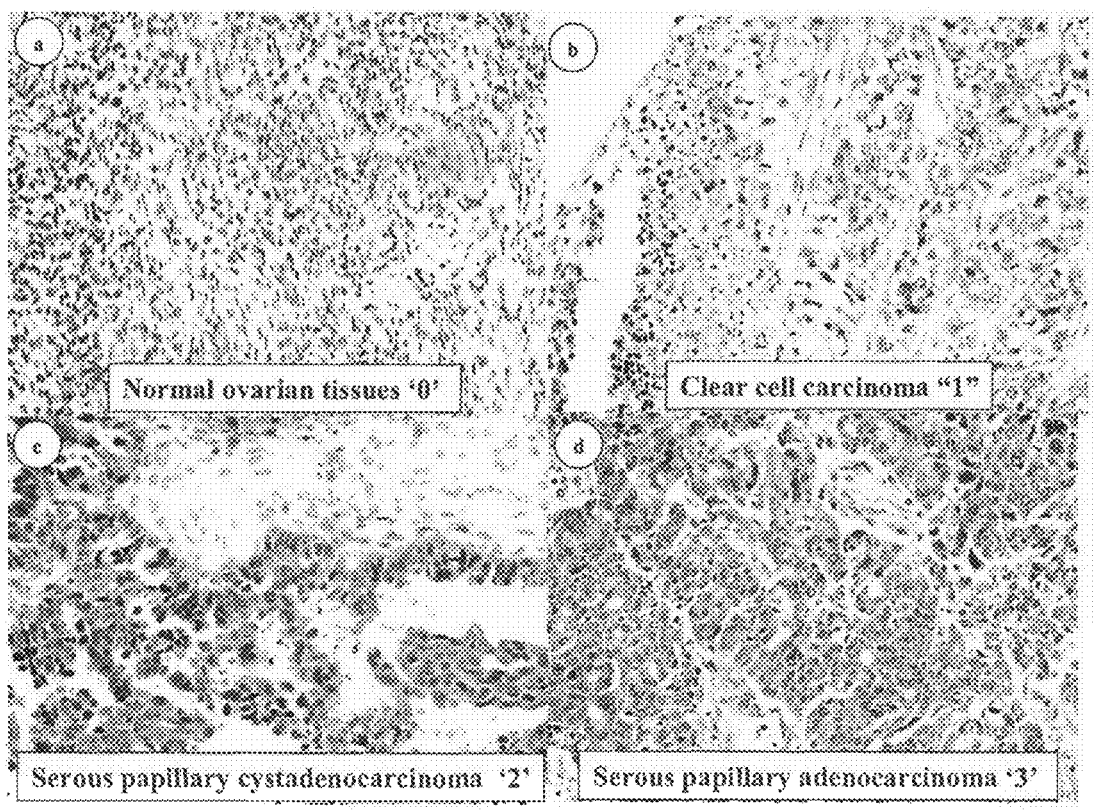

FIG. 8C are illustrations of samples exhibiting positive immunostaining for HERV-K from TMA1 microarray: a. Normal ovarian tissues (score "0"; 40×). b. Clear cell carcinoma (score "1"). c. Serous papillary cystadenocarcinoma (score "2"). d. Serous papillary adenocarcinoma (score "3").

Figure 8D:
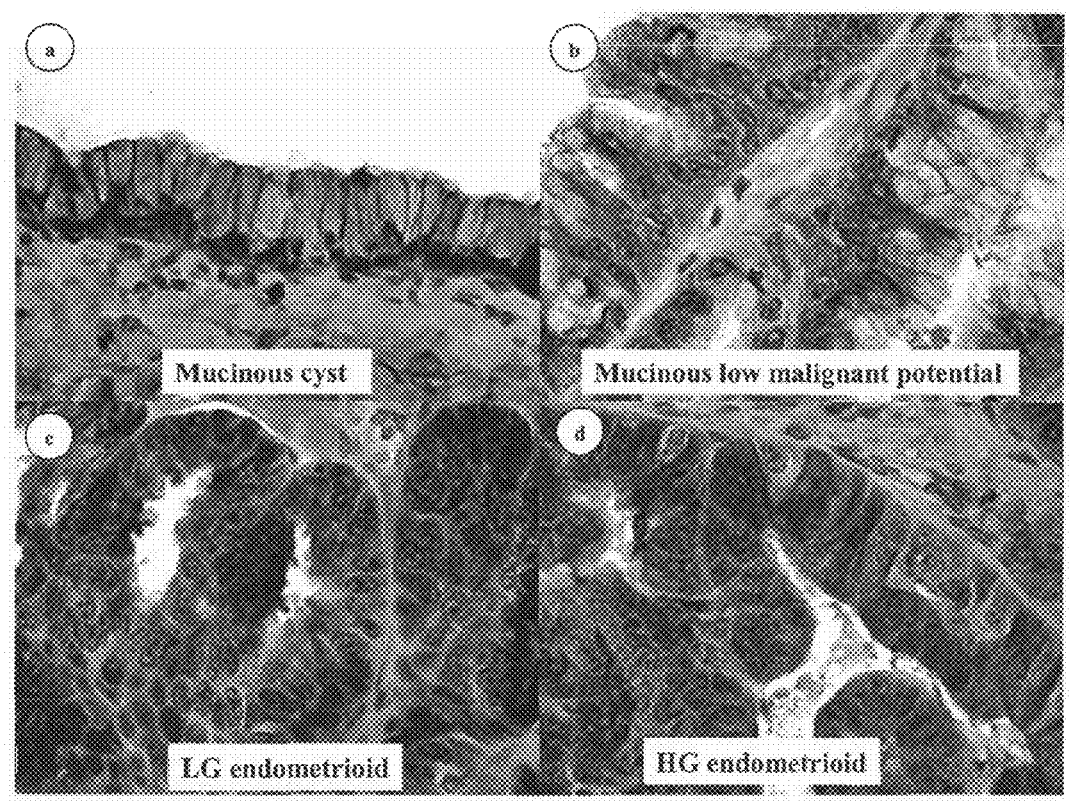

FIG. 8D are illustrations of samples exhibiting positive immunostaining for HERV-K from TMA2 microarray: a. Mucinous cyst. b. Mucinous LMP (low malignant potential). c. LG (Low-grade) endometrioid. d. HG (High-grade) endometrioid.

Figure 8E:
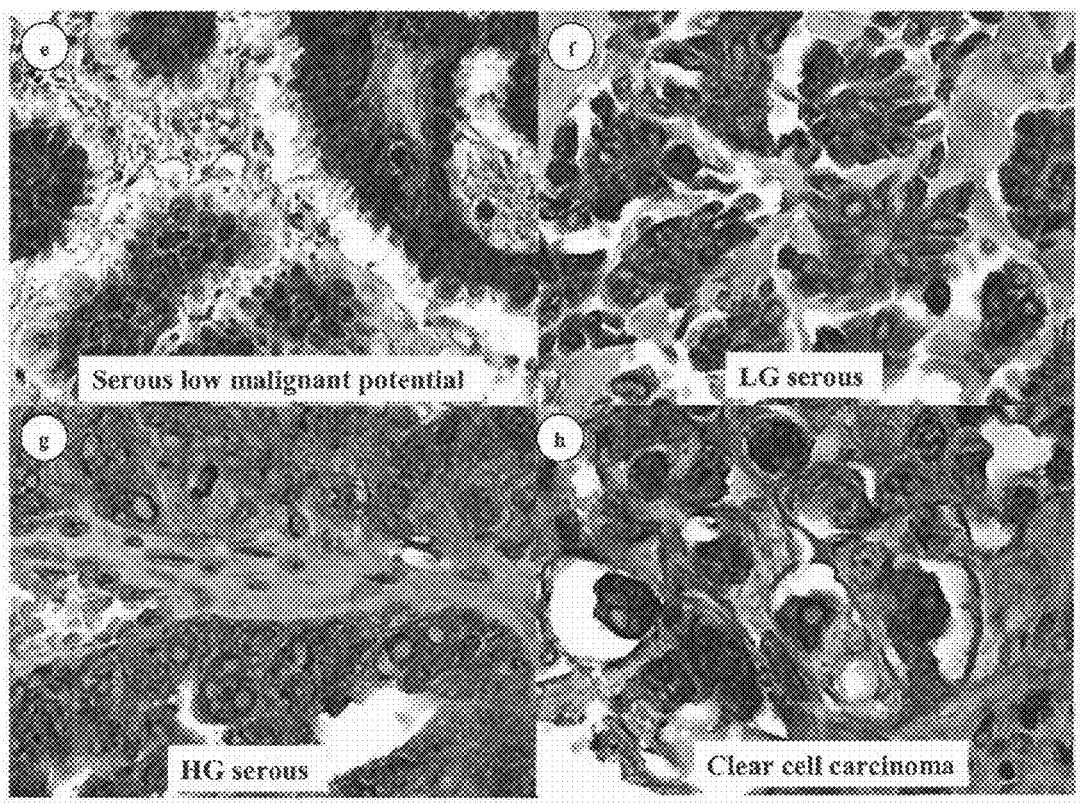

FIG. 8E are illustrations of are illustrations of samples exhibiting positive immunostaining for HERV-K from TMA2 microarray: e. Serous LMP. f. LG Serous. g. HG Serous. h. Clear cell carcinoma.

Figure 9A:
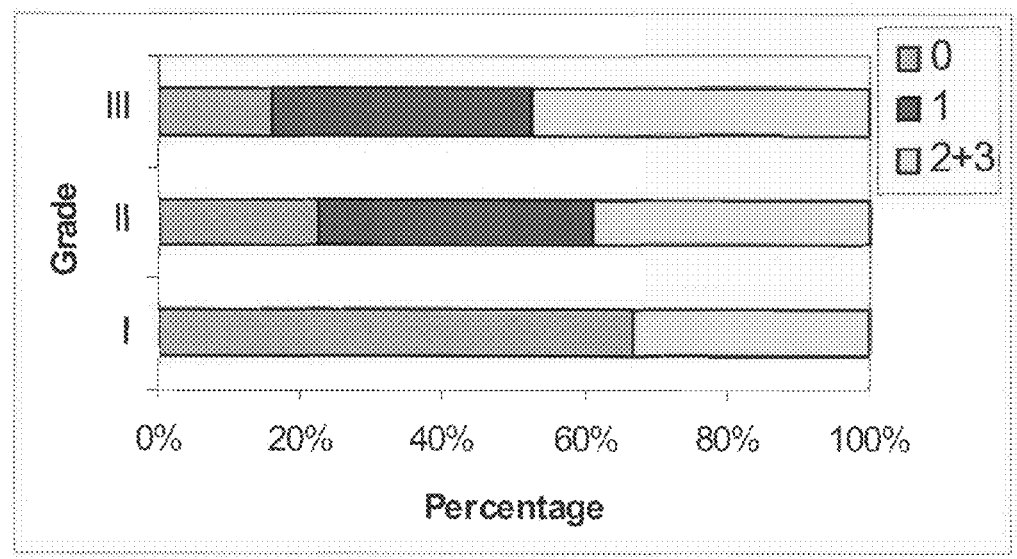

FIG. 9A is a graph of an expression profile of HERV-K env SU protein expression in serous papillary adenocarcinoma of various grades (I, II and III). Percentage of "no expression" progressively decreased from lower to higher grades, whereas percentage of "strong expression" progressively increased from lower to higher grades.

Figure 9B:
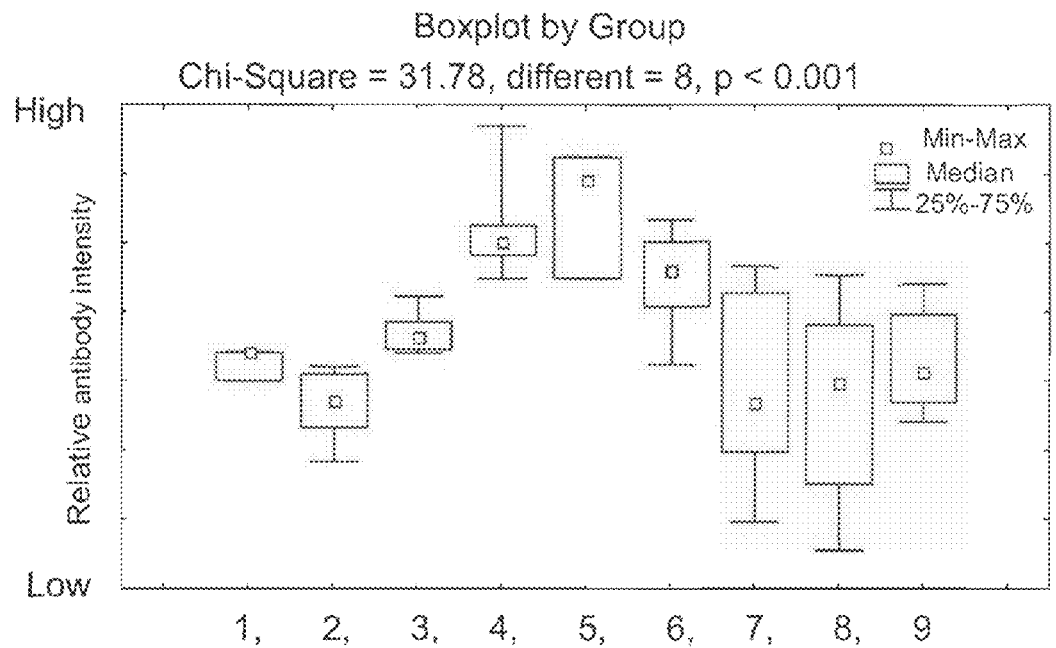

FIG. 9B is a graph of an analysis of ovarian cancer progression with tissue microarrays: 1. Normal ovary. 2. Mucinous cyst. 3. Mucinous tumor of low malignant potential. 4. Serous tumor of low malignant potential. 5. Low-grade serous carcinoma. 6. Low-grade endometrial carcinoma. 7. High-grade serous carcinoma. 8. High-grade endometrial carcinoma. 9. Clear cell carcinoma. Low malignant potential and low-grade tumors showed higher levels of expression compared to normal ovarian surface epithelial cells (Kruskall Wallis analysis p<0.001). High-grade tumors showed great variability in protein expression with a median expression slightly lower compared to normal ovaries.

Figure 10A:
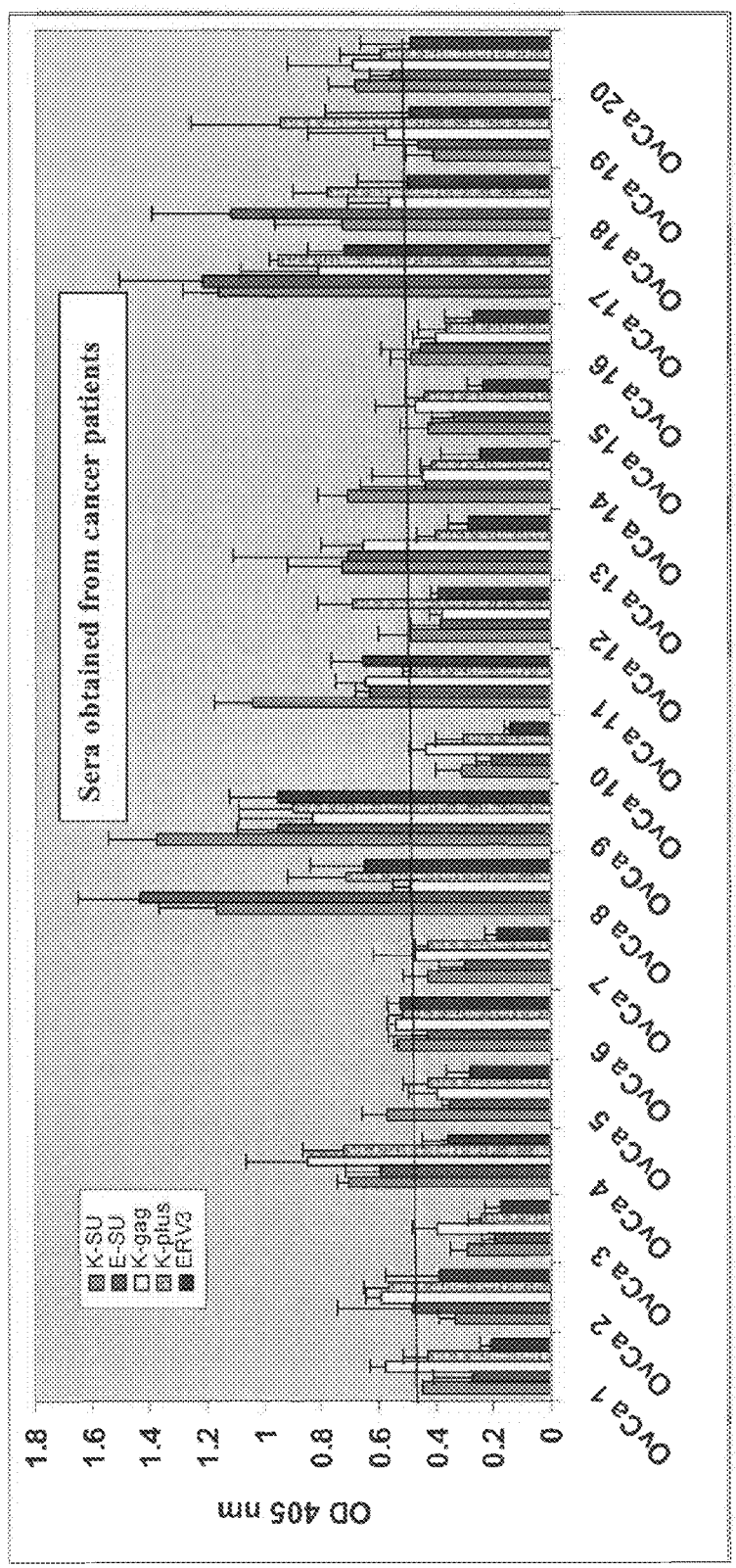

FIG. 10A is a graph of binding affinity and specificity of anti-HERV-K sera from 20 patients with ovarian cancer. An ELISA plate was coated with HERV env fusion proteins including HERV-K envelope surface protein (K-SU), HERV-E surface protein (E-SU), HERV-K gag protein (K-gag), HERV-K plus (a HERV-K spliced env product), and ERV3 env protein. Sera obtained from 20 patients with ovarian cancer were tested. The ELSIA plate was read at a wavelength of 405 nm. The cutoff value is 0.5 for OD at 405 nm.

Figure 10B:
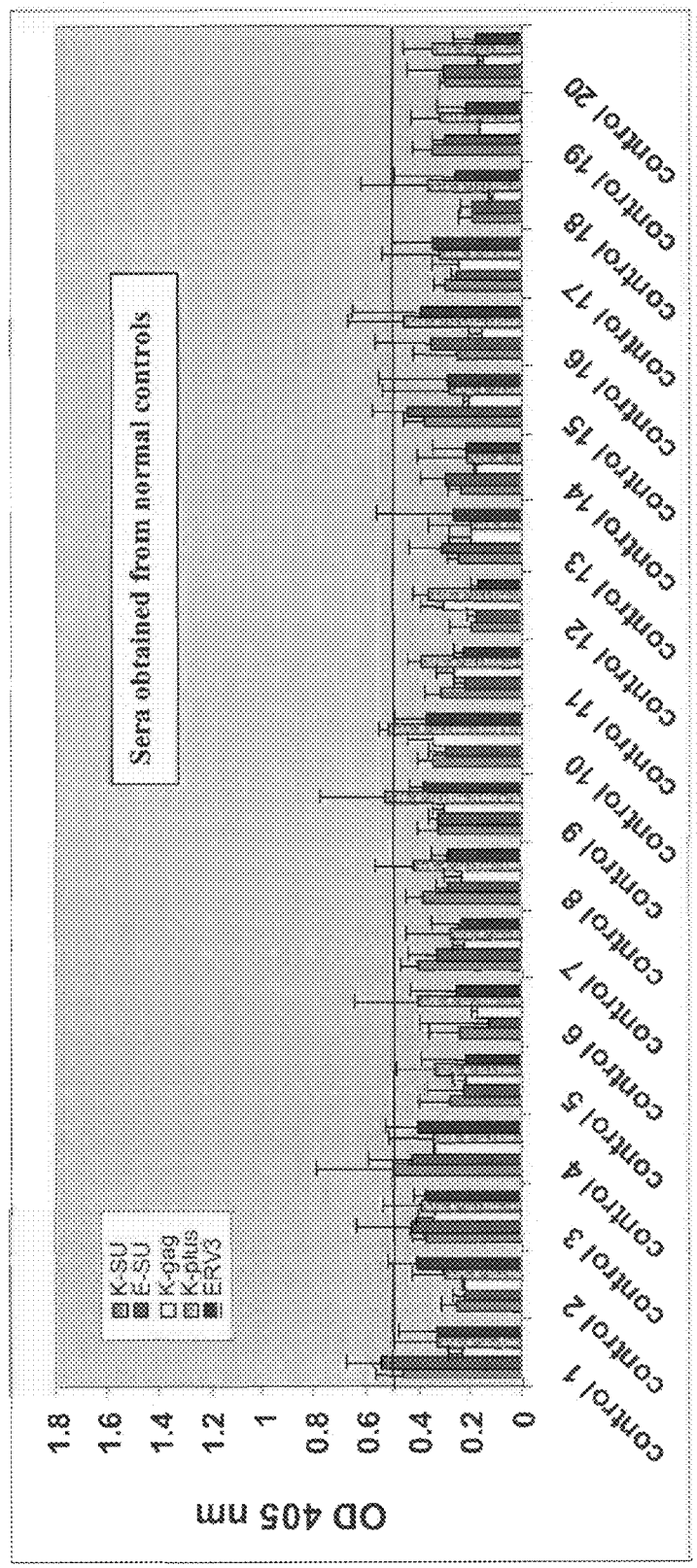

FIG. 10B is a graph of binding affinity and specificity of anti-HERV-K sera from 20 normal female controls. An ELISA plate was coated with HERV env fusion proteins including HERV-K envelope surface protein (K-SU), HERV-E surface protein (E-SU), HERV-K gag protein (K-gag), HERV-K plus (a HERV-K spliced env product), and ERV3 env protein. Sera obtained from 20 normal female controls were tested. The ELSIA plate was read at a wavelength of 405 nm. The cutoff value is 0.5 for OD at 405 nm.

Figure 11A:
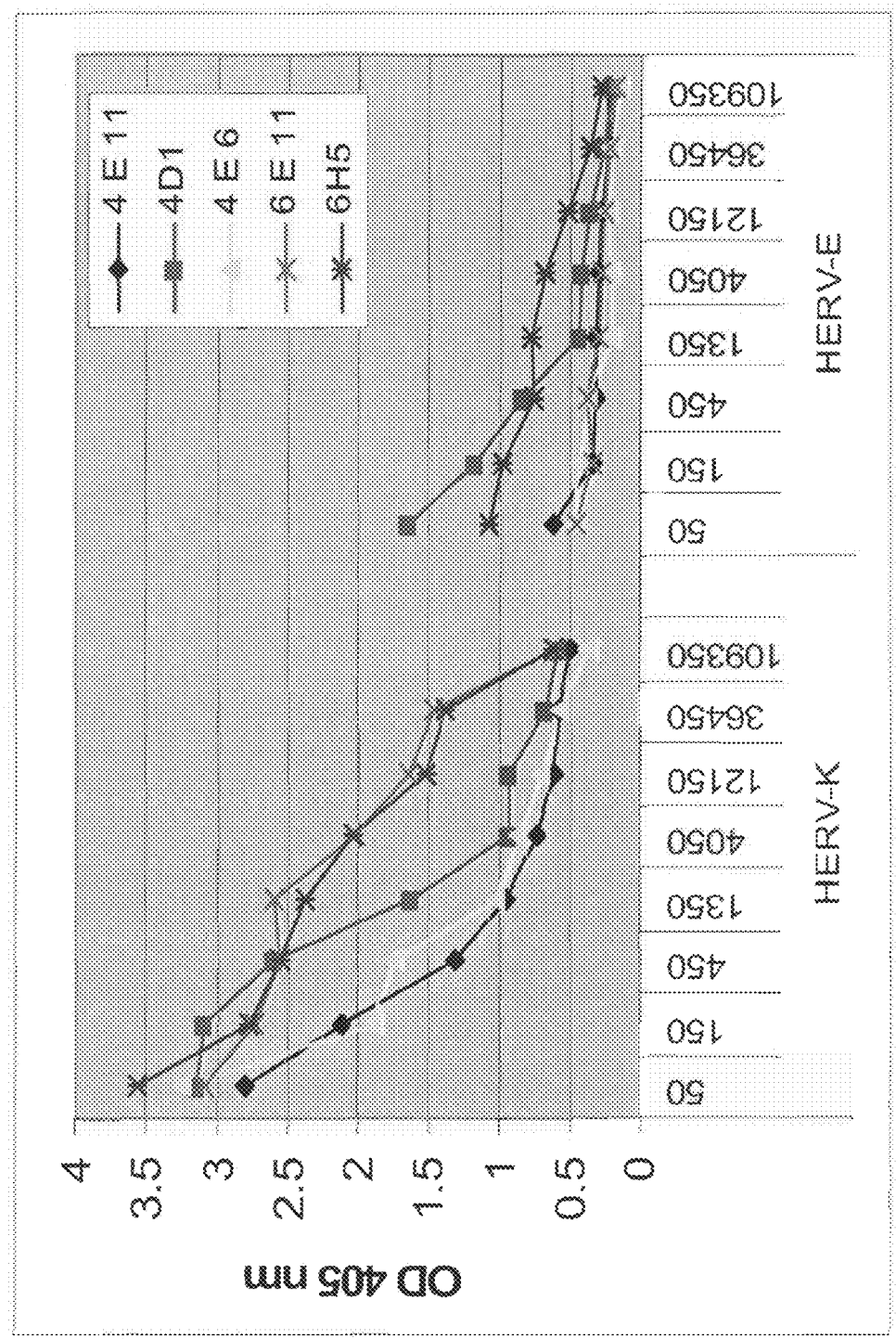

FIG. 11A is a graph of the binding affinity and specificities of anti-HERV-K monoclonal antibodies from an ELISA analysis of binding affinity and specificities of the positive clones derived from anti-HERV-K hybridoma cells. The ELISA plate was coated with HERV-K or HERV-E env fusion proteins (10 µg per ml, 100 µl per well). The media obtained from several positive clones were diluted from 1:50 to 1:109, 350. The ELISA plate was read at a wavelength of 405 nm.

Figure 11B:
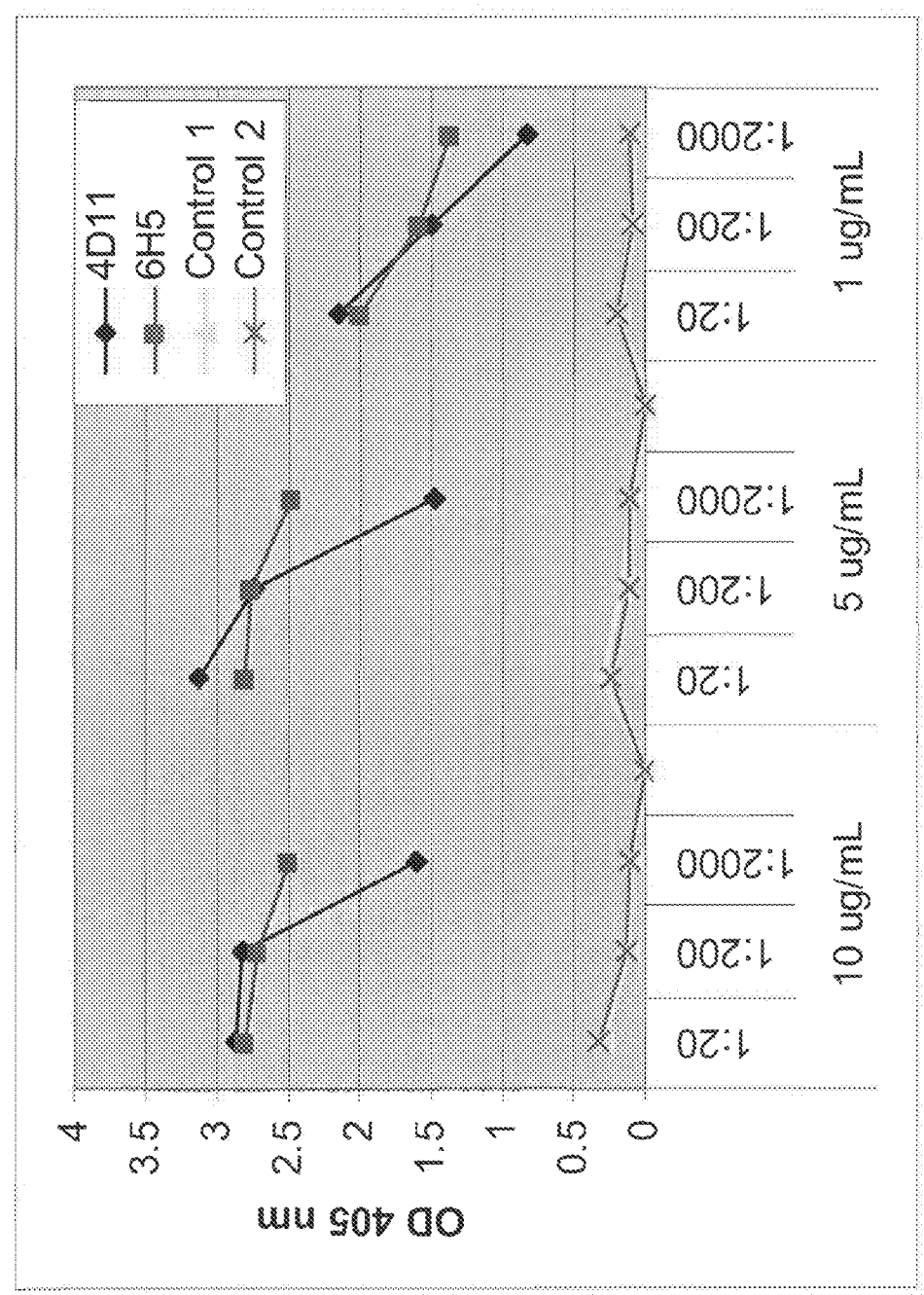

FIG. 11B is a graph of the binding affinity and specificities of anti-HERV-K monoclonal antibodies from an ELISA analysis of binding affinity and specificities of the positive clones derived from anti-HERV-K hybridoma cells. Various concentrations of HERV-K env protein were coated on ELISA plates, and the medium obtained from two hybridoma clones (4D11 and 6H5) and two negative controls were diluted from 1:20, to 1:2,000. These positive clones, but not two negative controls, reacted with only HERV-K env fusion protein.

Figure 11C:
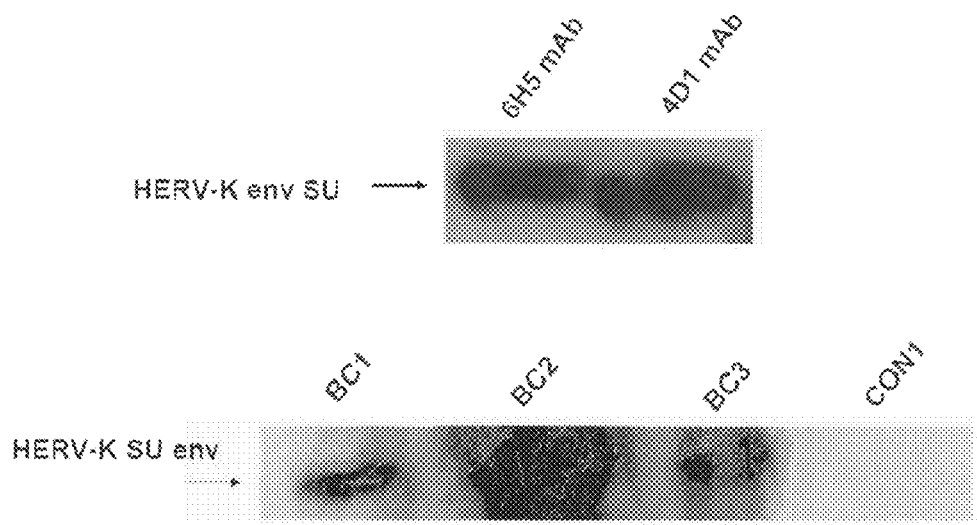

FIG. 11C is an image illustrating binding of mAb clones 4D1 or 6H5 to HERV-K env SU fusion protein, confirmed by Western blot. Antibodies against HERV-K env protein in sera obtained from patients with BC (BC1, BC2, and BC3), but not in sera from a normal donor (CON1) were demonstrated by Western blot.

Figure 11D:
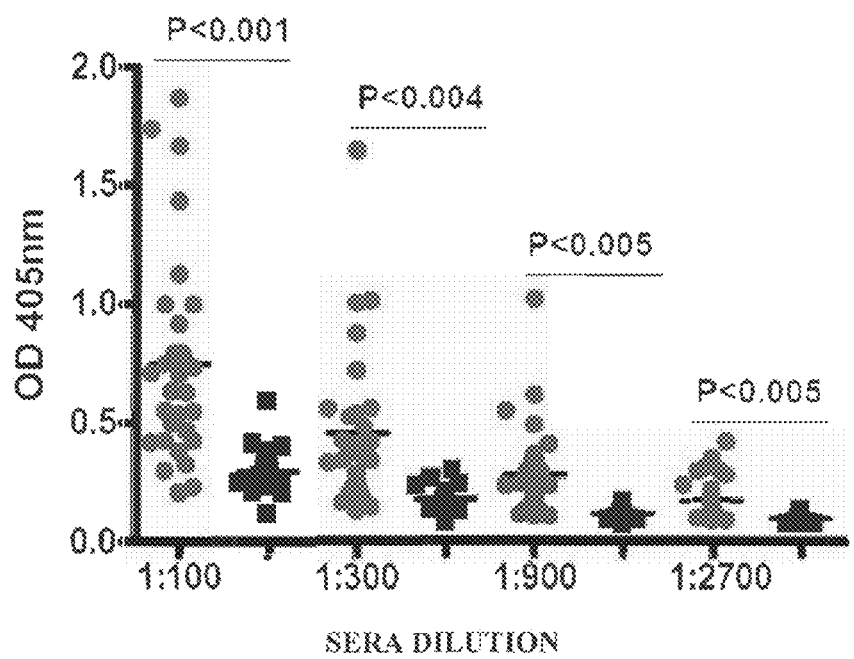

FIG. 11D is a graph illustrating titration of antibodies against HERV-K env SU protein in sera from BC patients, accomplished by ELISA. The sera obtained from normal female donors were used as controls. The frequency of antibodies detected in patients with BC (N=31) and normal donors (N=20) is shown. Anti-HERV-K SU antibody titers were significantly higher in BC patients than in normal donors.

Figure 12:
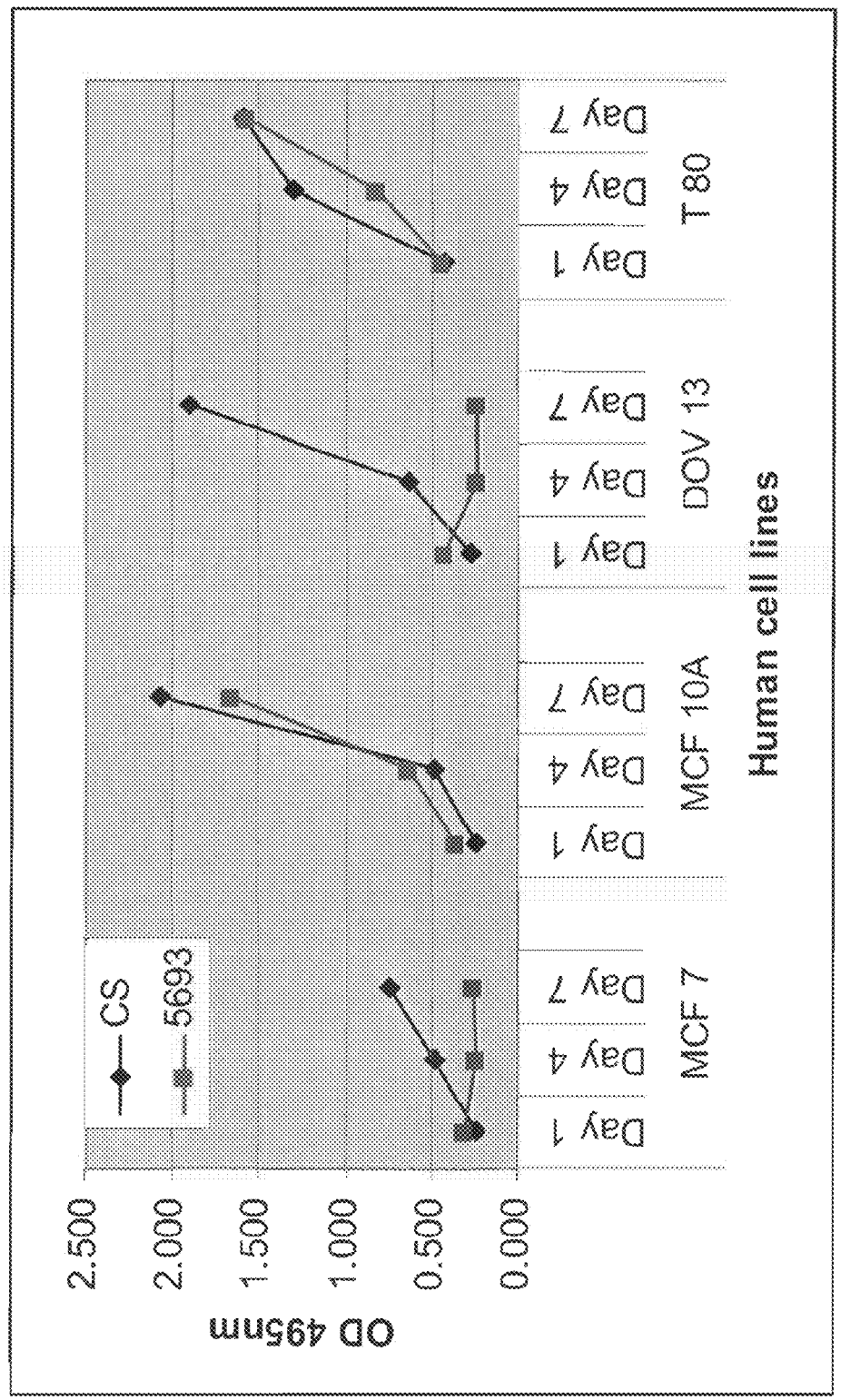

FIG. 12 is a graph showing that an anti-HERV-K antibody inhibits proliferation of breast (MCF-7) and ovarian (DOV13) cancer cell lines, but not normal breast (MCF-10A) or ovarian (T80) cell lines. Human epithelial cells were treated with anti-HERV-K antibody (5693) or preimmune sera (CS) on day 1 and day 4. Proliferation of cells was measured by the MTT assay. Values represent the mean of six replicate wells at days 1, 4, and 7 of culture.

Figure 13A:
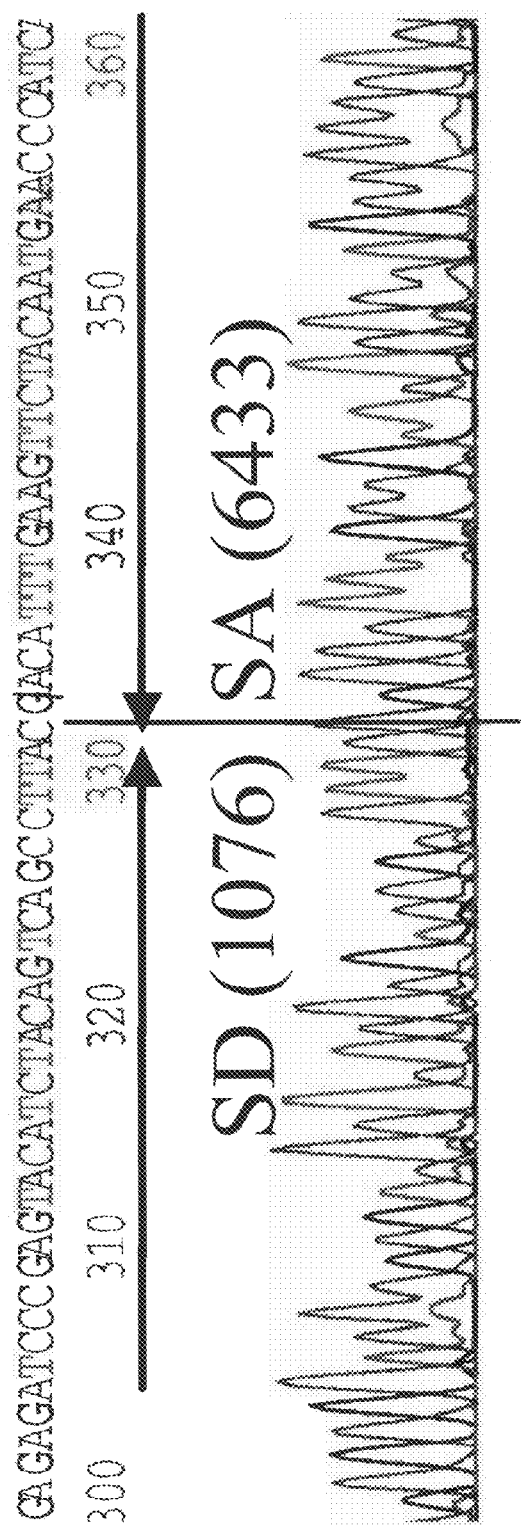

FIG. 13A is a graph showing splice donor (SD) (SEQ ID. NO:1) and splice acceptor (SA) sites (SEQ ID. NO:2) for HERV-K subgenomic transcripts from human breast cancer tissue. Samples #165U2 and #165U4 are located at by numbers 1076 and 6433, respectively, according to the type 2 HERV-K, HML-2.HOM sequence.

Figure 13B:
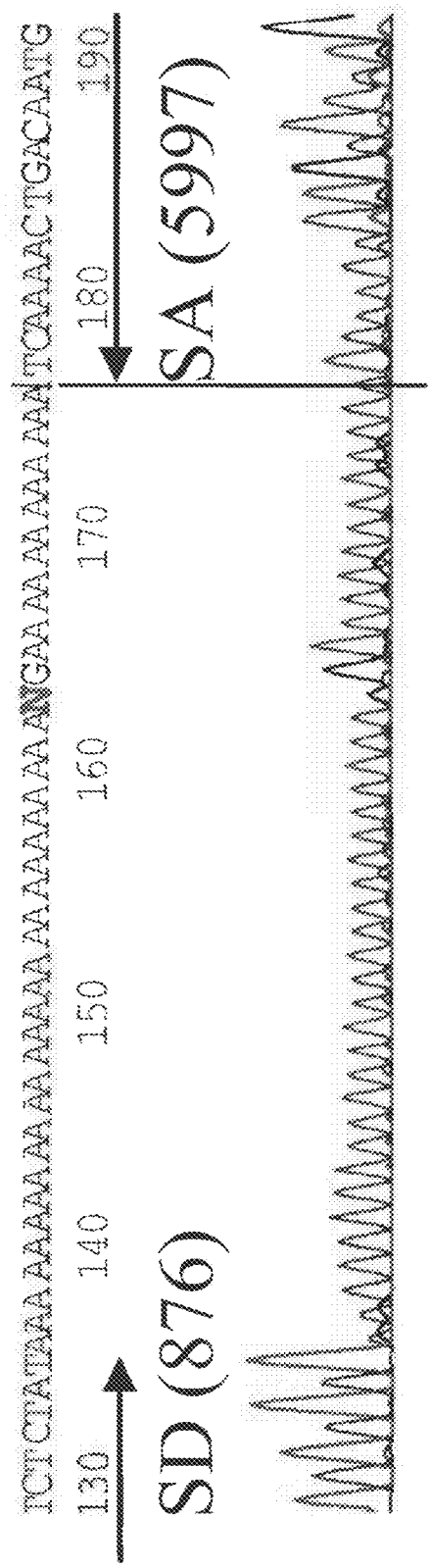

FIG. 13B is a graph showing SD (SEQ ID. NO:3) and SA (SEQ ID. NO:4) sites for HERV-K subgenomic transcripts from human breast cancer tissues. Samples #165U3 and 165U5 are located at by numbers 876 and 5997, respectively, according to the type 1 HERV-K, HERV-K102 sequence.

Figure 13C:
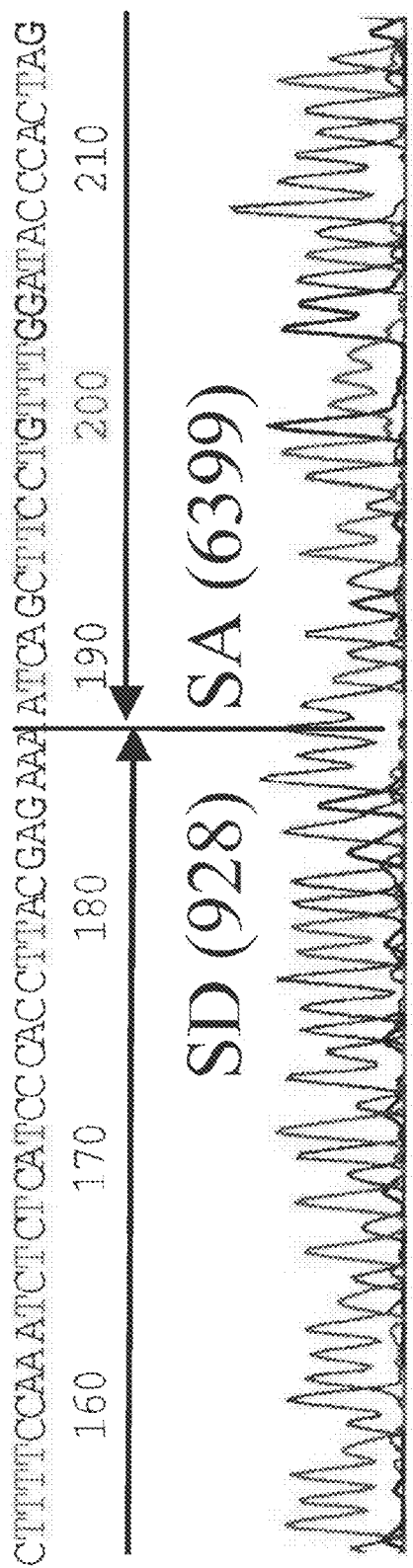

FIG. 13C is a graph showing SD (SEQ ID. NO:5) and SA (SEQ ID. NO:6) sites for HERV-K subgenomic transcripts from human breast cancer tissues. Samples #178U11 and 178U15 are located at by numbers 928 and 6399, respectively, according to the type 1 HERV-K, HERV-K102 sequence.

Figure 13D:
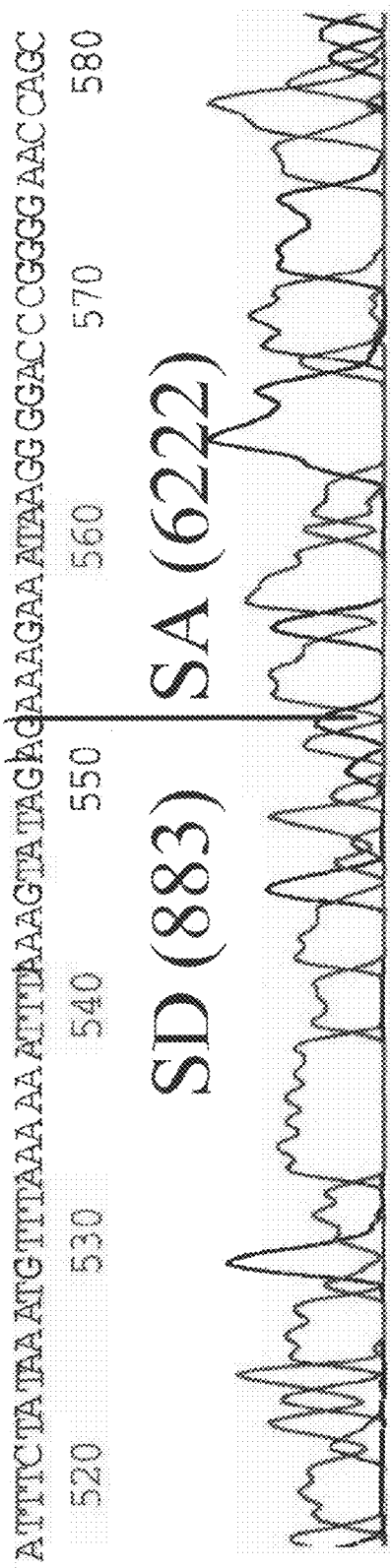

FIG. 13D is a graph showing SD (SEQ ID. NO:7) and SA (SEQ ID. NO:8) sites for HERV-K subgenomic transcripts from hormone-treated T47D cells located at by numbers 883 and 6222, respectively, according to the type 1 HERV-K102 sequence.

Figure 13E:
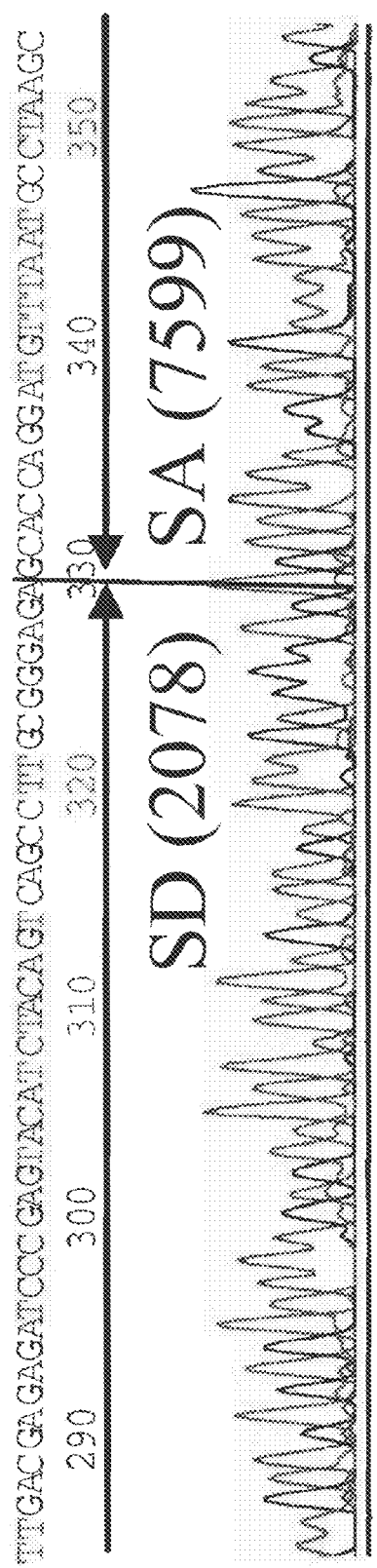

FIG. 13E is a graph showing SD (SEQ ID. NO:9) and SA (SEQ ID. NO:10) sites for HERV-K subgenomic transcripts from hormone-treated MCF-7 or MDA-MB-231 cells are located at by numbers 2078 and 7599, respectively, according to the type 1 HERV-K (II) sequence.

Figure 14A:
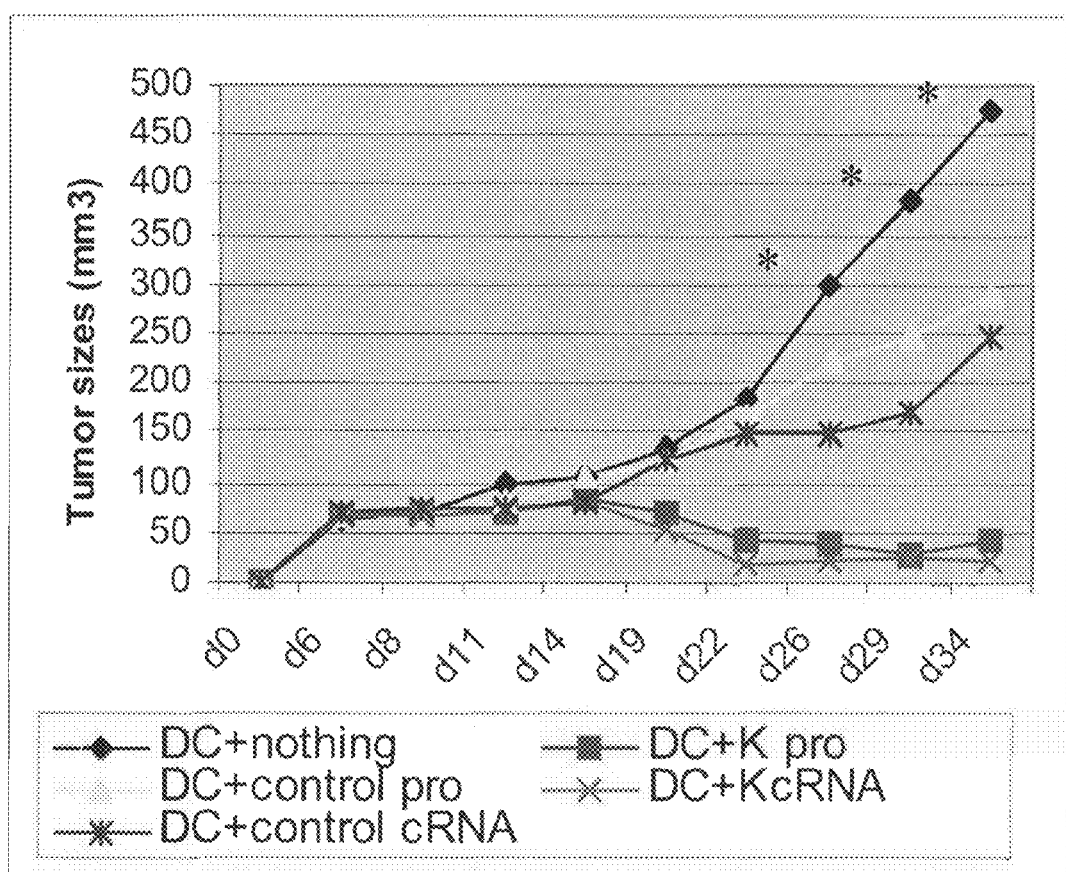

FIG. 14A is a graph showing the anti-tumor effect of HERV-K env protein antigen in mice. Mice were inoculated with B6DK cells ($5\times10^6$ cells) on day 0 and randomly divided into groups and treated with bone-marrow DC pulsed with nothing, HERV-K env protein (DC+K pro); control protein (DC+control pro), HERV-K cRNA (DC+KcRNA); or with control cRNA (DC+control cRNA) on day 3, day 10, and day 17 post-injection. Tumors were monitored twice per week and tumor sizes were compared between each group.

Figure 14B:
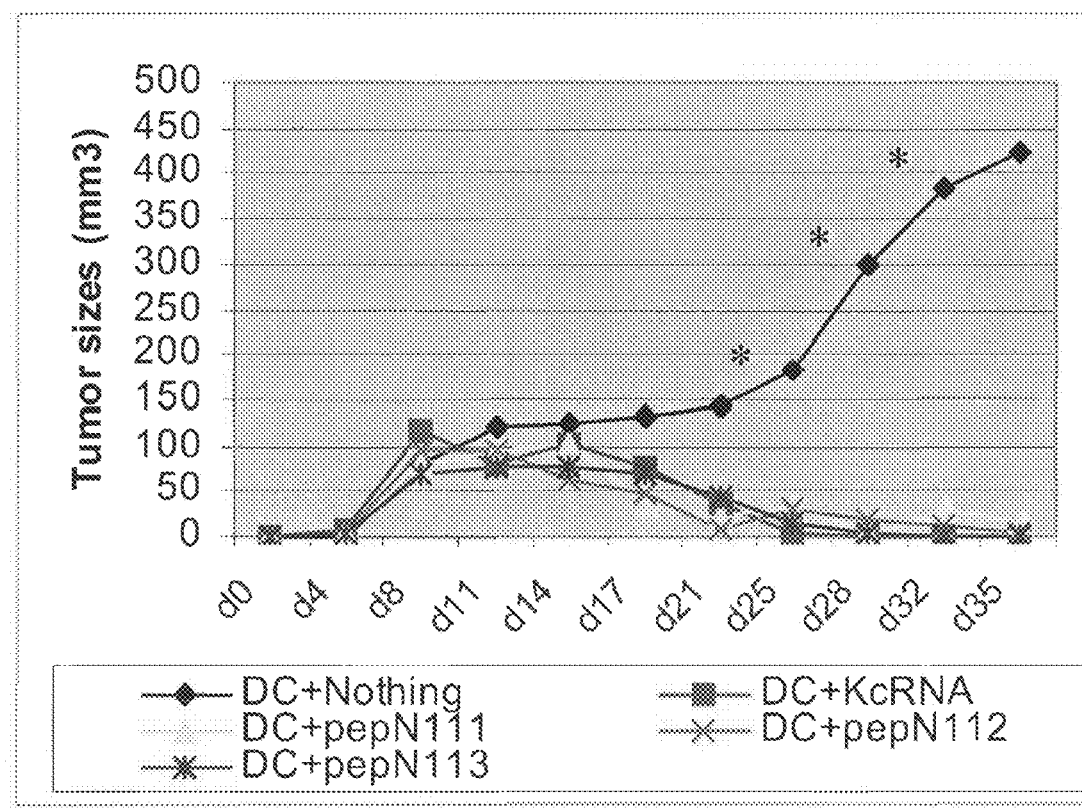

FIG. 14B is a graph showing is a graph showing the anti-tumor effect of HERV-K env protein antigen in mice. Mice were inoculated with B6DK cells ($5\times10^6$ cells) on day 0 and randomly divided into groups and treated with bone-marrow DC pulsed with HERV-K cRNA (DC+KcRNA), HERV-K env derived peptide for surface protein (Kp201) or transmembrane protein (Kp640), DNA methyl transferase I (p1028; as positive control), and nothing on day 7, day 14, and day 21 post-injection. DC pulsed with HERV-K env protein, cRNA, or even peptides elicit a strong antitumor response to B6DK ($*p<0.05$) compared with mice treated with DC only.

FIG. 15 are DNA and protein sequences of anti HERV-K scFv. (A) DNA sequences of anti HERV-K scFV (SEQ ID. NO:11); bold sequence at 5' end is restriction site for SfiI, and sequence at 3' end is restriction site for NotI. Bold sequence in the middle is linker sequence. Sequence between SfiI site and linker is heavy chain scFv sequence, and sequence between linker and NotI is light chain scFv sequence. (B) Amino acid sequences of anti HERV-K scFV (SEQ ID. NO:12).

Figure 16A:
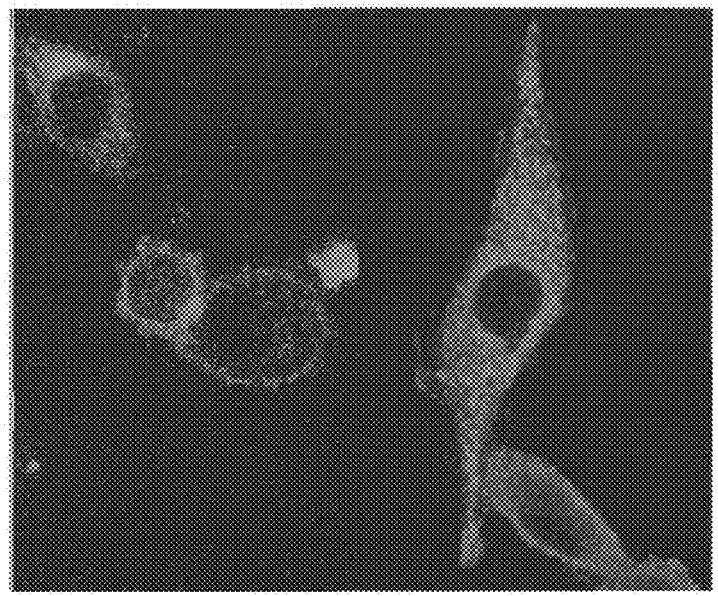

FIG. 16A illustrates HERV-K expression in BC cells. Surface (none-perm) and cytoplasmic (perm) expression of HERV-K env protein was detected on MDA-MB-231 BC cells by staining unpermeabilized (Non-perm) and permeabilized (Perm) cells, respectively.

Figure 16B:
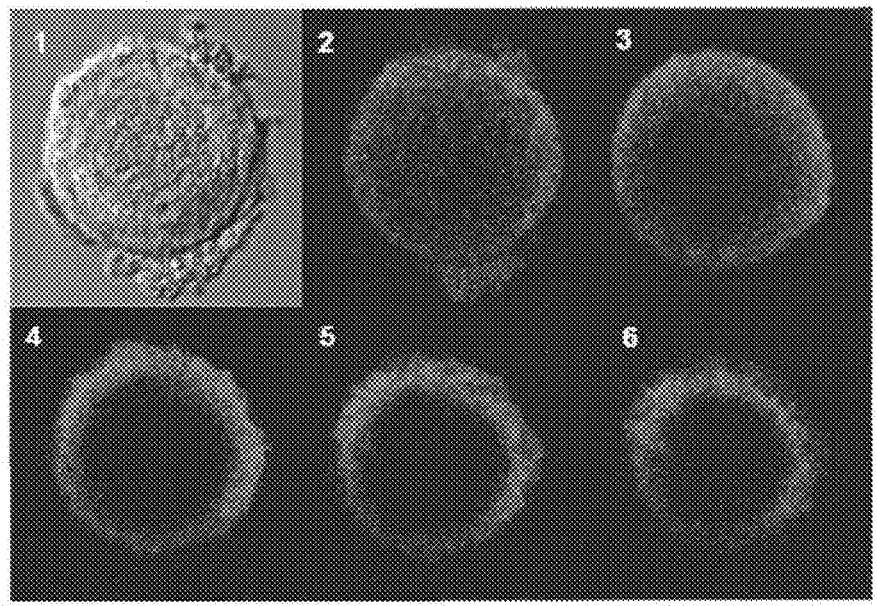

FIG. 16B illustrates HERV-K expression in BC cells. HERV-K env protein expression was detected on MCF-7 BC cells by immunofluorescence using a laser scanning confocal microscope and anti-HERV-K monoclonal antibody.

Figure 16C:
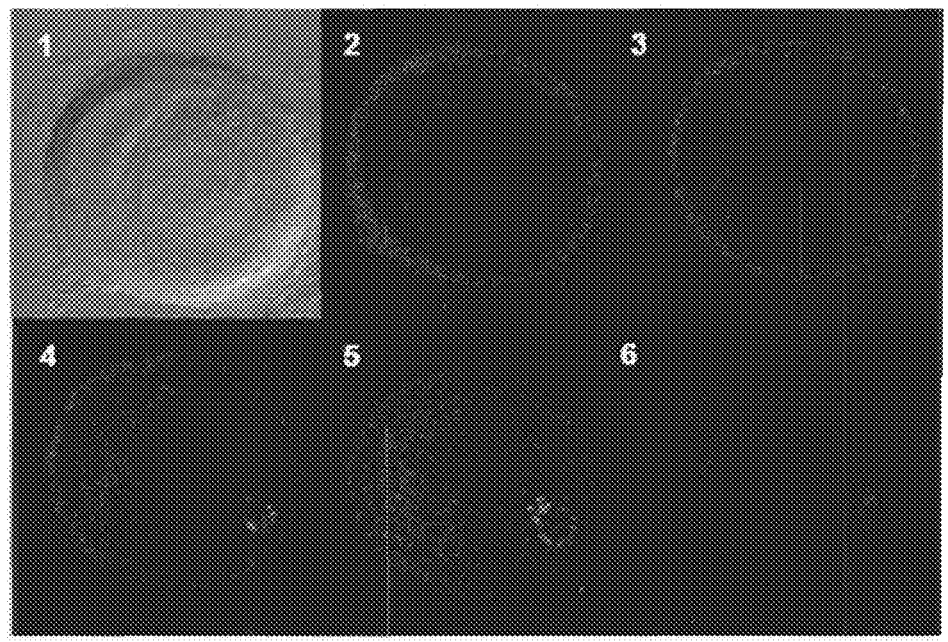

FIG. 16C illustrates HERV-K expression in BC cells. HERV-K env protein expression was not detected on benign MCF-10A breast cells. Observations were made under a laser scanning confocal microscope. Observations were made from top to bottom of the cells using z-sectioning.

Figure 16D:
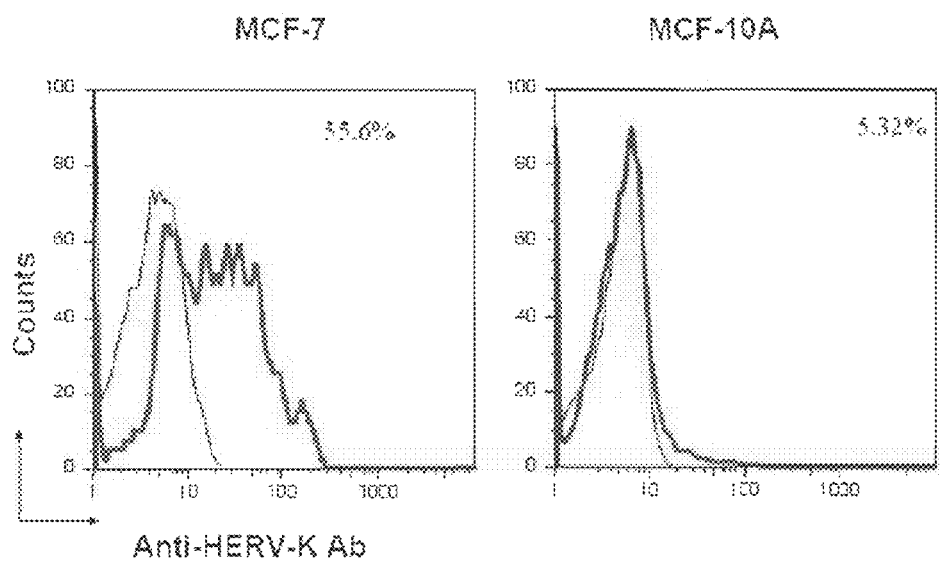

FIG. 16D illustrates HERV-K expression in BC cells. The percentage of positive surface expression of HERV-K env protein was greater on MCF-7 cells (55%) than on MCF-10A cells (5%), by FACS analysis.

FIG. 16E illustrates HERV-K expression in various cell lines. The expression of HERV-K env protein in various breast cell lines and an ovarian cancer cell line was detected by Western blot assay using 6H5 mAb against HERV-K env surface protein. β-actin was used as control. (top). FIG. 16E (bottom panel) shows that anti-HERV-K antibodies were detected in sera obtained from breast cancer patients.

FIG. 16F shows that anti-HERV-K antigen antibodies were detectable in breast cancer sera. Serial dilutions of patients were tested in ELISA assays for antibody activity against HERV-K, Np9, and Rec recombinant proteins.

Figure 17A:
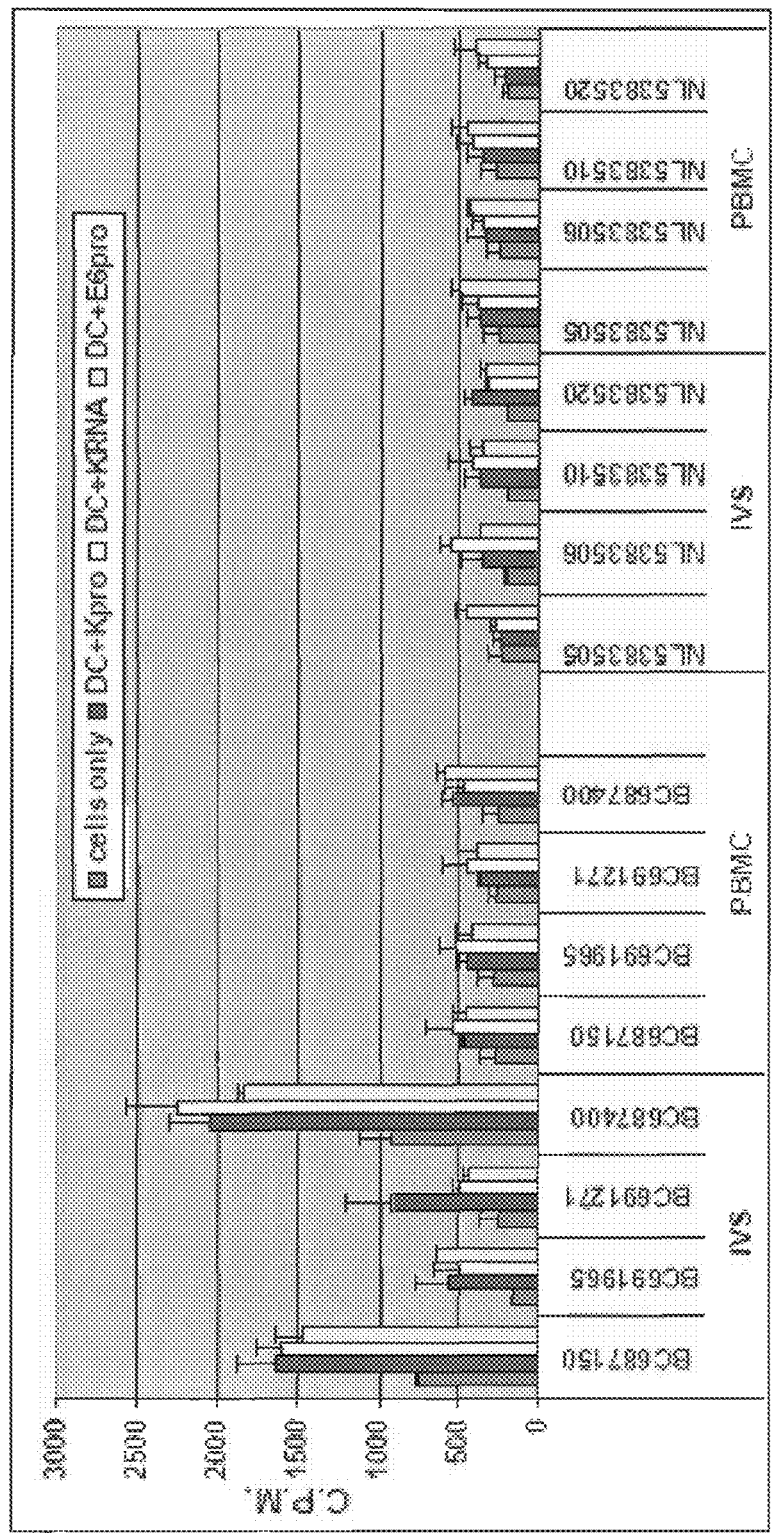

FIG. 17A shows detection of HERV-K-specific T cell proliferation. HERV-K-specific T-cell proliferation in BC patient PBMC compared to normal donor PBMC, as determined by $^3$H-thymidine incorporation in PBMC or IVS cells. Each donor was tested for stimulation of proliferation by DC pulsed with nothing (cell only), HERV-K SU protein (DC+K pro), HERV-K SU cRNA (DC+KRNA), and HPV16E6 protein (DC+E6pro). Proliferation was determined in IVS cells incubated one time with DCs pulsed with HERV-K env surface protein. T cell proliferation was increased in 3 of 4 IVS obtained from cancer patients compared to 0 of 4 IVS cells obtained from normal donors. No difference was observed in PBMC proliferation when BC patients and normal donors were compared. HPV16 E6 protein produced from a pQE30 expression vector or HERV-K env surface cRNA were used as controls.

Figure 17B:
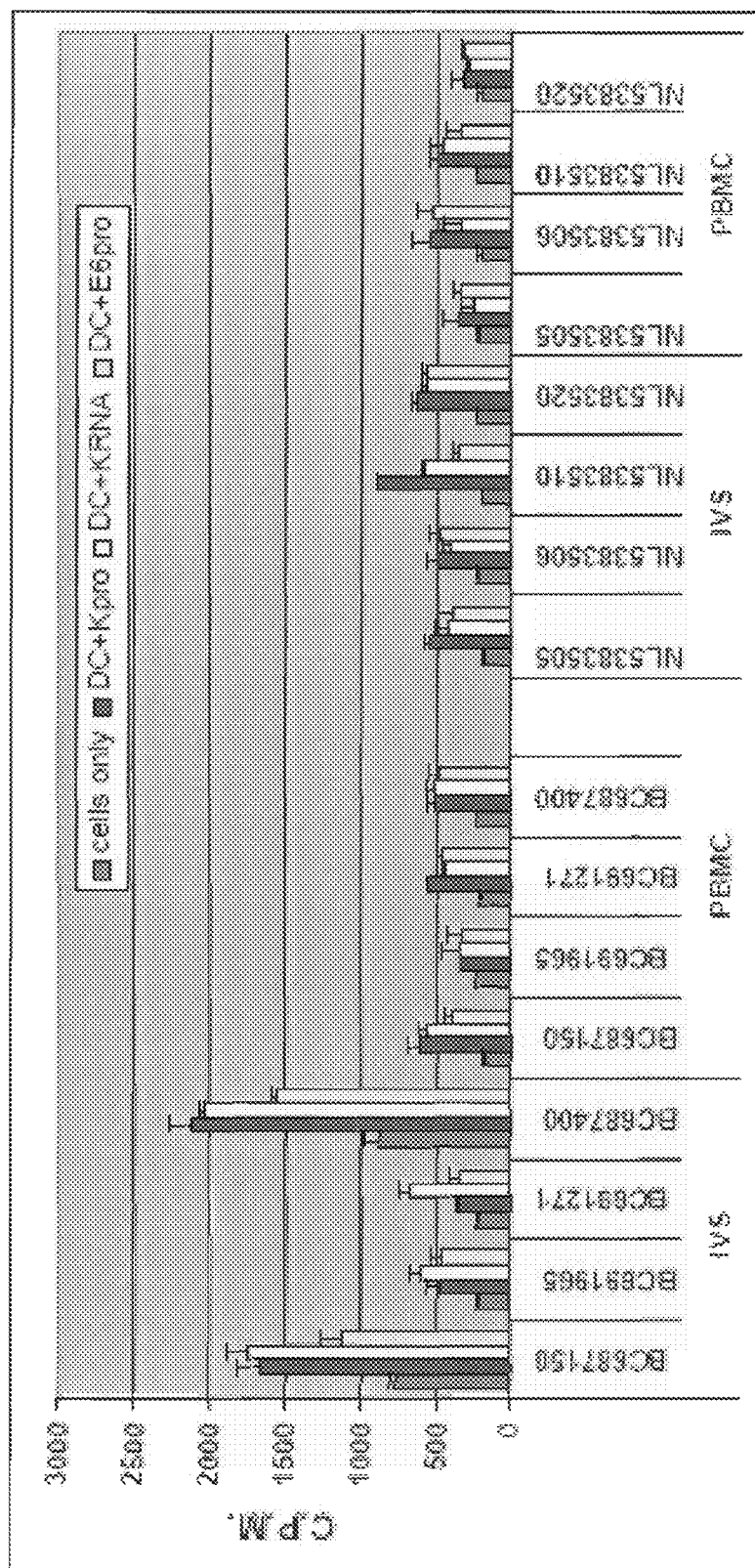

FIG. 17B shows detection of HERV-K-specific T cell proliferation. HERV-K-specific T-cell proliferation in BC patient PBMC compared to normal donor PBMC, as determined by $^3$H-thymidine incorporation in PBMC or IVS cells. Each donor was tested for stimulation of proliferation by DC pulsed with nothing (cell only), HERV-K SU protein (DC+K pro), HERV-K SU cRNA (DC+KRNA), and HPV16E6 protein (DC+E6pro). A similar T cell proliferation result was obtained for IVS cells incubated one time with DC pulsed with HERV-K env surface cRNA produced by in vitro transcription. HPV16 E6 protein produced by pQE30 vector or HERV-K env surface cRNA was used as control.

FIG. 17C shows detection of HERV-K-specific T cell proliferation. HERV-K-specific T-cell proliferation in BC patient PBMC compared to normal donor PBMC, as determined by $^3$H-thymidine incorporation in PBMC or IVS cells. Each donor was tested for stimulation of proliferation by DC pulsed with nothing (cell only), HERV-K SU protein (DC+K pro), HERV-K SU cRNA (DC+KRNA), and HPV16E6 protein (DC+E6pro). The T cell proliferation index was obtained from each donor's 1-week IVS, compared with PBMC stimulation by HERV-K-pulsed DC. The proliferation index was higher in BC patients (5.632±1.812; N=16) than in normal donors (1.388±0.4735; N=18; P=0.023; Student's t-test).

FIG. 18A illustrates detection of HERV-K-specific CD8+ T response. Antigen-specific GrB- or IFN-γ producing cells, as assessed by ELISPOT analysis. ELISPOT was performed on unstimulated PBMC from a BC patient (BC) and a normal control subject (NL) or after 1-week IVS with HERV-K-pulsed DC. DC pulsed HPV16 E6 protein served as the control. A greater number of GrB- or IFN-γ spots were detected in IVS cells produced from DC pulsed with HERV-K env surface protein obtained from BC patients than from normal donors.

Figure 18B:
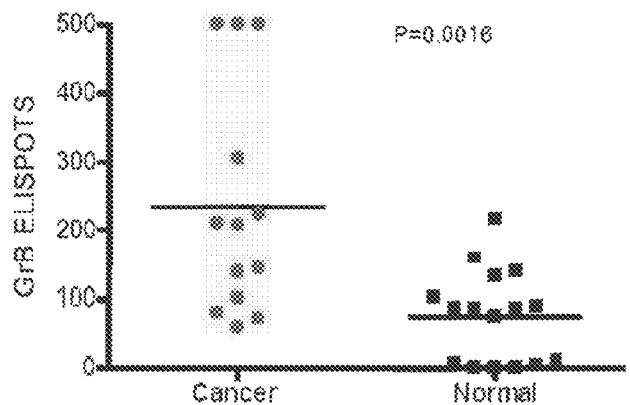

FIG. 18B illustrates detection of HERV-K-specific CD8+ T response. GrB spots obtained from IVS cells were compared between cancer patients and control subjects after stimulation with HERV-K-pulsed DC. The GrB spot numbers were higher in IVS cells obtained from cancer patients (233.9±46.26 N=13) than in IVS cells obtained from control subjects (74.73±16.67 N=16; P=0.0016; t tests).

Figure 18C:
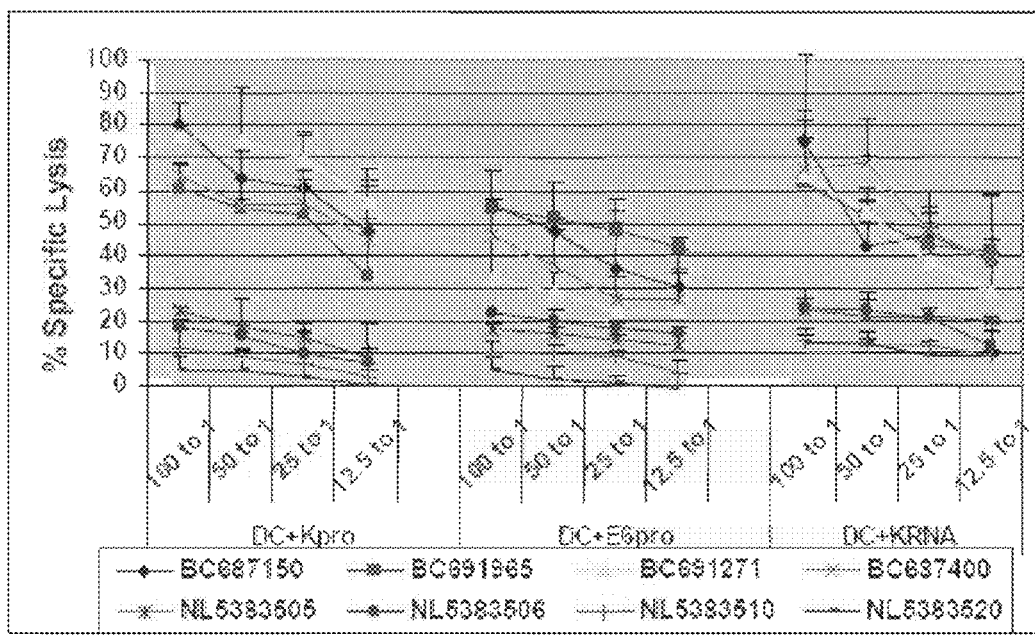

FIG. 18C illustrates detection of HERV-K-specific CD8+ T response. A CTL assay was performed after 1-week IVS from four BC patients and four healthy female donors. Autologous DC pulsed with HERV-K env protein (DC+Kpro) or cRNA (DC+KRNA), as well as DC pulsed with HPV16E6 protein (DC+E6pro) were used as target cells. Unlabeled K562 cells were used to correct for nonspecific lysis. The ratio of effector cells to target cells was 100:1, 50:1, 25:1, and 12.5:1.

Figure 19A:
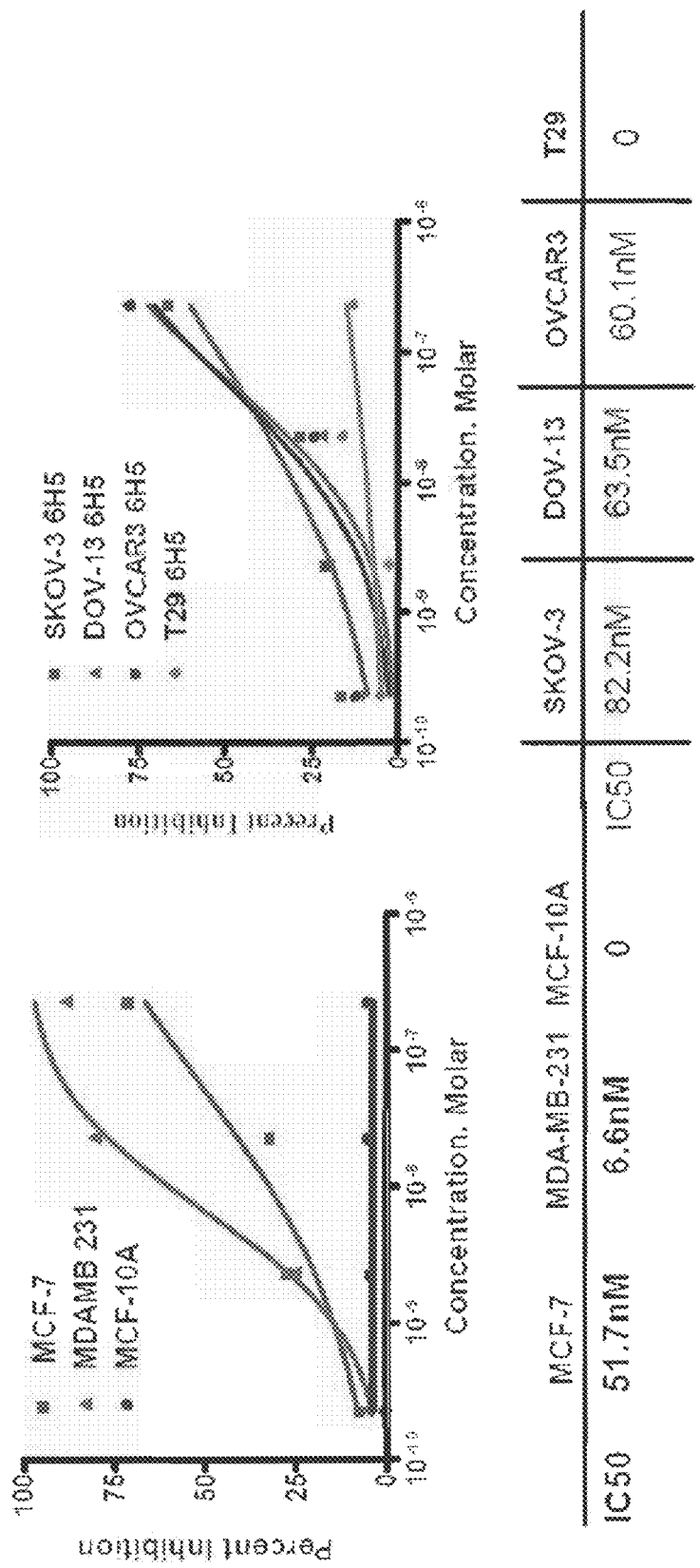

FIG. 19A shows comparative cytoxicity of 6H5 mAb towards breast cell lines (left) or ovarian cell lines (right). Cells were treated with medium containing different concentrations of 6H5 for 72 h, the cells were then stained with crystal violet and read at 595 nm. Cells without antibody treatment were used for controls. The percent inhibition of cell growth is shown. IC$_{50}$: 50% inhibitory concentration.

Figure 19B:
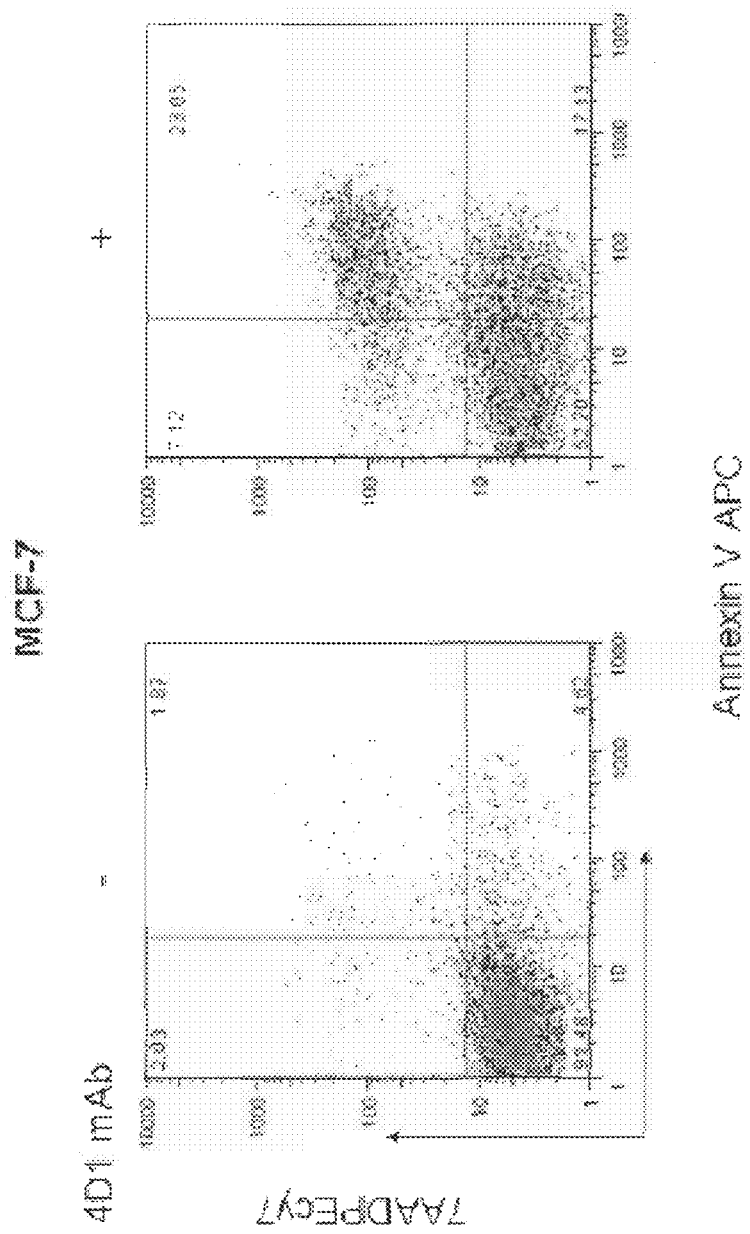

FIG. 19B illustrates that anti-HERV-K antibody is able to induce MCF-7 cells to undergo apoptosis, compared with cells without Ab treatment (control). The right bottom panel represents cells that are Annexin V+ and 7AAD− (17% in early apoptosis) and the right top panel represents cells that are Annexin V+ and 7AAD+ (23% in late apoptosis).

Figure 19C:
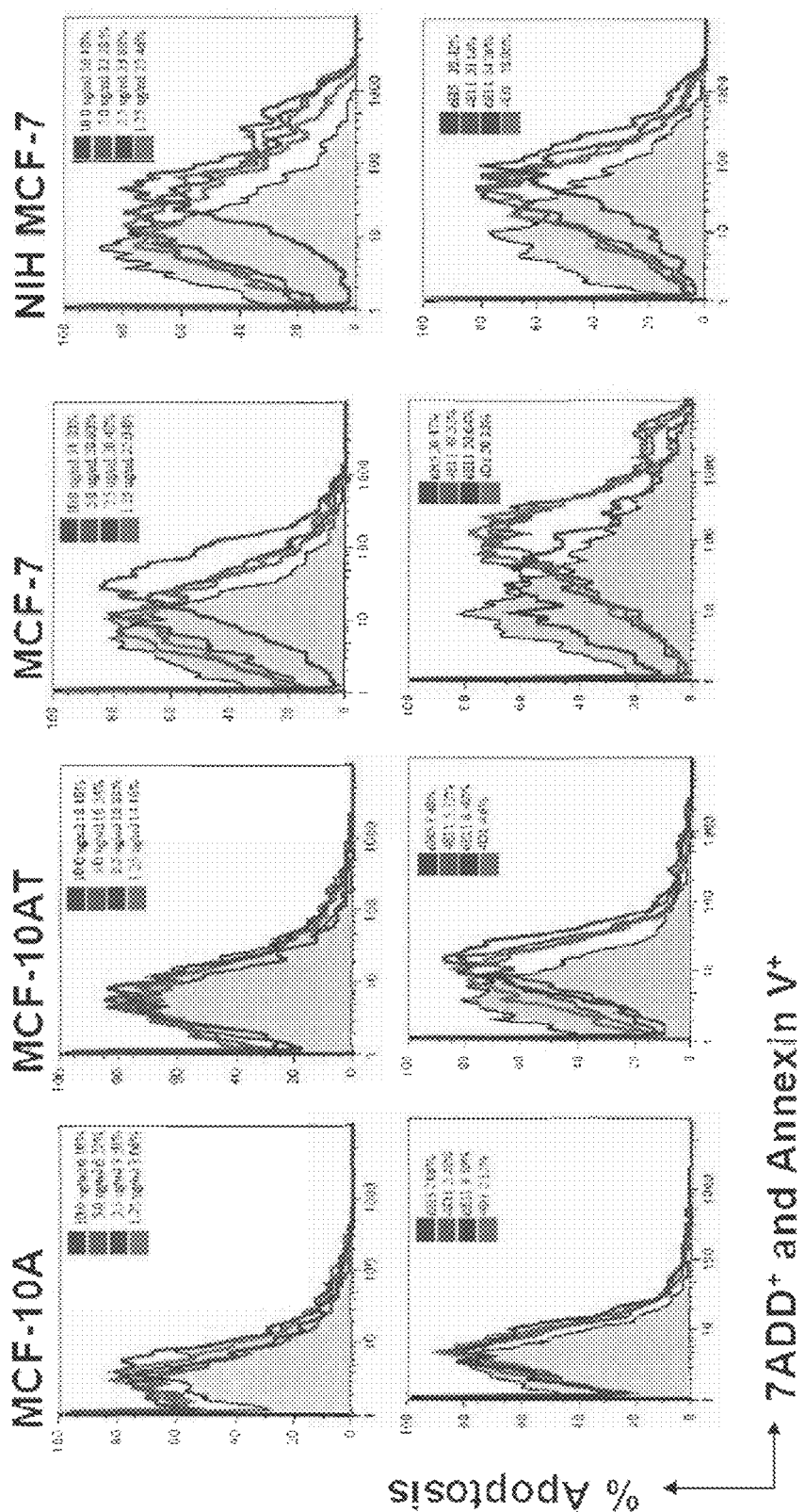
Figure 28A:
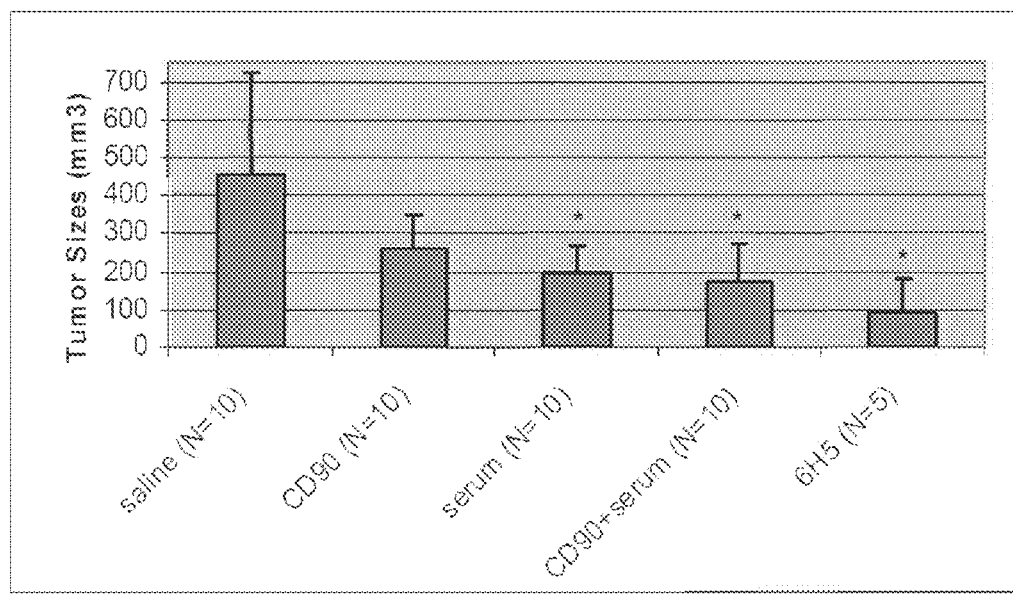
Figure 28B:
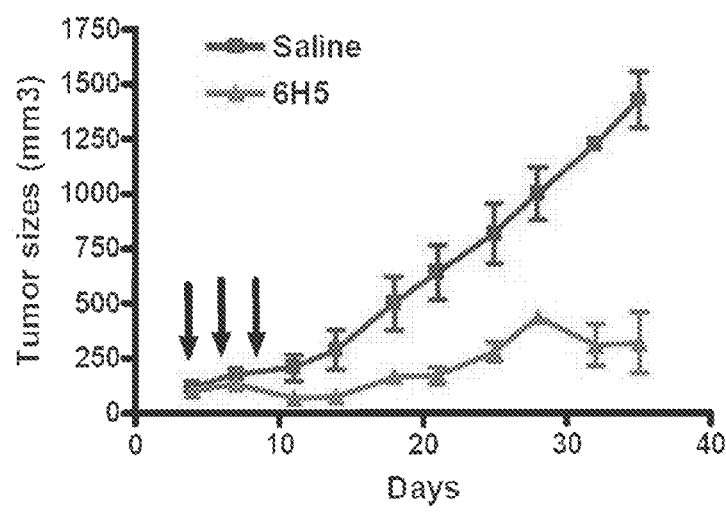

FIG. 19C summarizes the results of the apoptosis studies in breast cell lines. The top figures show a summary of the effect of dose of 6H5 on induction of breast cells to undergo apoptosis, compared with cells without Ab treatment (control). The bottom figures show a summary of the effect of various mAb clones on induction of apoptosis in breast cells.

FIG. 20A illustrates that adoptive T cell therapy in mice inhibited breast tumor growth.

FIG. 20B illustrates tumor formation in mice innoculated with MCF-7 cells on day 0 and treated with saline or 6H5 on days 4, 6, and 8 (arrows; 200 ug per mice). Mice treated with saline were used as control.

Figure 21:
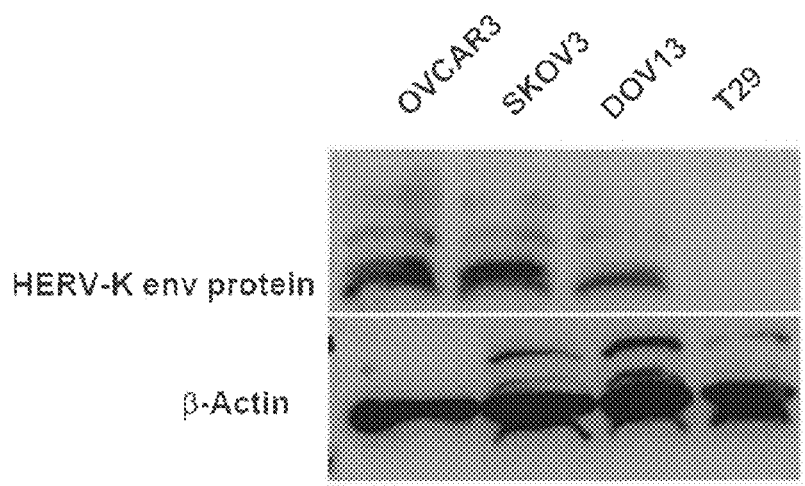

FIG. 21 illustrates western blot of various ovarian cancer cell lines using 6H5 mAb to detect expression of HERV-K env protein.

Figure 22:
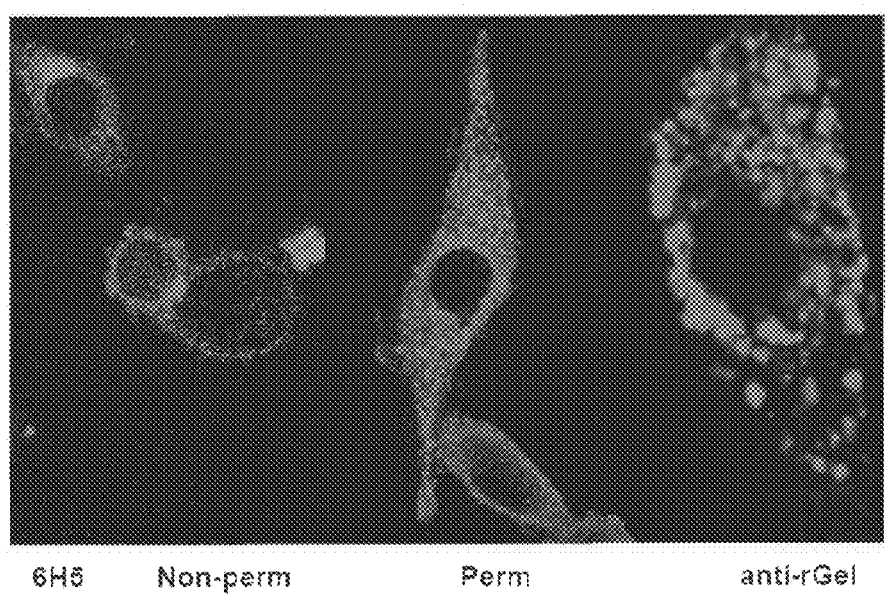

FIG. 22 illustrates detection of surface (Non-perm) and cytoplasmic (Perm) expression of HERV-K env protein in ovarian cancer cells by confocal microscopy using 6H5 mAb. rGel was delivered into DOV13 cells by 6H5, and was detected by anti-rGel Ab.

Figure 23:
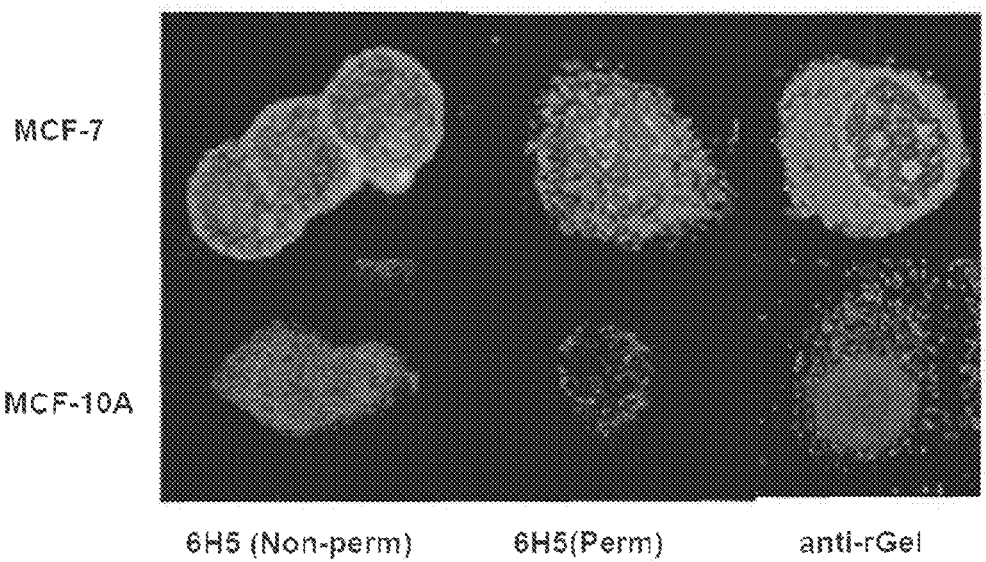

FIG. 23 illustrates detection of surface (Non-perm) and cytoplasmic (Perm) expression of HERV-K env protein in breast cell lines by confocal microscopy using 6H5 mAb. rGel was delivered into cells by 6H5, and was detected by anti-rGel Ab.

Figure 24:
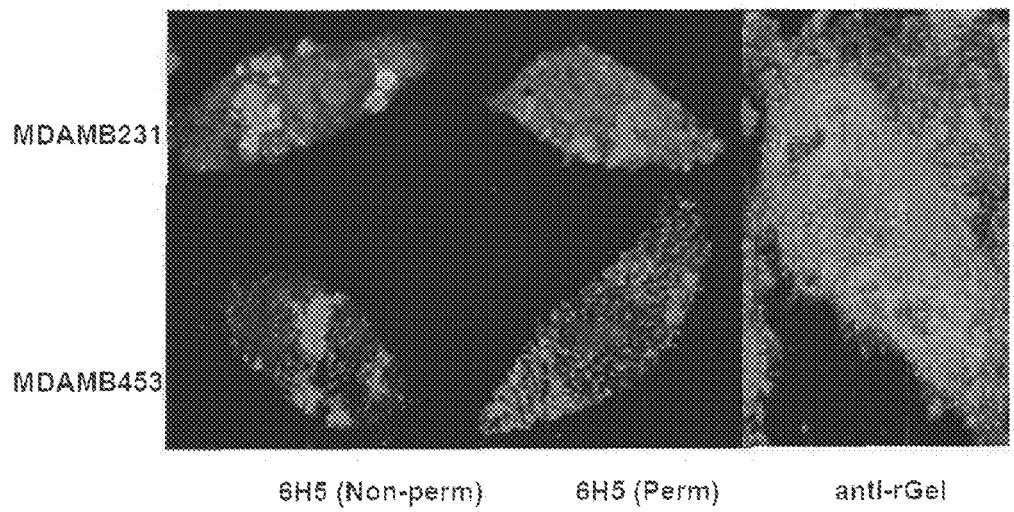

FIG. 24 illustrates detection of surface (Non-perm) and cytoplasmic (Perm) expression of HERV-K env protein in breast cell lines by confocal microscopy using 6H5 mAb. rGel was delivered into cells by 6H5, and was detected by anti-rGel Ab.

Figure 25:
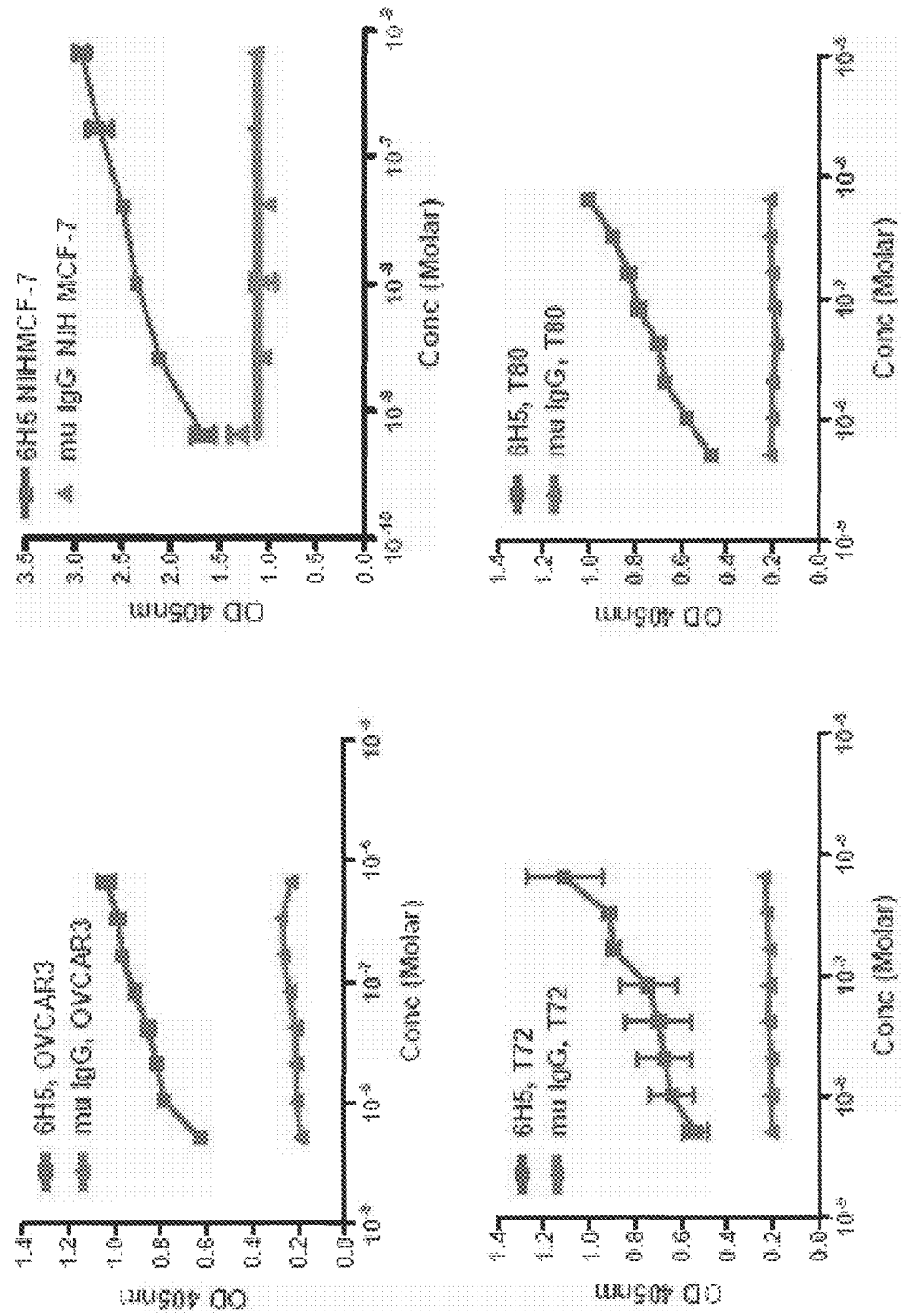

FIG. 25 illustrates quantitation of surface expression of HERV-K env protein in ovarian or breast cell lines by dry ELISA using 6H5 mAb. Murine IgG was used as a negative control.

Figure 26:
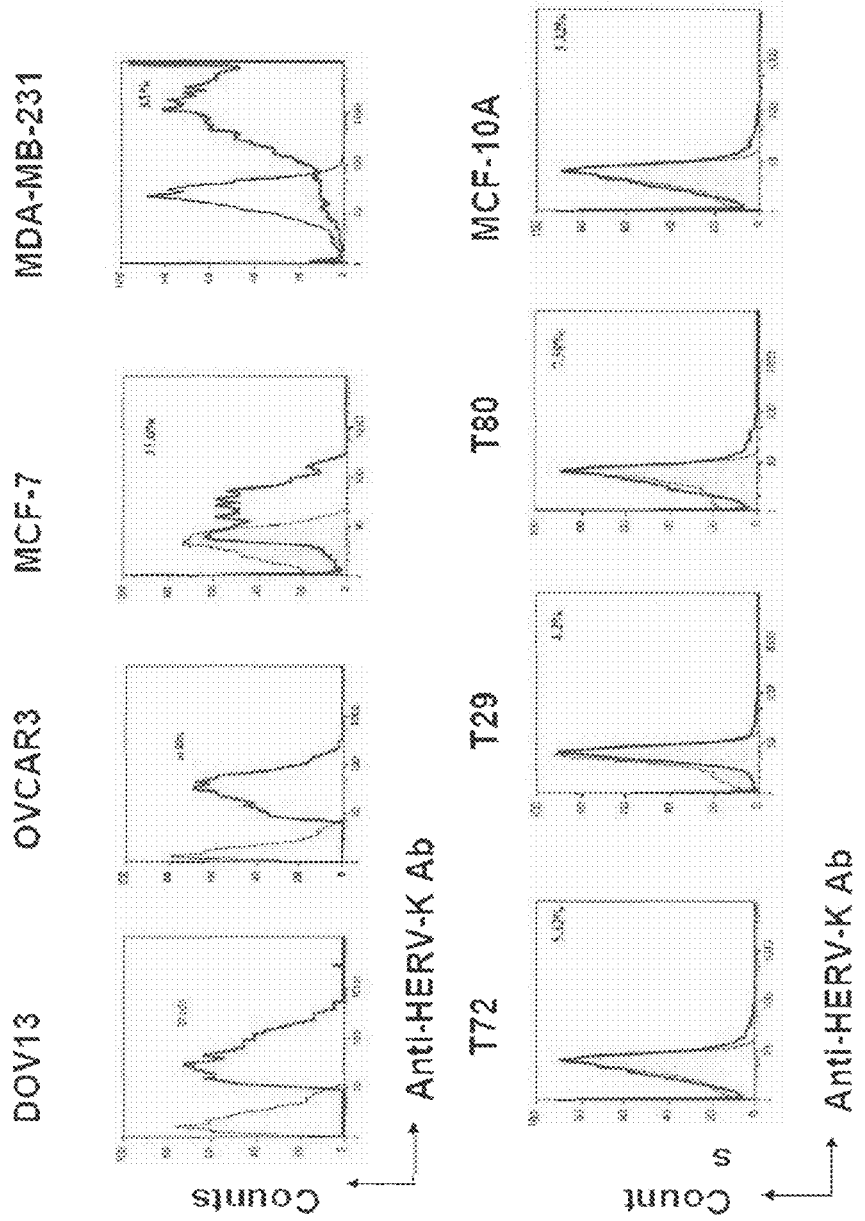

FIG. 26 illustrates quantitation of surface expression of HERV-K env protein in ovarian or breast cell lines by FACS using 6H5 mAb. Murine IgG was used as a negative control.

Figure 27:
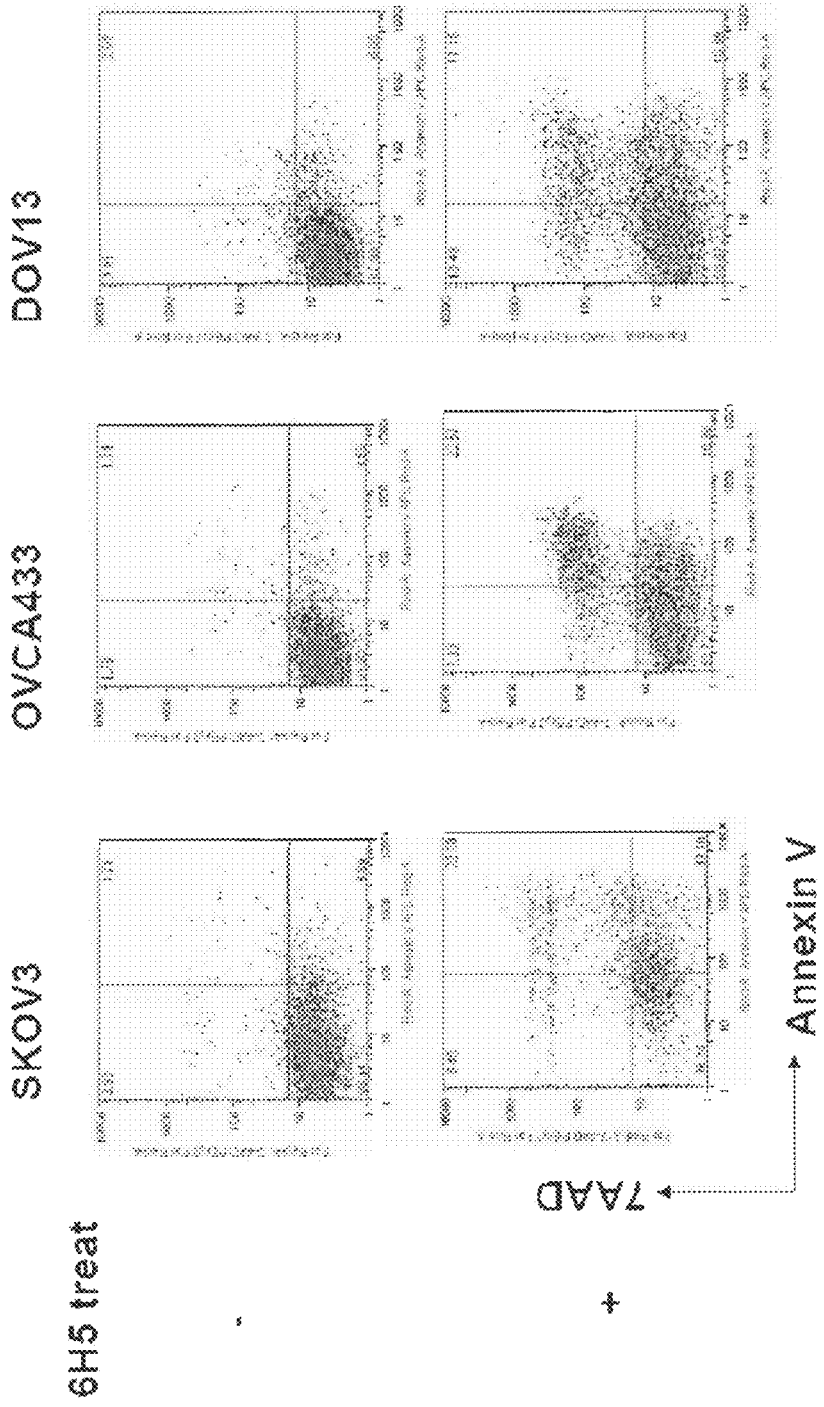

FIG. 27 illustrates that 6H5 mAb is able to induce ovarian cancer cells to undergo apoptosis, compared to cells without Ab treatment (control; top panels). The bottom panels represent cells that are Annexin V+ and 7AAD− (right bottom, in early apoptosis) and the right top panel represents cells that are Annexin V+ and 7AAD+ (right top, in late apoptosis).

Figure 28:
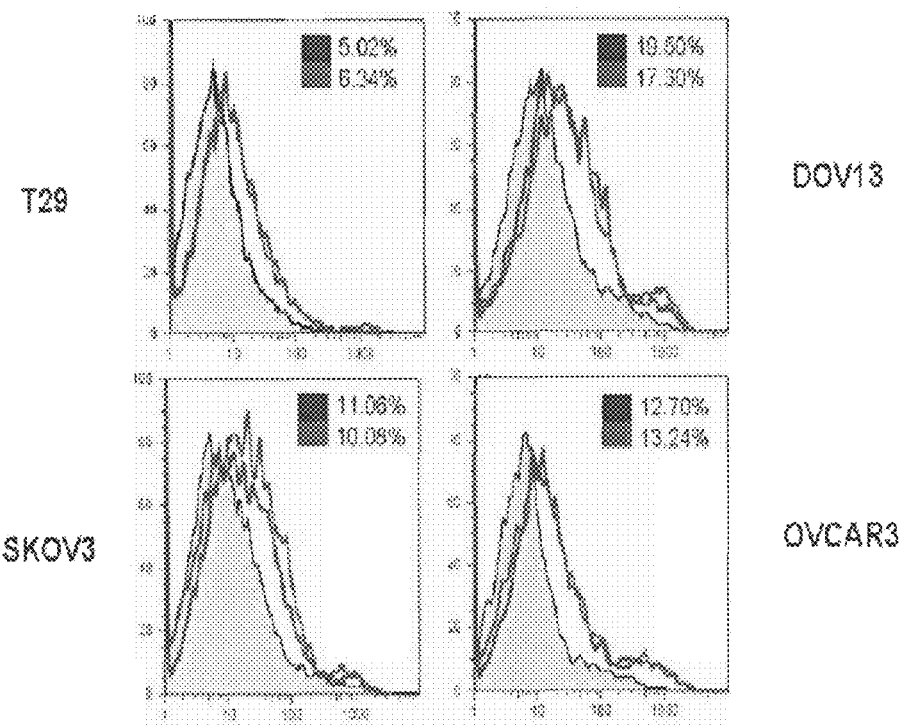

FIG. 28 shows a summary of 6H5 induction of ovarian cells to undergo apoptosis, compared to cells without Ab treatment (control.) Blue bar is early apoptosis and red bar is late apoptosis.

Figure 29:
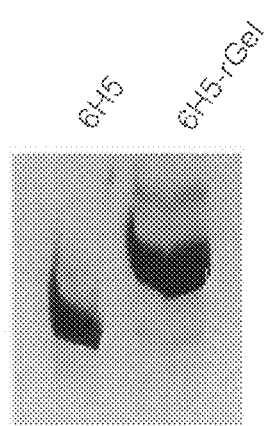

FIG. 29 illustrates Coomasie Blue staining of 6H5 mAb (lane 1) and 6H5-rGel conjugate (Lane 2) in non-reducing gel.

Figure 30:
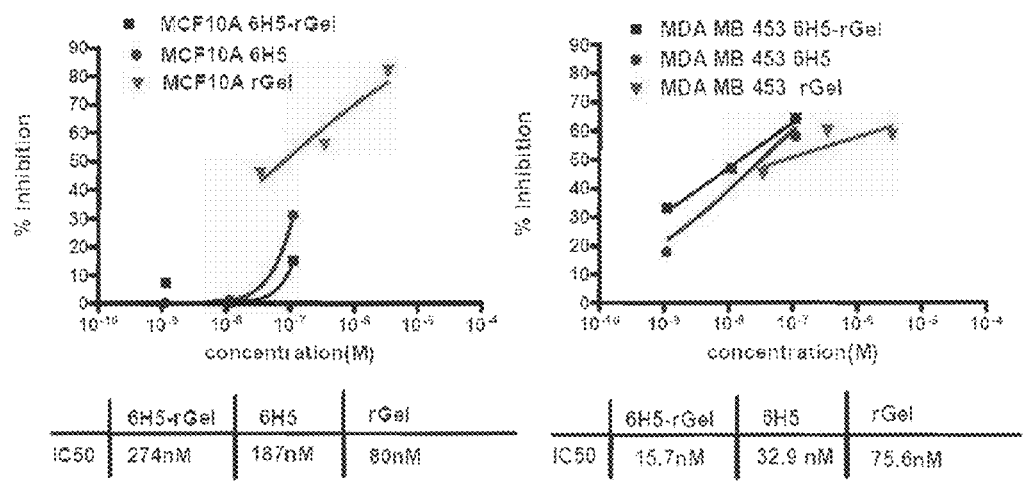

FIG. 30 illustrates comparative cytotoxicity of 6H5-rGel, 6H5, and rGel alone toward MCF-10A and MDA MB453 cells. Cells were treated with medium containing different concentrations of 6H5-rGel, 6H5, and rGel alone for 72 h and stained with crystal violet and read at 595 nm. The percentage of growth inhibition relative to control cell growth is shown. IC50 for each cell line is listed in the table.

Figure 31:
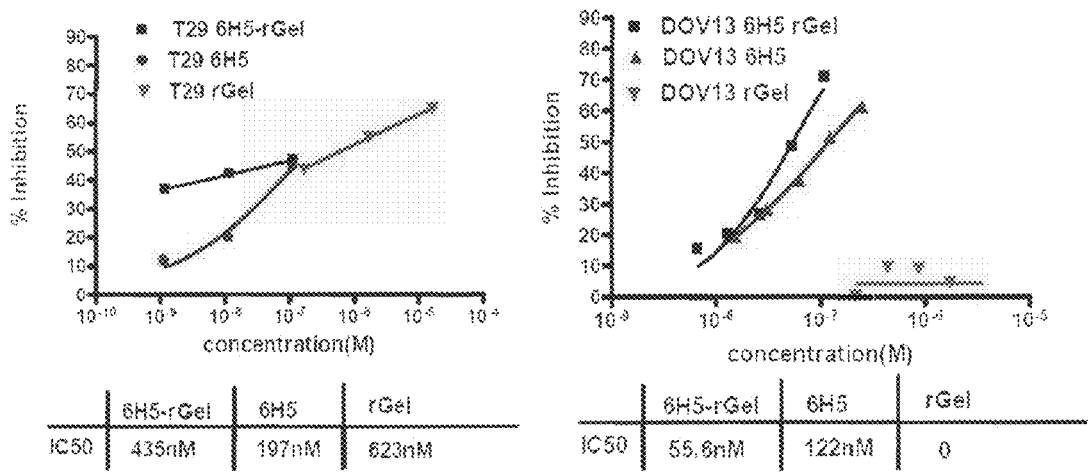

FIG. 31 illustrates comparative cytotoxicity of 6H5-rGel, 6H5, and rGel alone towards ovarian T29 and ovarian cancer DOV13 cells. Cells were treated with medium containing different concentrations of 6H5-rGel, 6H5, and rGel alone for 72 h and stained with crystal violet and read at 595 nm. The percentage of growth inhibition relative to control cell growth is shown. IC50 for each cell line is listed in the table.

FIG. 32A illustrates expression of HERV env RNAs in melanoma cell lines and tissues. HERV-K expression in normal melanocytes (HEMn-LP; lane 1 and HEMn-DP; Lane 2), in human malignant melanoma cells (SK-MEL-28 cells; lane 3 and SK-MEL-1; Lane 4), and in melanoma biopsies (lanes 5 and 6) obtained from patients. Expression of both of types of HERV-K env mRNAs was detected in melanoma cancer cells and biopsies (Lanes 3 to 6).

FIG. 32B illustrates expression of HERV env RNAs in melanoma cell lines and tissues. Purified Np9/GST and Rec/GST recombinant fusion proteins were detected by Coomassie blue staining.

FIG. 33 illustrates expression of HERV-K env protein in melanoma tissues. A. The expression of HERV-K env protein in malignant melanoma Case No. 4 (score "3"); B. metastasis to lymph node of case No. 4 (score "3"); C. HERV-K expression in melanoma (score "2"); and D. expression in melanoma metastasis to lymph node (score "1").

Figure 34A:
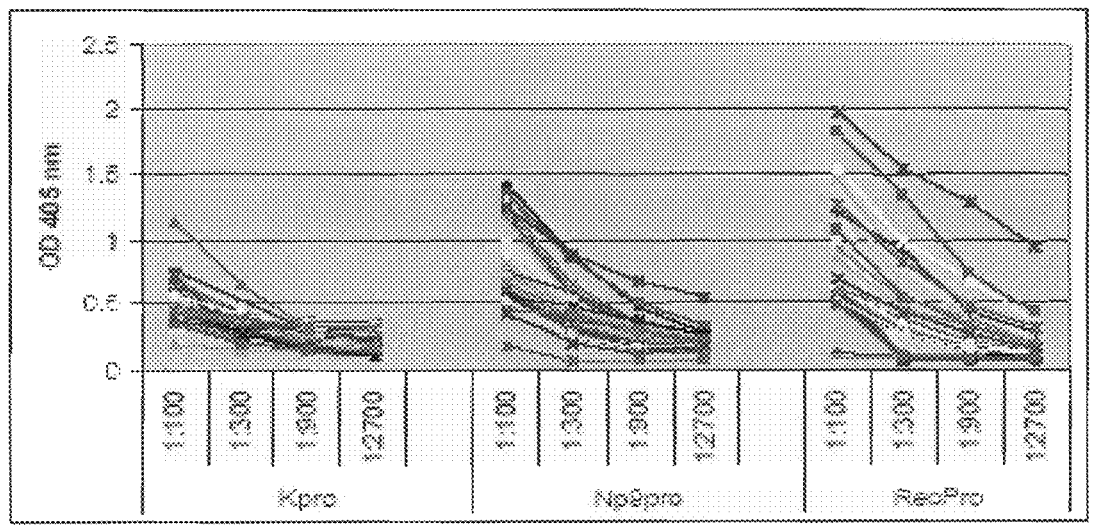

FIG. 34A illustrates detection of anti-HERV antigen antibodies in melanoma patient sera. Serial dilutions of patient sera were tested in ELISA for antibody activity against HERV K, Np9, and Rec recombinant proteins.

Figure 34B:
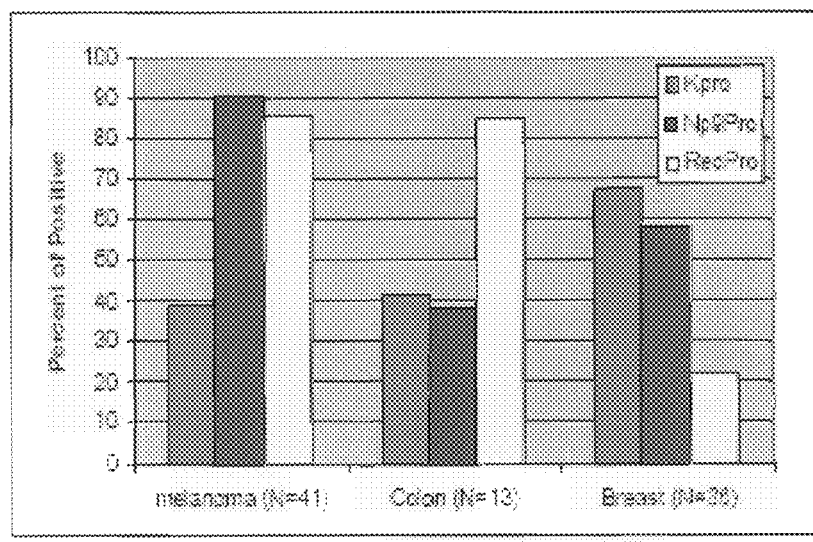

FIG. 34B illustrates detection of anti-HERV antigen antibodies in melanoma patient sera. An initial screen of sera from patients with different cancer types found that melanoma patients have enhanced antibody reactivity against HERV antigens, especially Np9 and Rec.

Figure 35:
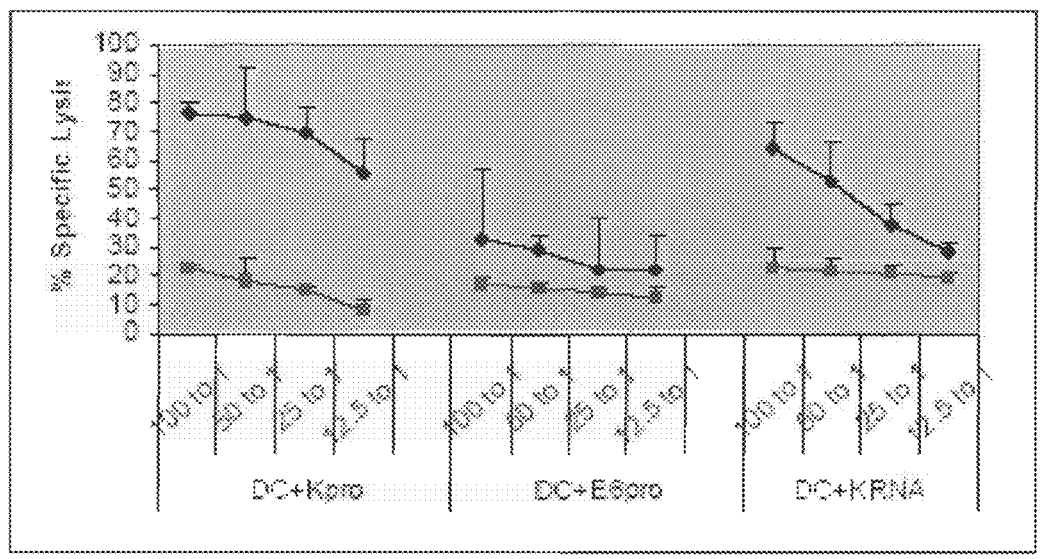

FIG. 35 illustrates the results of a CTL assay on HERV-K-specific T cells obtained after IVS with HERV-K Env protein or RNA. HERV-K specific T cells obtained from a melanoma patient (blue color) and one healthy donor (red) were used as effector cells, and autologous DC pulsed with HERV-K Env protein (DC+Kpro) or HERV-K RNA (DC+KRNA), DC pulsed with HPV16E6 protein (DC+E6 pro) or HPV16E6 RNA (DC+E6 RNA) were used as target cells. K562 cells were added to neutralize nonspecific lysis. The ratio of effector cells to target cells was 50:1, 25:1, 12.5:1 and 6.25:1.

Figure 36:
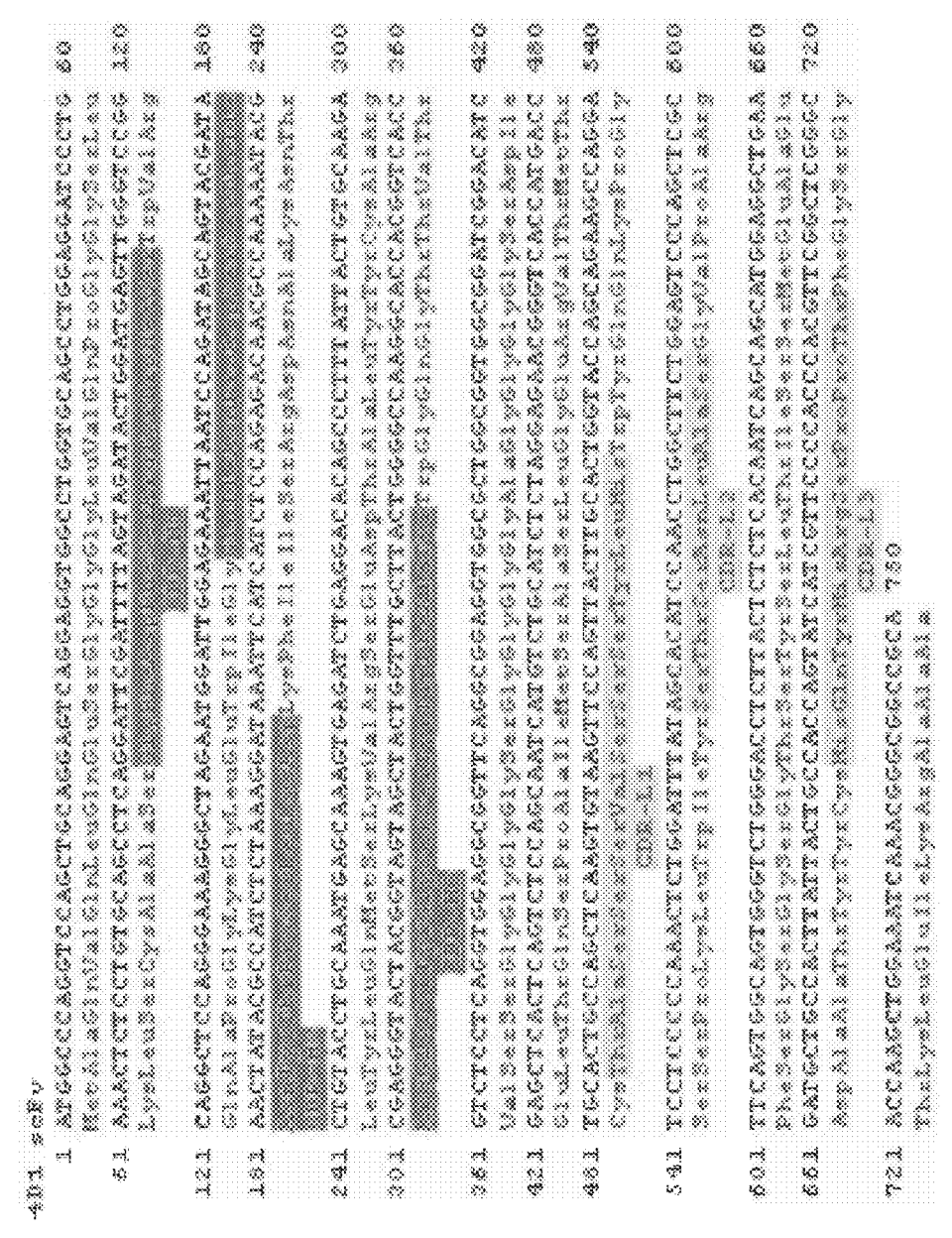

FIG. 36 depicts the amino acid and nucleotide sequences of the 4D1 scFv its variable heavy and light chains and CDRs. (SEQ ID NOS. 13, 14, 15, 16, 17, 18, 19, 20, 21, 22, 23, 24, 25, 26, 27, 28, 29, 30).

Figure 37:
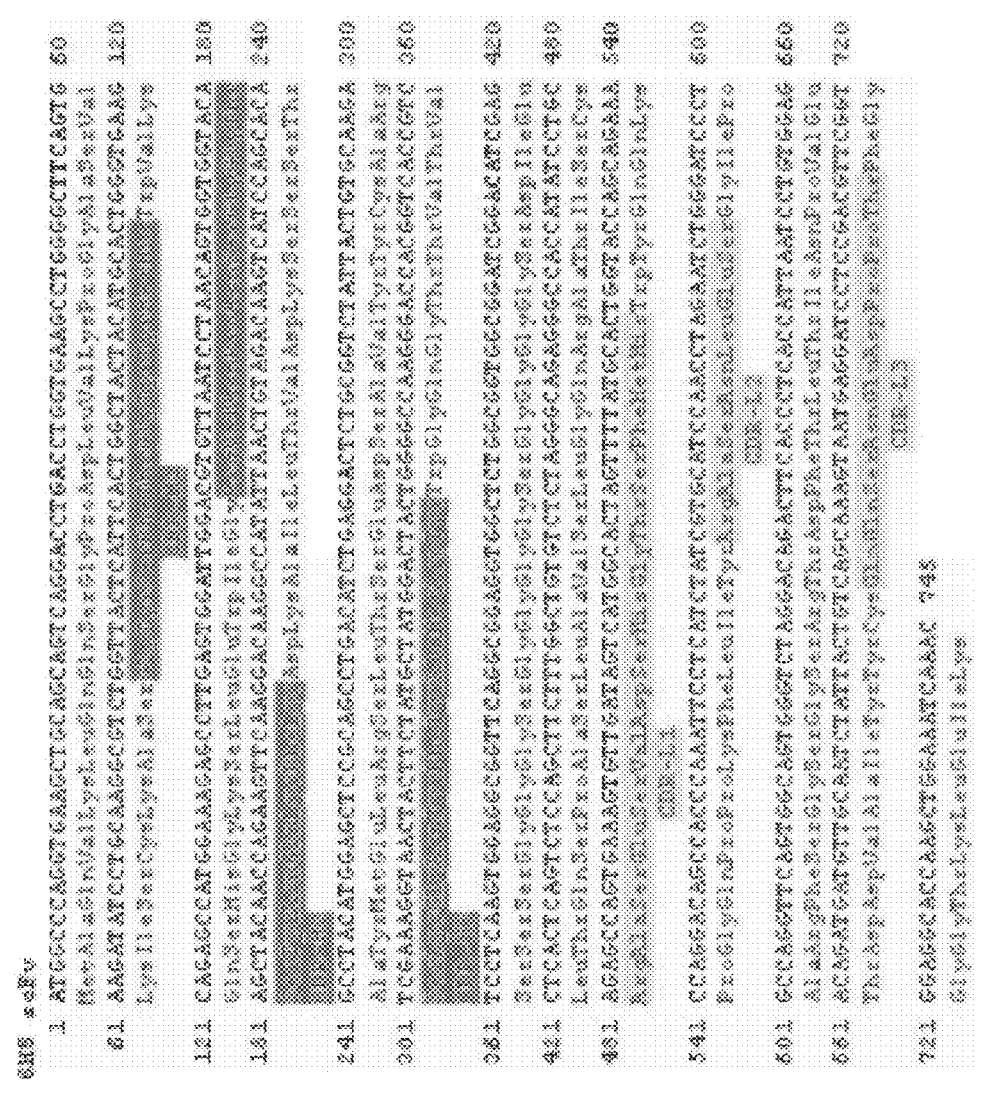

FIG. 37 depicts the amino acid and nucleotide sequences of the 6H5 scFv generated, its variable heavy and light chains, and CDRs. (SEQ ID NOS. 49, 50, 51, 52, 53, 54, 55, 56, 57, 58, 59, 60, 61, 62, 63, 64, 65, 66).

Figure 38:
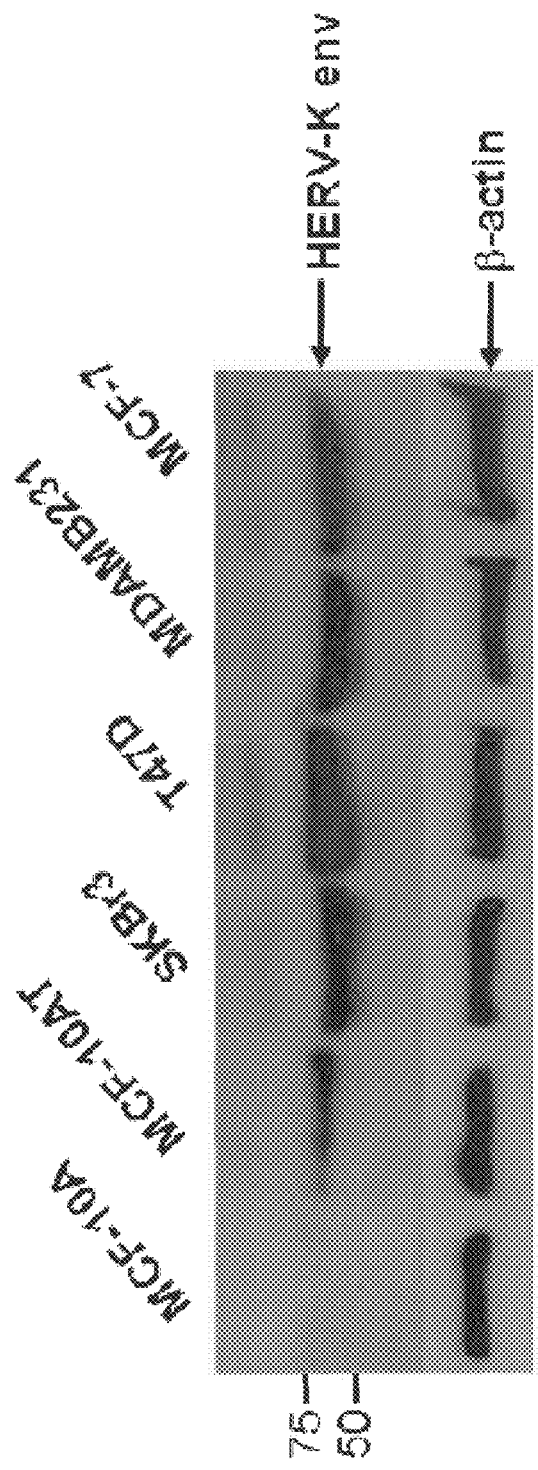

FIG. 38 shows HERV-K protein as expressed in breast cancer cells and detected by Western blot using 6H5 mAb.

Figure 39:
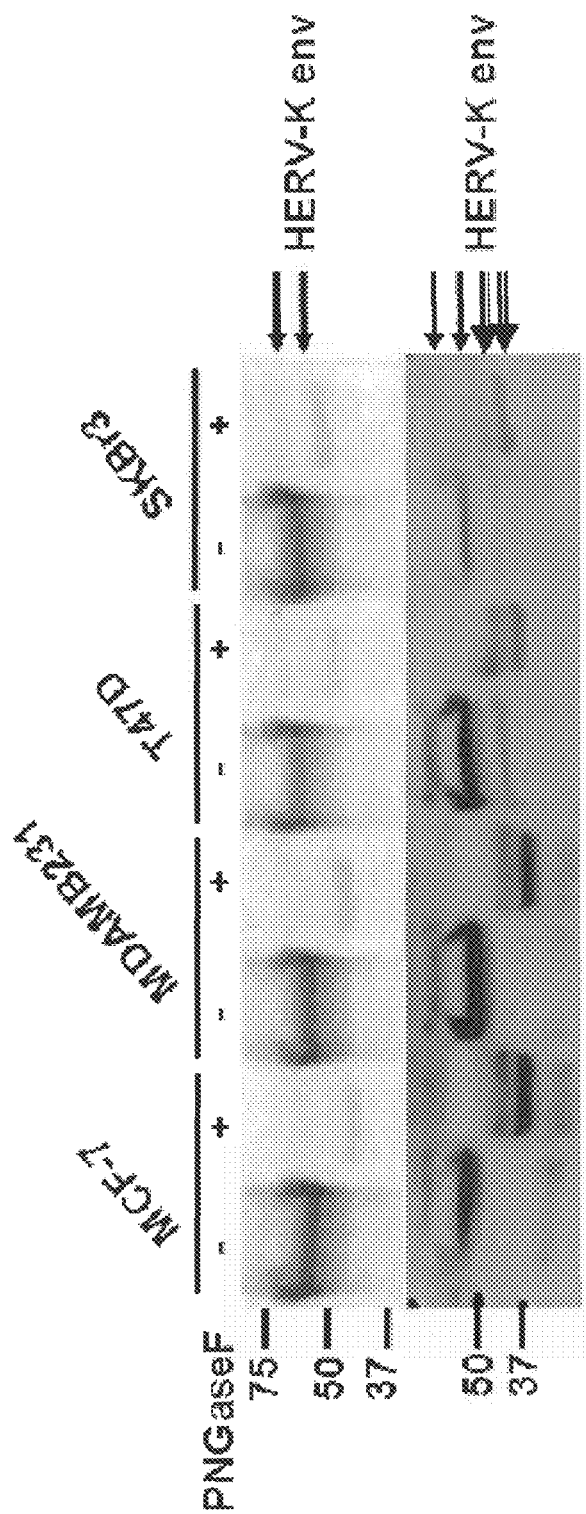

FIG. 39 shows HERV-K env glycoprotein in breast cancer cells as detected by Western blot using 6H5 mAb.

FIGS. 40a, 40b, 40c and 40d show the expression of HERV-K as detected in lung carcinoma (A), colonic adenocarcinoma (B), gallbladder carcinoma (C) and melanoma (D)

FIGS. 41a, 41b, 41c, and 41d show that HERV-K is not expressed in normal tissues including lung (A), heart (B), brain (C) and small intestine (D) using 6H5 mAb in a tissue array with multiple tissues including cancer and normal cells.

Figure 42:
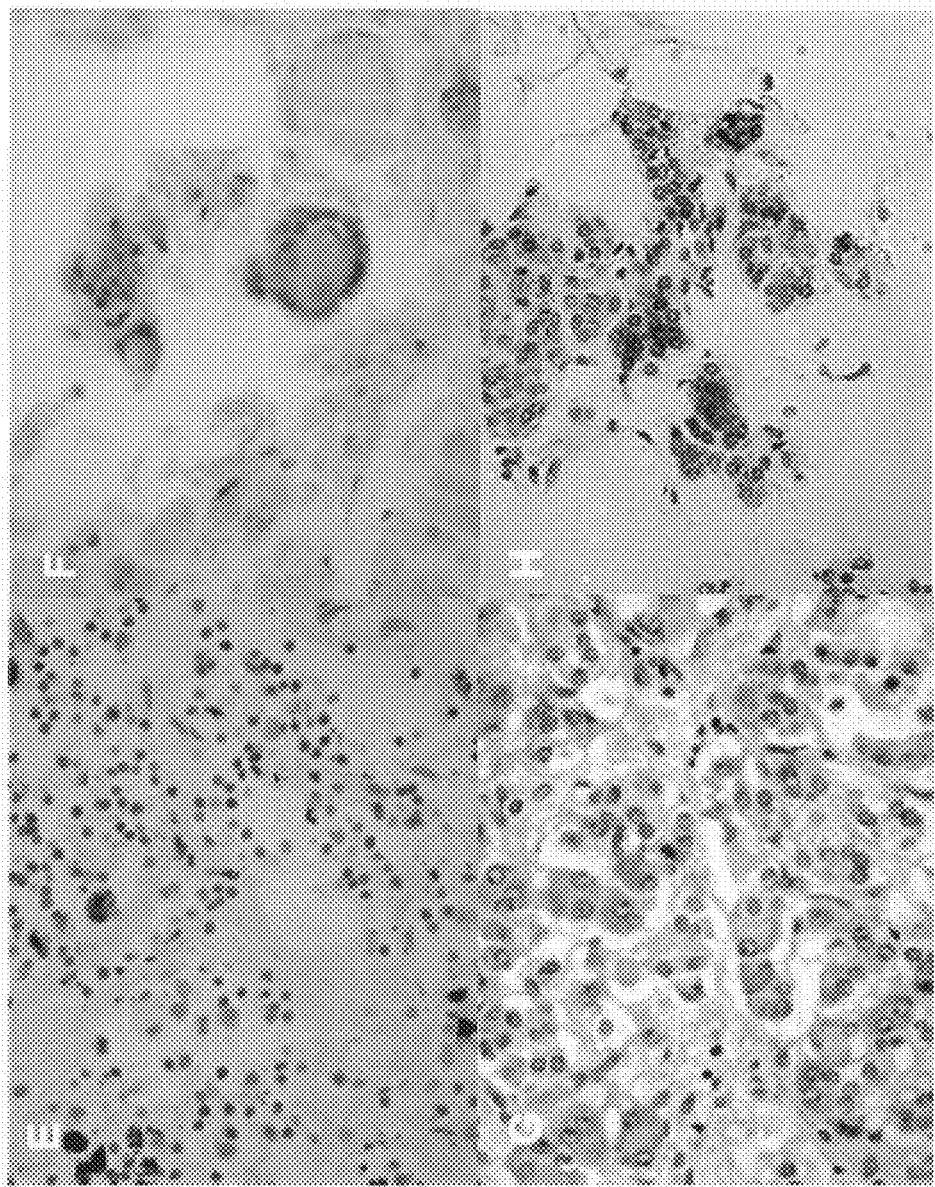

FIG. 42 shows that HERV-K is not expressed in normal tissues including lymph node (E), thyroid (F), pancreases (G) and salivary glands (H) using 6H5 mAb in a tissue array with multiple tissues including cancer and normal cells.

Figure 43:
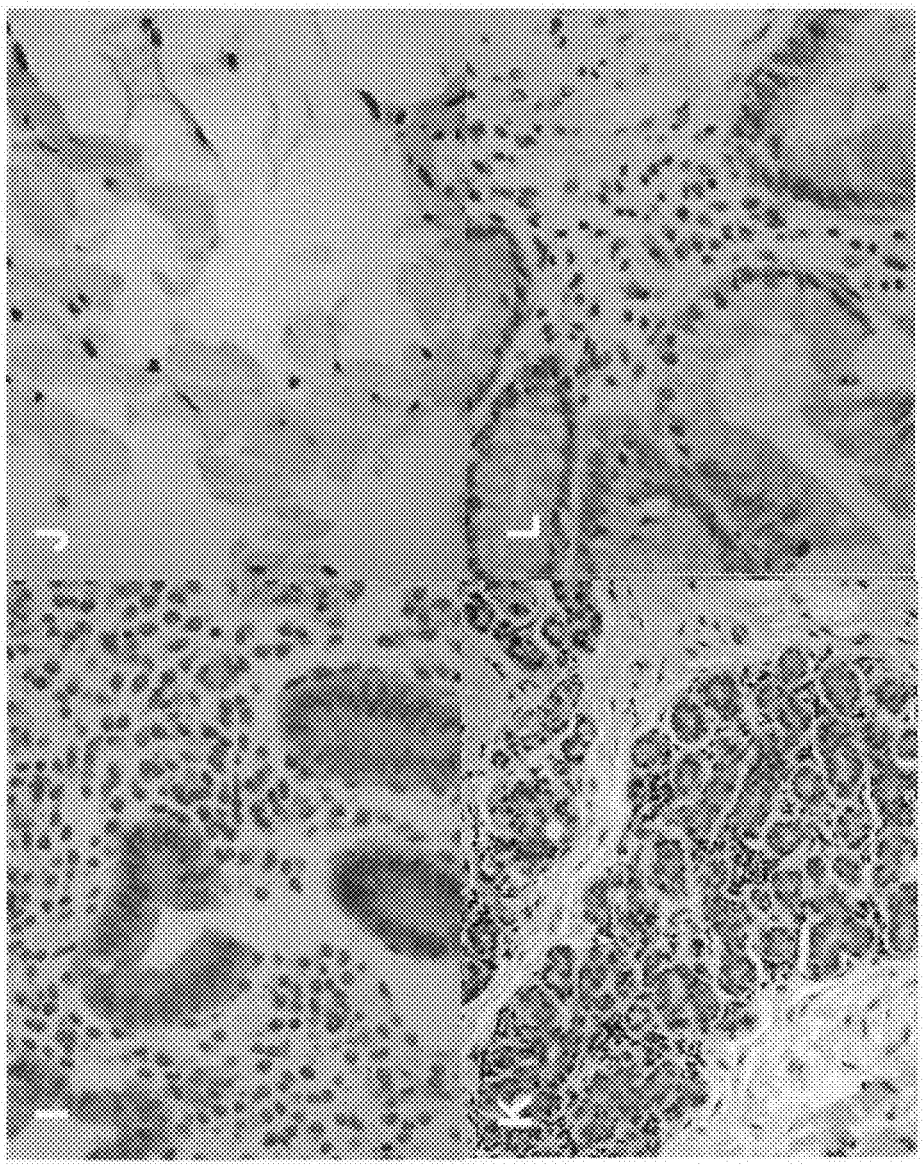

FIG. 43 shows that HERV-K is not expressed in normal tissues including endometrium (I), tongue (J), breast (K) and colon (L) using 6H5 mAb in a tissue array with multiple tissues including cancer and normal cells.

Figure 44:
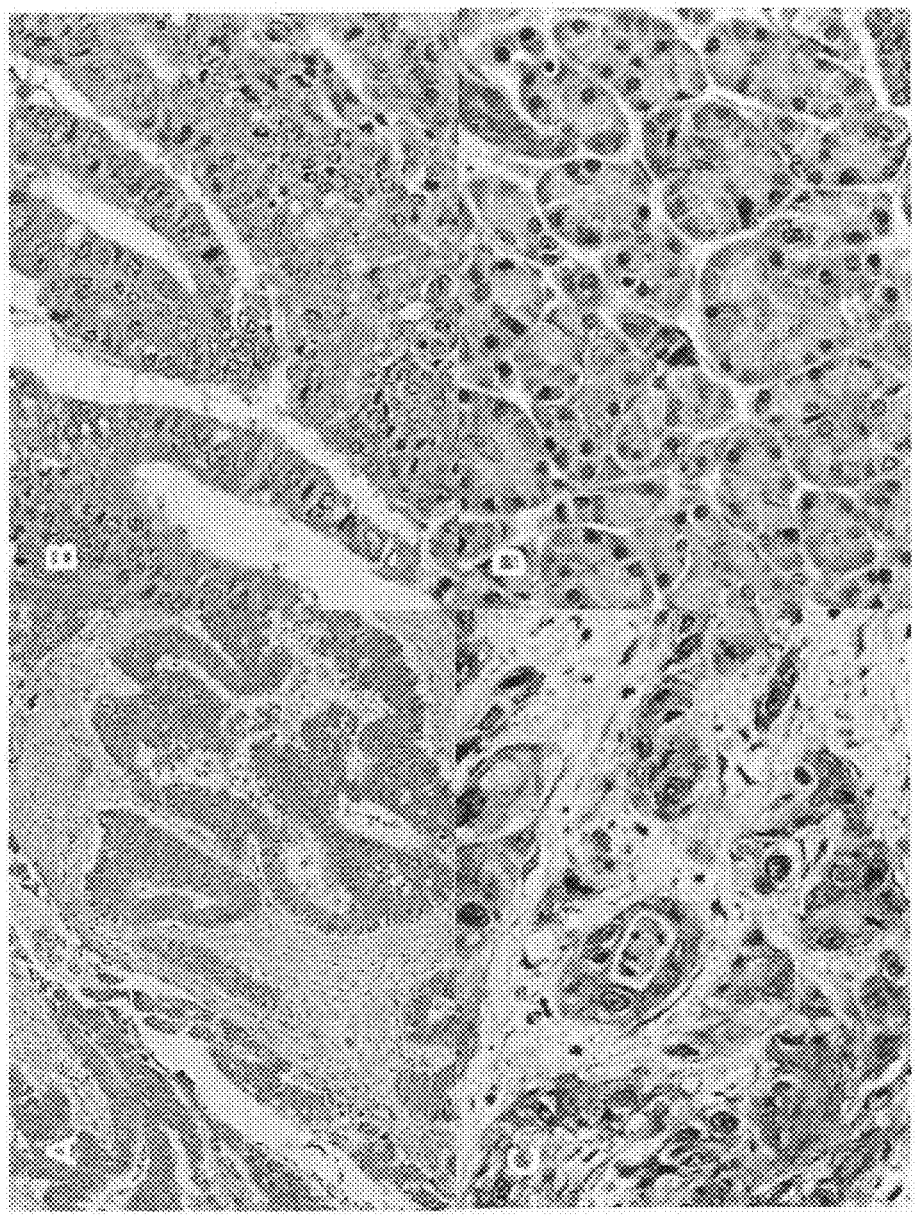

FIG. 44 shows that HERV-K env protein is expressed in colon cancer (A and B) and pancreas from cancer (C) and non-neoplastic (D) tissue by IHC using 6H5 mAb.

Figure 45:
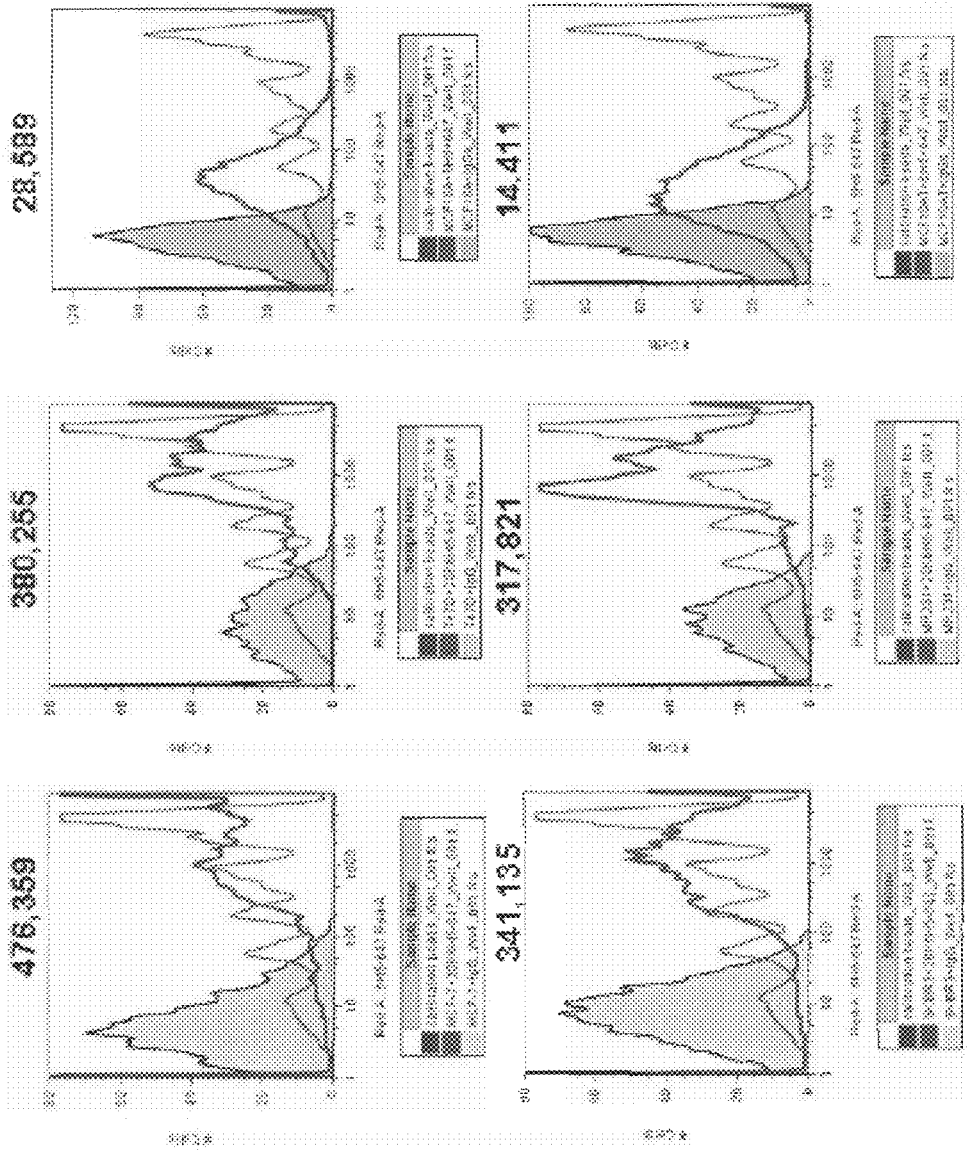

FIG. 45 shows the number of molecules of HERV-K surface env protein in various breast cells was quantified by QIFI assay using 6H5 mAb.

Figure 46:
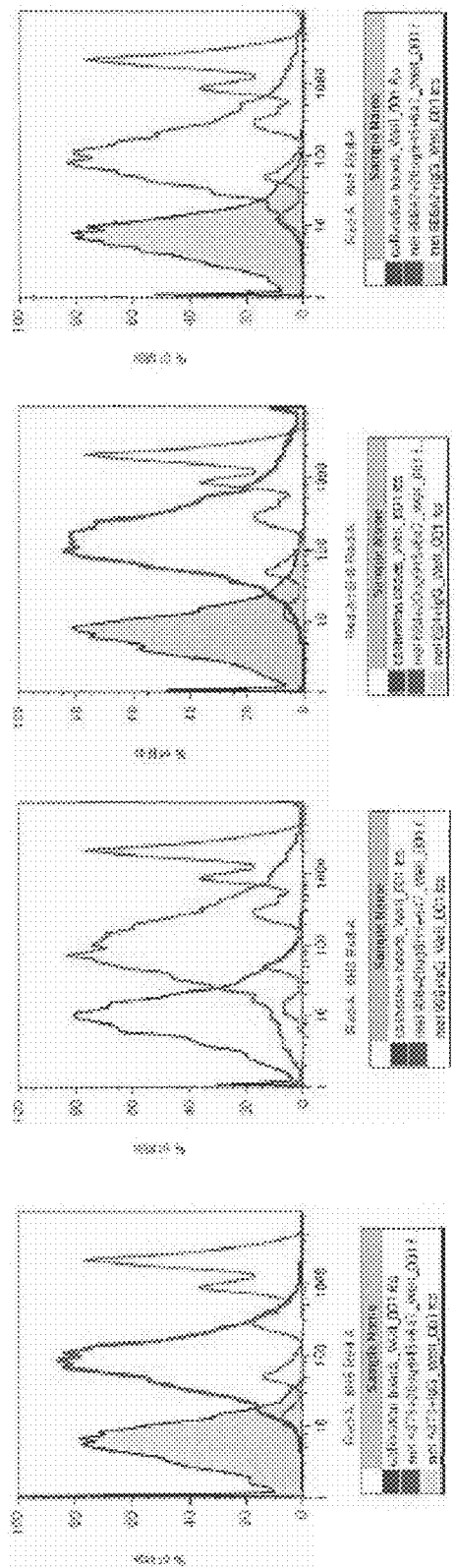

FIG. 46 shows the number of surface HERV-K env protein molecules in melanoma cell lines was determined by flow cytometry using 6H5 mAb. The MFI from each cell line was calculated according to the calibration equation.

Figure 47:
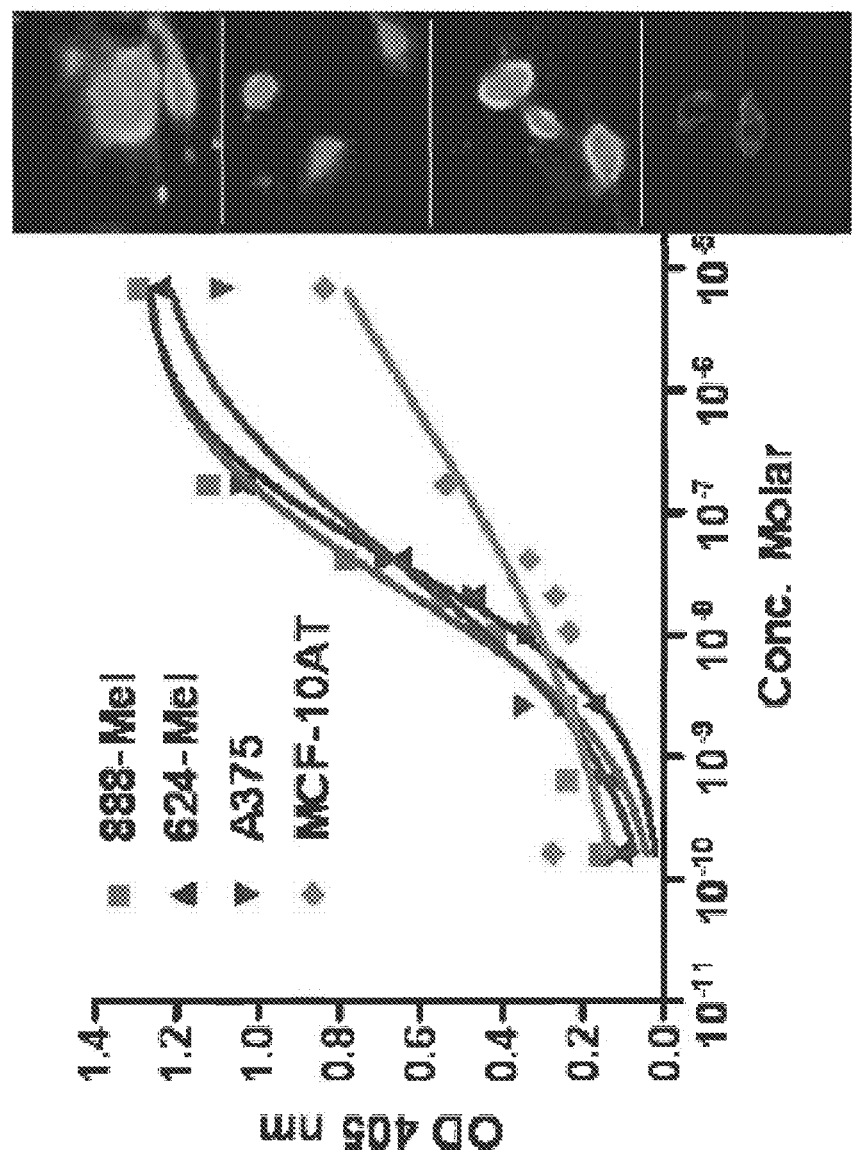

FIG. 47 shows that HERV-K env antigen was detected in several melanoma cell lines including 888A2-Mel (top panel), 624-Mel (2nd panel) and A-375 (3rd panel) cells by dry cell ELISA and immunofluorescence staining using 6H5 mAb. MCF-10AT breast cells 4th panel were used as a negative control.

Figure 48:
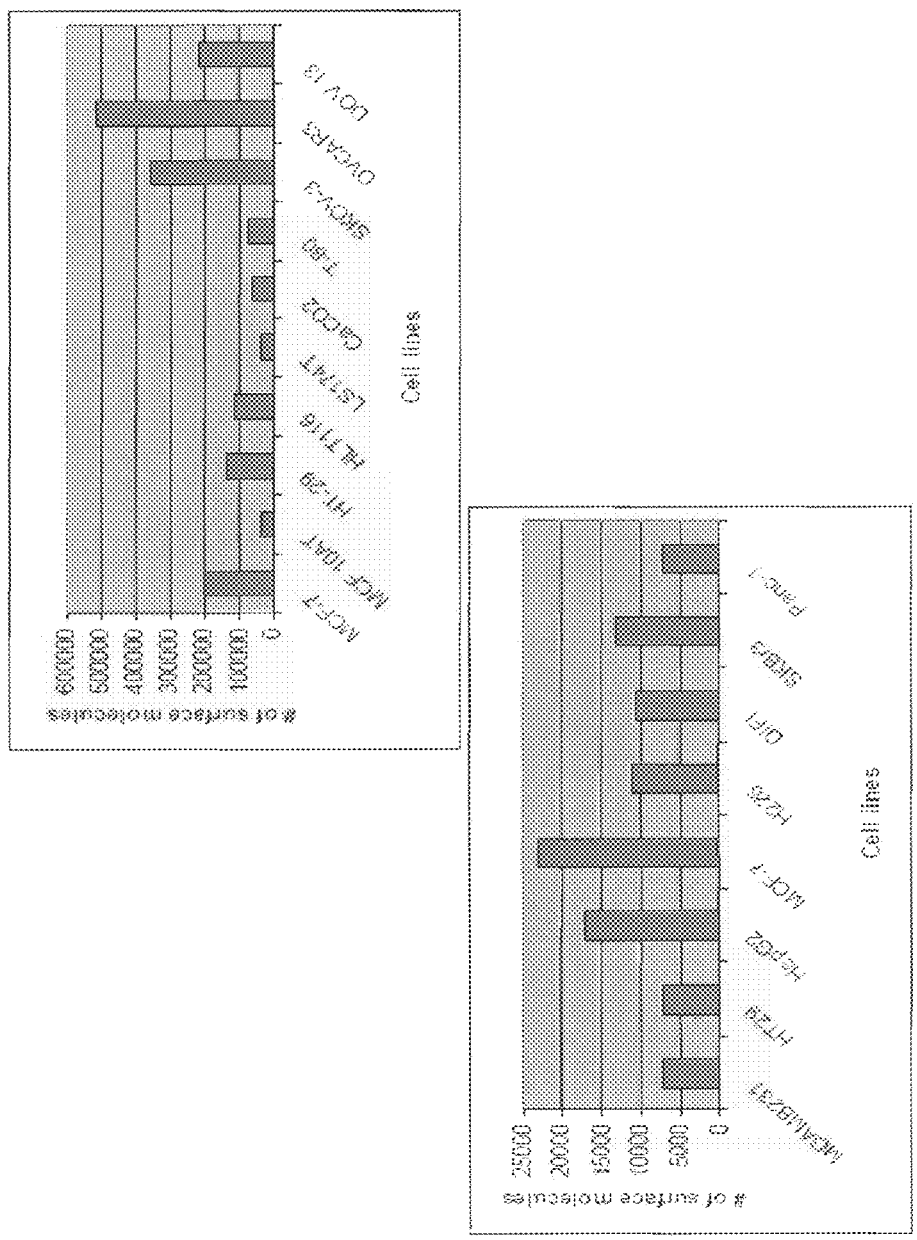

FIG. 48 shows the expression profiles of HERV-K env protein on the surface of various cancer cells or normal cells were evaluated and compared by Q1F1 assay using 6H5 mAB.

Figure 49:
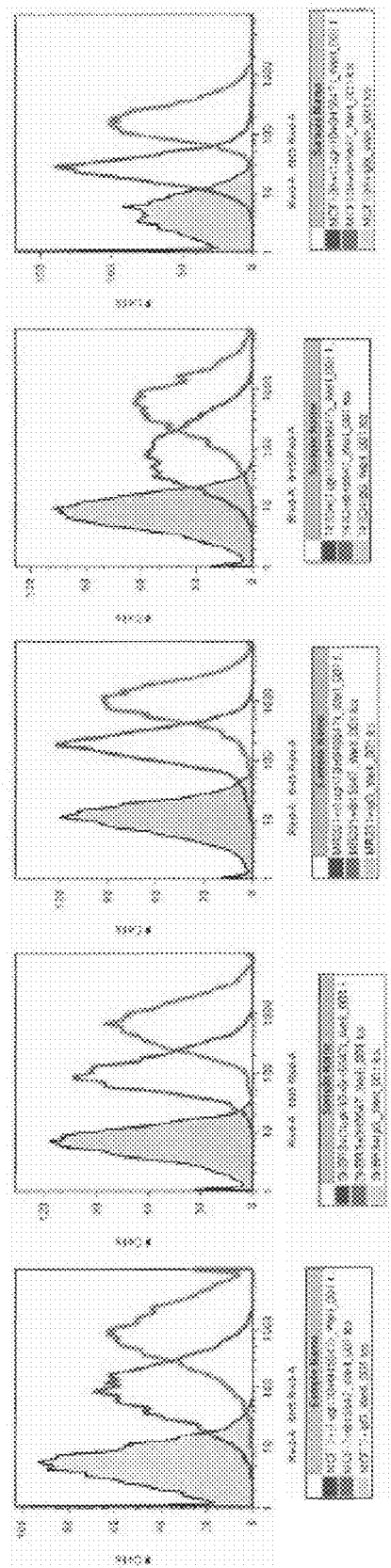

FIG. 49 shows the ability of HERV-K recombinant protein to block binding of anti-HERV-K antibodies to the cell surface was evaluated by pre-incubating the 6H5 with HERV-K recombinant protein (1 ug/10 ug 6H5).

FIG. 49 shows the ability of HERV-K recombinant protein to block binding of anti-HERV-K antibodies to the cell surface was evaluated by pre-incubating the 6H5 with HERV-K recombinant protein (1 ug/10 ug 6H5).

Figure 50:
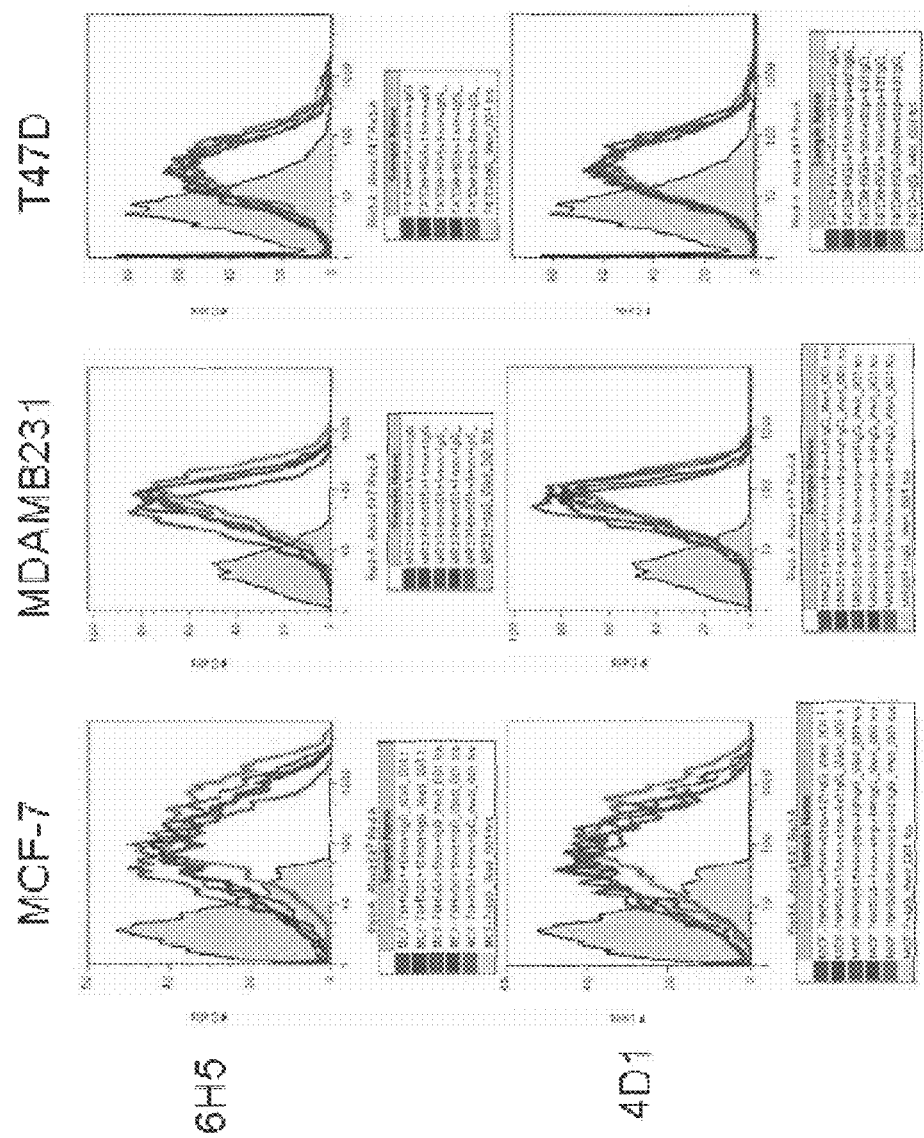

FIG. 50 shows the cycling of HERV-K env protein between the cell surface and intracellular stores in breast cells. The percentage of internalization at 45 min was 39% for T47D cells, 57.92% for MCF-7, and 64.52% for MDA-MB-231 cells, respectively.

Figure 51:
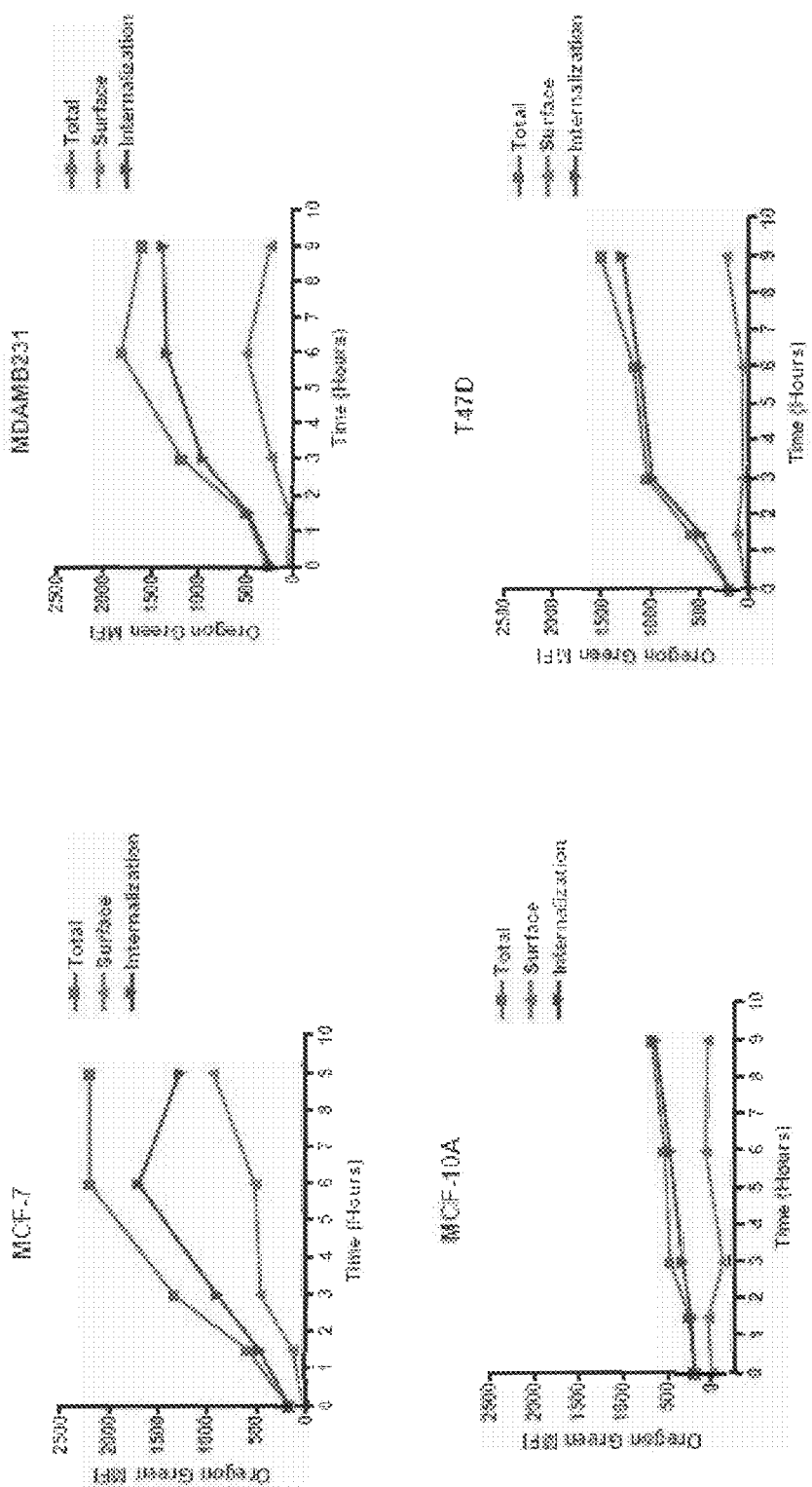

FIG. 51 shows the net cellular uptake rates of anti-HERV-K antibodies. Surface quenching allows for distinction of surface and internal antibody fractions. Total cellular fluorescence was measured at each time point by flow cytometry and the internal and surface fractions determined by surface quenching with an anti-Oregon green lgG.

Figure 52:
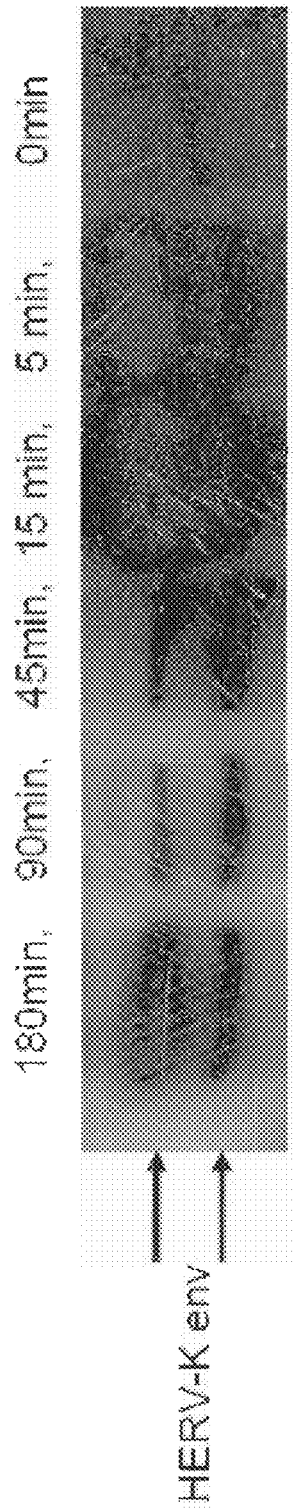

FIG. 52 shows cell surface proteins were pulsed with biotin using an HS-SS-biotin reagent and chased at 37° C. At each time point (0, 5, 15, 45, 90, and 180 minutes), cells were lysed, biotinylated proteins pulled down with streptavidin resin and the pull down blotted for HERV-K.

FIG. 53 shows the results of MTS and cytotoxicity assays of cells treated with anti-HERV-K mAbs. MCF-7 cells were treated with several concentrations of 6H5 or 6E11 mAb or mlgG on day 0, and cell proliferation was measured by MTS assay (OD 492 nm; left) or cytotoxicity assay (crystal violet staining; OD 600 nm; right) after 72 hr.

Figure 54:
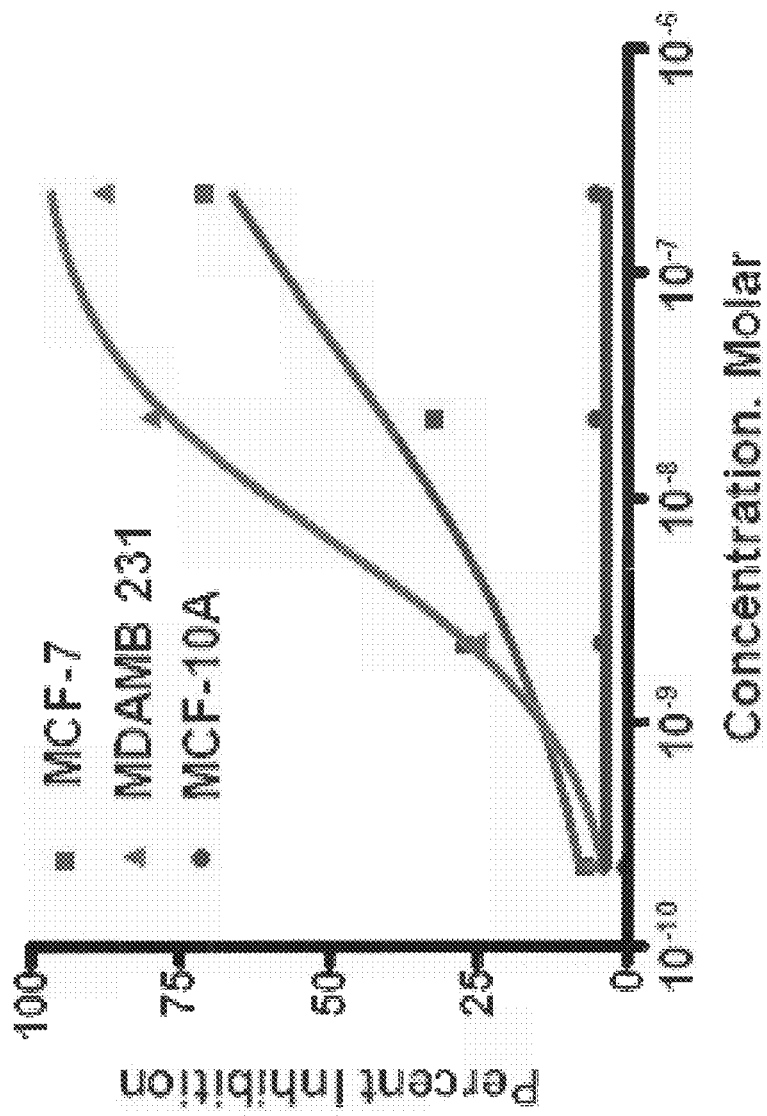

FIG. 54 provides the results of cytotoxicity assays of cells treated with anti-HERV-K mAbs. There was no cytotoxicity of 6H5 toward MCF-10A normal breast cells, in contrast to the significant cytotoxicity of 6H5 toward MCF-7 and MDA-MB-231 breast cancer cells.

Figure 55:
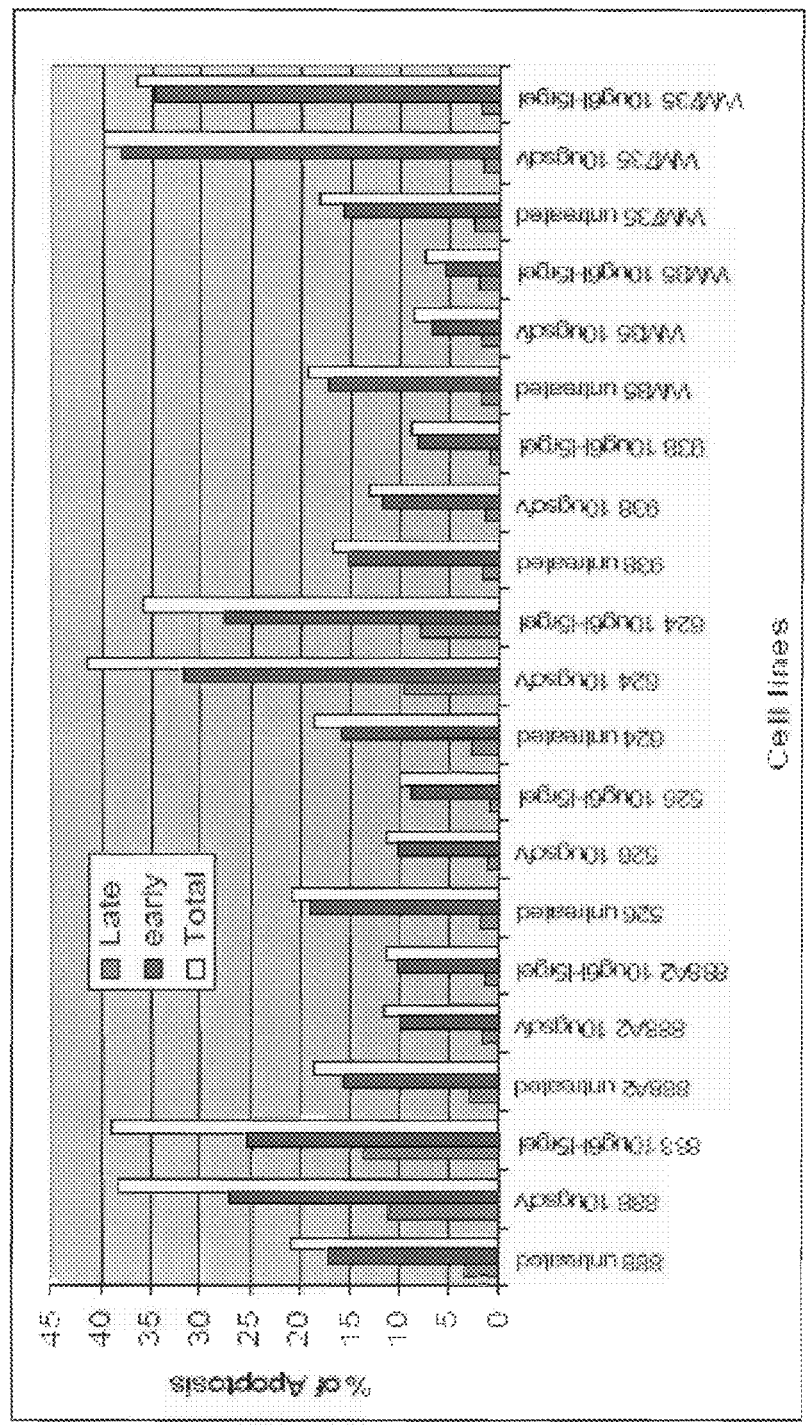

FIG. 55 shows the effect of antibody treatment on apoptosis of melanoma cells. "untreated" represents cells not exposed to 6H5 or its scFv, "6H5-rGel" or "scFv" represent cells treated with 10 µg per ml of the respective antibodies. The effect of 6H5-rGel (6H5 conjugated to rGel toxin) was not significantly different from the effect of its scFv on melanoma cell apoptosis.

Figure 56:
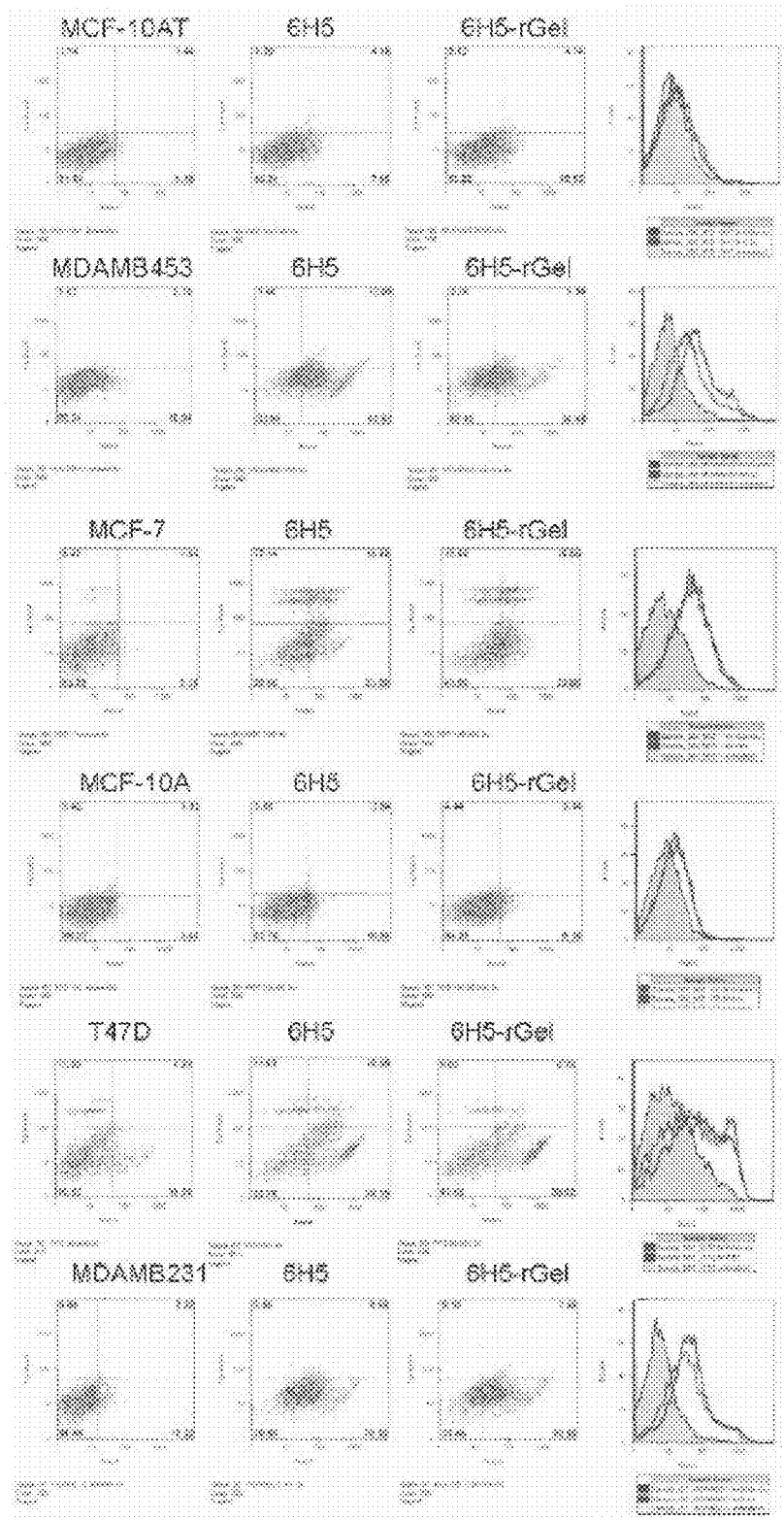

FIG. 56 shows the effect of 6H5 (red curve) or 6H5-rGel (blue curve) on induction of apoptosis in breast cells, in comparison to the same cells not treated with 6H5 or 6H5-rGel (cells stained with anti-mouse lgG; gray color region).

Figure 57:
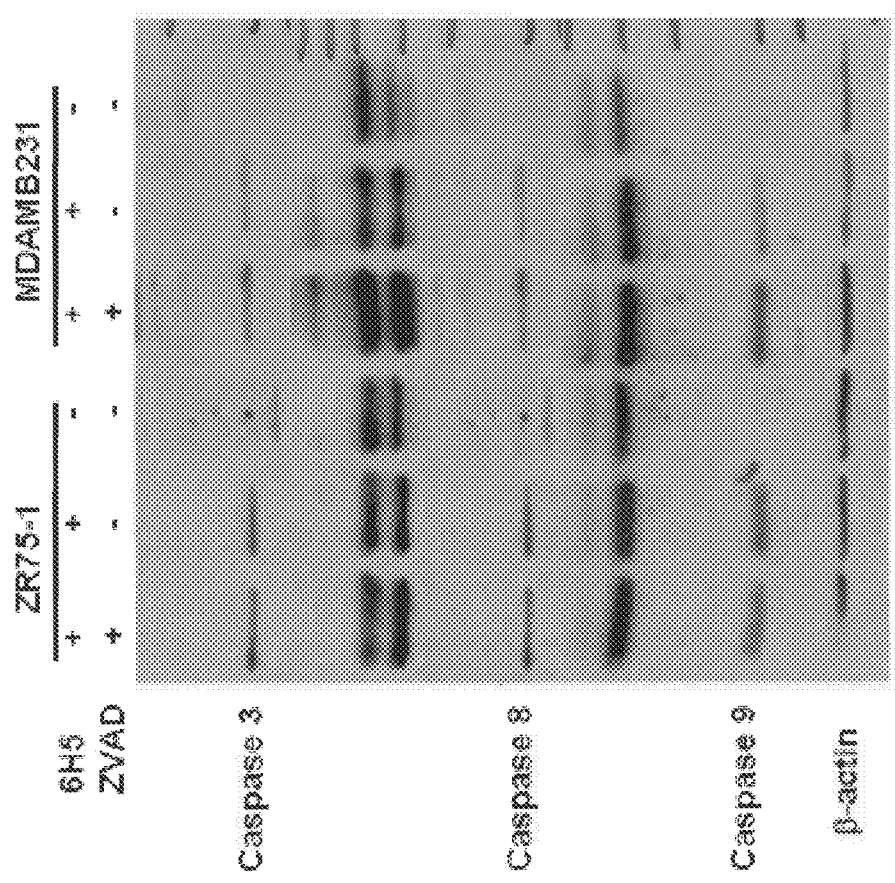

FIG. 57 shows the expression of caspase 3, 8, and 9 was detected in cancer cells treated with 6H5 (10 ug/ml) for 24 h by Western blot using antibodies for caspase 3, 8, and 9.

Figure 58:
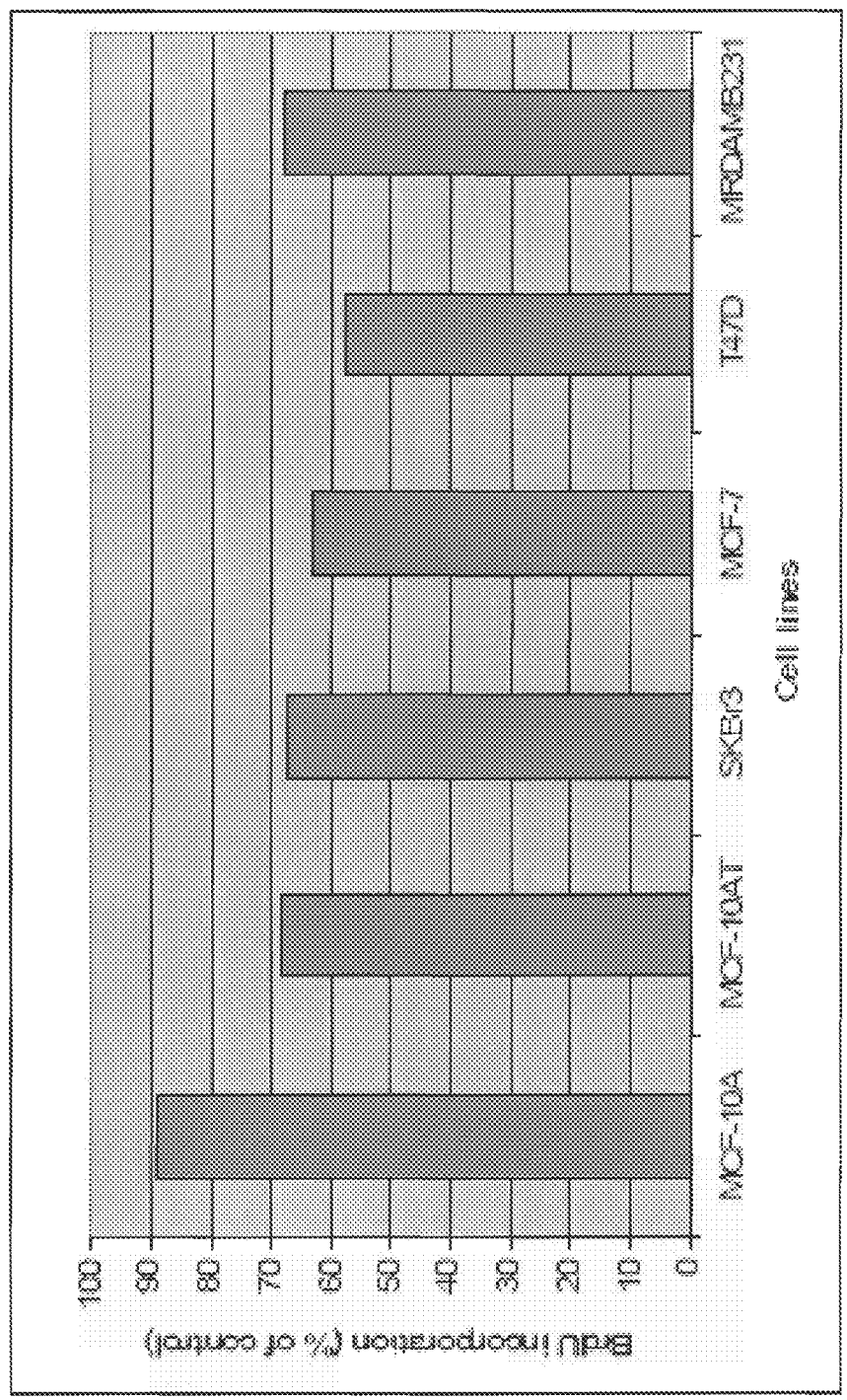

FIG. 58 shows breast cells were treated with 6H5 or mlgG (10 ug/ml) for 72 h and BrdU Incorporation was expressed as a % of control cells (cells treated with mlgG).

Figure 59:
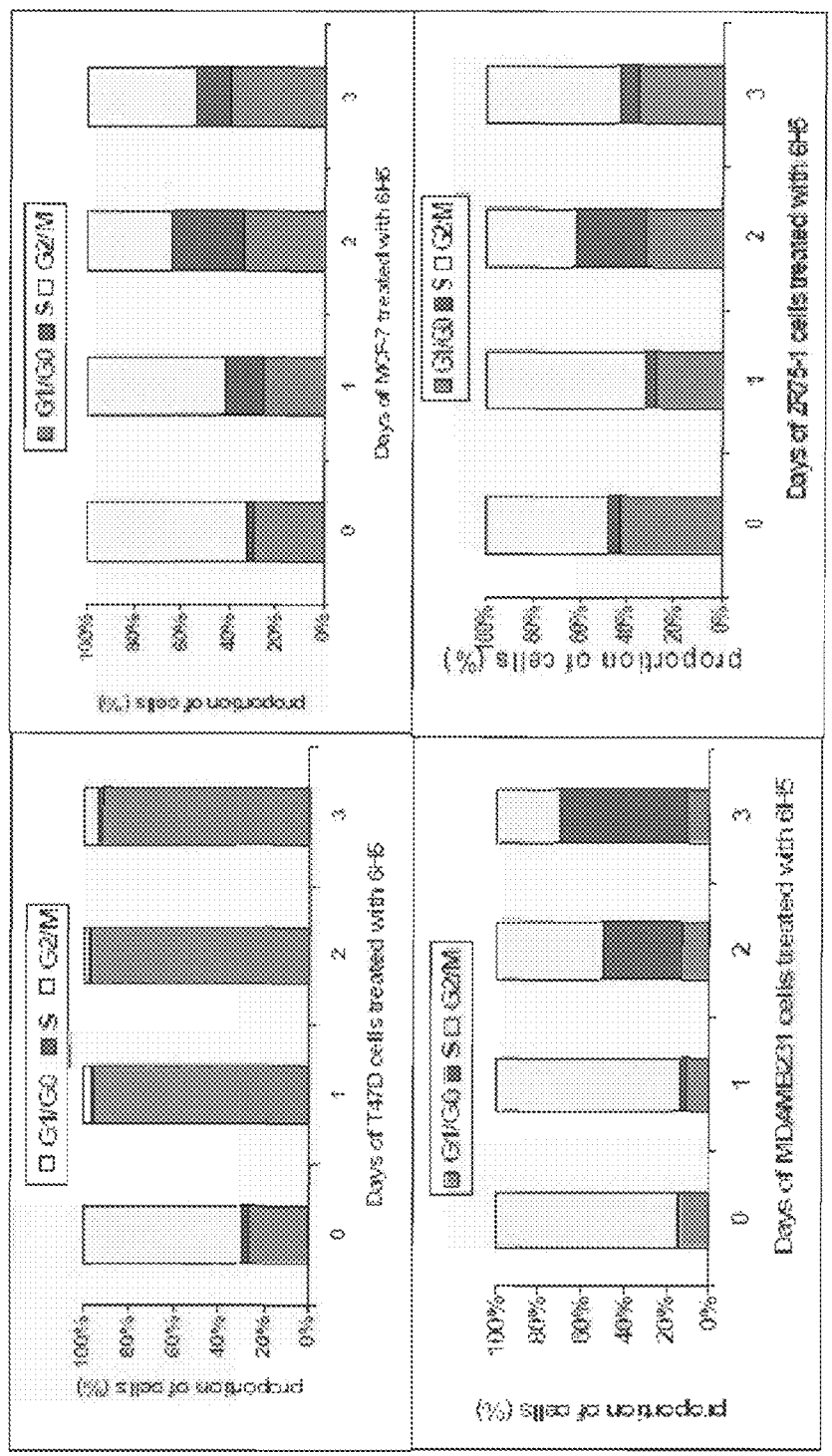

FIG. 59 shows the cell cycle arrest in the G1/G0 phase (T47D) and S phase (MCF-7, MDAMB231, and ZR75-1). Cells were induced with 6H5 mAb (10 ug/ml) on days 1, 2, and 3.

Figure 60:
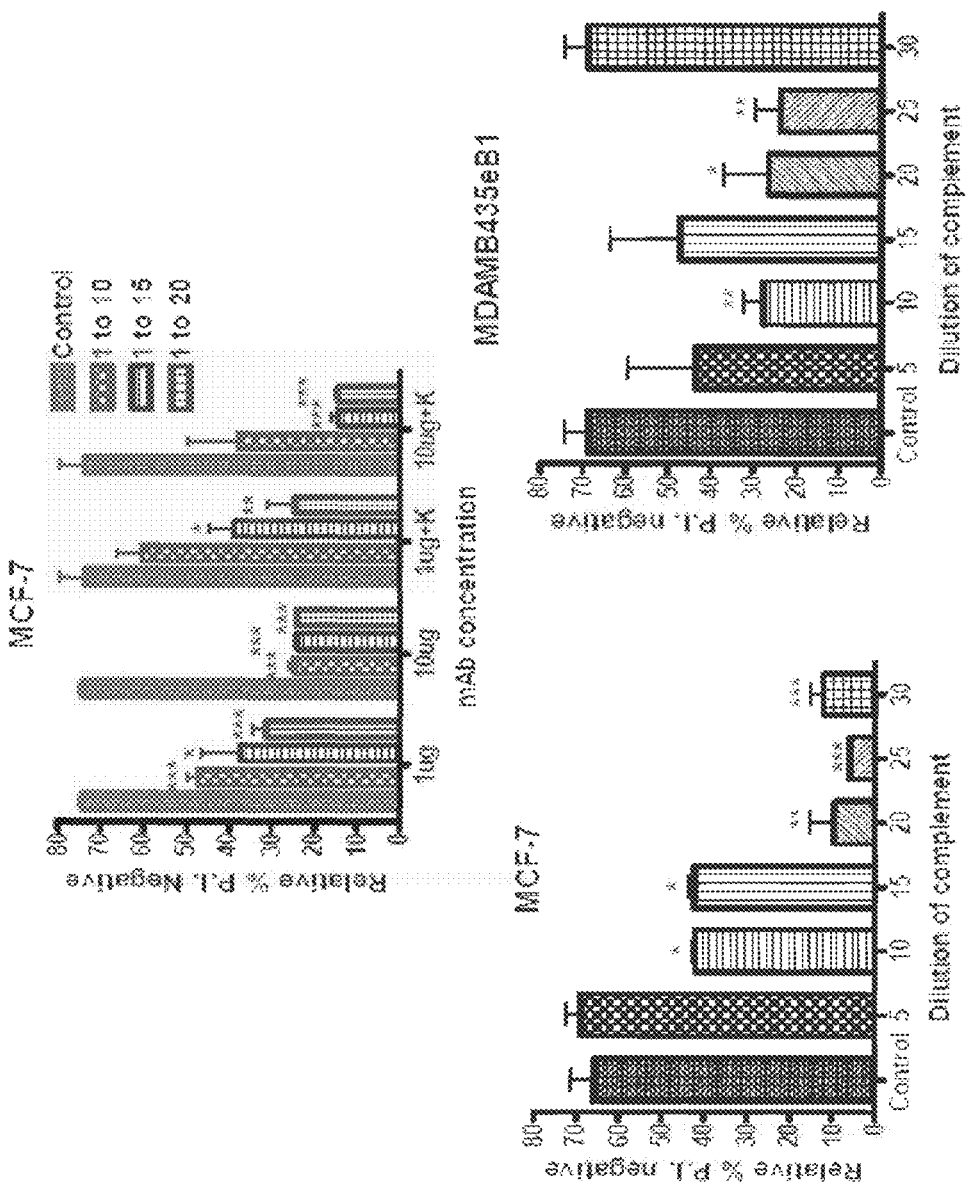

FIG. 60 shows the results of the CDC assay of breast cancer cell lines: Breast cells were treated with 6E11 mAb (1 or 10 µg/ml) in media with 1:5 to 1:30 dilutions of normal human sera complement. A greater percentage of negative P.I. staining is indicative of living cells.

Figure 61:
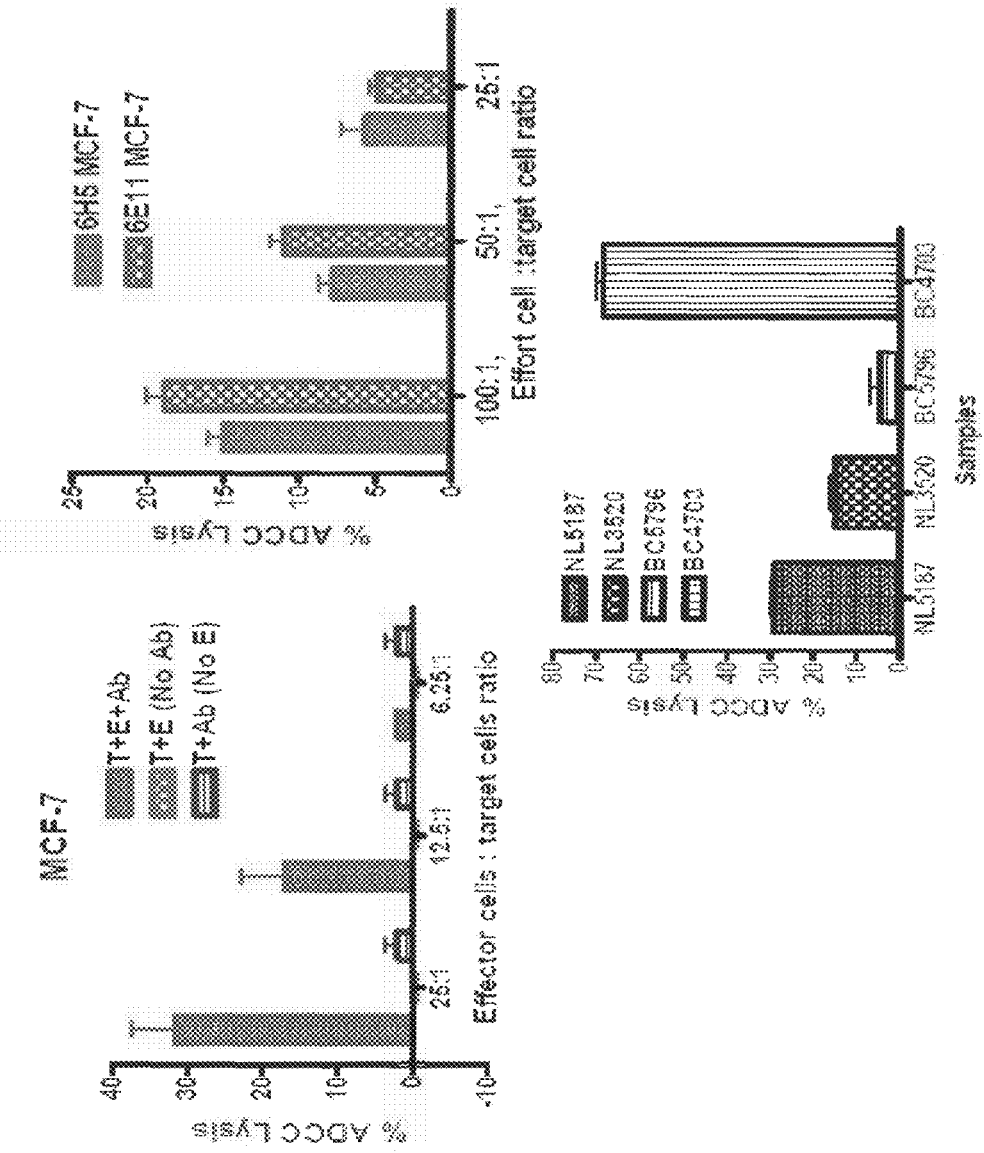

FIG. 61 shows both 6H5 and 6E11 mAbs (10 µg/ml) induced MCF-7 cell death by ADCC, using PBMCs from normal donors (top panel). Controls contained no mAb or no effector cells. The effector cell (E) to target cell (T) ratio was evaluated in the range of 25:1 to 6.25:1 (top left panel), and in the range of 100:1 to 25:1 (top right panel). The percentage of ADCC lysis differed among individuals.

Figure 62:
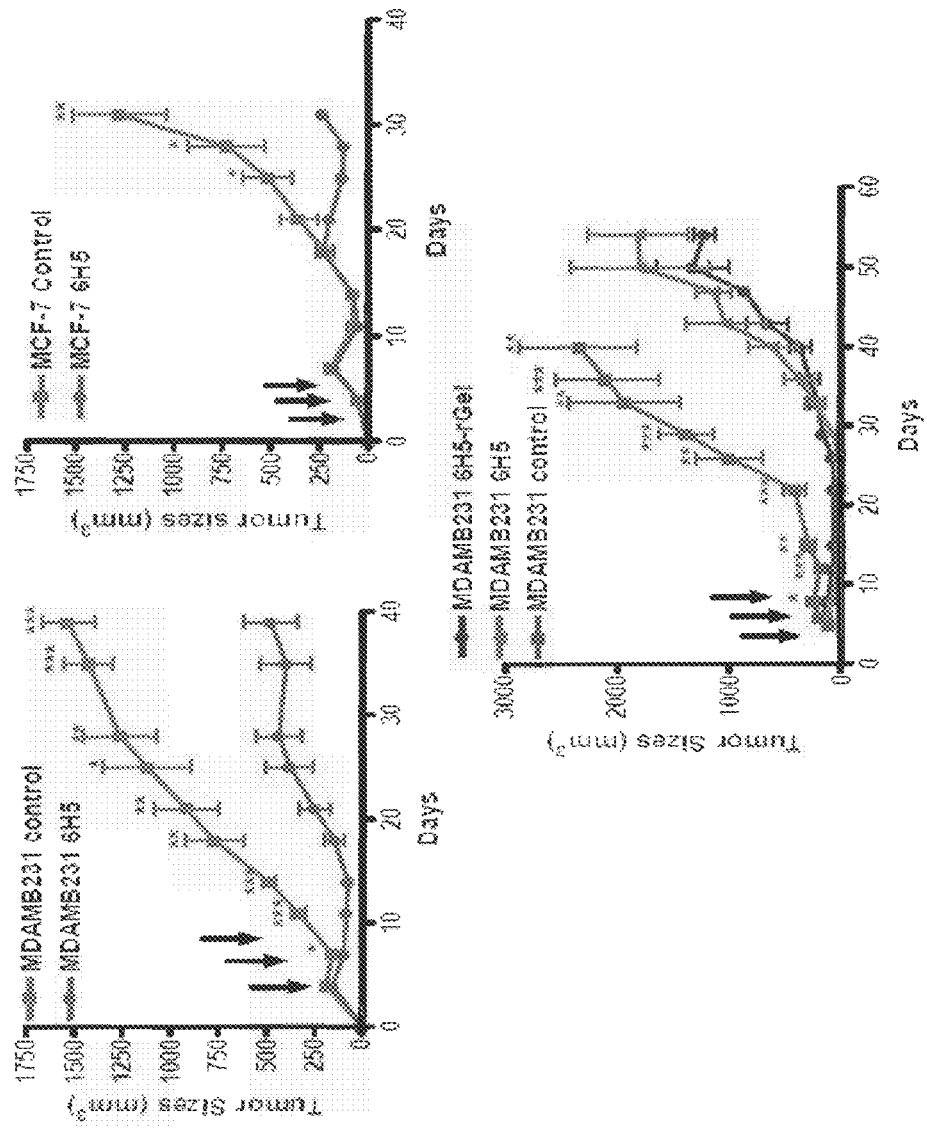
Figure 63:
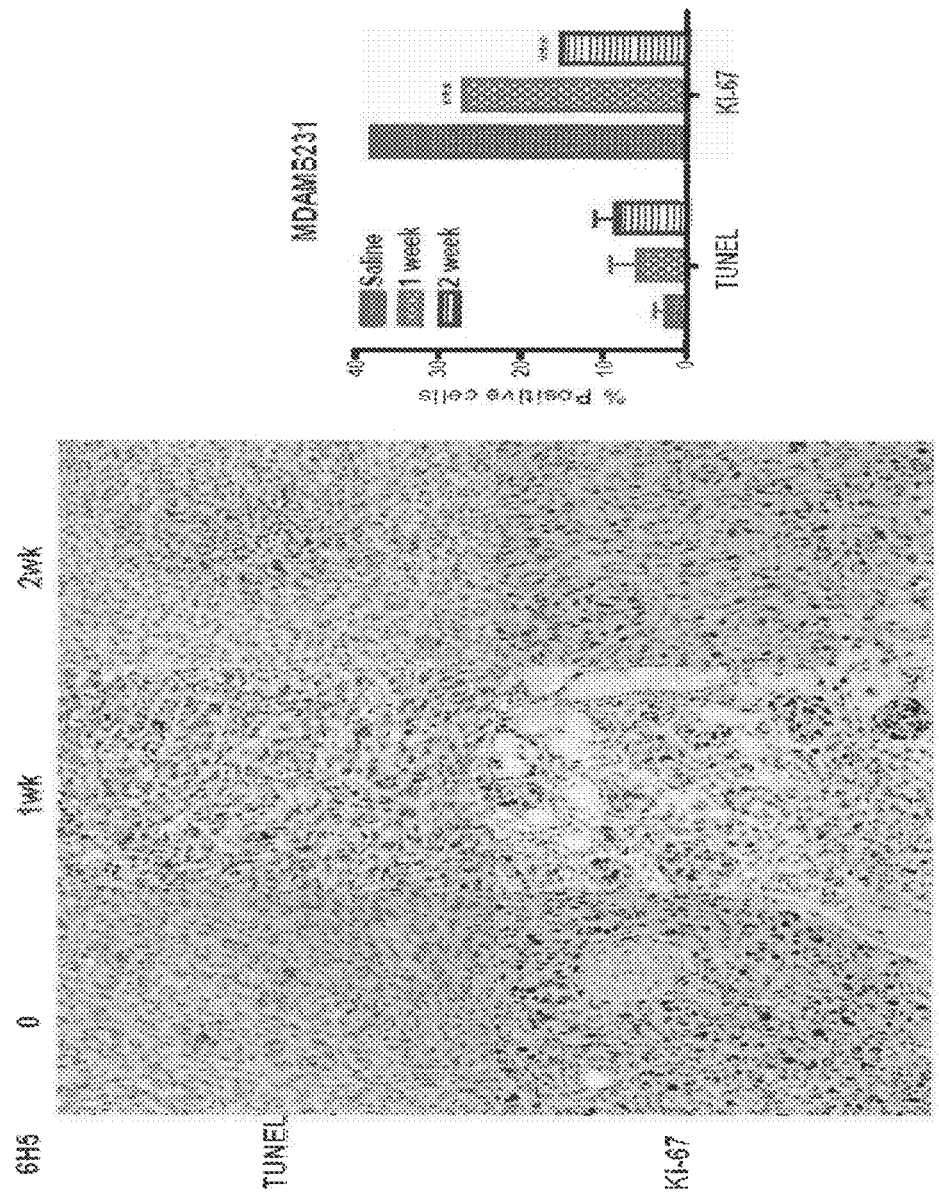

FIG. 62 provides the results of female SCID mice inoculated subcutaneously with MDA-MB-231 or MCF-7 (5×106 cells) on day 0 and treated with mlgG, 6H5 or 6H5-rGel on days 4, 6, and 8 (arrows). Tumor sizes were measured twice per week, and average tumor volumes (L×W×D) for each group were compared FIG. 63 shows the results of a TUNEL or Ki-67 assay was used for detection of apoptosis or cell proliferation, respectively, in MDA-MB-231 human breast cancer tumors from SCID mouse xenografts. Mice were treated with 6H5 mAb for 1 or 2 weeks, and comparisons were made between the tumors of 6H5 mAb treated mice and control mice treated with saline or mIgG (0).

Figure 64:
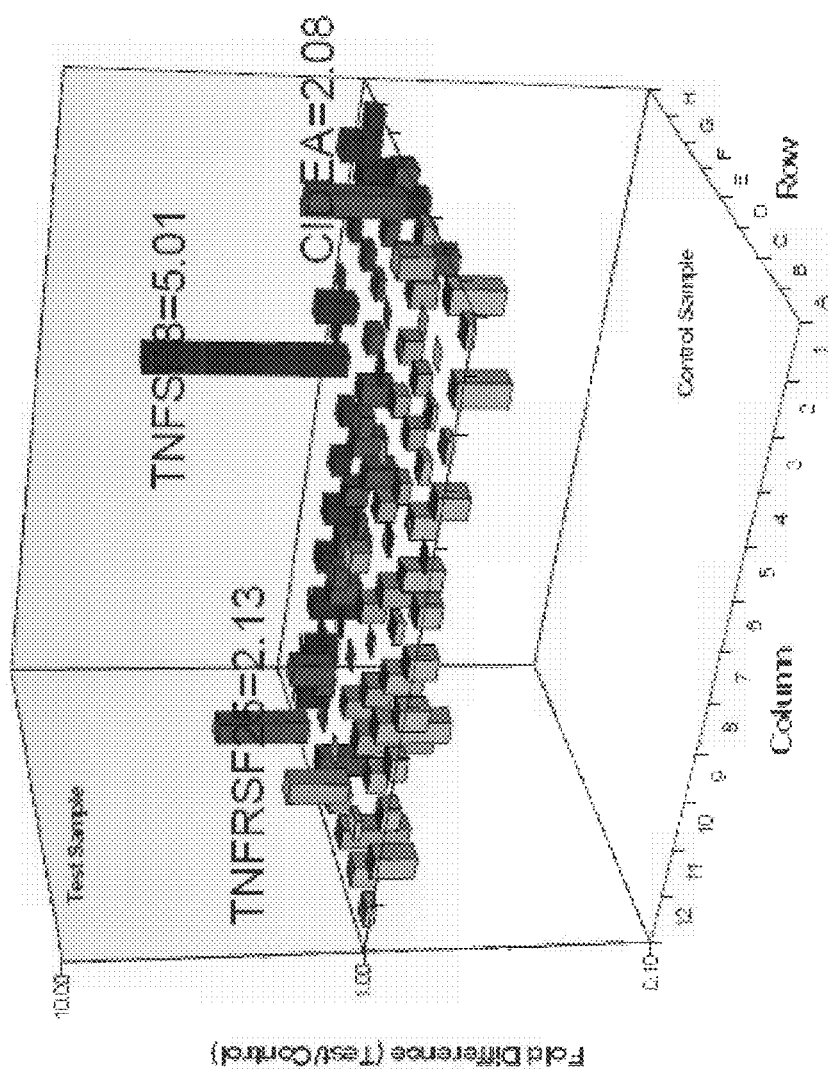

FIG. 64 shows the results of MCF-7 cells treated with 6H5 or mIgG (10 ug/ml) for 24 h, and 3 or 84 key genes involved in apoptosis, or programmed cell death were upregulated by 6H5 using human apoptosis PCR arrays. The fold changes in response to antibody treatment are shown.

Figure 65:
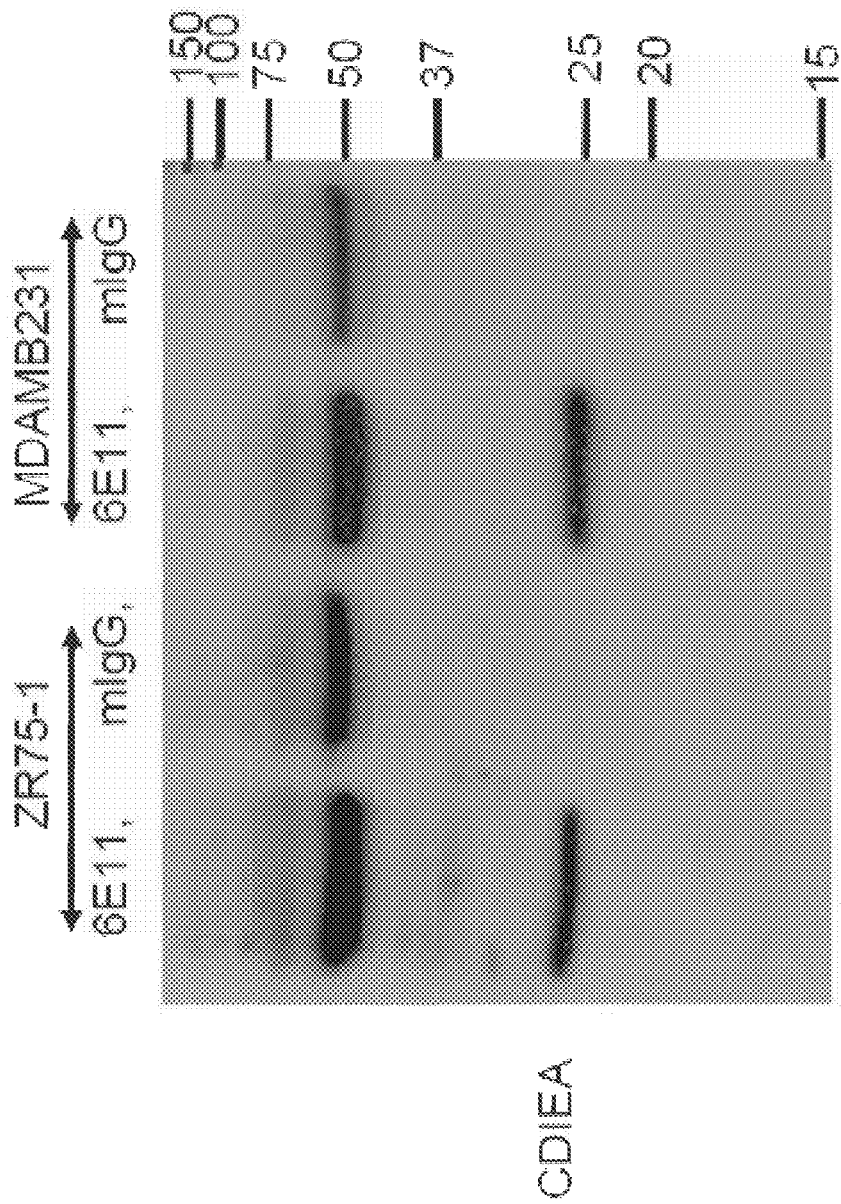

TNFRSF25: tumor necrosis factor receptor superfamily, member 25
TNFSF8: tumor necrosis factor (ligand) superfamily, member 8
CIDEA: cell death-inducing DFFA-like effector a FIG. 65 shows the detection of CIDEA in breast cancer cell lines ZR75-1 and MDAMB231. Cells were treated with 6H5 mAb, and compared to the same cells treated with mIgG.

Figure 66:
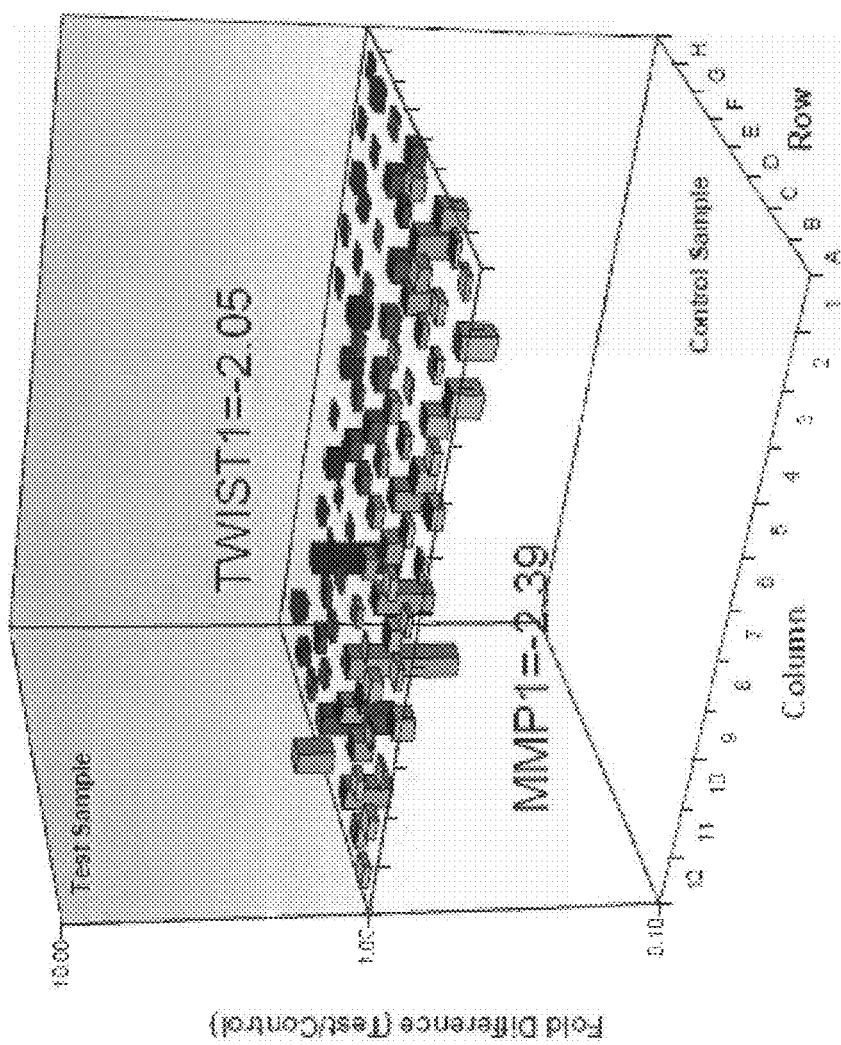

FIG. 66 shows the results of MCF-7 cells treated with 6H5 or mIgG (10 ug/ml) for 24 h, and TWIST1 and MMP1, genes involved in invasion and metastasis of cancer cells, were downregulated by 6H5 mAb. Data were obtained using the Cancer Finder Pathway Superarray, and the fold changes are shown in this graph.

TWIST1: Probably transcription factor
MMP1: collagenase-1

Figure 67:
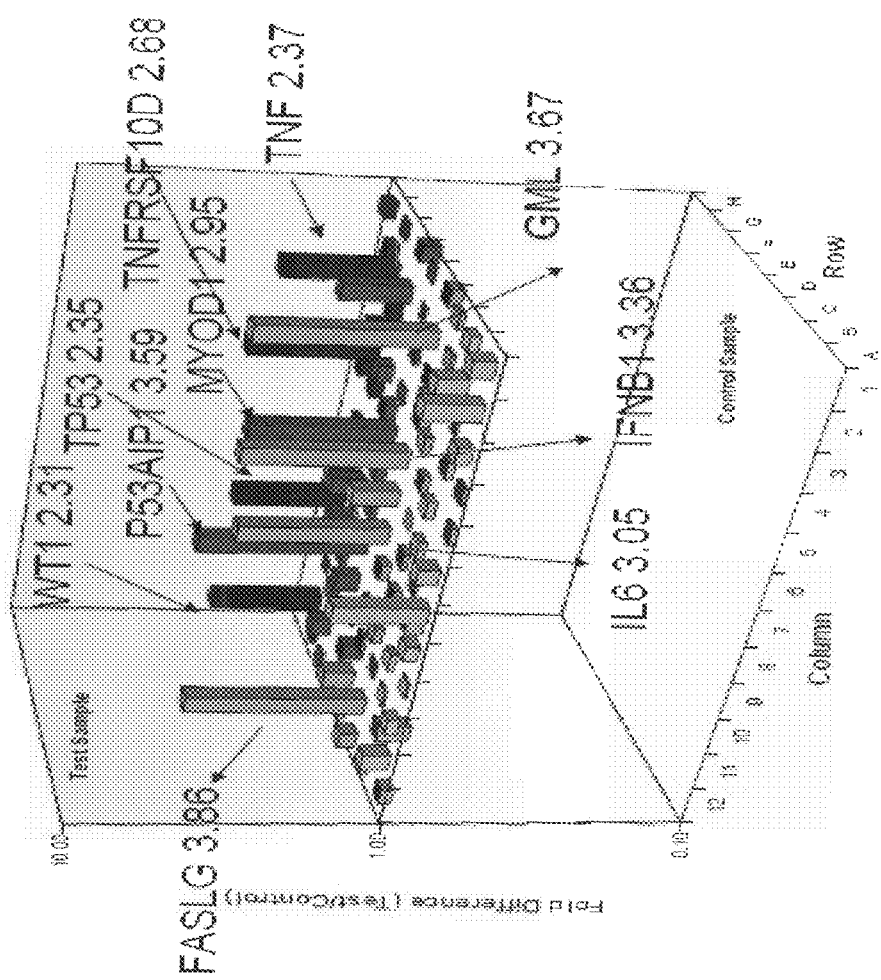

FIG. 67 shows the results of MCF-7 cells treated with 6H5 or mIgG (10 ug/ml) for 24 h and the expression of 84 genes related to p53-mediated signal transduction was evaluated using a p53 Signaling Pathway PCR Array. Genes on the array include p53-related genes involved in the processes of apoptosis, the cell cycle, cell growth, proliferation, and differentiation, and DNA repair.

FIG. 68 shows humanized 4D1 scFv as generated in a human antibody framework with murine CDRs as labeled (heavy chain is blue and light chain is yellow). (SEQ ID NOS. 31, 32, 33, 34, 35, 36, 37, 38, 39, 40, 41, 42, 43, 44, 45, 46, 47, 48, 49)

FIG. 69 shows humanized 6H5 scFv as generated in a human antibody framework with murine CDRs as labeled (heavy chain is blue and light chain is yellow) (SEQ ID NOS. 67, 68, 69, 70, 71, 72, 73, 74, 75, 76, 77, 78, 79, 80, 81, 82, 83, 84).

Figure 70:
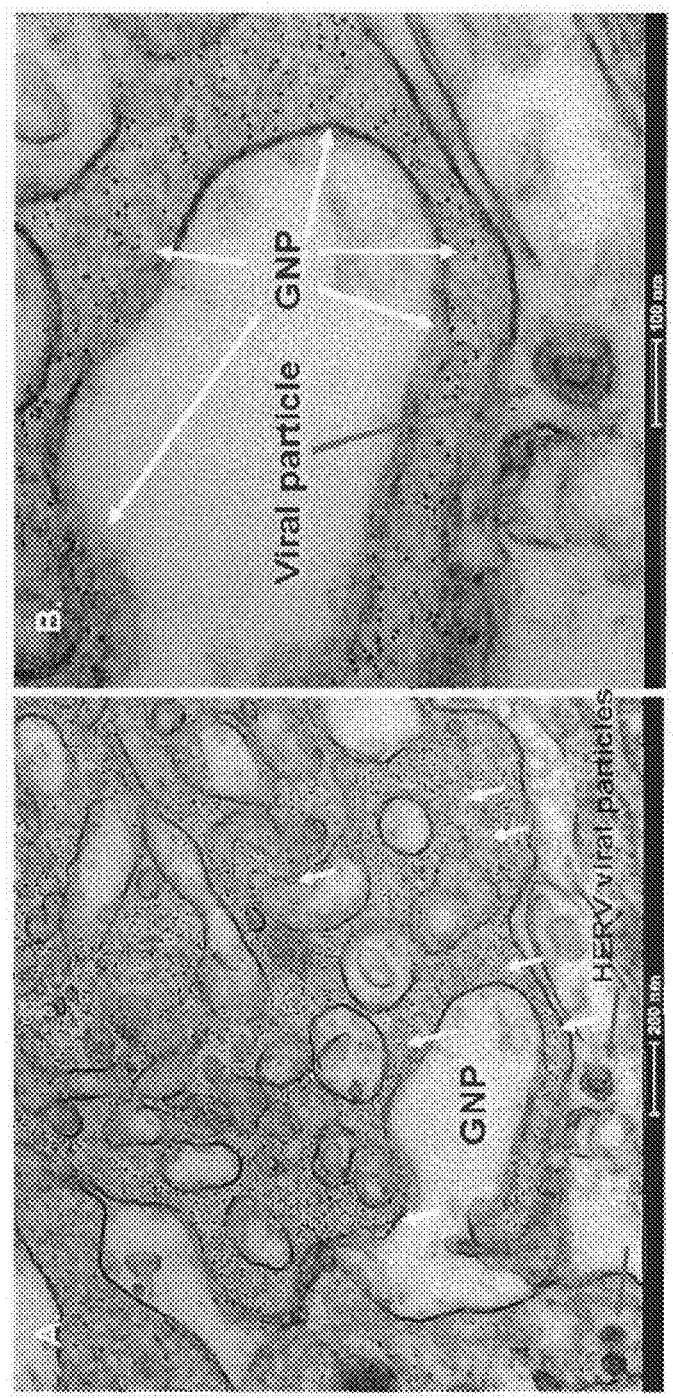

FIG. 70 shows GNP (white arrows) was detected by TEM in MDAMB231 cells of tumors isolated from mice 24 hr post-i.v.-injection with 6H5-GNP. HERV viral particles (green arrows) were observed adjacent to tumor cells.

While the present disclosure is susceptible to various modifications and alternative forms, specific example embodiments have been shown in the figures and are herein described in more detail. It should be understood, however, that the description of specific example embodiments is not intended to limit the disclosure to the particular forms disclosed, but on the contrary, this disclosure is to cover all modifications and equivalents as illustrated, in part, by the appended claims.

Description

Identification of unique cancer antigens enables the design of selective immunotherapy for neoplastic diseases. The capacity to utilize a determinant exclusively expressed by cancer cells, and which is devoid in normal tissues, ensures the targeting and elimination of the neoplastic cells while insulating the function of normal cells.

General Definitions

"human endogenous retrovirus" (HERV) is a retrovirus that is present in the form of proviral DNA integrated into the genome of all normal cells and is transmitted by Mendelian inheritance patterns. Such proviruses are products of rare infection and integration events of the retrovirus under consideration into germ cells of the ancestors of the host. Most endogenous retroviruses are transcriptionally silent or defective, but may be activated under certain conditions. Expression of the HERV may range from transcription of selected viral genes to production of complete viral particles, which may be infectious or non-infectious. Indeed, variants of HERV viruses may arise, which are capable of an exogenous viral replication cycle, although direct experimental evidence for an exogenous life cycle is still missing. Thus, in some cases, endogenous retroviruses may also be present as exogenous retroviruses. These variants are included in the term HERV for the purposes of the disclosure. In the context of the disclosure, human endogenous retrovirus includes proviral DNA corresponding to a full retrovirus comprising two LTRs, gag, pol, and env, and further includes remnants or "scars" of such a full retrovirus, which have arisen as a results of deletions in the retroviral DNA. Such remnants include fragments of the full retrovirus, and have a minimal size of one LTR. Typically, the HERVs have at least one LTR, preferably two, and all or part of gag, pol, or env.

The term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. Purity can be evaluated by chromatography, gel electrophoresis, immunoassay, composition analysis, biological assay, and other methods known in the art.

A "sample" refers to a biological material which can be tested for the presence of HERV-K env protein or HERV-K env protein nucleic acids. Such samples can be obtained from subjects, such as humans and non-human animals, and include tissue, especially mammary glands, ovaries, biopsies, blood, and blood products; plural effusions; cerebrospinal fluid (CSF); ascites fluid; and cell culture.

The term "non-human animals" includes, without limitation, laboratory animals such as mice, rats, rabbits, hamsters, guinea pigs, etc.; domestic animals such as dogs and cats; and, farm animals such as sheep, goats, pigs, horses, and cows.

The term "transformed cell" refers to a modified host cell that expresses a functional protein expressed from a vector encoding the protein of interest. Any cell can be used, but preferred cells are mammalian cells.

The term "assay system" is one or more collections of such cells, e.g., in a microwell plate or some other culture system. To permit evaluation of the effects of a test compound on the cells, the number of cells in a single assay system is sufficient to express a detectable amount of the HERV-K env protein mRNA and protein expression. The methods of the disclosure are suitable cells of the disclosure that are particularly suitable for an assay system for test ligands that modulate transcription and translation of the HERV-K env gene.

The terms "cancer" or "tumors" refers to group of cells that display uncontrolled division. In a specific embodiment, the cancer is a HERV-K$^+$ cancer. In a specific embodiment, the cancer is breast cancer and particularly infiltrating ductal and/or lobular carcinomas. In another specific embodiment, the cancer is ovarian cancer. Ovarian cancer refers to any cancer in any of the three kinds of ovarian tissue cell types, which include germ cells, stromal cells, or epithelial cells. The majority of epithelial tumor types are HERV positive. The term "cell proliferation" refers to the growth of a cell or group of cells.

The term "humanly acceptable" refers to compounds or antibodies that are modified so as to be useful in treatment of human diseases or disorders. In a specific embodiment, antibodies (polyclonal or monoclonal) are modified so that they are humanly acceptable. In one embodiment, this requires the antibodies to be humanized or primatized.

The use of italics generally indicates a nucleic acid molecule (e.g., HERV-K env protein cDNA, gene, and the like); normal text generally indicates the polypeptide or protein. Alternatively, whether a nucleic acid molecule or a protein is indicated, it can be determined by the content.

The term "amplification" of DNA refers to the use of polymerase chain reaction (PCR) to increase the concentration of a particular DNA sequence within a mixture of DNA sequences. For a description of PCR see Saiki et al., *Science*, 239:487, 1988.

The term "nucleic acid molecule" refers to the phosphate ester form of ribonucleosides (RNA molecules) or deoxyribonucleosides (DNA molecules), or any phosphoester analogs, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, among other things, in linear (e.g., restriction fragments) or circular DNA molecules, plasmids, and chromosomes. In discussing the structure of particular double-stranded DNA molecules, sequences may be described according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

The terms "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and antisense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thiouracil, thio-guanine and fluoro-uracil.

The polynucleotides may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described below.

Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. The genetic code has some redundancy, also called degeneracy, meaning that most amino acids have more than one corresponding codon.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.

A common type of vector is a "plasmid," which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct."

The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. See, Sambrook, Fritsch & Maniatis, *Molecular Cloning: A Laboratory Manual*, Second Edition (1989) Cold Spring Harbor Laboratory Press, Cold Spring Harbor, N.Y. The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived. See, Sambrook, Fritsch & Maniatis, *Molecular Cloning: A Laboratory Manual*, Second Edition (1989) Cold Spring Harbor Laboratory Press, Cold Spring Harbor, N.Y. For hybridization with shorter nucleic acids, i.e., oligonucleotides, the position of mismatches becomes more important, and the length of the oligonucleotide determines its specificity. See, Sambrook, Fritsch &

Maniatis, Molecular Cloning: A Laboratory Manual, Second Edition (1989) Cold Spring Harbor Laboratory Press, Cold Spring Harbor, N.Y. A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

The term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of HERV-K Env, or to detect the presence of nucleic acids encoding HERV-K Env. Generally, oligonucleotides are prepared synthetically, preferably on a nucleic acid synthesizer.

"Antibody-dependent cell-mediated cytotoxicity" and ADCC refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII An "epitope," as used herein is a portion of a polypeptide that is recognized (i.e., specifically bound) by a B-cell and/or T-cell surface antigen receptor. Epitopes may generally be identified using well known techniques, such as those summarized in Paul, *Fundamental Immunology*, 3rd ed., 243-247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present disclosure.

Cancers

As mentioned above, the term "cancer" refers to cells that display uncontrolled proliferation or division. The degree to which a cancer has spread beyond its original location is referred to as the "stage" of the cancer. Lower stages, such as stages I and II, are generally more confined to their site or region of origin than advanced stages (III and IV). See, e.g., The Merck Manual, 15$^{th}$ Ed., Merck, Sharp, & Dohme Research Laboratories (1987).

HERV-K$^+$ cancers refer to cancers that are characterized by expression of a HERV-K gene, or a polymorphism or sequence variant thereof, which results in an antigen derived from the HERV-K gene, or a polymorphism or sequence variant thereof. Examples of a HERV-K$^+$ cancer include, but are not limited to, breast cancers, ovarian cancers, teratocarcinomas, and melanomas.

Breast cancers refer to a class of cancers that are associated with development in the breast of women and men. The most common type of breast cancer is invasive ductal carcinoma. It occurs most frequently in women in their 50's and appears to spread from the breast into the lymph nodes. The HERV-K env gene may be expressed in breast cancer cell lines, tumors, and tissues.

Ovarian cancer refers to a class of cancers that are associated with development in the ovaries of women. Carcinoma of the ovary is most common in women over age 60. The most common type of ovarian cancer is epithelial ovarian carcinomas. The HERV-K env transcripts, as well as type 1 and type 2 HERV-K full length transcripts, may be detected in ovarian cancer cell lines.

Polypeptides

The present disclosure describes polypeptides that encompass amino acid sequences encoded by a polynucleotide having a HERV-K env sequence, and variants of such polypeptides. In specific embodiments, polypeptides also include polypeptides (and epitopes thereof) encoded by DNA sequences that hybridize to a HERV-K env sequence under stringent conditions, wherein the DNA sequences are at least 80% identical in overall sequence and wherein RNA corresponding to the nucleotide sequence is expressed at a greater level in a cancer tissue than in the corresponding normal tissue. Examples of such DNA sequences include, but are not limited to those shown in FIGS. 13A-E (SEQ ID. NO:1-SEQ ID. NO:10), and those listed in Table 5, and Table 6.

Cloning and Expression of HERV-K Env Protein

The present disclosure contemplates analysis and isolation any antigenic fragments of HERV-K env protein from any source, preferably human. It further contemplates expression of functional or mutant HERV-K env protein for evaluation, diagnosis, or therapy.

Conventional molecular biology, microbiology, and recombinant DNA techniques within the skill of the art may be employed in the use of this disclosure. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Antibodies

The present disclosure describes antibodies that bind HERV-K env protein in cells and specifically in cancer cells such as HERV-K$^+$ cancer cells, for example breast and ovarian cancers and melanoma. According to the disclosure, HERV-K env polypeptides produced recombinantly or by chemical synthesis, and fragments or other derivatives, may be used as an immunogen to generate antibodies that recognize the HERV-K env polypeptide or portions thereof. Such antibodies include, but are not limited to, polyclonal, monoclonal, humanized, primatized, chimeric, single chain, Fab fragments, and a Fab expression library. An antibody that is specific for human HERV-K env protein may recognize a wild-type or mutant form of HERV-K env protein. In particular embodiments, antibodies are produced to, but not limited to, HERV-K env proteins, and variants thereof. Specific examples of such antibodies include, but are not limited to, antibodies that are capable of binding to HERV-K env surface protein products from both types of HERV0K env regions, such as, HERV-K10 (HUMERVKA), HERV-K102 (AF164610), HERV-K103 (AF164611), HERV-K104 (AF164612), HERV-K107 (AF164613), HERV-K108 (AF164614), HERV-K109 (AF164615), HERV-K113 (AY037928.1), HERV-K115 (AY037929.1), and HML-2.HOM (AF074086.2).

Various procedures known in the art may be used for the production of polyclonal antibodies to polypeptides, derivatives, or analogs. For the production of antibody, various host animals, including but not limited to rabbits, mice, rats, sheep, goats, etc, can be immunized by injection with the polypeptide or a derivative (e.g., fragment or fusion protein). The polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, KLH, dinitrophenol, and potentially useful human adjuvants such as BCG (bacille Calmette-Guerin) and *Corynebacterium parvum*.

Monoclonal antibodies directed toward a HERV-K env polypeptide, fragment, analog, or derivative thereof, may be prepared by any technique that provides for the production of antibody molecules by continuous cell lines in culture may be used. These include but are not limited to the hybridoma technique originally developed by Kohler and Milstein *Nature* 256:495-497, 1975), as well as the trioma technique, the human B-cell hybridoma technique (Kozbor et al., *Immunology Today* 4:72, 1983; Cote et al., *Proc. Natl. Acad. Sci. U.S.A.* 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985). Accordingly, the present disclosure is also directed to hybridoma cell lines that produce a monoclonal antibody that specifically binds to an antigen (e.g., HERV-K env protein) of a HERV-K$^+$ cancer.

Additionally, "Chimeric antibodies" may be produced (Morrison et al., *J. Bacteriol.* 159:870, 1984; Neuberger et al., *Nature* 312:604-608, 1984; Takeda et al., *Nature* 314:452-454, 1985) by splicing the genes from a non-human antibody molecule specific for a polypeptide together with genes from a human antibody molecule of appropriate biological activity. For example, a chimeric antibody, wherein the antigen-binding site is joined to human Fc region, e.g., IgG1, may be used to promote antibody-dependent mediated cytotoxicity or complement-mediated cytotoxicity. In addition, recombinant techniques known in the art can be used to construct bispecific antibodies wherein one of the binding specificities is that of an antibody of the present disclosure (See, e.g., U.S. Pat. No. 4,474,893).

According to the present disclosure, techniques described for the production of single chain antibodies (U.S. Pat. Nos. 5,476,786; 5,132,405; and 4,946,778) can be adapted to produce HERV-K env protein antigen-specific single chain antibodies. An additional embodiment of the disclosure utilizes the techniques described for the construction of Fab expression libraries (Huse et al., *Science,* 246:1275-1281, 1989) to allow the rapid and easy identification of monoclonal Fab fragments with the desired specificity, or fragment derivatives, or analogs.

Antibody fragments which contain the idiotype of the antibody molecule can also be generated by known techniques. For example, such fragments include, but are not limited to, the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Anti-idiotypic monoclonal antibodies to the antibodies of the present disclosure are also contemplated.

In the production and use of antibodies, screening for or testing with the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc.

In a specific embodiment, antibodies of the present disclosure are conjugated to a secondary component, such as, for example, a small molecule, polypeptide, or polynucleotide. The conjugation may be produced through a chemical modification of the antibody, which conjugates the antibody to the secondary component. The conjugated antibody may allow for targeting of the secondary component, such as, for example, a cytotoxic agent or an anti-tumor agent or an imaging agent, to the site of interest. The secondary component may be of any size or length. Examples of secondary components include, but are not limited to, chemotherapeutic agents, toxins, photo-activated toxins (e.g., dihydropyridine- and omega-conotoxin), radioactive isotopes, mitotic inhibitors, cell-cycle regulators, and anti-microtubule disassembly compounds (e.g., taxol). For example, suitable cytotoxic agents include ricin A chain, abrin A chain, modeccin A chain, gelonin, melphalan, bleomycin, adriamycin, daunomycin, pokeweed antiviral proteins (PAP, PAPII, PAP-S), and granzyme B; and suitable anti-tumor agents include a lymphokine or oncostatin. In a specific embodiment, the secondary component is the toxin Gelonin (rGel), which is a potent inhibitor of cellular protein synthesis. For example, rGel may be fused to anti-HERV-K single-chain antibody (scFv) to produce a novel fusion protein, namely HERV-K scFv/rGel.

Those skilled in the art will realize that there are numerous radioisotopes and chemocytotoxic agents that can be coupled to tumor specific antibodies by well known techniques, and delivered to specifically destroy tumor tissue. See, e.g., U.S. Pat. No. 4,542,225. Examples of imaging and cytotoxic reagents that can be used include $^{125}$I, $^{111}$In, $^{123}$I, $^{99m}$Tc, $^{32}$P, $^{3}$H, and $^{14}$C; fluorescent labels such as fluorescein and rhodamine, and chemiluminescers such as luciferin. The antibody can be labeled with such reagents using techniques known in the art, for example, as described in Wenzel and Meares, *Radioimmunoimaging and Radioimmunotherapy,* Elsevier, N.Y. (1983) and Colcer et al., *Methods Enzymol.,*

121:802-16, 1986, and *Monoclonal Antibodies for Cancer Detection and Therapy*, Baldwin et al. (eds), pp. 303-16 (Academic Press 1985).

Other covalent and non-covalent modifications of the antibodies or antibody fragments of the present disclosure are embraced herein, including agents which are co-administered or administered after the antibody or fragments, to induce growth inhibition or killing of the cells to which the antibody or fragment has previously bound.

In another embodiment of the present disclosure, compositions are provided that comprise the monoclonal antibody, or antibody binding fragment as described herein, bound to a solid support. A solid support for use in the present disclosure will be inert to the reaction conditions for binding. A solid phase support for use in the present disclosure must have reactive groups or activated groups in order to attach the monoclonal antibody or its binding partner thereto. In another embodiment, the solid phase support may be a useful chromatographic support, such as the carbohydrate polymers SEPHAROSE®, SEPHADEX®, or agarose. As used herein, a solid phase support is not limited to a specific type of support. Rather, a large number of supports are available and are known to one of ordinary skill in the art. Solid phase supports include, for example, silica gels, resins, derivatized plastic films, glass beads, cotton, plastic beads, alumina gels, magnetic beads, membranes (including, but not limited to, nitrocellulose, cellulose, nylon, and glass wool), plastic and glass dishes or wells, and the like.

Antisense Constructs

The present disclosure provides antisense nucleic acids (including ribozymes and siRNAs), which may be used to inhibit expression of HERV-K env protein, particularly to suppress any effects on cell proliferation. An "antisense nucleic acid" is a single stranded nucleic acid molecule or oligonucleotide which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes, and RNase-H mediated arrest. Antisense nucleic acid molecules can be encoded by a recombinant gene for expression in a cell (e.g., U.S. Pat. Nos. 5,814,500 and 5,811,234), or alternatively they can be prepared synthetically (e.g., U.S. Pat. No. 5,780,607). Also contemplated are vectors which include these oligonucleotides or antisense constructs, for example, HERV-K1/1267 and K2/1267 lentiviral vectors.

Assay Systems

Any cell assay system that allows for assessing the presence of a HERV-K env protein is contemplated by the present disclosure. The assay may be used to screen for compounds that inhibit or prevent proliferation of a HERV-K$^+$ cancer cell. For example, such assays may be used to identify compounds that interact with a HERV-K env protein to regulate transcription and translation, which can be evaluated by assessing the effects of a test compound. In particular embodiments, changes in expression of unique splice variants of HERV-K may be used to monitor the effectiveness of test compounds that inhibit or prevent HERV-K$^+$ cancer cell proliferation.

Any convenient method permits detection of the expressed product. For example, the disclosure provides Northern blot analysis for detecting HERV-K env mRNA product. The methods comprise, for example, the steps of fractionating total cellular RNA on an agarose gel, transferring RNA to a solid support membrane, and detecting a DNA-RNA complex with a labeled DNA probe, wherein the DNA probe is specific for a particular nucleic acid sequence of HERV-K env under conditions in which a stable complex can form between the DNA probe and RNA components in the sample. Such complexes may be detected by using any suitable means known in the art, wherein the detection of a complex indicates the presence of HERV-K env protein in the sample.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labelled immunoassays, such as ELISA assays.

For in vitro assay systems, test compounds may be added to cell cultures of host cells, prepared by known methods in the art, and the level of HERV-K env protein mRNA and/or protein are measured. Various in vitro systems can be used to analyze the effects of a test compound on HERV-K env protein transcription and translation.

Nucleic Acid Assays

The DNA may be obtained from any cell source. DNA is extracted from the cell source or body fluid using any of the numerous methods that are standard in the art. It will be understood that the particular method used to extract DNA will depend on the nature of the source. Generally, the minimum amount of DNA to be extracted for use in the present disclosure is about 25 pg (corresponding to about 5 cell equivalents of a genome size of $4 \times 10^9$ base pairs). Sequencing methods are well known in the art.

In another alternate embodiment, RNA is isolated from biopsy tissue using standard methods well known to those of ordinary skill in the art such as guanidium thiocyanate-phenol-chloroform extraction (Chomocyznski et al., *Anal. Biochem.*, 162:156, 1987). The isolated RNA is then subjected to coupled reverse transcription and amplification by polymerase chain reaction (RT-PCR) or real time RT-PCR, using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, cDNA obtained from the RNA can be cloned and sequenced to identify a mutation.

In a specific embodiment, the presence or absence of a HERV-K$^+$ cancer in a patient may be determined by evaluating the level of mRNA encoding a HERV-K env polypeptide within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction.

Protein Assays

In an alternate embodiment, biopsy tissue is obtained from a subject. Antibodies that are capable of specifically binding to HERV-K env protein are then contacted with samples of the tissue to determine the presence or absence of a HERV-K env polypeptide specified by the antibody. The antibodies may be polyclonal or monoclonal, preferably monoclonal. Measurement of specific antibody binding to cells may be accomplished by any known method, e.g., quantitative flow cytometry, enzyme-linked or fluorescence-linked immunoassay, Western analysis, and the like.

Immunoassay technology, e.g., as described in U.S. Pat. Nos. 5,747,274 and 5,744,358, and particularly solid phase "chromatographic" format immunoassays, are preferred for detecting proteins in blood or blood fractions.

Diagnostic Tests

The antibodies of the present disclosure are also useful for diagnostic applications, both in vitro and in vivo, for the detection HERV-K env protein and HERV-K$^+$ cancers, for example, breast cancer, ovarian cancer, and melanoma. Therefore, one embodiment of the present disclosure is directed to the detection and/or measurement of HERV-K env protein in a sample and the use of such detection or measurement in the diagnosis, staging, determination of severity, and prognosis in general of the disorder.

In vitro diagnostic methods include immunohistological detection of tumor cells (e.g., on human tissue cells for excised tumor specimens), or serological detection of tumor-associated antigens (e.g., in blood samples or other biological fluids). Immunohistochemical techniques involve staining a biological specimen such as tissue specimen with the antibody of the disclosure and then detecting the presence of antibody complexed to its antigen as an antigen-antibody complex. The formation of such antibody-antigen complexes with the specimen indicates the presence of multiple ovarian, melanoma, or breast cancer cells in the tissue. Detection of the antibody on the specimen can be accomplished using techniques known in the art such as immunoenzymatic techniques, e.g., immunoperoxidase staining technique, or the avidin-biotin technique, or immunofluorescence techniques.

Serologic diagnostic techniques involve the detection and quantification of tumor-associated antigens that have been secreted or "shed" into the serum or other biological fluids of patients thought to be suffering from multiple myeloma. Such antigens can be detected in the body fluids using techniques known in the art such as radioimmunoassay (RIA) or enzyme-linked immunoabsorbant assays (ELISA) wherein antibody reactive with the shed antigen is used to detect the presence of the antigen in a fluid sample.

In a particular embodiment, the diagnostic techniques described can be used to follow the progress of therapy. In a subject undergoing therapeutic treatment that results in an increase or a decrease in the amount of HERV-K env protein bearing cells, the amount of HERV-K env protein bearing cells in a sample may serve as a useful measure for the success or failure of the treatment. Thus, the present disclosure provides a method for monitoring the effect of a therapeutic treatment in a subject which comprises measuring at suitable time intervals the amount of HERV-K env protein expressed in a sample of tissue suspected of containing HERV-K env protein expressing cells. The total amount of HERV-K env protein is compared to a baseline or control value which depending on the disease, and the treatment, may be the amount of HERV-K env protein in a similar sample from a normal subject, from the patient prior to disease onset or during remission of disease, or from the patient prior to the initiation of therapy. One of ordinary skill in the art will readily discern the appropriate baseline value to use in a particular situation without undue experimentation.

Any procedure known in the art for the measurement of analytes can be used in the practice of the measurement of HERV-K env protein in a sample using the compounds of the present disclosure. Such procedures include but are not limited to competitive and non-competitive assay systems using techniques such as radioimmunoassays, enzyme immunoassays (EIA), preferably the enzyme linked immunosorbent assay (ELISA), "sandwich" immunoassays, precipitin reactions, gel diffusion reactions, immunodiffusion assays, agglutination assays, complement-fixation assays, immunoradiometric assays, fluorescent immunoassays, protein A immunoassays, immunoelectrophoresis assays, and the like.

For diagnostic and prognostic applications, a compound of the present disclosure, typically a hybrid molecule as described above will be labeled with a detectable moiety and used to detect HERV-K env protein in a sample. Numerous labels are available which can be preferably grouped into the following categories:

(a) Radioisotopes, such as $^{35}$S, $^{14}$C, $^{125}$I, $^{3}$H, and $^{131}$I. The hybrid molecules can be labeled with the radioisotope using the techniques described in *Current Protocols in Immunology*, Volumes 1 and 2, Coligen et al., Ed., Wiley-Interscience, New York, N.Y., Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the hybrid molecules using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme preferably catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., *Methods for the Preparation of Enzyme-Antibody Conjugates for use in Enzyme Immunoassay*, Methods in Enzym. (ed J. Langone & H. Van Vunakis), Academic press, New York, 73: 147-166, 1981.

In the assays of the present disclosure also my use a solid phase support or carrier to which a hybrid molecule or an antigen is bound. By "solid phase support or carrier" is intended any support capable of binding an antigen or antibodies. Well-known supports, or carriers, include glass, polystyrene, polypropylene, polyethylene, dextran, nylon, amyloses, natural and modified celluloses, polyacrylamides, agaroses, and magnetite. The nature of the carrier can be either soluble to some extent or insoluble for the purposes of the present disclosure. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, and the like.

Kits comprising one or more containers or vials containing components for carrying out the assays of the present disclosure are also within the scope of the disclosure. For instance, such a kit can comprise reagents required for the immunohistochemical analysis of a sample such as a tumor biopsy. Reagents may include one or more binding partners, e.g. a hybrid molecule or an antibody. For histological assays the kit contains the chromogenic substrate as well as a reagent for stopping the enzymatic reaction when color development has occurred. The substrate included in the kit is one appropriate for the enzyme conjugated to one of the hybrid molecules of the present disclosure. These are well-known in the art. The kit can optionally also comprise a standard, e.g., a known amount of purified HERV-K env protein.

Pharmaceutical Compositions

The present disclosure is also directed to pharmaceutical compositions comprising a monoclonal antibody, or binding fragment thereof, which specifically binds to a HERV-K env protein, together with a pharmaceutically-acceptable carrier, excipient, or diluent. Such pharmaceutical compositions may be administered in any suitable manner, including parental, topical, oral, or local (such as aerosol or transdermal) or any combination thereof. Suitable regimens also include an initial administration by intravenous bolus injection followed by repeated doses at one or more intervals.

Pharmaceutical compositions of the compounds of the disclosure are prepared for storage by mixing a peptide ligand containing compound having the desired degree of purity with optional pharmaceutically acceptable carriers, excipients or stabilizers (*Remington's Pharmaceutical Sciences* 18th ed., 1990), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The compositions herein may also contain more than one active compounds as necessary for the particular indication being treated, preferably those with complementary activities that do not adversely affect each other. Alternatively, or in addition, the composition may comprise a cytotoxic agent, cytokine, growth inhibitory agent and/or cardioprotectant. Such molecules are suitably present in combination in amounts that are effective for the purpose intended.

Vaccines may comprise one or more such compounds in combination with an immunostimulant, such as an adjuvant or a liposome (into which the compound is incorporated). An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., *Vaccine Design (the subunit and adjuvant approach)*, Plenum Press (NY, 1995). Pharmaceutical compositions and vaccines within the scope of the present disclosure may also contain other compounds, which may be biologically active or inactive. For example, one or more immunogenic portions of other tumor-associated antigens may be present, either incorporated into a fusion polypeptide or as a separate compound, within the composition or vaccine. Humoral or cellular immune responses against tumor-associated antigen may provide a non-toxic modality to treat cancer. The presence of these antigens is also associated with both specific $CD4^+$ and $CD8^+$ T cell responses. The pharmaceutical compositions and vaccines within the scope of the present disclosure may capitalize on these responses to increase their clinical benefit.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745-1749 (1993), and reviewed by Cohen, *Science* 259:1691-1692 (1993). The uptake of naked DNA may be increased by coating the DNA onto biodegradable beads, which are efficiently transported into the cells.

Any of a variety of immunostimulants may be employed in the vaccines of this disclosure. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFNγ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Therapeutic Methods

The antibodies or binding fragments of the present disclosure may be used without modification, relying on the binding of the antibodies or fragments to the surface antigen(s) of HERV-K+ cancer cells in situ to stimulate an immune attack thereon. Alternatively, the aforementioned method may be carried out using the antibodies or binding fragments to which a cytotoxic agent is bound. Binding of the cytotoxic antibodies, or antibody binding fragments, to the tumor cells inhibits the growth of or kills the cells.

As mentioned above, HERV-K env protein may serve as a tumor-associated antigen which can be used to elicit T cell and B cell responses. In therapeutic applications, this may be used to reduce immune tolerance in, for example, a cancer patient. For example, HERV-K env protein is expressed on both the cell surface and cytoplasm of breast cancer cells, therefore providing a target for both B cells and T cells, and potentially greatly increasing the effectiveness of HERV-K as a tumor-associated antigen.

Autologous DCs pulsed with HERV-K env protein enables autologous professional antigen presenting cells to process and present one or more HERV-K epitopes in association with host human leukocyte antigen (HLA) molecules. Accordingly, in particular embodiments a therapeutic method of the present invention comprises pulsing autologous DCs with HERV-K env protein to treat a HERV-K+ cancer. In general, DCs pulsed with HERV-K env protein induce T cell responses, enhance granzyme B secretion, induce CTL responses, and increase the secretion of several T helper type 1 and 2 cytokines.

In particular embodiments, antibodies specific for HERV-K env protein may be used in conjunction with other expressed HERV antigens. This may be particularly useful for immunotherapy and antibody treatments of diseases in which several different HERVs are expressed. For example, HERV-E in prostate, ERV3, HERV-E and HERV-K in ovarian cancer, and ERV3, HERV-H, and HERV-W in other cancers.

The following examples are offered by way of illustration and not by way of limitation. The disclosures of all citations in the specification are expressly incorporated herein by reference.

EXAMPLES

To facilitate a better understanding of the present disclosure, the following examples of specific embodiments are given, which are provided by way of exemplification and not by way of limitation.

Example 1

Expression of HERV-K Env Surface Proteins in Breast Tumor Epithelial Cells

Figure 1A:
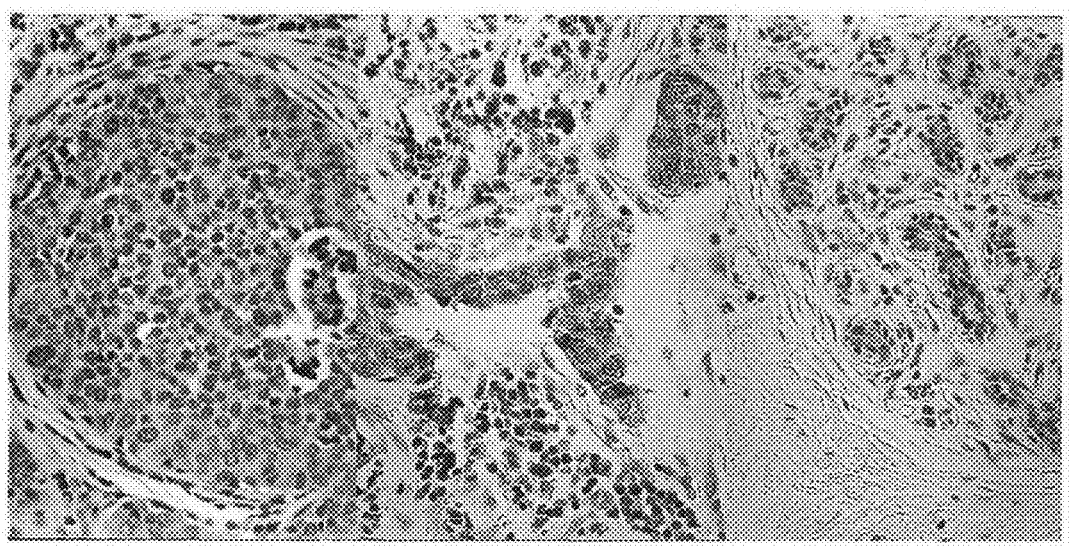

Since protein expression is a prerequisite for generating an immune response, we first confirmed the presence and localization of HERV-K env protein expression in breast cancer tissues by immunohistochemistry using anti-HERV-K-specific antibodies. Expression of HERV-K surface env protein was detected in breast tumor epithelial cells (more than 85% of breast tumor epithelial cells are HERV-K+), but not in normal or uninvolved breast epithelial cells (more than 90% of uninvolved breast epithelial cells are HERV-K−). Representative examples obtained from a breast biopsy are shown in FIG. 1A. FIG. 1A shows the detection of HERV-K env protein expression in tumor epithelial cells obtained from a patient with infiltrating ductal carcinoma. Serial breast tissue sections obtained from a breast cancer patient were assessed by immunohistochemistry using antibody specific against HERV-K env protein. The expression of HERV-K env protein was detected only in tumor epithelial cells, including ductal carcinoma in situ (DCIS) and invasive ductal carcinoma (IDC), but not in uninvolved normal epithelial cells obtained from the same tumor tissue section (Normal epithelial cells) (C).

We also compared the expression of HERV-K env protein in multiple tissue microarray slides under identical staining conditions. The slides were assigned a score of "0" to indicate no expression, "1" to indicate low expression, "2" to indicate intermediate expression, and "3" to indicate strong expression of HERV-K env protein. Examples of the staining patterns observed in tissue-microarray slides are shown in FIG. 1B. In FIG. 1B, Case #1 was a normal mammary lobule from a 43-year-old female; case #4 was a normal mammary lobule from a 50-year-old female; case #16 was a mammary gland tissue from a 61-year-old female; case #8 was a IDC (grade II) from a 45-year-old female; case #17 was a IDC (grade II; 49 year-old female); Case #11 was a intraductal carcinoma (grade II) from a 52-year-old female.

The three normal breast tissue samples shown in FIG. 1B (Case #1, #4, and #16) did not express HERV-K env protein; whereas, the three breast cancer tissues (Case #8, #11, and #17) had intermediate or strong expression of HERV-K env protein. The expression profiles of HERV-K env protein in the tissue microarray are summarized in FIG. 1C. The amount of HERV-K expression increased during the progression from normal to benign to cancerous (Table 1). Fisher's exact test shows expression levels are associated with tumor tissue types (e.g., cancer, benign, and normal) with P value<0.001. Specifically, all the cancer tissues expressed HERV-K protein with the majority (96%) displaying moderate or strong expression. In contrast, 92% of normal and benign tissues had no expression in HERV-K protein.

Figure 1D:
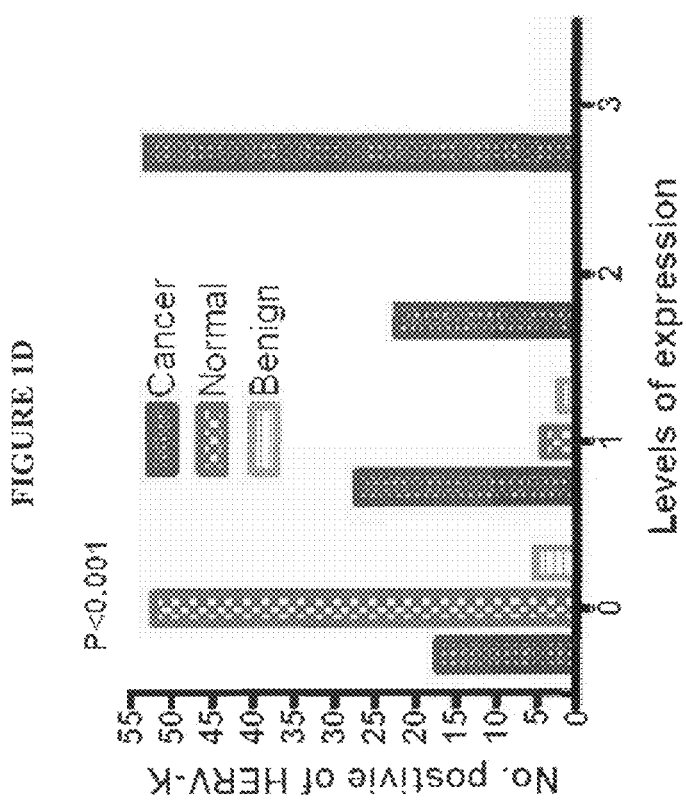

BC biopsies (case #17 and 11) had intermediate or strong expression of HERV-K env protein, whereas the normal breast tissue sample (case 4) did not express HERV-K env protein. The expression profiles of HERV-K env protein in the tissue microarray (N=182) are summarized in FIG. 1D. The amount of HERV-K expression increased during progression from normal (N=56) to benign (ductal epithelial hyperplasia; N=7) to cancerous (N=119), and levels of expression were significantly associated with tumor tissue type (cancer, benign, or normal) (P<0.001; Chi-square test). Overall, 85% of cancer tissues expressed HERV-K protein, with 63% displaying moderate or strong expression, while 92% of normal and benign tissues lacked HERV-K protein expression.

TABLE 1

The frequency of expression of HERV-K env protein in 126-breast-tissue microarrays

|  | Total | Age | 0[1] | 1[2] | 2[3] | 3[4] |
|---|---|---|---|---|---|---|
| Cancer[5] | 70 | 39.29 | 0[6] | 3 (4.29%) | 16 (22.86%) | 51 (72.86%) |
| Normal[7] | 44 | 48.71 | 42 (95.45%) | 2 (4.55%) | | |
| Benign[8] | 7 | 54.8 | 5 (71.43%) | 2 (28.57%) | | |
| P value[9] | | | <0.001 | | | |

[1] "0" no expression
[2] "1" is low expression
[3] "2" is moderate expression
[4] "3" is strong expression
[5] Cancer, infiltrating ductal carcinoma
[6] Values are numbers of samples in a given category, with percentage in parentheses
[7] Normal, normal breast tissues
[8] Benign, benign breast disease tissues
[9] P value calculated using Fisher exact test

TABLE 2

Patient characteristics

| Patient sample number | Age | Diagnosis | Lymph node status | Date of Diagnosis |
|---|---|---|---|---|
| C1 | 51 | IDC[1] | — | December 1992 |
| C2 | 59 | IDC | — | April 2004 |
| C3 | 40 | DCIS + ILC | — | June 2004 |
| C4 | 54 | DCIS + IDC | — | March 2003 |
| C5 | 41 | IDC stage 3 | — | September 2004 |
| C6 | 41 | IDC | — | April 2004 |
| C7 | 49 | IDC | — | January 2000 |
| C8 | 55 | DCIS | — | June 2005 |
| C9 | 32 | IDC | — | October 2003 |
| C10 | 55 | IDC + Colon C | positive | June 2005 |
| C11 | 38 | IDC | positive | June 2005 |
| C12 | 49 | DCIS | — | June 2005 |
| C13 | 42 | DCIS | — | November 2005 |
| C14 | 79 | IDC | — | 1994 |

[1] IDC, Infiltrating ductal carcinoma; DCIS, ductal carcinoma in situ; ILC, invasive lobular carcinoma; Colon C, colon cancer In our study, the expression of both types of HERV-K, including env transcripts (FIG. 1 and Table 5), spliced subgenomic env transcripts (FIG. 2, Table 1 and 2), and full-length HERV-K transcripts (FIG. 3 and Table 5), was detected in the majority of breast cancer tissues. We are the first report that both types of HERV-K env transcripts were capable of being spliced into subgenomic env transcripts, and various splice donor and acceptor sites (Table 5 and 6; FIG. 4) were detected in breast cancer tissues.

TABLE 5 cDNA sequence analysis of a breast cancer sample (invasive ductal carcinoma)

| Transcripts | Primer used | Clone No. | Homology | HERV-K | Accession | nt |
|---|---|---|---|---|---|---|
| Env region (type 1) | K1-5'&K1-3' | 165K10C3 | 100% | K102 | AF164610.1 | 6491-7552 |
|  | K1-5'&K1-3' | 165AC4E | 99% | K102 | AF164610.1 | 6491-7575 |
|  | K1-5'&K1-3' | 165KC2 | 99% | K102 | AF164610.1 | 6471-7575 |
| Env region (type 2) | K2-5'&K1-3' | 165K22EC | 98% | K109 | AF164615.1 | 6660-7501 |
|  | K2-5'&K1-3' | 165K22C11 | 97% | K (I) | AB047209.1 | 7533-8680 |
|  | K2-5'&K1-3' | 165K22C18 | 98% | K (I) | AB047209.1 | 7533-8680 |
|  | K2-5'&K1-3' | 165K22C6 | 98% | K109 | AF164615.1 | 6659-7194 |
| Full-Length (type 1) | P1&P3 | 165P1C2 | 98% | K102 | AF164610.1 | 6072-7690 |
|  | P1&P3 | 165P1C8 | 95% | K (II) | AB047240.1 | 7016-8632 |
| Spliced subgenomic type 1 & type 2 | U5 &Env A | 165U2 | 99% | cORF | X82271.1 | 12-533 |
|  | U5 &Env A | 165U3 | 99% | K102 | AF164610.1 | 833-878/5997-6658 |
|  | U5 &Env A | 165U4 | 99% | cORF | X82271.1 | 12-533 |
|  | U5 &Env A | 165U5 | 99% | K102 | AF164610.1 | 835-878/5997-6658 |
|  | U5 &Env B | 165EBC22 | 99% | K102 | AF164610.1 | 835-1076/8117-8186 |
|  | U5 &Env B | 165EBC23 | 99% | K102 | AF164610.1 | 835-1076/8117-8186 |

TABLE 6

Analysis of splice donor (SD) and acceptor (SA) in breast cancer cell lines and tissues

| Tissue | 165U2[1] | 165U3[2] | 165U4[1] | 165U5[2] | 177U26[1] | 177U29[1] | 178U11[2] | 178U15[2] | 165UB2[2] | 165UB2[3] |
|---|---|---|---|---|---|---|---|---|---|---|
| SD | 1076 | 876 | 1076 | 876 | 961 | 961 | 927 | 927 | 1076 | 1076 |
| SA | 6433 | 5997 | 6433 | 5997 | 6948 | 6948 | 6399 | 6399 | 8117 | 8117 |
| ORF[6] | ✓ | ✓ | ✓ | ✓ | ✓ | ✓ | ✓ | ✓ | ✓ | ✓ |

| Cell lines[9] | T47DU3[2] | T47DU4[2] | MCF7c28[3] | 231U3[3] | ZR75c33[8] | Tera2U2[2] | Tera2U3[2] | Tera1U13[1] | Tera1U15[1] | Tera1UB4[1] |
|---|---|---|---|---|---|---|---|---|---|---|
| SD | 883 | 883 | 2076 | 2076 | 1076 | 1076 | 1076 | 1076 | 1035 | 1076 |
| SA | 6222 | 6222 | 7599 | 7599 | 8410 | 6433 | 6433 | 6433 | 6756 | 6433 |
| 2$^{nd}$ SD[4] | | | | | | 6492 | 6492 | | | |
| 2$^{nd}$ SA[5] | | | | | | 6946 | 6794 | | | |
| ORF[6] | ✓ | ✓ | N/A[7] | N/A | N/A | X | X | ✓ | X | ✓ |

[1]Type 2 HERV-K, nt numbered according to HML-2.HOM sequence (AF074086.2).
[2]Type 1 HERV-K, nt numbered according to HERV-K102 sequence (AF164610).
[3]Type 1 HERV-K, nt numbered according to HERV-K (II) sequence (AB047240).
[4]second splice donor.
[5]second splice acceptor.
[6]ORF: Open reading frame. ✓ means ORF without stop codon, and X means ORF with one or more than one stop codon.
[7]N/A: could not be determined.
[8]Type 2 HERV-K, nt numbered according to HERV-K113 sequence (AY037928.1).
[9]231: MDA-MB-231; ZR75: ZR75-1.

Example 2

Detection of Anti-HERV Antibodies in Sera of Breast Cancer Patients

Figure 2A:
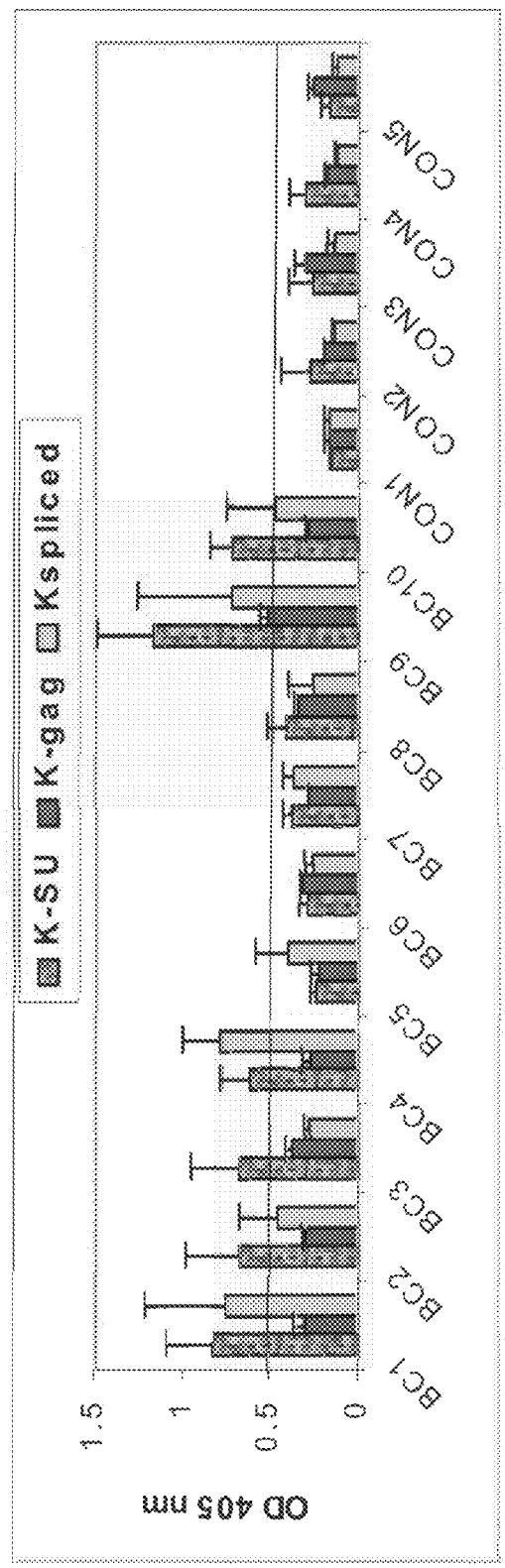
Figure 2B:
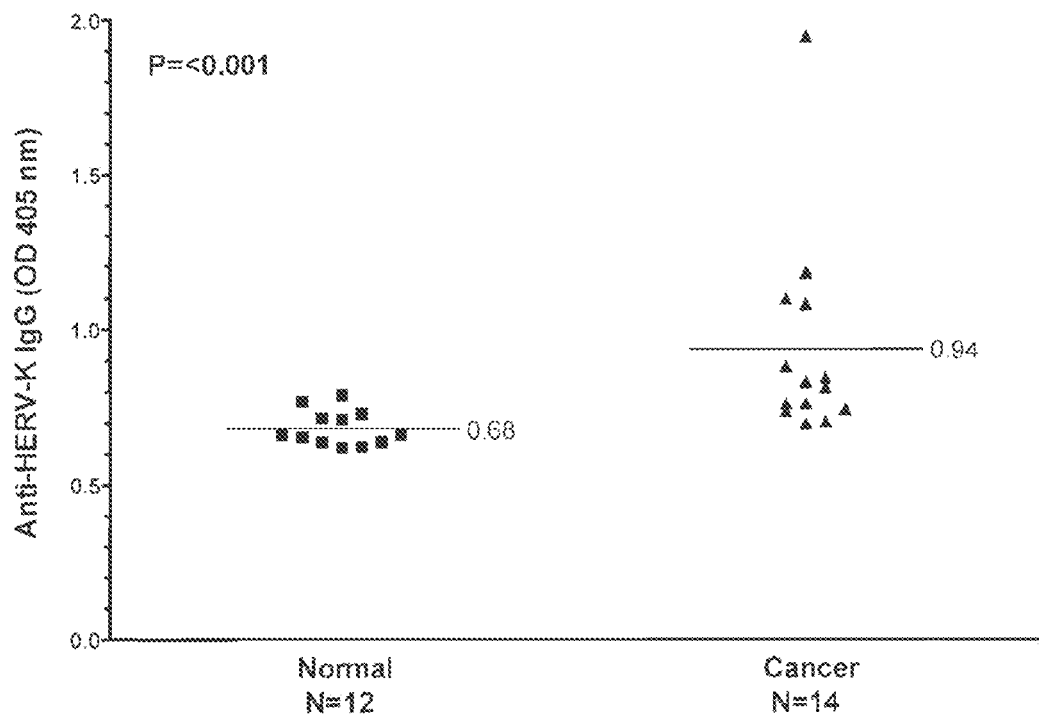

We assayed for anti-HERV antibodies in sera from patients with various cancers including breast cancer. ELISA analysis was used to determine the binding affinity and specificity of antibodies in the sera obtained from breast cancer patients (N=48) and normal female controls (N=50). The cutoff value was 0.5 for optical density at 405 nm. Approximately 50% of the 48 breast cancer patient samples were positive for antibodies against HERV-K env surface protein, 15% were positive for antibodies against HERV-K gag protein, and 35% were positive for antibodies against a splice variant of the env protein. In contrast, no anti-HERV-K antibodies were detected in the control samples. ELISA data obtained from 10 breast cancer and 5 control samples are shown in FIG. 2A. The presence of anti-HERV-K env protein antibodies, including anti-HERV-K surface env protein antibody (K-SU), anti-HERV-K gag protein (K-gag), and anti-HERV-K spliced env protein (Kspliced), provides indirect evidence of the presence of HERV-K env proteins in human breast cancer. We further tested for detection of potential serum IgG antibody against HERV-K in cancer patients or control subjects by ELISA. The proportion of seropositive patients whose tumors were HERV-K positive was higher than the proportion in control subjects without cancer (P=0.03; FIG. 2B).

Example 3

Phenotyping of Immature and Mature Human DCs

Figure 3A:
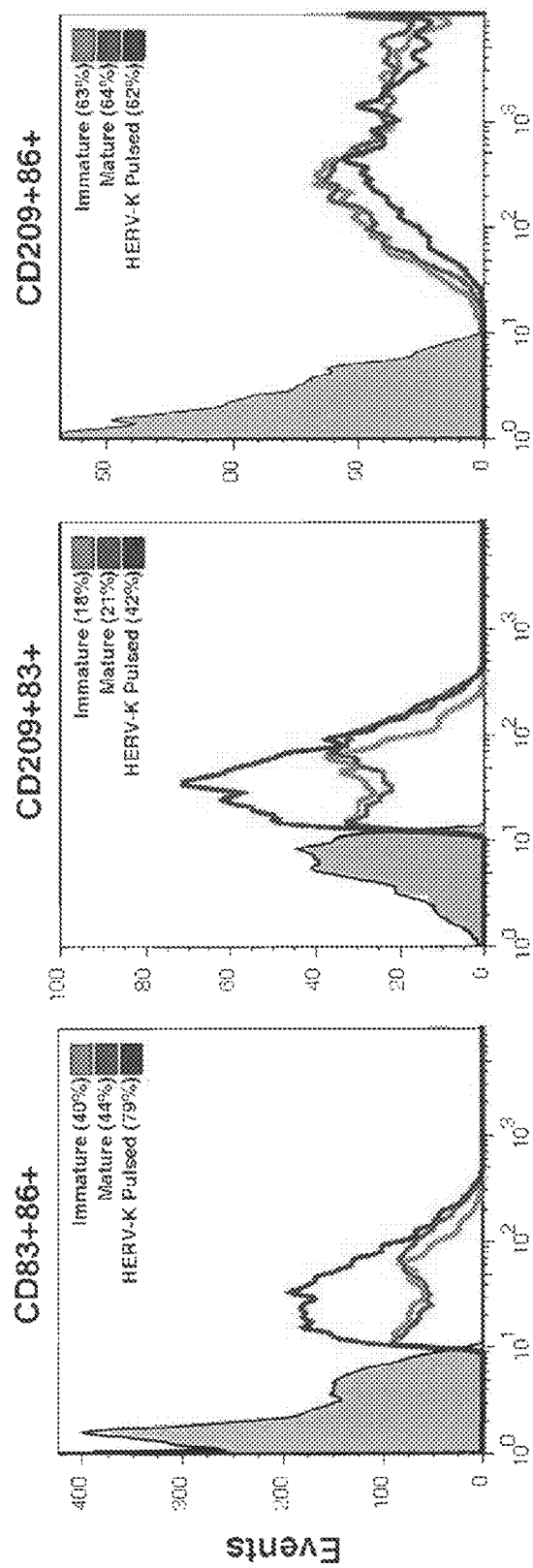

DCs were generated from PBMCs cultured in medium containing the cytokines GM-CSF and IL-4. Immature DCs were exposed to TNF-α overnight for maturation, with or without prior pulsing with HERV-K proteins. Characteristically, HERV-K-pulsed mature DCs showed enhanced CD83 expression, relative to immature DCs and mature DCs treated with TNF-α only. Expression of CD83+/CD209+ and CD83+/CD86+ was also higher in HERV-K pulsed mature DCs than in immature DCs and mature DCs (FIG. 3A).

We determined that HERV-K env protein is expressed in HERV-K pulsed DCs, by flow cytometry using anti-HERV-K antibody or anti-RGS mAb. More than 50% or 70% of DCs pulsed with HERV-K env surface protein became HERV-K antigen positive cells as assessed using anti-HERV-K or anti-RGS mAb, respectively (FIG. 3B).

Example 4

Surface Expression of HERV-K Env Protein on Breast Cancer Cells Lines

Figure 3C:
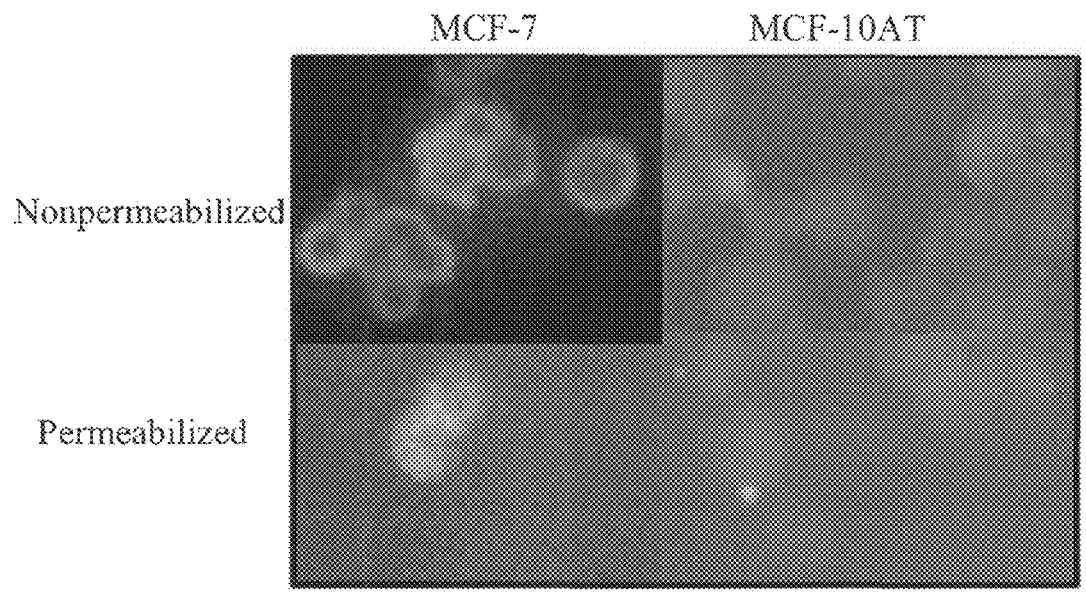

No report to date has provided direct evidence of the surface expression of HERV-K env protein in any non-transfected cell line. We therefore examined the expression of this protein on the surface and in the cytoplasm of breast cancer cells by flow cytometric analysis and fluorescence microscopy of cells stained with antibody against HERV-K env protein. Surface expression of HERV-K env protein was observed on nonpermeabilized malignant MCF-7 (50% positive surface expression) and T47D (25%) breast cancer cell lines, and cytoplasmic expression (95% of MCF-7 and 95% of T47D cells) was observed in cells permeabilized by Triton X-100 flow cytometry. In contrast, no surface or cytoplasmic expression of HERV-K was observed in benign MCF10A or premalignant MCF10AT breast epithelial cells (1% to 3% surface expression and 3% to 5% cytoplasmic expression, respectively). The observation was further confirmed by fluorescence microscopy (FIG. 3C).

Using immunofluorescence microscopy, we found HERV-K env protein expression on the surface of non-permeabilized BC cell lines such as MCF-7, T47D, MDA-MB-231 BC cells as well as in the cytoplasm following permeabilization with Triton X-100 (FIG. 16A; MDA-MB-231 cells). However, HERV-K env protein expression was not observed in benign MCF10A or premalignant MCF10AT breast epithelial cells under these conditions (data not shown). Surface expression of HERV-K env protein on MCF-7 (FIG. 16B), but not on MCF-10A cells (FIG. 16C), was detected using confocal microscopy and the percentage of surface expression in the cells was determined by flow cytometric analysis (FIG. 16D). HERV-K env protein was detected in several BC cell lines, but not in MCF-10A and MCF-10AT non-cancer breast cells (FIG. 16E) by Western blot using anti-K-SU antibody.

Example 5

T-Cell Proliferation Assay

Figure 4A:
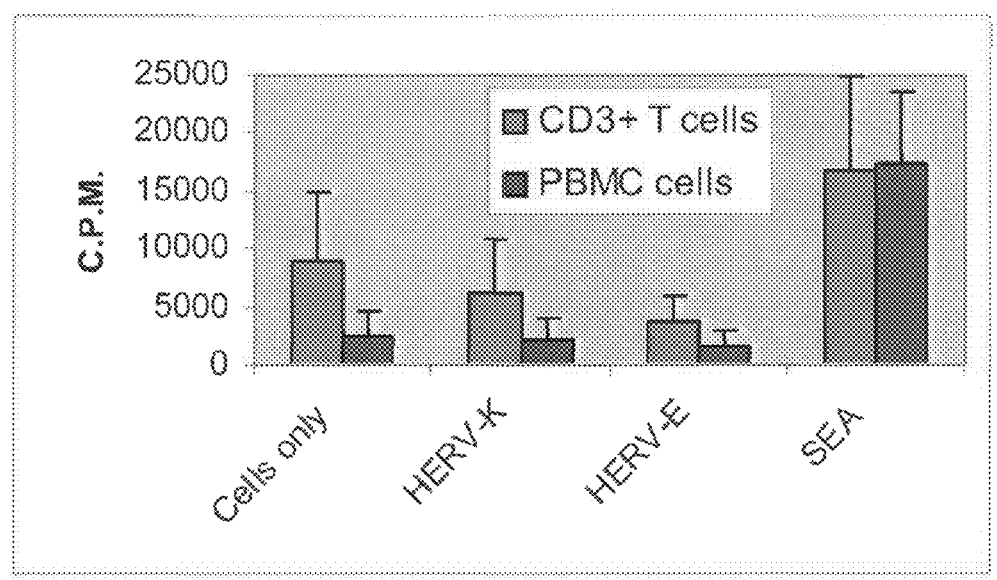

Non-IVS PBMCs or CD3+ cells obtained from normal donors (N=7) were stimulated with HERV-K or HERV-E env surface protein and tested for activation of human T cell proliferation. We found that HERV-K or HERV-E env surface protein does not stimulate human T cell proliferation in a manner similar to the bone fide superantigen *Staphylococcal enterotoxin* A (SEA; FIG. 4A).

Figure 4B:
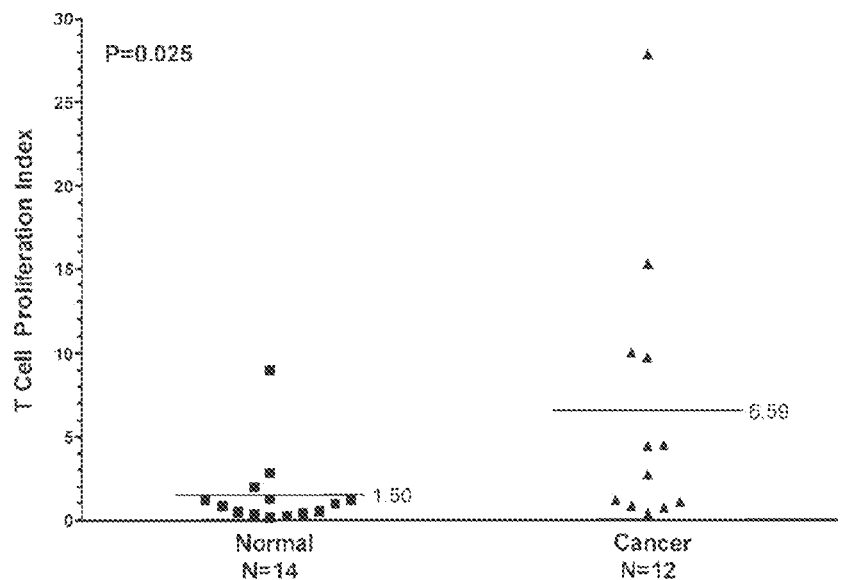
Figure 4C:
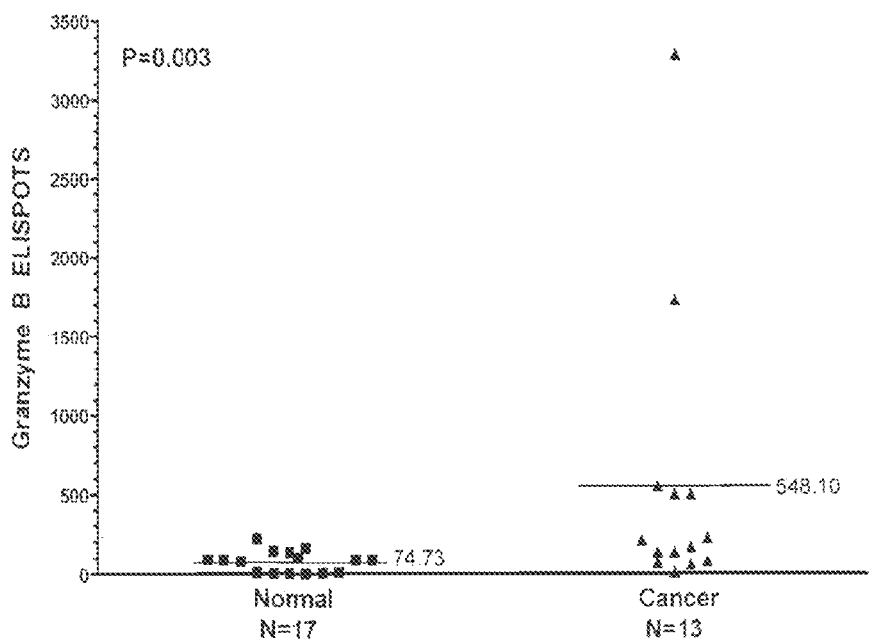

We stimulated PBMCs with autologous DCs pulsed with HERV-K env antigen, matured the PBMCs to produce antigen specific 1-week or 3-week IVS and assessed the ability of the PBMCs to stimulate T-cell proliferation. The fold-increase in proliferation of HERV-K specific T cells was significantly greater in IVS cells from cancer patients than in those from normal female control subjects, compared with autologous PBMCs (FIG. 4B).

Example 6

Granzyme B ELISPOT Assays with IVS or PBMCs from Cancer Patients

PBMCs (stimulated with unpulsed-DCs), 1-week IVS cells, or 3-week IVS cells obtained from cancer patients and normal donors were used in ELISPOT assays to quantitate cells producing granzyme B (GrB), an important effector molecule of CTL and natural killer cells. GrB spots detected in 1-week or 3-week IVS were higher in cancer patients than in normal controls (FIG. 4C) (1-week IVS P=0.004; 3-week IVS P=0.003). Very few or no GrB spots were detected from PBMCs stimulated with unpulsed DCs obtained from normal donors or cancer patients.

Example 7

HERV-K Specific CTL Cytotoxic Responses

Figure 4D:
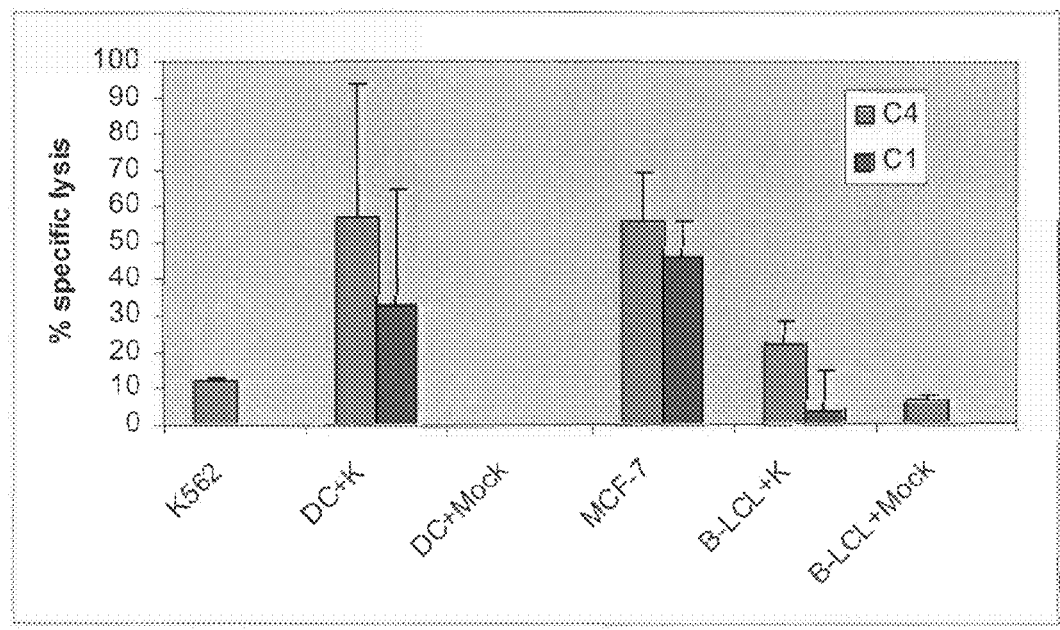

51Cr release cytotoxicity assay was used to assess the immunogenicity of HERV-K from IVS cells obtained from control and cancer samples. HERV-K specific cytotoxicity resulted in 20% to 60% lysis of HERV-K expressing cells in the cancer patients only, with nonspecific cytotoxic activity below 15% (FIG. 4D). Natural killer (NK) cell activity was assessed by cytotoxicity against K562 cells, which are susceptible to NK cells. IVS cells stimulated with HERV-K-pulsed DCs were capable of killing HERV-K-loaded autologous DCs or B-LCL cells, but not DCs or B-LCL cells loaded with an irrelevant mock protein (human LMP2A, purified from the same expression vector). HERV-K-specific IVS cells from cancer patients that were stimulated with HERV-K-pulsed DCs did not increase lysis of K562 cells; whereas HERV-K-specific IVS cells obtained from normal donors did increase cytotoxicity toward K562 cells (data not shown). CTLs obtained from two breast cancer patients showed strong lytic activity against the HERV-K positive breast cancer cell line MCF-7. The higher cytotoxicity against MCF-7, relative to HERV-K-loaded DCs or B-LCL cells, is probably due to the higher expression of the naturally processed HERV-K proteins at the surface of MCF-7 cells relative to DCs or B-LCL cells (lower transfection efficiency), as assessed by flow cytometry with anti-HERV-K antibody (data not shown).

Thus, HERV-K env protein does not suppress NK cell responses, and the lack of suppression would provide a potential mechanism for breaking tolerance by the host immune system.

Example 8

Detection of Cytokines in HERV-K Specific IVS Cells

Figure 5A:
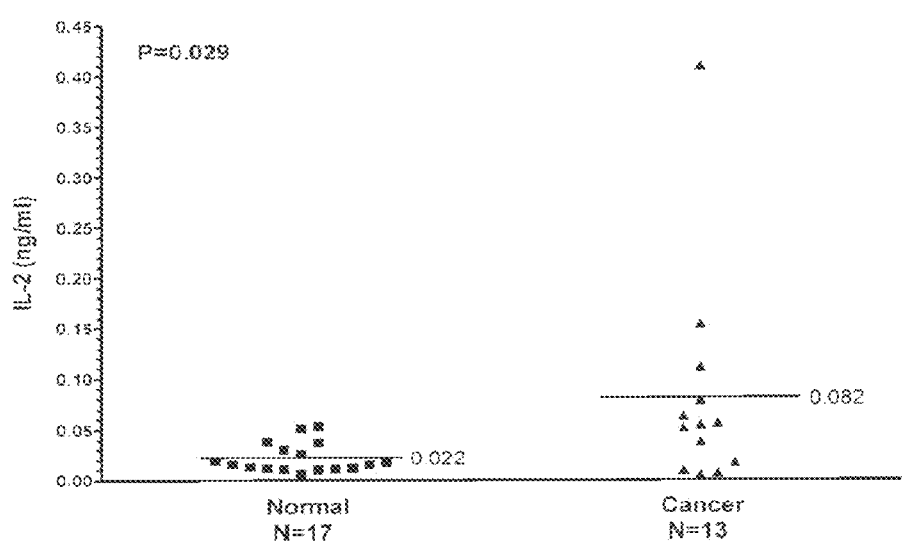
FIG. 5B is a graph of cytokine secretion by IVS cells obtained from breast cancer patients and normal control subjects showing the mean values of IFN-γ secretion from cancer patients (535 pg/ml) and normal subjects (144 pg/ml). IFN-γ secretion is significantly higher (P=0.028) in IVS cells from breast cancer patients than in IVS from normal female donors.
FIG. 5C is a graph of cytokine secretion by IVS cells obtained from breast cancer patients and normal control subjects showing the mean values of IL-6 secretion from breast cancer patients (7,448 pg/ml) and normal subjects (1,306 pg/ml). IL-6 secretion was higher (P=0.038) in IVS cells from breast cancer patients (Cancer) than in IVS from normal female donors (Normal).
FIG. 5D is a graph of cytokine secretion by IVS cells obtained from breast cancer patients and normal control subjects showing the mean values of IL-8 secretion from breast cancer patients (16,360 pg/ml) and normal subjects (8,793pg/ml). IL-8 secretion was higher (P=0.028) in IVS cells from breast cancer patients (Cancer) than in IVS from normal female donors (Normal).
Figure 5B:
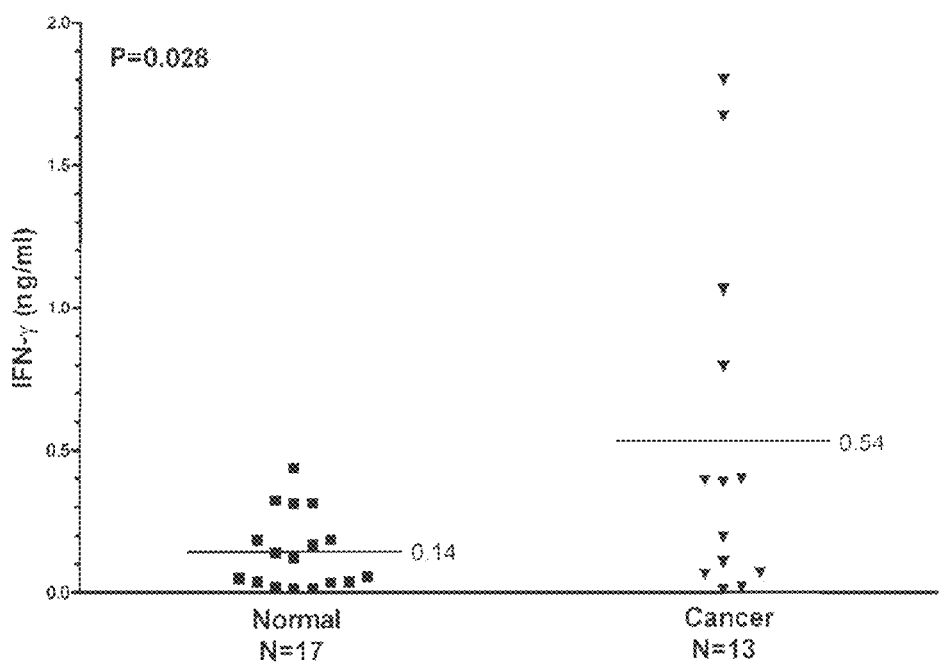
Figure 5C:
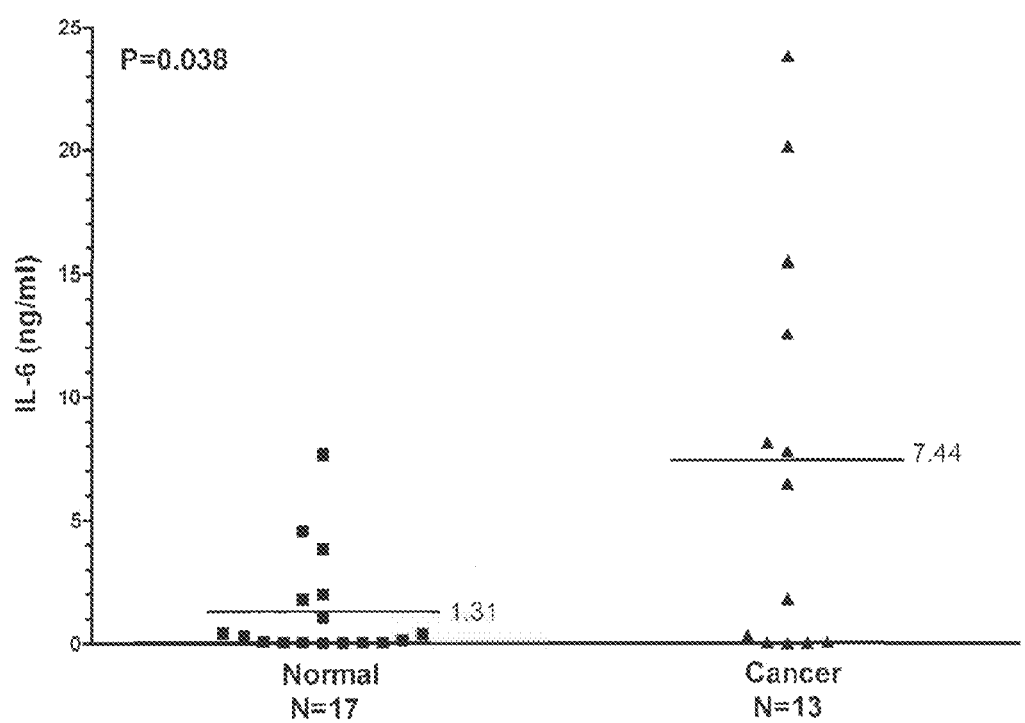
Figure 5D:
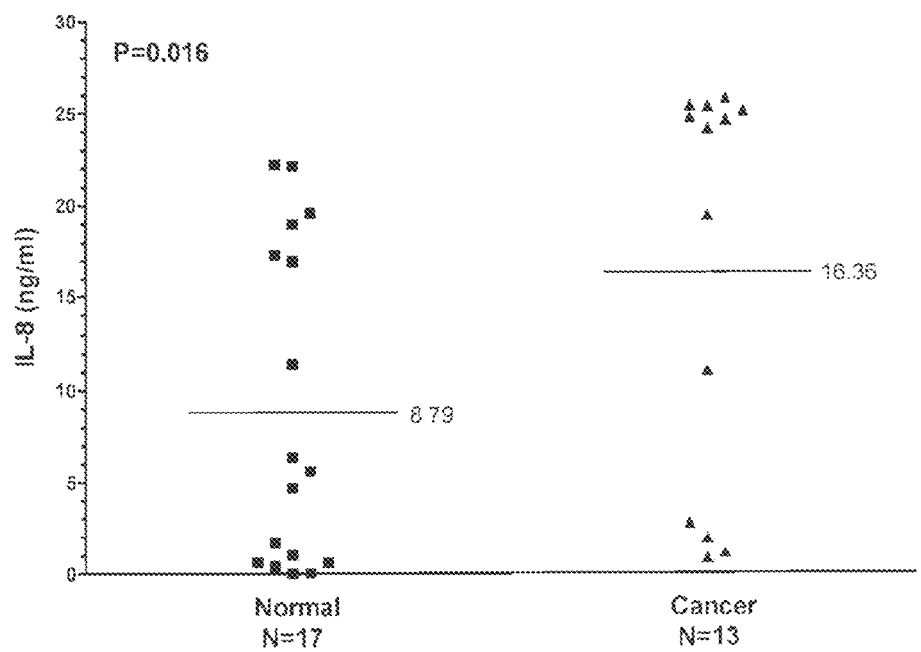

Cytokine bead array assays for human cytokines were used to detect the secretion of cytokines by PBMCs treated with unpulsed DCs or IVS cells (PBMCs stimulated with DCs pulsed with HERV-K env surface proteins). IL-2 secretion (P=0.001) and IFN-γ secretion (P<0.001) were markedly increased in IVS obtained from cancer patients, when compared to the patients' PBMCs (N=12). IL-2 secretion (P=0.021) and IFN-γ secretion (P=0.061) were greater in IVS than in PBMCs obtained from normal control subjects (N=11), but the increase was not as great as in cancer patients. IL-2 (P=0.029; FIG. 5A), IFN-γ (p=0.028; FIG. 5B), IL-6 (P=0.038; FIG. 5C), and IL-8 (P=0.016; FIG. 5D) secretion were higher in HERV-K-specific IVS cells obtained from cancer patients, than in IVS cells from control subjects. TNF-α secretion was non-significantly increased (P=0.063) in HERV-K-specific IVS cells obtained from cancer patients, relative to IVS cells from control subjects. IL-1β secretion or IL-4 secretion was unchanged in HERV-K-specific IVS cells obtained from cancer patients, in comparison to IVS cells from control subjects.

Example 9

Intracellular Cytokine Expression by T Cells Specific for HERV-K Human Isotype Control To evaluate whether TNF-α, IL-2, or IFN-γ expression are increased in HERV-K-stimulated IVS cells, intracellular cytokine expression was assessed at the single-cell level. PBMCs treated with unpulsed DCs, or IVS cells obtained from the same PBMCs stimulated with HERV-K pulsed DCs, were left unactivated as negative controls, were nonspecifically activated with a leukocyte activation cocktail which included PMA, ionomycin and brefeldin A (positive controls; non-specific), or were activated with HERV-K plus brefeldin A (HERV-K-stimulated). Intracellular expression of TNF-α, IL-2, and IFN-γ by CD3+ T cells was analyzed by four-color flow cytometry. As shown in FIG. 6, activated IVS cells had higher intracellular TNF-α and IFN-γ, but not IL-2, than their autologous unactivated PBMCs. Similar results were consistently obtained in several similar experiments. APC-labeled anti-IgG2a or anti-IgG1 antibodies, and a PE-labeled isotype control cocktail did not stain either the activated or unactivated cells (data not shown).

Cytokine production after HERV-K antigen stimulation. Human cytokine bead array assays were used to detect the secretion of T-helper 1 (Th1) and Th2 in PBMC or IVS obtained from PBMC stimulated with DC pulsed with K-SU protein. The secretion of each cytokine was induced significantly by antigen-pulsed DC over secretion levels of unpulsed control DC (data not shown). We compared cytokine secretion in PBMC and IVS, in both BC patients and normal donors. Secretion of a number of cytokines was altered after HERV-K stimulation. Secretion of the Th1 cytokines IL-2 and IFN-γ was significantly enhanced in BC patient K-SU-stimulated IVS cells, in comparison to K-SU-stimulated PBMC. IFN-γ secretion was significantly lower in BC patients than in normal donors before HERV-K env stimulation. A summary of IL-2 and IFN-γ secretion is presented in FIGS. 6C and 6D. Interestingly, elevated IP10 secretion was also observed in cancer patients (data not shown). Other cytokines including IL-6 and 11-8 were increased in BC patients (data not shown). We also analyzed cytokine production ex vivo from freshly-isolated PBMC from BC patients and normal healthy donors by intracellular cytokine staining (ICS). PBMC were activated with HERV-K-pulsed or unpulsed DC for 6 h and fixed and subjected to ICS. As shown in FIGS. 6A and 6B, a markedly increased frequency of TNF-α, IL-2 and IFN-γ-secreting $CD8^+$ T cells were detected in the HERV-K-stimulated cultures.

Thus, T cells isolated from BC patients exhibit HERV-K-specific proliferation, pro-inflammatory cytokine secretion, and cytotoxic activity against HERV-K target cells not found in normal healthy controls.

Materials and Methods for Examples 1-9

Synthesis of HERV-K Env Fusion Proteins and Antibodies. HERV-K env surface cDNAs obtained from breast cancer tissue, as described in Wang-Johanning F, et al. Clin Cancer Res 7(6):1553-60 (2001), were cloned into the corresponding enzyme-digested QIA expression vector (pQE30; Qiagen; Valencia, Calif.), which contains a 6-His tag at the N-terminus. Colonies positive for HERV-K env expression were further identified by restriction enzyme analysis and characterized by sequencing with vector-specific primers to confirm that the clones produced the desired HERV-K env proteins. The colonies confirmed by sequencing were induced with isopropyl-B-D-thiogalactopyranoside and the HERV-K env fusion proteins were purified by affinity chromatography using Ni-nitrilotriacetic acid (Ni-NTA; Qiagen) agarose for the pQE vector. HERV-E env surface cDNAs obtained from prostate cancer tissue, as described in Wang-Johanning F, et al. Cancer 98(1):187-97 (2003), were cloned into pQE30 to produce HERV-E env surface protein. The purified HERV env fusion proteins were used to immunize rabbits or mice for the production of polyclonal or monoclonal anti-HERV-K env antibodies, respectively, using standard techniques. The antibodies were further purified using Protein G Sepharose 4 Fast Flow (Amersham Pharmacia Biosciences; Piscataway, N.J.) and tested for specificity and sensitivity against various HERV env proteins by enzyme-linked immunosorbent assay (ELISA) and/or immunoblot analysis.

HERV-K Expression in Breast Cancer Cell Lines, Breast Cancer Patient Tissues, and Breast Tissue Microarrays. The human breast cell lines MCF-7, T47D, MCF-10A and MCF-10AT, as well as the human chronic myelogenous leukemia cell line K562 and Epstein-Ban virus (EBV)-transformed tamarin cells B95-8, were obtained from the American Type Culture Collection (Rockville, Md.) and were cultured in the media recommended by the manufacturer. MCF10A cells were gifts obtained from Dr. Robert Pauley, and were cultured in his recommended media. For immunohistochemistry, formalin-fixed, paraffin-embedded tissues were used. Two tissue microarrays, each with 63 breast tissue samples from normal women and women with benign, malignant, or other breast diseases, were obtained from US Biomax, Inc (Rockville, Md.). Human breast tissues and peripheral blood mononuclear cells from breast cancer patients or normal female controls (Table 7) were obtained from The University of Alabama at Birmingham and The MD Anderson Cancer Center with approval from both of the Institutional Review Boards.

Immunohistochemical Analysis of Multiple Tissue Microarray Slides. Immunohistochemistry was performed on tissue microarray slides using an LV-1 Autostainer universal staining system (DAKO; Carpinteria, Calif.) compatible with currently available reagents for the staining of paraffin-embedded and frozen tissue sections. These multiple tissue microarray slides allowed us to compare the expression of HERV-K env surface (SU) protein in multiple tissues under identical staining conditions. Slides were incubated for 5 minutes with 3% $H2O2$, for 10 minutes with horse serum, and for 30 minutes with anti-HERV-K env antibodies (1:750 dilution). This was followed by a 15-minute incubation with horseradish peroxidase (HRP)-conjugated anti-rabbit or anti-mouse immunoglobulin G (IgG) secondary antibody (DAKO), a 5-minute incubation with diaminobenzidine for color development, and a 5-minute incubation with the counterstain hematoxylin.

ELISA. ELISA assays were used to detect various anti-HERV antibodies in human sera, as described previously in Wang-Johanning F, et al. Cancer Res 58(9):1893-900 (1998). Briefly, a 96-well ELISA plate was coated with various HERV fusion proteins (10 μg per ml, 100 μl per well) in phosphate-buffered saline (PBS) and incubated overnight at 4° C. The plate was then blocked for 1 hour with 5% nonfat dry milk (Sigma; St. Louis, Mo.) and 3% bovine serum albumin at room temperature. Human sera (diluted 1:200 with PBS) were added to the coated wells, and the plate was incubated overnight at 4° C. After washing six times with PBS-T (0.5 ml of Tween 20 in 1000 ml of PBS), 100 μl of HRP-conjugated anti-human IgG antibody (1:2000 dilution, Sigma) was added to each well of the plate to detect the serum antibody, followed by incubation for 1 hour at room temperature. The plate was washed again with PBS-T, and color was developed using 2,2'-Azino-bis(3-ethylbenzothiazoline-6-sulfonic acid (ABTS; Sigma). After 10 to 30 minutes, the absorbance of the plate wells was measured on a microplate reader at 405 nm. Anti-human IgG antibody was used for negative controls and anti-RGS monoclonal antibody (mAb) was used for positive controls (Qiagen Inc.; used to detect 6-His protein produced from pQE30 vector). The cutoff value for a negative reaction is 0.5 OD at 405 nm. For determining anti-HERV-K antibody isotype, anti-human IgG antibody (5 μg per ml) was coated on the plate, human plasma samples (1:100 dilution; 100 μl per well) were added, followed by incubation for 1 hour at room temperature. HERV-K surface env fusion protein (10 μg per ml) was then added, followed by anti-RGS mAb (1:1,000 dilution), and then HRP conjugated-anti-mouse IgG (1:2,000 dilution). Additionally, all samples were tested on two wells not coated with HERV-K fusion protein or anti-IgG mAb to define non-specific reactivity. The final ELISA value was calculated by subtracting the non-specific reactivity mean absorbance from the sample triplicate mean absorbance. To control for inter-assay variation, positive IgG controls selected from a previous study were included in each plate and tested as described. All ELISA analyses were performed at least three times for each serum sample. The means of the threshold values were used for the final analysis, as described in Wang-Johanning F, et al. Cancer Res 58(9):1893-900 (1998).

Preparation of DCs from Human PBMC. DCs were generated from adherent or CD14-positive PBMCs isolated by magnetic cell sorting with CD14 MicroBeads (Miltenyi Biotec; Auburn, Calif.). The isolated cells were incubated in AIM-V medium (Gibco Life Technologies; Gaithersburg, Md.) with 10% human AB serum (Gemini Bioproducts; Woodland, Calif.) in the presence of interleukin (IL)-4 (1000 IU/ml; R&D Systems; Minneapolis, Minn.) and granulocyte macrophage colony-stimulating factor (GM-CSF; 1000 IU/ml; R&D Systems; Minneapolis, Minn.) for 6 days. Culture media were changed after 3 days. Following the 6-day incubation period, the immature DCs were harvested and transfected with HERV-K env surface protein or control proteins by lipofection with N-[1-(2,3-Dioleoyloxy)propyl]-N,N,N-trimethylammonium methyl-sulfate (DOTAP). After a four-hour incubation, cells were replenished with new media containing the pro-inflammatory cytokine tumor necrosis factor (TNF)-α (R&D Systems), and incubated for 18 additional hours to obtain mature DCs. The mature DCs were harvested, washed once and mixed with autologous PBMCs for IVS or for assays. CD3+ cells were separated from PBMCs by magnetic cell sorting with an autoMACS separator (Miltenyi Biotech) using human CD3 beads according to the manufacturer's instructions. B95-8 culture supernatants containing the transforming strain of Epstein-Ban virus EBV were used to establish the B lymphoblastoid cell lines (B-LCL). B-LCL express type 3 latency genes (EBNA-2 and LMP-1) and were maintained in RPMI medium 1640 with 10% FCS.

Phenotyping of Immature and Mature DCs and Determination of Surface Expression of HERV-K Surface Protein. Immature or mature DCs with or without prior pulsing with HERV-K env protein were phenotyped on day 7 using a multicolor kit with CD86PE/CD209 PerCP-Cy5.5/CD83 APC kit (BD Biosciences; San Jose, Calif.). The DCs were stained with monoclonal antibodies for 30 minutes at room temperature and analyzed by flow cytometry. To confirm that the env-pulsed DCs had become HERV-K specialized antigen-presenting cells, expression of HERV-K env surface protein in pulsed DCs was determined by flow cytometry using anti-HERV-K env antibody (1:200 dilution). As a positive control, anti-RGS mAb (1:200; Qiagen) was used to detect His-target protein produced from the pQE30 vector. The DCs were incubated with the primary antibodies at 4° C. for 30 minutes and then with anti-IgG-FITC secondary mAb (1:1000 dilution) at 4° C. for 15 minutes. DCs stained with only secondary antibody served as negative controls. After being washed with PBS, the cells were fixed with 3% paraformaldehyde in PBS. Samples were analyzed on a BD FACSCalibur™ system (BD Biosciences). After confirming the specificity of anti-HERV-K antibody to HERV-K env protein, cultured breast cells were incubated with the antibody as described above. For staining of permeabilized cells, the cells were treated with 0.1% Triton X-100 in PBS, and then incubated with primary and secondary antibodies. Controls samples were incubated with anti-IgG-FITC secondary antibody.

In Vitro Sensitization. DCs were pulsed with antigen and matured as described above. Autologous PBMCs ($1 \times 10^6$ cells/ml) were added to the loaded DCs at a DC:PBMC ratio of 1:20. Cells were incubated for 6-7 days in AIM-V medium (Gibco) containing 10% human AB serum (Gemini Bioproducts), 1000 U/ml penicillin (Gibco), 1000 µg/ml streptomycin (Gibco), and 10 IU/ml IL-2 (eBioscience; San Diego, Calif.) to produce 1-week IVS cells. The 1-week IVS cells were restimulated on day 14 with autologous DCs previously pulsed with antigen to produce 3-week IVS cells. The enriched IVS cells were then assessed with proliferation or Enzyme-Linked ImmunoSPOT (ELISPOT) assays. As unstimulated controls for WS, PBMCs were cultured under the same conditions but with nonpulsed DCs.

T-Cell Proliferation Assay. T cell proliferation was evaluated for PBMC and IVS cells. Autologous monocyte-derived DCs were loaded, matured, and added to PBMCs at a DC:PBMC ratio of 1:20. These cultures were set up in triplicate wells of 96-well plates at 100,000 cells/well in RPMI medium containing 10% (v/v) human AB serum. A new set of DCs was pulsed on day 6 with experimental or control antigens, matured and added either to the IVS cultures (T cell proliferation assay with IVS) or to fresh PBMCs (assay without IVS). The cultures were incubated for 5 days at 37° C. Methyl-[3H]thymidine (ICN Biomedicals; Costa Mesa, Calif.) was added and the cultures were incubated for another 18 hours. The cells were then collected and the incorporation of [$^3$H]thymidine into cells was measured as an indicator of cell proliferation using a liquid scintillation β counter. Results were expressed as counts per minute (CPM) per $1 \times 10^5$ splenocytes.

ELISPOT Assays. A granzyme B ELISPOT assay to detect and quantitative cytokine-secreting cells in response to antigen was performed using commercial kits (Biosource International; Camarillo Calif.), following the manufacturer's recommendations. The spots were evaluated using an automated ELISPOT reader system (Carl Zeiss; Thornwood, N.Y.) with KS ELISPOT Software 4.5+ (ZellNet Consulting). Only spots with fuzzy or diffuse borders were scored as positive. Net frequencies of spot-forming cells were calculated.

Cytotoxic T-Lymphocyte Release Assay. To determine whether HERV-K env surface proteins are potential targets for a breast tumor vaccine, CTL assays were performed in round-bottomed 96-well plates using a standard 4-hour 51Cr-release assay, as described in Dolbier C L, et al. J Behav Med 24(3):219-29 (2001). Five thousand 51Cr-labeled target cells were added to serial dilutions of effector cells in effector to target cell ratios (E/T) up to 20:1. K562 cells were used as target cells in the same experiment to detect natural killer cell activity. After a 4-hour incubation at 37° C., 25 µl of the supernatants were collected and radioactivity was quantitated using a gamma counter. To block cytotoxicity, effector cells were pre-incubated for 30 minutes at room temperature with an anti-human CD3 mAb (10 µg/ml; Ortho Pharmaceutical Corp; Raritan, N.J.).

Cytokine Bead Array Analysis. PBMCs or IVS cells from cancer patients or normal control subjects were cultured with HERV-K env protein (10 µg/ml), human papillomavirus 16 E6 protein (10 µg/ml; purified from the same expression vector as control protein), concanavalin A (10 µg/ml; used as control protein), or no protein for 48 hours at 37° C. in a 5% $CO_2$ atmosphere, under the previously described conditions for evaluating T cell proliferation. After incubation, the supernatants were collected and stored at −20° C. for cytokine bead array analysis using a LINCOplex multiplex immunoassay-based protein array system (LINCO Research; St. Charles, Mo.), which contains microspheres conjugated with mAbs specific for target proteins. Triplicate samples of cell culture supernatants (25 µl) were assayed for the human cytokines IL-1β, IL-2, IL-4, IL-6, IL-8, TNF-α, and interferon (IFN)-γ. Antibody-coupled beads were incubated with the supernatants (antigen) overnight at 4° C., and were subsequently incubated with a biotinylated detection antibody at room temperature for 1 hour. Incubation with streptavidin-phycoerythrin was performed at room temperature for 30 minutes. Data were reported as the mean±standard deviation (SD) of triplicate wells. A standard curve ranging from 0 to 10,000 pg/ml, in which mean fluorescence intensity was plotted against cytokine concentration, was generated from known concentrations of various cytokines using a Luminex 100 instrument, which employs fluorescent bead-based technology (Luminex Corporation; Austin, Tex.).

Intracellular Cytokine Staining. Cytokines produced by CD4+ and CD8+ T cells, including TNF-α, IL-2, and IFN-γ, were assayed by cytokine flow cytometry as previously described in Martins S L, et al. Blood 104(12):3429-36 (2004) and Komanduri K V, et al. Nat Med 4(8):953-6 (1998). PBMCs and IVS cells were activated by incubation with HERV-K env protein and GolgiPlus (BD Biosciences) at 37° C. in a humidified 5% $CO_2$ atmosphere for 4 hours. Cells activated with a Leukocyte Activation Cocktail (BD Biosciences) served as positive controls; whereas unstimulated cells served as negative controls. After the 4-hour incubation, the cells were blocked for 15 minutes and stained with surface antibodies against CD4, CD8, and CD3 (BD PharMingen; San Diego, Calif.) for 20 minutes. The activated cells were permeabilized with BD Cytofix/Cytoperm buffer for subsequent intracellular staining with PE-conjugated TNF-α, IL-2, and IFN-γ (BD PharMingen). APC-labeled anti-IgG2a or IgG1, and a PE-conjugated isotype control cocktail were used as single color controls. The samples were acquired and analyzed on a FACSCalibur system (BD Biosciences).

Statistical Analysis. Each assay was performed in triplicate and analyzed using SigmaStat 3.0 software. To evaluate the differences between the proportions of positive samples in the different groups, data were arranged in the form of two-by-two contingency tables and analyzed by Fisher's exact test to calculate the odds ratios, 95% confidence intervals and P values. Differences among groups were analyzed by the Kruskal-Wallis One Way Analysis of Variance on Ranks. The mean, standard deviation (SD) and coefficient of variation were calculated for sample triplicates. A P value<0.05 indicated a significant difference among treatments.

Example 10

Expression of Multiple HERV Env Transcripts in Human Ovarian Cancer Cells and Tissues The expression of env transcripts of type 1 (1,104 bp) and type 2 (1,194 bp) HERV-K surface domains was detected in ovarian cancer cell lines (PA1, SKOV3, OVCA 429, OVCA 433, OVCAR3, DOV 13, and OVCA 420), but not in normal ovarian epithelial cells (NOE 113, 114, 116, and 119). An example of the RT-PCR results is depicted in FIG. 7A. HERV-K expression was not detected by RT-PCR in normal and uninvolved ovarian tissues. Some ovarian cancer tissues expressed only type 1 HERV-K env region transcripts, some expressed only type 2 and some expressed both types of HERV-K env transcripts with the same or varying intensities (data not shown). The expression of multiple HERV families, which included ERV3 (1,744 bp), HERV-E (1,348 bp), and HERV-K types 1 and 2, was detected in ovarian cancer tissues more than in matched uninvolved ovarian tissues (FIG. 7B). Expression of both of cORF (437 bp) and np9 (256 bp) RNA, as well as full-length HERV-K env reading-frame transcripts, was detected in ovarian cancer cells or some specimens (FIG. 7C).

Spliced np9 and/or cORF mRNA was expressed in ovarian cancer tissues and the ovarian cancer cell lines DOV13, OVCAR 3, OVCA 429, and OVCA 433. Proteins cORF (type 2) located in the nucleus and with functions similar to the Rev protein of HIV (Boese A, et al. FEBS Lett 468:65-67, 2000; Tonjes R R, et al. J Acquir Immune Defic Syndr Hum Retrovirol 13:S261-267, 1996), were shown in earlier studies to support cell transformation and to induce tumor formation in nude mice (Boese A, et al. Oncogene 19:4328-4336, 2000). Not wishing to be limited by theory or mechanism, splice variants may promote cell transformation, as was observed for cORF and np9; or the variants may inhibit the host immune response, as was found when expression of a retroviral envelope protein or transmembrane subunit led to tumor growth in vivo (Blaise S, et al., 2001). These results provide evidence that both types of HERV-K mRNA, as well as multiple HERV family mRNAs, are transcribed in ovarian cancer cell lines and tissues.

In order to quantitate the expression of HERV-K in human ovarian biopsies, 254 ovarian tissue RNAs isolated from various ovarian specimens were quantified for the expression of HERV-K env transcripts by real time RT-PCR. The results of real-time RT-PCR analyses of these samples are presented in FIG. 7D. Lower CT values (HERV-K/S9 ratios) represent higher expression of HERV-K env transcripts. HERV-K env expression was significantly greater in tissues from epithelial tumor without metastasis (p=0.012; N=121) and greater but not statistically significant in tissues from epithelial tumor with metastasis (p=0.058; N=46), relative to expression in normal and benign ovarian tissues (N=19), using a two-sample t-test.

Example 11

Characterization of HERV-K Surface Env Fusion Protein and Anti HERV-K Antibody

Various HERV env cDNAs derived from cancer tissues were cloned in the bacterial expression vector systems pQE (with 6-His; Qiagen Inc.) and GST (Pharmacia). Some clones produced recombinant fusion proteins, such as HERV-K-His fusion surface protein (40,000 daltons;), HERV-K gag fusion protein (84,460 daltons), and HERV-K env splice product protein (cORF-His; 14,000 daltons). Several other HERV env proteins have been also produced in our laboratory including ERV3 and HERV-E env proteins (data not shown). The authenticity of HERV env fusion proteins was further confirmed by sequence analysis using vector specific primers. These purified HERV fusion proteins were used to detect the various anti-HERV antibodies in human sera. These HERV fusion proteins were also used to produce antibodies. These positive antibodies were used to test for their specificity or sensitivity against HERV env surface proteins by ELISA analysis or Western blot analysis.

Example 12

Surface Expression of HERV-K Env Protein on Ovarian Cancer Cells Lines

Our data suggest that HERV-K env is expressed in ovarian cancer cells and tissues at the transcriptional level. To evaluate the significance of HERV-K env protein in ovarian cancer, we examined expression of this protein in cell surface and cytoplasmic compartments of ovarian cancer cells by flow cytometric analysis of cells stained with anti-HERV-K env surface protein specific antibody. Both cell surface and cytoplasmic expression of HERV-K env protein was detected in ovarian epithelial carcinoma cells including DOV13 (53% surface expression of HERV-K; FIG. 8A; No-perm), SKOV3 (22%), OVCAR3 (25%), OVCA429 (16%), OVCA433 (15%), OVCA430 (16%), and OVCA420 cells (20%), but not in three normal ovarian surface epithelial cell lines. The observation was further confirmed by fluorescence microscopy (FIG. 8A). Surface expression of HERV-K env protein was observed on nonpermeabilized malignant DOV13 and OVCA420 ovarian cancer cell lines, and cytoplasmic expression was observed in DOV13 (FIG. 8A; Perm; 86%) and OVCA420 cells permeabilized by Triton X-100 by flow cytometry. In contrast, no surface or cytoplasmic expression of HERV-K was observed in T29 or T80 epithelial cells, respectively.

Example 13

Expression of HERV-K Env Proteins in Ovarian Tumor Epithelial Cells

Our data demonstrate the expression of HERV env transcripts in human ovarian cancer tissues. It is essential to test for HERV-K protein expression in these cancer tissues, because protein expression is a prerequisite for generating an immune response.

Multiple tissue microarrays TMA1, TMA2, and TMA3 contained 72, 85, and 484 multiple ovarian tissues, respectively, and were stained with a DAKO autostainer universal staining system using anti-HERV-K env protein antibody. A score of "0" indicates no expression, "1" indicates low expression and "2+3" indicates intermediate and strong expression of HERV-K env protein, respectively. Examples of samples in TMA1 with 0, 1, 2 and 3 scores after staining for HERV-K are shown in FIG. 8B. Normal ovarian tissues had a "0" score, clear cell carcinoma had a score of "1", serous papillary cystadenocarcinoma had a score of "2", and serous papillary adenocarcinoma had a score of "3". The expression profiles of HERV-K env protein detected from TMA1 are summarized in Table 3. Positive staining samples from TMA2 were mucinous cyst (FIG. 8C), low malignant potential, low-grade, high-grade (HG) endometrioid, serous LMP, LG serous, HG serous, and clear cell carcinoma.

TABLE 3

The expression profile of HERV-K env SU protein in ovarian tissue microarray slide TMA1 containing 72 tissues.

| | [2]Age (range) | N | Histotype[1] 0 | 1 | 2 + 3 |
|---|---|---|---|---|---|
| [3]NL | 45 (43-47) | 3 | 3 (100%)[4] | | |
| [5]GCT | 35.2 (12-49) | 5 | 3 (60%) | | 2 (40%) |
| [6]Stroma T | 49.5 (40-48) | 4 | 4 (100%) | | |
| [7]Krukenberg T | 46.6 (24-66) | 5 | 3 (60%) | 1 (20%) | 1 (20%) |
| Brenner T | 57 | 1 | 1 (100%) | | |
| Borderline T | 75 | 1 | | 1 (100%) | |
| [8]Mets. AdCa | 44.6 (30-70) | 5 | 1 (20%) | | 4 (80%) |
| [9]Mucous P AdCa | 55.5 (42-69) | 2 | 1 (50%) | | 1 (50%) |
| Serous P AdCa | 48.3 (22-66) | 40 | 13 (33%) | 10 (25%) | 17 (43%) |
| Other carcinoma | 47.7 (35-62) | 3 | 2 (66.7%) | | 1 (33.3%) |
| [10]CCC | 43.6 (40-48) | 2 | | 2 (100%) | |
| Endometrioid C | 40 | 1 | 1 | | 1 (100%) |
| Total | | 72 | 31 (43%) | 16 (19%) | 28 (38%) |

[1]A score of 0 indicates no expression, 1 indicates low expression and 2 + 3 indicates intermediate and strong expression
[2]Age: Average age and range of ages of patients
[3]NL: Normal ovarian tissues
[4]Number and percent with the given score
[5]GCT: Germ cell tumors
[6]Stroma T: Granular cell tumors
[7]Krukenberg T: Krukenberg tumors
[8]Mets. AdCa: Metastatic adenocarcinoma
[9]Mucous P AdCa: Mucous papillary adenocarcinoma
[10]CCC: Clear cell carcinoma Expression of HERV-K env SU protein increased in a stepwise fashion from grade I (33%) to grade II (38%) to high-grade (47%) serous papillary adenocarcinoma (FIG. 9A) for 40 serous papillary adenocarcinoma tissues obtained from the TMA1 tissue microarray. Microarray TMA2 contained normal, mucinous cyst, LMP, LG, and HG carcinomas, and this array was used for analysis of progression of ovarian cancer (FIG. 9B). LMP serous, LG serous, and LG endometrial tumors showed higher levels of expression compared to normal ovaries (p<0.001). HG serous and endometrial tumors showed great variability in protein expression with a median expression slightly lower than normal ovaries. Furthermore, tissue microarray TMA3, containing 484 cases of various ovarian cancer tissues with clinical follow-up information, was used to assess whether activation of HERV-K env surface protein correlated with clinical or histological characteristics, or with prognostic factors associated with the patients. The parameters evaluated included patient demographics, hormone receptor status, tumor type, tumor stage, and survival. A statistically significant increase in HERV-K expression was observed for histotypes with a diagnosis of ovarian cancer (Table 4). There were no significant increase in tumor grade, stage, patient age, and level of cytoreduction achieved (data not shown). Clear cell and mucinous carcinomas showed lower levels of expression compared to other ovarian cancers. Patients with low expression of HERV-K env SU protein had the highest survival rate. However, patients with mid-level expression of HERV-K env SU protein had lower survival rate than patients with high expression (data not shown).

TABLE 4

Ovarian cancer tissue microarray: HERV-K envelope surface protein expression and clinicopathological characteristics.

| Histotype | 0 | 1 | 2 + 3 | Total |
|---|---|---|---|---|
| Endometrioid adenocarcinoma | 6 (12.8%) | 11 (23.4%) | 30 (63.8%) | 47 |
| Serous carcinoma | 38 (10.4%) | 109 (29.8%) | 219 (59.8%) | 366 |
| Malignant mixed mullerian tumor | 1 (5.9%) | 7 (41.2%) | 9 (52.9%) | 17 |
| Clear cell carcinoma | 5 (26.3%) | 8 (42.1%) | 6 (31.6%) | 19 |
| Poorly differentiated carcinoma | 4 (25%) | 2 (12.5%) | 10 (62.5%) | 16 |
| Mucinous adenocarcinoma | 4 (40%) | 4 (40%) | 2 (20%) | 10 |
| Transitional cell carcinoma | | 3 (33.3%) | 6 (66.7%) | 9 |
| p value* | 0.01 | | | |

TABLE 4-continued

Ovarian cancer tissue microarray: HERV-K envelope surface protein expression and clinicopathological characteristics.

|  | 0 | 1 | 2 + 3 | Total |
|---|---|---|---|---|
| Tumor grade |  |  |  |  |
| 1 | 4 (18.2%) | 10 (45.5%) | 8 (36.4%) | 22 |
| 2 | 4 (16.7%) | 5 (20.8%) | 15 (62.5%) | 24 |
| 3 | 49 (11.5%) | 129 (30.2%) | 249 (58.3%) | 427 |
| missing | 1 (9.1%) |  | 10 (90.9%) | 11 |
| p value | 0.24 |  |  |  |
| Stage |  |  |  |  |
| Stage 1 | 6 (15%) | 12 (30%) | 22 (55%) | 40 |
| Stage 2 | 3 (8.3%) | 11 (30.6%) | 22 (61.1%) | 36 |
| Stage 3 | 36 (12.9%) | 77 (27.5%) | 167 (59.6%) | 280 |
| Stage 4 | 11 (11.8%) | 34 (36.6%) | 48 (51.6%) | 93 |
| missing | 2 (5.7%) | 10 (28.6%) | 23 (65.7%) | 35 |
| p value | 0.7 |  |  |  |
| Age |  |  |  |  |
| <55 | 20 (12.2%) | 44 (26.8%) | 100 (61%) | 164 |
| >55 | 34 (12.1%) | 89 (31.6%) | 159 (56.4%) | 282 |
| missing | 4 (10.5%) | 11 (28.9%) | 23 (60.5%) | 38 |
| p value | 0.5 |  |  |  |
| Level of cytoreduction achieved |  |  |  |  |
| suboptimal | 25 (12.1%) | 65 (31.4%) | 117 (56.5%) | 207 |
| optimal | 27 (12.4%) | 63 (28.9%) | 128 (58.7%) | 218 |
| unknown |  | 2 (66.7%) | 1 (33.3%) | 3 |
| missing | 6 (10.7%) | 14 (25%) | 36 (64.3%) | 56 |
| p value | 0.8 |  |  |  |

*P values calculated using chi-square test of independence.

Example 14

Detection of Anti-HERV Antibodies in Sera of Ovarian Cancer Patients

To determine whether HERV proteins expressed in ovarian cancer tissues are immunogenic in ovarian cancer patients, we assayed for anti-HERV antibodies in sera from patients with various cancers including ovarian cancer. ELISA analysis was employed to determine the binding affinity and specificity of the sera obtained from ovarian cancer patients (n=60) and normal female controls (n=50). The cutoff value is 0.5 for OD at 405 nm. Approximately 55% of the 60 ovarian cancer patient samples were positive for antibodies against HERV-K surface protein, 40% were positive for antibodies against HERV-E surface protein, 55% were positive for antibodies against HERV-K gag protein, 50% were positive for antibodies against an env protein splice variant, and 30% were positive for antibodies against ERV3 env protein. ELISA results obtained from 20 ovarian cancer patients and 20 normal female controls are shown in FIGS. 10A and B. The presence of anti-HERV env protein antibodies provides indirect evidence of the presence of HERV proteins in human ovarian cancer. Further, the occurrence of these antibodies in the circulation of cancer patients but not normal subjects indicates that HERV may be an unrecognized tumor-associated antigen in ovarian cancer.

Materials and Methods for Examples 10-14

Cells and tissues. The human ovarian cancer cell lines PA1 and SKOV3 were obtained from the American Type Culture Collection (ATCC; Rockville, Md.) and were cultured in the media recommended by the manufacturers. The human ovarian surface epithelial cancer cell lines OVCA 430, OVCA 433, OVCA 420, OVCAR3, DOV 13 and OVCA 429, and the normal human ovarian epithelial cell lines NOE 114, NOE 116, NOE 113, and NOE 119 were gifts from Dr. Robert C. Bast Jr., University of Texas M. D. Anderson Cancer Center. The normal human ovarian epithelial cell lines T29, T72, and T80 were generated from human ovarian surface epithelial cells that had previously been transfected with the SV40 early region expressing large T and small t antigens, and which were infected subsequently with a retrovirus containing a full-length hTERT cDNA, as described in Liu J, et al. Cancer Res 64:1655-1663 (2004). The human ovarian cancer cell lines were maintained in minimal essential medium supplemented with 10% Bovine Growth Serum (BGS; HyClone), penicillin and streptomycin, glutamine, non-essential amino acids and sodium pyruvate. For hormone stimulation, cells were treated with β-estradiol on day 1 and progesterone on day 2 as described in Rininsland F H, et al., J Immunol Methods 240(1-2):143-55, 2000. The normal human surface ovarian epithelial cell lines were cultured in a 1:1 mixture of MCDB 105 medium (Sigma) and Medium 199 (Life Technologies, Inc.) supplemented with 10 ng/ml epidermal growth factor (Sigma), 15% BGS, L-glutamine, penicillin and streptomycin. Tissue samples were snap-frozen and stored at −70° C. until RNA isolation. For in situ hybridization or immunohistochemistry, formalin-fixed, paraffin-embedded tissues were used.

PCR primers. Oligonucleotide primers derived from the sequences encoding the env surface proteins of HERV-K, ERV3 and HERV-E were used to amplify cDNA prepared from human ovarian tissues and cell lines as described in Wang-Johanning F, et al. Clin Cancer Res 7:1553-1560, 2001. The 5' sense primer of the HERV-K env gene has between one and four base-pair (bp) mismatches with most type 2 HERV-K env genes. In this study, a sense primer (nucleotide [nt] 6674-6698; Accession number: AF074086 (Mayer J, et al, Nat Genet 21:257-258, 1999)) specific for type 2 HERV-K env genes was also used to detect type 2

HERV-K env mRNA transcripts, as described in Wang-Johanning F. Oncogene 22:1528-1535, 2003. Previously-described primer pairs were used to amplify env reading frame transcripts that include np9. Armbruester V, et al. N. Clin Cancer Res 8:1800-1807, 2002.

RT-PCR. RNA was prepared and treated with DNase as described in an earlier study. Wang-Johanning F, et al. Clin Cancer Res 7:1553-1560, 2001. Briefly, isolated total RNA was incubated at 65° C. for 10 minutes followed by incubation on ice for 2 minutes prior to reverse transcription. Reverse transcription was carried out for 1 h at 37° C. using cDNA synthesis beads (Amersham Pharmacia Biotech Inc., Piscataway, N.J.) as per the manufacturer's instructions. The reverse transcribed samples were amplified in a volume of 50 µl using the HERV env sense and antisense primer pairs described in Wang-Johanning F, et al. Clin Cancer Res 7:1553-1560, 2001. The same reverse-transcribed RNA sample was analyzed using primers that recognize human β-actin to confirm equivalent loading. One microgram of RNA from the same sample without reverse transcriptase addition was amplified in parallel to ensure that no genomic DNA was present in the samples.

Real-time RT-PCR. One-step RT-PCR was performed using an ABI PRISM 7900HT sequence detector to quantitate the expression of HERV-K env gene in various ovarian specimens. The optimized concentrations of HERV-K primers and probes were determined and used for real-time RT-PCR as described in Wang-Johanning F. *Oncogene* 22:1528-1535, 2003. *Homo sapiens* ribosomal protein S9 (GenBank accession number XM 008957.2) was used as an endogenous control. Wang-Johanning F, et al. *Cancer* 94:2199-2210, 2002. Briefly, the amplification reactions were performed in 25 µl final volume containing 1× TaqMan buffer (Perkin-Elmer Applied Biosystems, Foster City, Calif.) plus dNTPs (0.3 mM each), 0.625 units of AmpliTaq Gold, RNase inhibitor (5 units), 2% glycerol, and 0.625 units of MuLV reverse transcriptase. All RT-PCR reactions were performed in optical reaction tubes (Perkin-Elmer) designed for the ABI PRISM 7900HT sequence detector system. Reverse transcription and thermal cycling conditions were 30 min at 48° C. followed by 10 min at 95° C., and 40 cycles of 15 s at 95° C. and 1 min at 60° C. PCR premixes containing all reagents except for total RNA were used as no a template control. Linear extrapolation of the cycle threshold (CT) values of HERV-K were obtained from ovarian specimens, and were then divided by the relative amounts of S9, which were quantitated by linear extrapolation from the CT values of the same unknown samples.

Synthesis of HERV env fusion proteins and production of anti-HERV env protein antibodies. HERV cDNAs obtained from cancer tissues were cloned into the corresponding enzyme-digested QIA expression vector (pQE30; Qiagen Inc.), which contains a 6-His tag at the N-terminus, or pGEX vector (4T1; Amersham Pharmacia), which contains glutathione S-transferase (GST). After screening for protein production on a small-scale, the HERV env-positive colonies were further identified by restriction enzyme analysis and characterized by sequencing using vector-specific primers to confirm that the clones produced the desired HERV env proteins. The HERV env-positive colonies were induced with isopropyl-B-D-thiogalactopyranoside and purified by affinity chromatography using Ni-nitrilotriacetic acid agarose (Qiagen) for the pQE vector, or Glutathione Sepharose 4B (Amersham Pharmacia) for the pGEX vector. These purified HERV env fusion proteins were used to immunize rabbits for polyclonal or mice for production of anti HERV env protein monoclonal antibodies using standard techniques. The antibodies were further purified using Protein G Sepharose 4 Fast Flow (Amersham Pharmacia) and tested for specificity and sensitivity against various HERV env proteins by ELISA and/or immunoblot analysis.

Flow cytometry. Cultured cells were incubated with anti-HERV-K antibody (5691; 1:200 dilution) at 4° C. for 30 min, followed by anti-rabbit IgG-FITC secondary mAb (1:1000 dilution) at 4° C. for 15 min. For staining in permeabilized conditions, cells were treated with 0.1% Triton X-100 in PBS, then incubated with primary antibody, followed by secondary antibody. After washing with PBS, the cells were fixed with 3% paraformaldehyde in PBS. Samples were analyzed on a BD FACSCalibur™ system (BD Biosciences). For controls, samples were incubated with anti-rabbit IgG-FITC secondary mAb.

Immunohistochemistry for ovarian tissue slides. Immunohistochemistry was performed on a range of human ovarian tumor and non-tumor tissues using pre-immune serum and various anti-HERV antibodies. Paraffin-embedded ovarian tissue specimens were cut into serial 5 µm sections, melted, deparaffinized in xylene, rehydrated in ethanol and then fixed in 4% paraformaldehyde. The slices were incubated with horse sera, anti-HERV-K env polyclonal antibody (1:200 dilution), pre-immune serum (as a negative control; 1:200 dilution) or NCL-5D3 monoclonal antibody for cytokeratin 8/18 (Vector Laboratories Inc., Burlingame, Calif.) as a positive control to identify glandular epithelium or adenocarcinomas (1:40 dilution). This was followed by incubation with anti-rabbit IgG biotin conjugate antibody (1:1,000 dilution) or anti-mouse IgG biotin conjugate antibody, and finally with ABC (ABC kit, Vector) as described by the manufacturer. Diaminobenzidine (Vector Laboratories) substrate was used for color development. Slices were then counterstained with hematoxylin.

Tissue microarray (TMA) slides. Multiple tissue microarray slide TMA1, containing 72 ovarian tissues from patients with various ovarian diseases, was obtained from US Biomax, Inc (Catalog # CC11-01-002; Rockville, Md.). Slide TMA2 contains 85 ovarian tissues that included normal, mucinous cyst, low malignant potential, low-grade, and high-grade carcinomas obtained from The University of Texas M. D. Anderson Cancer Center Department of Pathology. TMA3 contain 484 cases of various ovarian cancer tissues obtained from University of Texas M. D. Anderson Cancer Center, with clinical follow-up information.

Immunohistochemistry for multiple tissue microarray slides. Immunohistochemistry was performed on tissue microarray slides using a DAKO autostainer universal staining system (Model: LV-1). The DAKO Autostainer System is an automated slide processing system compatible with currently available reagents for the staining of paraffin-embedded and frozen tissue sections. These multiple tissue microarray slides provided us with a means to compare the expression of HERV-K env SU protein in multiple tissues under identical conditions of staining. The protocol has been programmed into the system, and the slices were incubated with 3% $H_2O_2$ (5 min), horse sera (10 min), and antibodies (1:750 dilution for anti-HERV-K antibodies and 1:100 dilution for NCL-5D3) (30 min). This was followed by incubation with anti-rabbit or anti-mouse IgG HRP conjugate antibody (DAKO) (15 min), incubation with diaminobenzidine (5 min) for color development, and counterstaining with hematoxylin (5 min).

ELISA. ELISA assays were used to detect anti-HERV antibody in human sera, and were carried out as described in Wang-Johanning F, et al. Cancer Res 58: 1893-1900, 1998. Briefly, a 96-well ELISA plate was coated with various HERV env fusion proteins (10 µg per ml, 100 µl per well) in PBS and incubated overnight at 4° C. The plate was then blocked for 1 h with 5% nonfat dry milk (Sigma) and 3% BSA at room temperature. Human sera (1:200 dilution with PBS) were added to the coated wells, and the plate was incubated overnight at 4° C. After washing 6 times with PBS-T (0.5 ml of Tween 20 in 1000 ml of PBS), 100 µl of HRP-conjugated anti-human IgG antibody (1:2000 dilution, Sigma) was added to each well of the plate to detect the serum antibody, followed by incubation for 1 h at room temperature. The plate was washed again with PBS-T, and color was developed using ABTS (Sigma). After 10 min, absorbances of the plate wells were measured on a microplate reader at 405 nm. All ELISA analyses were performed at least three times for each serum sample. The means of the threshold values (Wang-Johanning F, et al. *Cancer Res* 58: 1893-1900, 1998) were used for the final analysis.

Example 15

Specificity and Sensitivity of Anti-HERV-K Antibodies

Monoclonal antibodies against HERV were also produced in our laboratory, including anti-HERV-K env, and anti-HERV-E env mAbs. Anti-HERV-K or HERV-E positive clones were used to test for their specificity or sensitivity against HERV-K env (FIG. 11A) or HERV-E env (FIG. 11B) proteins by ELISA analysis. Several other anti-HERV protein monoclonal antibodies, including anti-HERV-E and anti-ERV3 antibodies, have been produced, including anti-HERV-K spliced-env antibodies, anti-HERV-K gag antibody, anti-ERV3 env antibody, and anti-HERV-E env antibody.

Example 16

Investigation of the In Vitro and In Vivo Antitumor Effect of Anti-HERV-K Antibodies Anti-HERV-K antibody has been observed to inhibit proliferation of breast cancer cells (MCF-7) and ovarian cancer cells (DOV13), but not normal or benign breast (MCF-10A and MCF-10AT) or ovarian (T 80) cell lines, as shown in FIG. 12.

The anti HERV-K antibody alone induces MCF-7 cancer cells (25%) and DOV13 (20%) to undergo apoptosis. Testing revealed that these antibodies are pure and have high specificity for their targets.

The antitumor effect of anti-HERV-K antibody has been demonstrated in mice bearing murine mammary tumors expressing HERV-K env protein, where 60% of mice treated with antibody remained tumor free. No antitumor effect was detected in mice treated with control antibody or in mice bearing HERV-K negative tumors.

Both B6D and B6DK cells ($5 \times 10^6$) were injected s.c. into the right flank of mice (H-$2^b$), and average tumor sizes in mice were compared. Tumors sizes were 2.42-fold greater in mice with B6DK cells than their parent cells (at 40 days post-injection). However, mice that were immunized with HERV-K env surface proteins were protected from subsequent tumor challenge. No change in tumor growth rate was detected in mice bearing B6D cells, which are HERV-K negative parent cells. Furthermore, bone marrow-derived DCs were administrated as vaccines to improve the antitumor activity. DCs were pulsed with HERV-K env surface protein, control protein (such as HPV16E6 protein in the same expression vector; pQE30), HERV-K env cRNAs constructed by in vitro transcription, or control cRNA (such as HPV16E6 cRNA in the same vector; pcDNA3). Results of a representative study are depicted in FIG. 14A. In addition, the antitumor effect was observed in the mice bearing B6DK mammary tumor expressing HERV-K env protein treated with DC pulsed with KcRNA and peptides Kp201 and Kp640. No protection was observed in animals treated with nonpulsed DCs (FIG. 14B). p1028 peptide was used as positive control.

Example 17

Construction of a Single-Chain Anti-HERV-K Antibody (Designated HERV-K sFv) and Fusion to the Recombinant Toxin Gelonin (rGel)

Cloning of the VH and VL domains of anti-HERV-K antibody from mice hybridomas (monoclonal antibodies) or Spleen Cells. mRNA from murine hybridoma 4D1 expressing anti-HERV-K antibody (IgG2A) or spleen cells obtained from Balb/c mice has been isolated and reverse-transcribed to cDNA, and spleen cells obtained from HLA-A2 transgenic mice will be isolated and reverse-transcribed to cDNA. Amplification of antibody light- and heavy-chain variable regions was carried out using the V heavy chain or light chain primers as described in Wang-Johanning F, et al. *Cancer Res* 58: 1893-1900, 1998. DNA amplified using this procedure was then cloned into the Invitrogen T/A cloning vector pCR II without further purification, transformed into *Escherichia coli* XL1-Blue, and identified using blue-white screening procedures. Positive clones (five each from the heavy- and light-chain libraries) were sequenced using the T-7 and SP6 promoter primers (see sequence in FIG. 15) (SEQ ID. NO:11), and antibody domains will be identified by homology to other immunoglobulin sequences.

Construction of genes encoding the single-chain antibody HERV-K sFv and the immunotoxin HERV-K sFv-rGel. A two-step splice-overlap extension PCR method (Rosenblum, M. G. *Cancer Res* 63, 3995-4002, 2003) will be used to construct the single-chain antibody HERV-K sFv using light- and heavy-chain DNA clones as templates. The clones will then be fused together using the splice-overlap extension PCR method with gelonin DNA as templates. PCR products will be purified and digested with BamHI and HindIII as described previously, and cloned into vector pQE-30. Sequenced DNA clones will be subsequently transformed into *E. coli* strain M15 obtained from Qiagen for expression of the fusion toxin. The colony-blot procedure will be used for identification of clones expressing anti-HERV-K antibody. After the positive clones expressing anti-HERV-K are identified, the clones will be sequenced to confirm that the sequence is correct.

Protein expression in *E. coli*. The positive bacterial cultures will be incubated at 37° C. in 2×LB growth medium with strong antibiotic selection (200 µg/ml ampicillin, and 15 µg/ml kanamycin) and grown until early log phase (A600 nm=0.4-0.8). The cultures will then be induced at 37° C. by the addition of 0.1 mM IPTG for 4 h. Induced bacterial cultures will be centrifuged and purified by affinity chromatography as described previously (F Wang-Johanning, 2001, Clinical Cancer Research).

Internalization and immunofluorescence staining. Antigen-positive (MCF-7 or DOV13) cells will be added to polylysine-coated 16-well chamber slides (Nunc) at 104 cells/chamber and incubated at 37° C. overnight under 5% $CO_2$ atmosphere. Cells will be treated with 50 µg/ml HERV-K sFv-rGel fusion construct for various time intervals. Cells will be washed briefly with PBS, and proteins bound to the cell surface will be stripped by 10-min incubation with glycine buffer (500 mM NaCl and 0.1 M glycine (pH 2.5)), neutralized for 5 min with 0.5 M Tris (pH 7.4), washed briefly with PBS, and then fixed in 3.7% formaldehyde (Sigma) for 15 min at room temperature, followed by a brief rinse with PBS. Cells will then be permeabilized for 10 min in PBS containing 0.2% Triton X-100, washed three times with PBS, and incubated with PBS containing 3% BSA for 1 h at room temperature. After a brief wash with PBS, cells will be incubated with rabbit anti-rGel polyclonal antibodies diluted 1:500 in PBS containing 0.1% Tween 20 and 0.2% BSA for 1 h at room temperature. Cells will be washed three times in PBS containing 0.1% Tween 20 for 10 min and blocked for 1 h at room temperature with PBS containing 3% BSA, followed by a 1:100 dilution of FITC-coupled antirabbit IgG (Sigma) containing 2.5 µg/ml of propidium iodide (PI). Control cells will be incubated only with the secondary FITC-coupled antirabbit IgG (1:100) plus 2.5 µg/ml of PI. After three final washes with PBS containing 0.1% Tween 20, cells will be washed once with PBS for 10 min and mounted in DABCO mounting medium containing 1 µg/ml of PI. Slides will then be analyzed with a fluorescence microscope.

In Vitro cytotoxicity assay. Samples will be assayed using a standard 72-h cell proliferation assay with log-phase (5000 cells/well) antigen-positive MCF-7 and DOV13 cells, and antigen-negative MCF-10A and T80 cell monolayers, using crystal violet staining procedures as described in Rosenblum, M. G. *Cancer Res* 63, 3995-4002, 2003.

TUNEL Assay. Log-phase MCF-7 cells will be plated into 16-well chamber slides (10,000 cells/well) and incubated overnight at 37° C. in a 5% CO2 atmosphere. Cells will be treated with the fusion protein HERV-K sFv-rGel or rGel at a final concentration of 87 nM for different time periods (24 and 48 h) and washed briefly with PBS. Cells will be fixed with 3.7% formaldehyde at room temperature for 20 min, rinsed with PBS, then permeabilized with 0.1% Triton X-100 and 0.1% sodium citrate on ice for 2 min, and washed twice with PBS. Cells will be incubated with TUNEL reaction mixture at 37° C. for 60 min, followed by incubation with Concerter-AP at 37° C. for 30 min, and finally reacted with Fast Red substrate solution at room temperature for 10 min. After a final wash step, the slides will be mounted in mounting medium and analyzed under a light microscope. Positive controls will be included in each experimental set up. Fixed and permeabilized cells will be incubated with 1 mg/ml DNase I for 10 min at 37° C. to induce DNA strand breaks.

In vivo cytotoxicity studies. Athymic (nude) female mice or HLA-A2 transgenic female mice (4-6 weeks old) will be divided into groups of 5 mice/cage. Log-phase MCF-7 or DOV13 human cancer epithelial cells ($5 \times 10^6$ cells/mouse) will be injected s.c. in the right flank, and tumors will be allowed to establish. Ovarian cancer cells expressing green fluorescent protein as a result of transfection with a PG13-GFP expression vector will also be injected by an i.p. route, and these tumors can be detected using a fluorescence flashlight. Once tumors are measurable (~30-50 mm$^2$), animals will be treated (i.v. via tail vein) with either saline (control) or various concentrations of the HERV sFv-rGel fusion toxin for 4 consecutive days. Animals will be monitored, and tumors will be measured for an additional 30 days.

Example 18

Determination of Specificity and Sensitivity of Anti-HERV-K Antibody

Bacterial colonies positive for HERV-K env expression, characterized by sequencing, were induced with isopropyl-B-D-thiogalactopyranoside and purified by affinity chromatography using Ni-NTA Resin (Qiagen Inc.) or Glutathione Sepharose 4B by AKTAprime plus (GE Healthcare Bio-Sciences Corp). The purified HERV-K env fusion proteins were used for production of IVS cells, or to immunize rabbits or mice for the production of polyclonal or monoclonal anti-HERV-K env antibodies, respectively, using standard techniques. The antibodies were further purified and tested for specificity and sensitivity.

HERV-K env surface (K-SU) protein was cloned into two expression vectors (pQE30 and PGEX4T1) to generate HERV-K recombinant fusion proteins K10Q18 and K10G17, respectively, as described previously (Wang-Johanning, F., A. R. Frost, G. L. Johanning, M. B. Khazaeli, A. F. LoBuglio, D. R. Shaw, and T. V. Strong. 2001. Expression of human endogenous retrovirus k envelope transcripts in human breast cancer. Clin Cancer Res 7:1553-1560; Wang-Johanning, F., J. Liu, K. Rycaj, M. Huang, K. Tsai, D. G. Rosen, D. T. Chen, D. W. Lu, K. F. Barnhart, and G. L. Johanning. 2006. Expression of multiple human endogenous retrovirus surface envelope proteins in ovarian cancer. Int J Cancer.) K10Q18 was used to immunize animals to generate antibodies and K10G17 was used to screen for specificity and sensitivity of these antibodies. Several polyclonal and monoclonal anti-HERV-K antibodies were produced by standard methods. The positive clones were tested for their specificity and sensitivity against K-SU protein by ELISA and Western blot. Sample ELISA and Western blot results are shown, respectively, in FIG. 11A and FIG. 11C (top panel). Five hybridoma clones (4E11, 4D1, 4E6, 6E11, and 6H5) had higher sensitivity against K-SU protein than against HERV-E env surface protein, another HERV family member (cloned into pQE30 vector). Also, HERV-K fusion protein K10G17 was detected by two anti-HERV-K monoclonal clones, 4D1 and 6H5, which were generated by immunization with K10Q18 fusion protein. Anti-GST mAb was the positive control (data not shown).

Detection of anti-HERV antibodies in bc patients. The reactivity of anti-HERV-K antibodies obtained from BC patients and healthy female controls toward recombinant K-SU protein was determined by Western blot. Three patients with invasive ducal carcinoma, but not a healthy female donor, had anti-HERV-K serum antibodies which detected K10G17 protein (FIG. 11C, bottom panel), just as did monoclonal antibodies 6H5 and 4D1 (FIG. 11C, top panel). The sensitivity and specificity of antibodies in sera or plasma of BC patients toward K-SU was determined by ELISA. ELISA results for one series of serum dilutions (FIG. 11D) revealed higher K-SU antibody titers (p<0.001 to 0.005; Student's t test) in BC patients than in control subjects. The cut-off value was 0.5 for optical density at 405 nm. Approximately 50% of the BC patient samples (n=48) were positive for antibodies against K-SU protein, 15% had antibodies against HERV-K gag protein, and 35% had antibodies against type 2 HERV-K env protein with a 292 by insert. In contrast, anti-HERV-K antibodies were not detected in control samples (N=50). The presence of anti-HERV-K env protein antibodies provides indirect evidence of the presence of HERV-K env proteins in human BC, which indicates that there was a humoral response to HERV-K.

HERV-K-Specific CD4$^+$ T cell responses. Dendritic cells (DC) were generated from PBMC cultured in medium containing the cytokines GM-CSF and IL-4. Immature DC were exposed to TNF-α overnight for maturation, with or without prior pulsing with HERV-K proteins. Fluorescence-activated cell-sorting (FACS) analysis revealed that HERV-K-pulsed mature DC had enhanced CD83 expression compared with immature DC and mature DC treated with TNF-α only.

Expression of $CD83^+/CD209^+$ and $CD83^+/CD86^+$ was also higher in HERV-K-pulsed mature DC than in immature DC (data not shown).

PBMC obtained from BC patients (Table 7) or normal matched age female donors were stimulated with autologous mature DC pulsed with HERV-K env antigen for 1 week and assessed for proliferation using a $^3$H-thymdine incorporation assay. T cell proliferation was detected in one week IVS obtained from BC patients but not normal donors. Similar results were obtained when DC were pulsed with either K-SU protein (FIG. 17A) or HERV-K env surface RNA produced by in vitro transcription (IVT) using HERV-K env surface cDNA as a template (FIG. 17B). As shown in the scatter plots in FIG. 17C, the fold increase in HERV-K-specific T cell proliferation relative to autologous PBMC was significantly higher in IVS cells from cancer patients (N=16) than in those from healthy control subjects (N=18; p=0.023; Student's t test). In addition, when total PBMC or isolated $CD3^+$ cells obtained from healthy donors (N=7) were stimulated with HERV-K or HERV-E env surface protein (another HERV family), neither HERV-K nor HERV-E env surface protein stimulated human T cell proliferation to a similar extent as the superantigen *Staphylococcal enterotoxin* A (data not shown). These results indicate that T-cell proliferative responses against HERV-K are found only in BC patients and not in individuals without cancer.

TABLE 7

Patient characteristics

| Patient sample number | Age (years) | Diagnosis | Lymph node status | Date of diagnosis (month/year) |
|---|---|---|---|---|
| C1 | 51 | IDC[1] | | December 1992 |
| C2 | 59 | IDC | | April 2004 |
| C3 | 40 | DCIS[2] + ILC[3] | Negative | June 2004 |
| C4 | 54 | DCIS + IDC | | March 2003 |
| C5 | 41 | IDC stage 3 | | September 2004 |
| C6 | 41 | IDC | Negative | April 2004 |
| C7 | 49 | IDC | Negative | January 2000 |
| C8 | 55 | DCIS | Negative | June 2005 |
| C9 | 32 | IDC | Negative | October 2003 |
| C10 | 55 | IDC + colon C[4] | Positive | June 2005 |
| C11 | 38 | IDC | Positive | June 2005 |
| C12 | 49 | DCIS | Negative | June 2005 |
| C13 | 42 | DCIS | Negative | November 2005 |
| C14 | 79 | IDC | Negative | 1994 |
| BC 687150 | 64 | IDC + SCC[5] | | July 2006 |
| BC 691965 | 66 | IDC | | September 2006 |
| BC 691271 | 49 | IDC | | August 2006 |
| BC 684700 | 43 | DCIS | | August 2006 |
| BC 695606 | 55 | DCIS + IDC + ILC | | October 2006 |

[1]IDC, infiltrating ductal carcinoma,
[2]DCIS, ductal carcinoma in situ,
[3]ILC, invasive lobular carcinoma,
[4]colon C, colon cancer,
SCC[5], squamous cell carcinoma HERV-K Specific $CD8^+$ T cell responses. We then determined HERV-K specific Granzyme B (GrB) or IFN-γ release using an ELISPOT assay or $^{51}$Cr CTL assays. Results from a representative experiment are shown in FIG. 18A. HERV-K-specific GrB (top panel) or IFN-γ spot numbers (bottom panel) detected by ELISPOT after 3-week IVS (PBMC were stimulated twice with DC pulsed with K-SU) were significantly higher in cancer patients than in healthy controls. Similar results were obtained with PBMC stimulated in 1-week IVS assays (data not shown). Very few or no GrB spots were detected from PBMC stimulated with unpulsed DC obtained from healthy donors or cancer patients. A significantly greater number of GrB spots were produced in BC patients (N=13) than in normal female donors (N=16), regardless of whether they were subjected to 1 week IVS or 3 week IVS (FIG. 18B).

$^{51}$Cr-release CTL assays were employed to compare HERV-K specific $CD8^+$ T cell responses between BC patients and normal donors. An example of a CTL assay after 1 wk IVS is shown in FIG. 18C. IVS from four normal donors stimulated with HERV-K-expressing DC had lower antigen-specific CTL activity than IVS from four cancer patients. Higher cytotoxic activity in BC patients than in normal donors against K-SU protein (DC+Kpro) or RNA (DC+KRNA) was observed, with lesser cytotoxic activity against HPV16 E6 protein (DC+E6pro) or RNA (DC+E6RNA which obtained by IVT using E6 DNA a template; data not shown). Other human proteins produced in the pQE30 expression vector, including LMP2A and HPV16 E7, had lesser cytotoxic activity than K-SU protein (data not shown). PBMC from normal donors stimulated with HERV-K-expressing DC in IVS assays did not exhibit any antigen-specific CTL activity (FIG. 18C).

Anti-HERV-K antibody inhibited BC cell proliferation and induced BC cells to undergo apoptosis. The antitumor effect of α-K antibodies in BC cells was determined by an MTS cell proliferation assay. Antibodies were able to inhibit BC, but not normal or benign breast cell proliferation. Anti-HERV-K pAb 5693 inhibited proliferation of MCF-7 BC cells, but not benign MCF-10A breast cells (FIG. 19A). The cytotoxicity of α-K mAb 6H5 toward BC cell lines was compared. The $IC_{50}$ of 6H5 mAb for MCF-7 and MDA-MB-231 was 51.7 nM and 6.6 nM, respectively, and 6H5 showed no cytotoxicity toward MCF-10A cells (FIG. 12). Furthermore, we investigated whether α-K mAbs induce apoptosis in BC cells. Breast cells treated with α-K mAb (6H5; 0, 1.25, 2.5, 5, 10 μg/ml) for 24 hr were subjected to FACS analysis of Annexin V-APC and 7AAD-PEcy7 expression, to assay for apoptosis. 6H5 induced apoptosis in a dose-response fashion in MCF-7 cells, and the response in MCF-7 cells was greater than in MCF-10AT; MCF-10A did not undergo apoptosis in response to 6H5 (FIG. 19B). Apoptosis in these breast cell lines is summarized in FIG. 19C. Several α-K mAb clones were able to induce apoptosis in T47D and NIH MCF-7 BC cells, but not in MCF-10A or MCF-10AT breast cell lines. Anti-HERV-K mAb induced apoptosis to a greater extent in BC cells than in premalignant breast cells, but had no effect on apoptosis in benign breast cells.

Example 19

Adoptive T Cell Therapy Inhibits Breast Tumor Growth in Mice

We evaluated whether a combination of HERV-K specific CTLs and α-K antisera function synergistically in tumor regression in vivo by evaluating influences of immunization on the course of tumor appearance. We first induced anti-K-SU immune responses in HLA-A2 mice (A2 mice), and then used the CTLs and antisera from these mice for adoptive T cell therapy in SCID mice. These experiments provide essential information as to whether HERV-K proteins can serve as tumor targets for development of a vaccine against breast cancer in vivo. The tumor sizes were reduced by 61% in SCID mice treated with $CD90^+$ T cells from A2 mice, plus antisera from A2 mice (174 mm$^3$) (P<0.05) compared with untreated controls (452 mm$^3$). In addition, tumor sizes were reduced by 80% in the 6H5 mAb group (93 mm$^3$) (P<0.05) relative to controls. The tumor sizes showed no significant difference relative to controls in the mice treated with antisera alone (199 mm³) or CD90⁺ T cells alone (293 mm³). (FIG. 20A.) FIG. 20B illustrates tumor formation in mice innoculated with MCF-7 cells on day 0 and treated with saline or 6H5 on days 4, 6, and 8 (arrows; 200 ug per mice). Mice treated with saline were used as control.

Example 20

Studies with Anti-HERV-K Antibody, 6H5

Many studies were performed on various breast and ovarian cell lines using anti-HERV-K Antibody, 6H5. ELISA and Western Blot were performed on the samples to determine monoclonal antibody specificity and protein expression, as described previously. Immunofluorescence staining, confocal microscopy, flow cytometry, and dry cell ELISA were performed to determine the surface expression of the viral protein. Internalization assays were performed to detect toxin entry into target cells; immunohistochemistry was performed to protein expression in tumor biopsies. Cytoxicity analysis was conducted to determine $IC_{50}$ of mAb or mAb-rGel in various cells. Nude or SCID mice were treated with mAB to test for protection against tumor growth. Western blot of various breast cell lines and an ovarian cell line using 6H5 mAb to detect HERV-K env expression can be seen in FIG. 16E. FIGS. 16E and 16F show that anti-HERV-K antibodies were detected in sera obtained from breast cancer patients. Western blot of various ovarian cell lines using 6H5 mAb to detect expression of HERV-K env protein can be seen in FIG. 21.

Surface and cytoplasmic expression of HERV-K env protein in ovarian cancer cells was detected by confocal microscopy using 6H5 mAb. rGel was delivered into DOV13 cells by 6H5, and was detected by anti-rGel Ab. Coomasie blue stain of 6H5 mAb and 6H5-rGel conjugate can be seen in FIG. 29. The results of this study are illustrated in FIG. 22. Surface and cytoplasmic expression of HERV-K env protein in breast cell lines detected by confocal microscopy using 6H5 mAb are illustrated in FIGS. 23 and 24. rGel was delivered into MCF-7 cells by 6H5, and was detected with anti-rGel Ab.

Surface expression of HERV-K env protein in ovarian cell lines was quantitated by ELISA using 6H5 mAb. Murine IgG was used as a negative control. These results can be seen in FIG. 25. Quantitation of surface expression of HERV-K env protein in ovarian cell lines by FACS using 6H5 mAb can be seen in FIG. 26. Murine IgG was used as a negative control.

The ability of 6H5 to induce ovarian cells to undergo apoptosis was assessed, as compared to cells that were not treated with antibody. FIG. 27 shows the results of this study. The results indicated that the antibody against HERV-K is able to induce cancer cells to undergo apoptosis. Apoptosis in these ovarian cell lines is summarized in FIG. 28. The results of comparative cytotoxicity studies with breast cell lines and ovarian cell lines can be seen in FIGS. 30 and 31.

The results of this study indicate that 6H5 mAb is able to inhibit cancer cell proliferation by the MTT assay. 6H5 mAb is also able to induce cancer cells to undergo apoptosis. 6H5 mAb-rGel is cytotoxic to cancer cells, but not normal cells. Expression of HERV-K env protein was observed only in cancer cells of biopsies by immunohistochemistry using 6H5. HERV-K envelope protein is a tumor specific antigen, and can be used for detection, diagnosis, and as a target for immunotherapy. Both surface and cytoplasmic expression of HERV-K env protein is observed on cancer cells only, which suggests that HERV-K can stimulate both T cell and B cell responses. 6H5, a mAb against HERV-K env protein, is able to treat HERV-K positive cancers. 6H5 is useful as an immunotoxin, and can also be used for radiotherapy and as an imaging agent.

Methods for Examples 15-20.

ELISA and Western blot assays. ELISA and Western blot assays were performed as described previously (Wang-Johanning, F., J. Liu, K. Rycaj, M. Huang, K. Tsai, D. G. Rosen, D. T. Chen, D. W. Lu, K. F. Barnhart, and G. L. Johanning. 2006. Expression of multiple human endogenous retrovirus surface envelope proteins in ovarian cancer. Int J Cancer; Wang-Johanning, F., G. Y. Gillespie, J. Grim, C. Rancourt, R. D. Alvarez, G. P. Siegal, and D. T. Curiel. 1998. Intracellular expression of a single-chain antibody directed against human papillomavirus type 16 E7 oncoprotein achieves targeted antineoplastic effects. Cancer Res 58:1893-1900.) The specificity and sensitivity of anti-HERV-K-positive clones against HERV-K env proteins were tested by an ELISA as described previously. In brief, HERV-K env proteins (10 μg per mL, 100 μL per well) or HERV-E env proteins (as controls) were coated in wells of 96-well plates. The supernatants obtained from several positive clones (1:50 to 1:109,350 dilution with PBS) were added to the coated wells and incubated for 1 h at ambient temperature. HRP-conjugated antimouse IgG antibody (100 μL, 1:2000 dilution) was added to each well for another 1 h at ambient temperature. The color was developed, and the plate was read on a microplate reader at 405 nm. ELISA was also used to detect various anti-HERV antibodies in human sera, as described previously. Anti-human IgG antibody was used as a negative control, and anti-RGS mAb (Qiagen, Inc.; used to detect 6-His protein produced from pQE30 vector) or anti-HERV-K mAb was used as a positive control. The cut-off value for a negative reaction was 0.5 OD at 405 nm. The means of the threshold values were used for the final analysis. For Western blot, purified HERV-K proteins (20 μg/well) were loaded onto 10-15% SDS gels. After transfer to membranes, mAbs (1:1,000 dilution) or human sera (1:200 dilution) were used as primary antibodies and incubated overnight at 4° C. Anti-mouse or human IgG HRP mAb (1:1,000 dilution) was added and incubated at room temperature for 1 hr and visualized using ECL (Upstate). Anti-RGS mAb (1:1,000 dilution, which detects 6-His protein produced from pQE30 vector) or anti-GST mAb (1:1,000 dilution, which detects GST protein produced from pGEX-4T1 vector) was used as a positive control.

Preparation of DC and EBV-transformed lines from human PBMC. DC were generated from adherent or CD14-positive PBMC isolated by magnetic cell sorting with CD14 MicroBeads (Miltenyi Biotec, Auburn, Calif.). The isolated cells were incubated for 6 days with GM-CSF and IL-4. After the 6-day incubation period, the immature DC were harvested and transfected with K-SU protein or control proteins by DOTAP, and TNF-α was added to the medium to obtain mature DC. To generate EBV-induced B lymphoblastoid lines (B-LCL) CD3⁺ cells were removed from PBMC by magnetic cell sorting with an autoMACS separator (Miltenyi Biotech) using human CD3 beads according to the manufacturer's instructions. B95-8 culture supernatants containing the transforming strain of EBV were then used to establish the B-LCL.

FACS analysis of DC phenotypes. Immature or mature DC with or without prior pulsing with HERV-K env protein were phenotyped on day 7 using a multicolor CD86-PE/CD209-PerCP-Cy5.5/CD83-APC kit (BD Biosciences, San Jose, Calif.) and analyzed on a BD FACSCalibur system. DC stained with only secondary antibody served as negative controls.

In vitro sensitization of T Cells and T-cell proliferation assay. DC were pulsed with antigen and matured as described above. Autologous PBMC ($1\times10^6$ cells/mL) were added to the loaded DC at a DC to PBMC ratio of 1:30 on day 0. Recombinant human IL-2 (10 U/ml) was added and the cultures incubated for 7 days to generate 1-week IVS cells. The 1-week IVS cells were restimulated on day 14 with autologous DC previously pulsed with antigen to produce 3-week IVS cells. T cell proliferation was evaluated in the PBMC or IVS cells that were stimulated with DC (pulsed for 72 hr with no added protein, K-SU protein or E6 protein, at a DC to PBMC or IVS ratio of 1:30. Results are expressed as counts per minute per $1\times10^5$ PBMC or IVS cells.

ELISPOT assays. A GrB ELISPOT assay to detect and quantitate cytokine-secreting cells in response to antigen was performed using a commercial kit (Biosource International, Camarillo Calif.), following the manufacturer's instructions. The spots were evaluated using an automated ELISPOT reader system (Carl Zeiss, Thornwood, N.Y.) with KS ELISPOT software 4.5+ (ZellNet Consulting). Only spots with fuzzy or diffuse borders were scored as positive. Net frequencies of spot-forming cells were calculated.

Cytotoxic T-lymphocyte assay. CTL assays were performed in round-bottomed 96-well plates using a standard 4-h $^{51}$Cr-release assay (Dolbier, C. L., R. R. Cocke, J. A. Leiferman, M. A. Steinhardt, S. J. Schapiro, P. N. Nehete, J. E. Perlman, and J. Sastry. 2001. Differences in functional immune responses of high vs. low hardy healthy individuals. J Behav Med 24:219-229) using $1\times10^5$ target cells. Target cells were either MCF-7 BC cells or HERV-K (or control antigen) transduced autologous DC or B-LCL cells. Unlabeled K562 cells ($1\times10^5$ cells/well) were added to assess nonspecific lysis. To block cytotoxicity, effector cells were pre-incubated for 30 min at ambient temperature with an anti-human CD3 mAb (10 μg/mL; Ortho Pharmaceutical Corp, Raritan, N.J.).

Multiplex cytokine bead array analysis. The supernatants obtained from T cell proliferation were collected after 7 days of IVS and stored at −20° C. for cytokine bead array analysis using a LINCOplex multiplex immunoassay-based protein array system (LINCO Research, St. Charles, Mo.), which contains microspheres conjugated with mAb specific for target proteins. Fluorescence intensity was measured using a Luminex 100 instrument (Luminex Corporation, Austin, Tex.).

Intracellular cytokine staining. Cytokines produced by CD4$^+$ and CD8$^+$ T cells, including TNF-α, IL-2, and IFN-γ, were assayed by cytokine flow cytometry as previously described (Martins, S. L., L. S. St John, R. E. Champlin, E. D. Wieder, J. McMannis, J. J. Molldrem, and K. V. Komanduri. 2004. Functional assessment and specific depletion of alloreactive human T cells using flow cytometry. Blood 104:3429-3436; Komanduri, K. V., M. N. Viswanathan, E. D. Wieder, D. K. Schmidt, B. M. Bredt, M. A. Jacobson, and J. M. McCune. 1998. Restoration of cytomegalovirus-specific CD4+T-lymphocyte responses after ganciclovir and highly active antiretroviral therapy in individuals infected with HIV-1. Nat Med 4:953-956.). The activated cells were permeabilized with BD Cytofix/Cytoperm buffer for subsequent intracellular staining with PE-conjugated anti-TNF-α, anti-IL-2, or anti-IFN-γ (BD Pharmingen). APC-labeled anti-IgG2a or IgG1 and a PE-conjugated isotype control cocktail were used as single color controls. The samples were acquired and analyzed on a FACSCalibur system.

Statistical analysis. Each assay was performed in triplicate. Statistical significance between groups was determined by the unpaired, two-tailed student's t-test using Prism software (GraphPad). To compare HERV-K expression during progression from normal to cancerous, we used Chi-square test. A P value of <0.05 indicated a significant difference among treatments.

Example 21

Expression of HERV in Melanoma Cell Lines

Detection of the Env region of HERV transcripts in melanoma cells. Total RNA was isolated from cells or tissues and treated with DNase to remove DNA contamination. Reverse transcription and PCR amplification were performed by standard protocols using various HERV Env outer sense and antisense primer pairs including ERV3, HERV-E4-1 and HERV-K type 1, as described previously, and HERV-K type 2.

Expression of HERV-K env protein in melanoma biopsies. We have generated several anti-HERV-K env protein mAb (including 6H5, 4D1, 6E11, 4E11 and 6E5) in our laboratory against recombinant HERV env protein products such as HERV-K Env surface protein, Np9 and Rec proteins (see FIG. 32). Anti-HERV-K Env protein mAb 6H5 was used to detect the expression of HERV-K env protein in melanoma biopsies. More than 75% of melanoma biopsies were HERV-K positive (Table 8 and FIG. 33). Stronger expression of HERV-K was detected as the Clark's level and Breslow thickness increased. All metastatic lymph nodes stained positive for HERV-K expression, even though some skin biopsies were negative. In all of the positive skin expression cases, at least 40% of tumor cells were HERV-K positive.

In summary, the extent of expression of HERV-K is associated with severity of melanoma. We observed no expression in melanoma in situ and nor-tumorigenic melanoma. There was focal expression in the deep tumor cluster of tumorigenic invasive melanoma in complex primary melanoma, where histology showed a tumorigenic compartment adjacent to a non-tumorigenic compartment. When the melanoma progressed to the vertical growth phase there were more positive cases with the strongest HERV-K staining in two desmoplastic types (spindle cell type).

TABLE 8

The expression profile of HERV-K env protein in melanoma biopsies

| No. | ARS[1] | Primary | Metastasis to LN[2] | histology type | Breslow | Clark | HERV-K LN expression | HERV-K skin expression | % HERV-K positive |
|---|---|---|---|---|---|---|---|---|---|
| 1 | 61WM | Skin | | Superficial sprd[3] | 2 | II | | 0-1[4] | |
| 2 | 63WF | Skin | | Superficial sprd | 0.4 | I | | 0 | |
| 3 | 61M | Skin | | nodular type | 4 | IV | | 2 to 3 | 40% |
| 4 | 62WM | Skin | N2[5] | nodular type | 8 | IV | Positive | 3 | 70% |
| 5 | 29WM | Skin | | nodular type | >10 | V | | 2 | >70% |
| 6 | 35WF | Skin | N1 | Superficial sprd | <2 | | Positive | 0 | |
| 7 | 60HM | Skin | | spindle cell | | V | | 3 | 70% |

TABLE 8-continued

The expression profile of HERV-K env protein in melanoma biopsies

| No. | ARS[1] | Primary | Metastasis to LN[2] | histology type | Breslow | Clark | HERV-K LN expression | HERV-K skin expression | % HERV-K positive |
|---|---|---|---|---|---|---|---|---|---|
| 8 | 58HF | | N2 | | | | Positive | 2 to 3 | 70% |
| 9 | 50HM | Skin | N3 | nodular type | | | Positive | 1 | 40% |
| 10 | 61M | Eyelid | | nodular type | 2 | IV | | 1 | |
| 11 | 70WM | Skin | | nodular type | 10 | IV | | 3 | >70% |
| 12 | 72HM | Skin | | spindle cell | >10 | V | | 3 | 50% |

[1]ARS: Age, Race, and Sex.
[2]LN: lymph nodes.
[3]Superficial sprd: Superficial spreading.
[4]0: no expression of HERV-K; 1: low expression; 2: intermediate expression; 3: strong expression.
[6]N: number of lymph nodes affected: N1, 1-4 LN; N2, 4-9 LN; N3, >10 LN. Case No. 1 is negative with a few deeply invaded tumor clusters staining positive.

Detection of anti-HERV antibodies in melanoma patients. Patient sera was serially diluted and tested by ELISA using recombinant purified fusion proteins. Approximately 90% of melanoma patients (37/41 patients) had elevated anti-Rec titers, 85% (35/41) had elevated anti-Np9 titers, and 39% (16/41) had elevated anti-HERV-K antibody titers (FIG. 34A). In comparison with other human cancers such as colon cancer and breast cancer, melanoma patients had the highest antibody titers against both Rec and Np9 protein (FIG. 34B).

Induction of immune response in human cells. We have tested for the presence of anti-HERV-K T-cell responses in human PBMC in cancer patients and normal donors. We used an in vitro system to determine if a CTL immune response can be elicited in cancer patients. DCs were generated from adherent PBMC in cultures containing the cytokine combination of GM-CSF and IL-4. Immature DCs were pulsed with or without HERV-K proteins (Kpro) or RNA (KRNA) and TNF-α for maturation. (FIG. 35).

Examples Summary

Overall, we found that one human retroviral gene product, HERV-K env, is produced as a full-length protein in many BC cell lines and primary human BC specimens and is not found in normal tissue. HERV-K protein was detected in 85% of invasive ductal carcinomas stained by IHC. In addition, immunofluorescence microscopy and FACS analysis demonstrated that the HERV-K env product is not only expressed in the cytoplasm of BC cells, but is also present as a transmembrane cell surface protein detectable in non-permeabilized cells. The expression of HERV-K in BC was found to be associated with the presence of HERV-K-specific CD8$^+$ T-cell responses in patient PBMC-derived T cells, while healthy donors did not exhibit considerable anti-HERV-K activity. These responses were manifested in T cell proliferation, GrB secretion, elevated Th1 cytokine (IL-2 and IFN-γ) secretion, and lysis of HERV-K$^+$ target cells, suggesting that T cells in these patients had been primed in vivo to HERV-K env protein derived from their tumors.

HERV-K env protein may overcome the immunosuppression that is observed in cancer patients. Helper T cell activation results in secretion of interleukin-2 (IL-2), which augments CTL response, and we show increased IL-2 secretion in BC patient K-SU stimulated IVS cells. Our results also show significantly decreased IFN-γ secretion in BC patients relative to normal female donors, which was reversed by K-SU stimulation of BC patient IVS to give increased IFN-γ secretion relative to normal control females, who showed no response to K-SU stimulation.

The cellular immune responses were induced by HERV-K env protein, and not by other viral proteins produced by the same expression vector, such HPV16 E6, HPV16 E7 or LMP2A. The HERV-K specific T cell immune responses, including CD4$^+$ and CD8$^+$ T cell responses, were likely due to HERV-K env protein itself and not to bacterial contamination for two reasons. First, HERV-K mRNA produced by in vitro transcription, independent of expression in a bacterial system, also induced immune response relative to control proteins. Second, control HPV16 E6 and HPV16 E7 proteins produced in bacteria did not promote immune response to nearly as great an extent as did HERV-K protein. Importantly, the immune response could be induced by only a single in vitro sensitization, which led to a recall response.

Only 23.5% of BC patients (4/17) secreted IFN-γ at levels 50 pg/mL before HERV-K in vitro sensitization. After IVS, more than 94% of the BC patients (16/17) had increased IFN-γ secretion. The production of IFN-γ in response to HERV-K is significant because IFN-γ secretion at levels≥50 pg/mL in response to TAA in PBMC from cancer patients was previously reported to be associated with an increase in median cancer patient survival of 88 to 470 days. The production of IL-2, which is used in cancer vaccines to boost immune response to specific cancer antigens, was also significantly increased in BC patients after IVS (71.89±23.06 pg/ml) compared to levels before IVS (12.89±2.242 pg/ml; N=17) (FIG. 6C). These results suggest that HERV-K env surface protein activates an immunostimulatory response against neoplasms.

CD8$^+$ T cells have traditionally been the main focus of tumor immunologists developing anti-cancer vaccines. However, more recently the critical role of antigen-specific CD4$^+$ T-cell responses in generating more effective anti-tumor responses has been recognized. This appreciation for the role of CD4$^+$ T cells stemmed from the discovery of antibodies in patients against tumor antigens including cancer testis antigens such as MAGE-3 and NY-ESO-1 using "SEREX," and the identification of HLA class II-binding epitopes from the same tumor antigens that are recognized by CD4$^+$ T cells. Optimal anti-tumor responses against a specific TAA have been found in cases where both CD8$^+$ and Th1 CD4$^+$ tumor antigen-specific responses are generated. The expression of HERV-K at the surface of BC cells also suggests that the protein can be shed from and internalized by B cells and trigger CD4$^+$ T-cell responses and HERV-K-specific IgG production. Indeed, we found significant titers of anti-HERV-K env IgG in the sera of BC patients while insignificant titers were found in normal donor sera. The presence of these antibodies also suggests that soluble retroviral envelope proteins such as HERV-K may circulate in the blood of cancer patients and may be a diagnostic marker for BC. The presence anti-HERV-K IgG is indicative of the activation of CD4+ T-helper cells. The activation of CD4+ T-helper cells along with CD8+ T cells against HERV-K is significant especially in light of the growing importance of T-helper cells in driving and maintaining CTL responses through the provision of cytokines and signals activating DC antigen presentation to CD8+ T cells.

The precise mechanism by which cancer cells respond to processed peptides of HERV-K env proteins has not been elucidated. The presence of gene polymorphisms or sequence variants, which are exemplified by the expression of HERV-K-MEL in melanoma tumors and HERV-K in BC, and the presence of variants of human teratocarcinoma-derived virus (HTDV)/HERV-K in teratocarcinoma cell lines, may help explain the response of cancer cells to HERV-K peptides. Importantly, multiple HERV-K env spliced products obtained from human BC tissues encode open reading frames without stop codons, suggesting the opportunity for translation of variant HERV-K proteins and subsequent processing of their peptides. Thus, T cell responses against multiple HERV-derived epitopes may exist in cancer patients. Anti-HERV-K antibody can inhibit BC cell, but not benign breast cell proliferation and induce BC cells to undergo apoptosis (data not shown). These data support the idea that HERV-K env surface protein and its antibody suppress cancer through several mechanisms.

Moreover, the examples provide direct evidence that HERV-K Env proteins are immunogenic in melanoma patients. Importantly, these studies are the first to directly show that these viral antigens induce T-cell and CTL capable of killing HERV-K-expressing target cells. We have also found that PBMC from ovarian and breast cancer patients secrete several Th1 or Th2 cytokines in response to HERV-K antigens.

In summary, we report here for the first time the presence of cellular and humoral immune responses against a human endogenous retroviral env protein in breast cancer, ovarian cancer, and melanoma and its ability to recognize and kill cancer cells in vitro. HERV-K env protein expression was found to be highly expressed specifically in cancer with protein expression in >80% of human breast ductal carcinomas and no expression in normal tissues. The re-activation of endogenous retroviral gene products and synthesis of mature protein products in cancer makes these a potentially valuable new pool of tumor associated antigens for targeting in therapeutic vaccines in cancers. The silencing of retroviral gene expression throughout our lifetime and their reactivation specifically in cancer cells suggests that immunological self-tolerance mechanisms against HERV-K and other retroviral proteins may be limited or that the immune system exists in a state of ignorance towards these antigens until cancer develops. Accordingly, prophylactic vaccination may be used to prevent primary tumor development. Similar to anti-viral vaccines now used to prevent cervical cancer and other tumors such as liver cancer, prophylactic vaccines against non-expressed retroviral antigens may elicit long-lived retroviral antigen-specific T cell responses (T-central memory) in an otherwise ignorant host that can eradicate early malignancies re-expressing these retroviral gene products.

Additional Data

Monoclonal, chimeric, humanized, primatized, single chain, Fab fragments and other similar types of antibodies are not found naturally in humans. While HERV-K positive cancer patients may have anti-HERV-K antibodies, until this teaching, no antibody has been discovered, isolated and/or tested for their antitumor effects, especially the antibody that binds HERV-K env proteins expressed only on cancer cells and tumor biopsies and as obtained from HERV-K+ cancer patients.

For example, monoclonal and scFv antibodies are only produced in mice using HERV-K env recombinant protein obtained from tumor biopsies made in the lab by molecular biology techniques. Also, multiple copies HERV-K genes exist in the human genome, but not every gene copy can be actively transcribed or translated into proteins. Several hundred HERV-K env cDNAs isolated from human tumor biospies have been sequenced and selected to generate our antibodies. The monoclonal antibodies were selected and tested for their specificity and sensitivity against HERV-K env protein by multiple assays and five clones were chosen to test for antitumor effects in vitro and in vivo. In addition, scFv for the antibody identified herein as 4D1 with sequences provided in FIG. 16 and the antibody identified herein as 6H5 with sequences provided in FIG. 17 were both generated by a multiple panning process and functionally selected. Their CDRs for heavy chain and light chain are as shown in FIGS. 36 and 37 respectively. More specifically, FIG. 36 depicts the 4D1 scFv nucleotide and amino acid sequences. The 4D1 scFv nucleotide sequence illustrated in FIG. 36 is comprised in SEQ ID NO 11 which sequence includes the consensus sequence sites for two restriction enzymes, Sfi I and the NotI, at the 5' and 3' ends respectively. SEQ ID NO: 13 also comprises a 4D1 scFv nucleotide sequence as shown in FIG. 36 but is missing the 5' Sfi I consensus sequence. The amino acid sequences depicted in FIG. 36 correspond to the amino acids of SEQ ID NO: 12 (with both the restriction sites, 251 amino acid long) and SEQ ID NO:14 (with only the Not I restriction site, 247 amino acids in length). Also depicted in FIG. 36 (from nucleotide 1-337) is the nucleotide sequence of SEQ ID NO: 15, which comprises the heavy chain variable region of 4D1 scFv. The amino acid sequence of SEQ ID NO: 16 (112 amino acids long) corresponds to the protein encoded by SEQ ID NO: 15.

FIG. 36 further shows the nucleotide sequence of SEQ ID NO: 17 (303 nucleotides long), which is the light chain variable region of 4D1 scFv. The amino acid sequence of SEQ ID NO: 18 (101 amino acids long) corresponds to the protein encoded by SEQ ID NO: 17. The three heavy chain complementarity determining regions (CDR) of 4D1 scFv are depicted in FIG. 36, highlighted in blue and denoted as CDR-H1 (SEQ ID NO: 19 (nucleotide); SEQ ID NO: 20 (amino acid); CDR-H2 (SEQ ID NO: 21 (nucleotide); SEQ ID NO: 22 (amino acid); and CDR-H3 (SEQ ID NO: 23 (nucleotide); SEQ ID NO: 24 (amino acid). The three light chain CDRs of 4D1 scFv are also depicted in FIG. 36, highlighted in yellow and denoted as CDR-L1 (SEQ ID NO: 25 (nucleotide); SEQ ID NO: 26 (amino acid); CDR-L2 (SEQ ID NO: 27 (nucleotide); SEQ ID NO: 28 (amino acid); and CDR-L3 (SEQ ID NO: 29 (nucleotide); SEQ ID NO: 30 (amino acid).

FIG. 37 depicts the 6H5 scFv nucleotide and amino acid sequences. The 6H5 scFv nucleotide sequence of FIG. 37 is comprised in SEQ ID NO 49. The entire amino acid sequence depicted in FIG. 37 corresponds to the amino acids of SEQ ID NO: 50. Also depicted in FIG. 37 is the nucleotide sequence of SEQ ID NO: 51 (334 nucleotides in length), which is the heavy chain variable region of 6H5 scFv. The amino acid sequence of SEQ ID NO: 52 (111 amino acids long) corresponds to the protein encoded by SEQ ID NO: 51.

FIG. 37 also shows the nucleotide sequence of SEQ ID NO: 53 (310 nucleotides long), which is the light chain variable region of 6H5 scFv. The amino acid sequence of SEQ ID NO: 54 (103 amino acids long) corresponds to the protein encoded by SEQ ID NO: 53. The three heavy chain complementarity determining regions (CDR) of 6H5 scFv are depicted in FIG. 37, highlighted in blue and denoted as CDR-H1 (SEQ ID NO: 55 (nucleotide); SEQ ID NO: 56 (amino acid); CDR-H2 (SEQ ID NO: 57 (nucleotide); SEQ ID NO: 58 (amino acid); and CDR-H3 (SEQ ID NO: 59 (nucleotide); SEQ ID NO: 60 (amino acid). The three light chain CDR of 6H5 scFv are also depicted in FIG. 37, highlighted in yellow and denoted as CDR-L1 (SEQ ID NO: 61 (nucleotide); SEQ ID NO: 62 (amino acid); CDR-L2 (SEQ ID NO: 63 (nucleotide); SEQ ID NO: 64 (amino acid); and CDR-L3 (SEQ ID NO: 65 (nucleotide); SEQ ID NO: 66 (amino acid). FIG. 68 depicts the humanized 4D1 scFv (Hu 4HD1 scFv) nucleotide and amino acid sequences. The Hu 4D1 scFv nucleotide sequence of FIG. 68 is comprised in SEQ ID NO 31.

The entire amino acid sequence depicted in FIG. 68 corresponds to the amino acids of SEQ ID NO: 32 (254 amino acid long). Also FIG. 68 shows the nucleotide sequence corresponding to SEQ ID NO: 33, which is the heavy chain variable region of Hu 4D1 scFv. The amino acid sequence of SEQ ID NO: 34 comprise the protein encoded by SEQ ID NO: 33. FIG. 68 further identifies the nucleotide sequence of SEQ ID NO: 35 (327 nucleotides long), which is the light chain variable region of Hu 4D1 scFv. The amino acid sequence of SEQ ID NO: 36 (109 amino acids long) corresponds to the protein encoded by SEQ ID NO: 35. The three heavy chain complementarity determining regions (CDR) of Hu 4D1 scFv are depicted in FIG. 68, highlighted in blue and denoted as muCDR-H1 (SEQ ID NO: 37 (nucleotide); SEQ ID NO: 38 (amino acid); muCDR-H2 (SEQ ID NO: 39 (nucleotide); SEQ ID NO: 40 (amino acid); and muCDR-H3 (SEQ ID NO: 41 (nucleotide); SEQ ID NO: 42 (amino acid). The three light chain CDR of Hu 4D1 scFv are depicted in FIG. 68, highlighted in yellow and denoted as muCDR-L1 (SEQ ID NO: 43 (nucleotide); SEQ ID NO: 44 (amino acid); muCDR-L2 (SEQ ID NO: 45 (nucleotide); SEQ ID NO: 46 (amino acid); and muCDR-L3 (SEQ ID NO: 47 (nucleotide); SEQ ID NO: 48 (amino acid).

FIG. 69 depicts the humanized 6H5 scFv (Hu 6H5 scFv) nucleotide and amino acid sequences. The Hu 6H5 scFv nucleotide sequence of FIG. 69 is comprised in SEQ ID NO 67. The entire amino acid sequence depicted in FIG. 69 corresponds to the amino acids of SEQ ID NO: 68 (254 amino acid long). Also FIG. 69 identifies the nucleotide sequence corresponding to SEQ ID NO: 69 (328 nucleotides), which is the heavy chain variable region of Hu 6H5 scFv. The amino acid sequence of SEQ ID NO: 70 (109 amino acids) comprise the protein encoded by SEQ ID NO: 69. FIG. 69 shows the nucleotide sequence of SEQ ID NO: 71 (334 nucleotides long), which have the light chain variable region of Hu 6H5 scFv. The amino acid sequence of SEQ ID NO: 72 (111 amino acids long) corresponds to the protein encoded by SEQ ID NO: 71. The three heavy chain complementarity determining regions (CDR) of Hu 6H5 scFv are also depicted in FIG. 69, highlighted in blue and denoted as muCDR-H1 (SEQ ID NO:73 (nucleotide); SEQ ID NO: 74 (amino acid); muCDR-H2 (SEQ ID NO: 75 (nucleotide); SEQ ID NO: 76 (amino acid); and muCDR-H3 (SEQ ID NO: 77 (nucleotide); SEQ ID NO: 78 (amino acid). The three light chain CDR of Hu 6H5 scFv are further depicted in FIG. 69, highlighted in yellow and denoted as muCDR-L1 (SEQ ID NO: 79 (nucleotide); SEQ ID NO: 80 (amino acid); muCDR-L2 (SEQ ID NO: 81 (nucleotide); SEQ ID NO: 82 (amino acid); and muCDR-L3 (SEQ ID NO: 83 (nucleotide); SEQ ID NO: 84 (amino acid).

Figure 40:
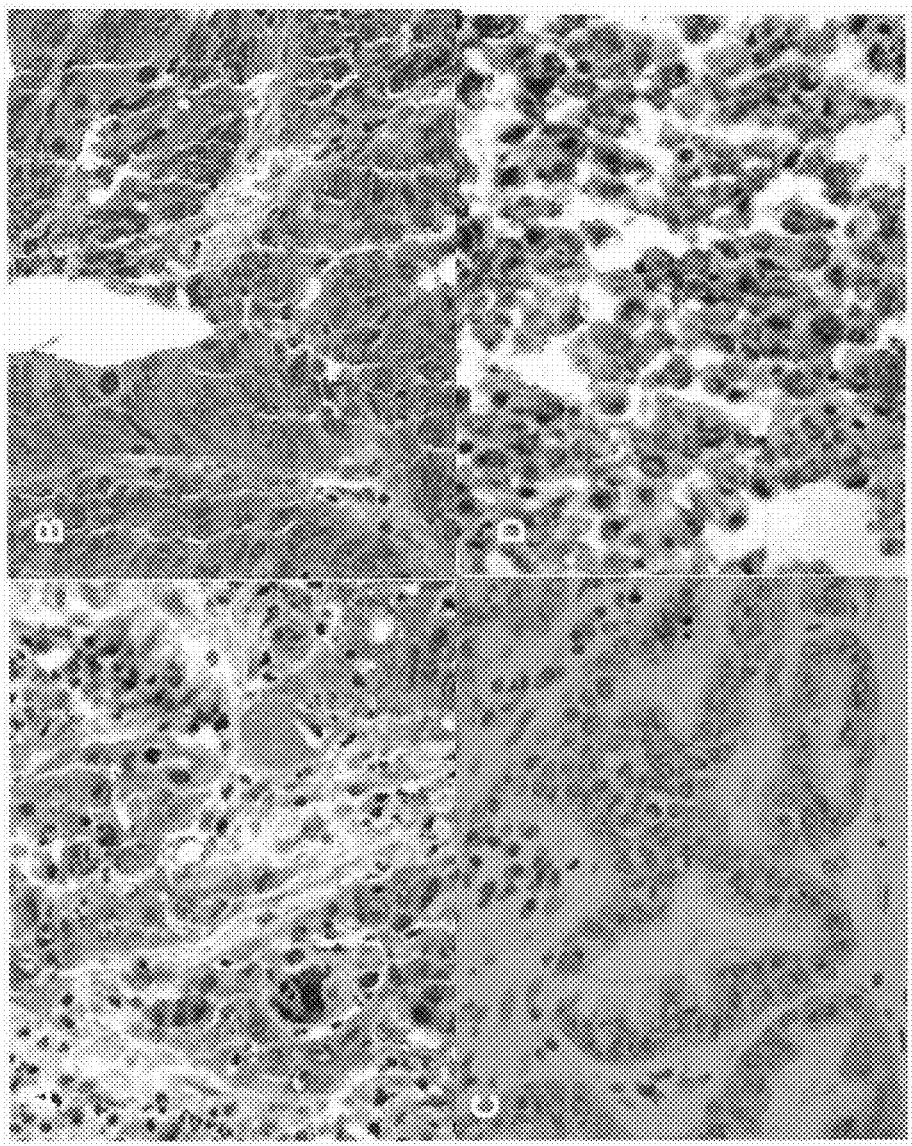
Figure 41:
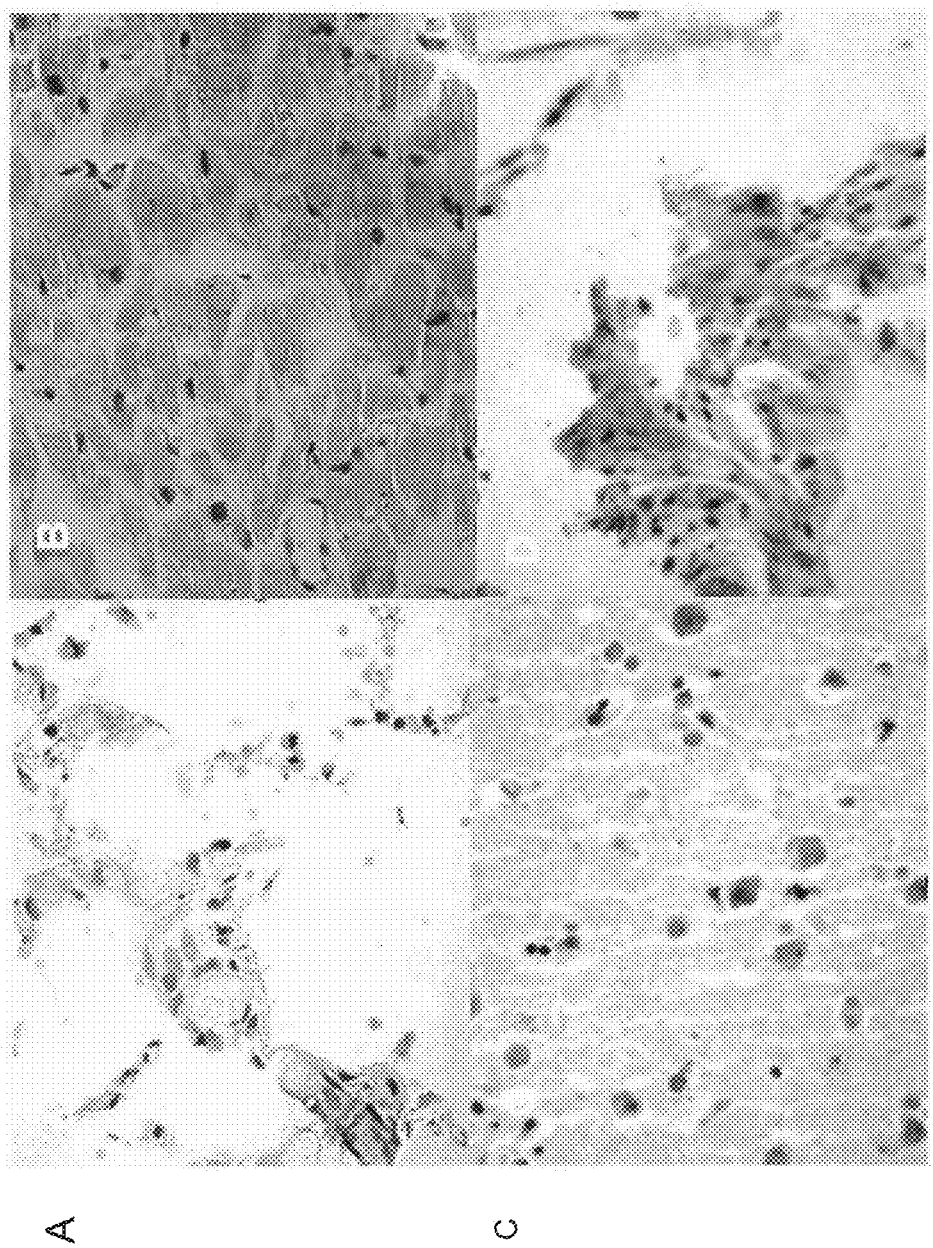

Western blot using 6H5 mAb revealed that HERV-K env protein was expressed only in breast cancer (SKBR3, T47D, MDA-MB-231 and MCF-7). Expression in breast cancer was greater than in early transformed breast cell lines (MCF-10AT), and was not observed at all in an immortalized non-neoplastic breast epithelial cell line (MCF-10A) (FIG. 38). HERV-K env protein in breast cancer cells was sensitive to PNGase F cleavage (FIG. 39; Pink gel), leading to a shift in the mobility of the band recognized by 6H5 (Blue gel), and confirming that HERV-K env protein is a glycoprotein. The antibodies detected the expression of HERV-K env protein only in cancer tissues (including breast, colon, lung, lymphoma, melanoma, and prostate, with the exception of brain tumor), but not in normal (no expression in a total of 38 normal tissues obtained from 33 organs; FIGS. 41 to 43) or uninvolved normal tissues adjacent to cancer tissue array samples stained with 6H5 under identical staining conditions (FIG. 40 and Table 9). This array contained 492 tissues on a single slide. Until this teaching, no one has yet reported that HERV-K env protein is expressed in other cancers, including lung (Table 10 and 11), colon (FIG. 44 top), pancreas (FIG. 44 bottom), and others in FIG. 44 and Tables 9, 10 and 11). Table 12 shows the expression profile of HERV-K in melanoma biopsies.

The antibodies disclosed herein prevent the proliferation of an already existing cancer cell, and, therefore, prevent the proliferation of cancer cells from forming cancer tissues. Furthermore, these antibodies bind to the HERV-K antigen on the cell surface of any HERV-K$^+$ cancer including breast (FIG. 45), melanoma (FIGS. 46 and 47), colon, ovarian, lung, liver, pancreatic, and others (FIG. 48). HERV-K negative cells were detected in most non-malignant cells including breast cell lines MCF-10A, MCF-10AT, and ovarian cell lines T80, T29, and T72 (data not shown). The numbers of surface molecules of HERV-K env protein in breast cancer cells and non-cancer breast cells was quantified by flow cytometry with a QIFI kit using calibration beads (FIGS. 45, 47 and 48), dry cell ELISA (FIG. 46 left), or immunofluorescent staining (FIG. 46 right). Cell surface expression of the HERV-K antigen in several types of cancer cells has also been shown. Specifically, low surface expression of HERV-K env protein was found in LS174T and CaCO2 colon cancer cells.

The ability of HERV-K recombinant protein to block binding of anti-HERV-K antibodies to the cell surface was evaluated by pre-incubating the mAbs with HERV-K recombinant protein (FIG. 49). Anti-mIgG AF647 only was used as control. Furthermore, cycling of HERV-K env protein was observed between the cell surface and intracellular stores in breast cells. Cells were first incubated with 6H5 mAb at 4° C., and HERV-K env protein membrane expression at 0 time was determined. After 1, 5, 15, and 45 min incubation at 37° C., samples were evaluated for membrane expression to assess time-dependent endocytosis of HERV-K env protein. Half of the cells were labeled with anti-mouse-IgG AF647 to detect HERV-K env protein remaining on the cell surface (top panel). The other half were treated with an acid buffer to strip the 6H5 from the membrane, and were re-incubated with another anti-HERV-K env mAb, 4D1-555, to detect the change in HERV-K cell-surface binding level (bottom panel). Time-dependent internalization of HERV-K env protein was observed on MCF-7, MDA-MB-231, and T47D breast cancer cells (FIG. 50). The disappearance of 6H5 was presented as percentage of internalization calculated by the following ratio: (mean fluorescence at 0 min-mean fluorescence at each time point)/(mean fluorescence at 0 min). The percentage of internalization at 15 and 45 min was 36.6% and 39% for T47D cells, 47.96% and 57.92% for MCF-7, and 41.94% and 64.52% for MDA-MB-231 cells, respectively. No significant change in cell-surface binding level of the conformationdependent 4D1 antibody was detected (bottom panel). Furthermore, net cellular uptake rates of anti-HERV-K antibodies were determined in HERV-K$^+$ cells (FIG. 51). Surface quenching allows for distinction of surface and internal antibody fractions. Total cellular fluorescence was measured at each time point by flow cytometry and the internal and surface fractions determined by surface quenching with an anti-Oregon green IgG. The internal fluorescence was then calculated as total MFI-surface MFI. Total, surface, and internalized HERV-K env protein in MCF-7, MDA-MB-231, T47D, and MCF-10A cells were compared at 0, 1.5, 3, 6, and 9 hr. The rank in expression of HERV-K env protein from high to low was MCF-7, MDA-MB-231, T47D, and MCF-10A. In addition, metabolic turnover of HERV-K env protein was assayed to determine the HERV-K env protein internalization rate (FIG. 52). HERV-K was degraded with a half amount between 15 to 45 min, similar to the internalization rate of the anti-HERV-K antibodies. Of interest, an increase in surface expression of HERV-K env protein was detected at 180 min. The two bands of surface proteins detected correspond to type 2 (top band) and type 1 of HERV-K env protein. The difference in band size is due to the presence or absence of a 292 by sequence in the env gene.

MCF-7 cells were treated with several concentrations of 6H5 or 6E11 mAb or mIgG on day 0, and cell proliferation was measured by MTS assay (OD 492 nm; top left) or cytotoxicity assay (crystal violet staining; OD 600 nm; top right) after 72 hr (FIGS. 53 and 54). 6H5 and 6E11 inhibited MCF-7 cell proliferation, compared to cells treated with mIgG. In addition, both mAbs were cytotoxic toward the breast cancer cell lines, compared to cells treated with mIgG. HERV-K 6H5 and 6E11 mAbs (≤0.1 µg/ml) inhibited MCF-7 cell proliferation (p<0.0001). Both 6H5 and 6E11 also showed significant cytotoxicity toward MCF-7 cells (p=0.0069 for 6H5; p=0.0002 for 6E11). There was no cytotoxicity of 6H5 toward MCF-10A normal breast cells, in contrast to the significant cytotoxicity of 6H5 toward MCF-7 and MDA-MB-231 breast cancer cells (FIG. 54).

As to cell death, FIGS. 53, 54, 55 and 56 provide data showing conclusively that the antibodies of the subject invention induces apoptosis (cell death). The annexin V assay allows for the rapid, specific, and quantitative identification of apoptosis in individual cells. Viable cells are Annexin V− and 7AAD−; cells in early apoptosis are Annexin V+ and 7AAD−; dead cells or cells in late apoptosis are Annexin V+ and 7AAD+. Untreated cells or cells treated with mIgG were used as controls. The effect of 6H5 on induction of apoptosis in melanoma cells is shown in FIG. 55. The effect of 6H5 (red tracing) or 6H5-rGel (blue tracing) on induction of apoptosis in breast cells, in comparison to the same cells not treated with 6H5 or 6H5-rGel (cells stained with anti-mouse IgG; gray color) is shown FIG. 56. The breast cancer cell lines MDA-MB-453 (52.28% or 33.82% apoptosis, after treatment with 6H5 or 6H5-rGel, respectively), MCF-7 (43.68% or 39.32%), T47D (33.14% or 23.29%), and MDA-MB-231 (63.6% or 53.02%) were induced to undergo apoptosis to a much greater extent than MCF-10A non-malignant breast (6.48% or 4.96%) or MCF-10AT preneoplastic breast (8.4% or 9.42%) cells, after 6H5 (10 g/ml) or 6H5-rGel (10 g/ml) treatment. This 6H5-induced apoptosis is followed by the elimination of dead cells and thereby eliminates cancer cells.

These anti-HERV mAbs affect expression of a major death receptor on breast cancer cells. Caspases play an important role in programmed cell death. Caspase-3 is a key executioner of apoptosis, whose activation is mediated by the initiator caspases, caspase-8 and caspase-9. There was increased expression of active caspases 3, 8, and 9 in breast cancer cells treated with 6H5 or 6E11 compared with cells treated with control mIgG (FIG. 57). Expression of these caspases in breast cancer cells treated with 6E11 or 6H5 did not decrease after treatment with Z-VAD (150 µM), which indicates that 6H5 and 6E11 induce breast cancer cells to undergo apoptosis through caspase 3 independent pathways.

BrdU is incorporated instead of thymidine into the DNA of proliferating cells and subsequently detected by fluorescent activated cell sorting (FACS) using a Beckton Dickinson FACSarray instrument. Cells were treated with 6H5 (10 µg/ml) for 72 h and DNA-BrdU incorporation was determined (FIG. 58). BrdU incorporation in breast cells was expressed as a percentage of control (the cells treated with mIgG). BrdU incorporation in all cancer cells was lower than MCF-10A (non-malignant breast cells). Breast cancer cells treated with 6H5 revealed a time-dependent decrease in DNA synthesis in various breast cancer cell lines (data not shown). HERV-K env protein activation and cell cycle responses were also observed after treatment with the mAbs. To test whether an induction of cell cycle arrest contributed to the antiproliferative potency of 6H5 in breast cancer cell lines, we performed cell cycle analyses. Incubation breast cancer cells with 10 µg/ml for 24, 48, 72 hr led to arrest of the cells in various phases. For example, G0/G1 arrest was found in T47D breast cancer cells treated with 6H5, whereas S arrest was observed for MCF-7 breast cancer cells, and G2 arrest for other breast cancer cells (FIG. 59).

IgG type antibodies containing the Fc portion usually mediate immunological cytotoxicity via antibody-dependent cell-death cytotoxicity (ADCC) or complement-dependent cytotoxicity (CDC). Murine IgG2a and IgG3 mAbs are the most effective in mediating ADCC, and both 6H5 and 6E11 are IgG2a. We demonstrated that both 6H5 and 6E11 are reactive against breast cancer cell lines in CDC (FIG. 60) and ADCC (FIG. 61) assays. There was a greater reduction in cell viability when MCF-7 cells were treated with 10 µg 6E11 than with 1 µg, or when MCF-7 cells transfected with HERV-K surface recombinant protein were treated with 10 µg 6E11 (10 µg+K) than with 1 µg (10 µg+K). In addition, cell viability decreased when the dilutions of complement were increased to 1:10, 1:15 or 1:20, compared to controls (no mAb, or heat-inactivated complement) (FIG. 60 top panel). A significant reduction in cell viability was observed in many instances when MCF-7 or MDA-MB-435eB1 cells were treated with mAb in the presence of 1:10 to 1:30 dilutions of complement, in CDC assays (FIG. 60; bottom left and right panels). The percent lysis in ADCC assays ranged from 15% to 30% after treatment with 6H5 or 6E11, using normal donor PBMC (FIG. 61, top left and top right panels). No mAb (T+E) or no effector cells (T+Ab) were used as controls. Higher cytotoxicity toward MCF-7 was observed if we used PBMC from breast cancer patients (BC4703; IDC) than from normal donors (NL5187 or NL3520) (FIG. 61, bottom panel). However, not every breast cancer patient's PBMC had higher cytotoxicity toward MCF-7 (BC5796). In addition, we noted that increased cell lysis was detected in target cells (T) that expressed HERV-K env protein by transfection. The above results clearly demonstrate a biological effect of our HERV-K anti-tumor antibody. Our results and others suggest that HERV-K plays a role in regulation of cell growth and tumor progression, which prompted us to investigate the specific contribution of HERV-K env protein to tumorigenicity in vivo. Tumor sizes were significantly reduced, and the appearance of tumors was significantly delayed, in groups of immunodeficient mice inoculated with MDA-MB-231 (FIG. 62, top left and top right panels) and MCF-7 (top right panel), and treated with 6H5 only (top left and top right panels) or 6H5 and 6H5rGel (bottom panel). A significant tumor size reduction was observed in mice treated with 6H5 (P=0.0051 for MCF-7 or P=0.0275 for MDA-MB-231; paired t-test), or with 6H5 and 6H5-rGel (P=0.0020 for one-way analysis of variance or P<0.0001 for Bartlett's test for equal variances). Tumor tissues obtained from mice treated with 6H5 for 0, 1 or 2 weeks were compared using TUNEL or Ki-67 assays. As shown in FIG. 63, there were 2.5 and 3.6-fold increases in TUNEL-positive cells, and a 29.3 and 60.3% decrease in Ki-67-positive cells, in tumors from mice treated with 6H5 after 1 week and 2 week periods, respectively, in comparison to control mice (FIG. 7d; P<0.0001, one way analysis of variance). In general, there was decreased expression of HERV-K env protein and Ki67, and increased apoptosis in breast cancer cells treated with 6H5, and these effects were greater when cells were treated twice with mAb.

Further, the epitopes of the antibodies of prior art such as Herve et al. are not the same as the epitopes described herein. Herve et al. found the antibodies in 32-47% of 84 sera from patients with autoimmune rheumatic disease, and 29% of 35 normal controls. Herve et al. discovered an immunodominant epitope (GKTCPKEIPKGSKNT) using patient serum, but Herve et al. did not isolate the antibody. While the antibodies of Herve et al. can be isolated, they cannot be modified to produce the antibodies described herein. It is only through the teaching provided in this specification that it is known which antibodies are effective in treating cancer. Herve et al only reported on the presence and epitopes of antibodies and such antibodies were not useful to treat disease. This is especially true because Herve et al. did not isolate these antibodies, which are contained in the milieu of many thousands of proteins present in human cells. Herve et al. found that the antibody exists in the sera of humans, which is not equivalent to isolating it. Multiple HERV-K alternatively-spliced proteins are present in humans, and we are the only group who has reported and isolated those HERV-K variants that are active in cancer.

In addition, Herve et al. does not present evidence that the antibodies disclosed could be used to treat any disease when administered to another individual. Nor is there a reason to believe this. An antibody may bind to an antigen on a cancer cell. However, it does not necessary follow that such antibody will kill the cancer cell. In fact, it is conceivable that binding will promote the growth of the cell via activation of growth-stimulatory cell signaling pathways. On the other hand, as noted above, the antibodies described herein have been shown not only bind to the antigen, but to promote cell death. For example, approximately twenty copies of endogenous betaretroviruses (enJSRVs) are present in the genome of sheep and goats, but only one sheep pulmonary adenomatosis virus (Jaagsiekte sheep retrovirus) induces a naturally occurring lung cancer. More than 170 copies of HERV-K are present in the genome of humans, but the expressed copies that induce naturally occurring cancer are not known yet. Five individual anti-HERV-K antibodies were selected from a library and they have common properties such as greater reactivity toward cancer cells than non-malignant cells; however, they have different sensitivity to various cell lines or epitopes of HERV-K env proteins. The role(s) of HERV-K play in tumorgenesis are not clear. They are silent in normal, but expressed in cancers to activate other genes.

For example, in our experiments, MCF-7 cells were treated with mIgG or 6H5 (10 μg/ml) for 24 hr, and three Superarray PCR array kits were used to determine how blocking of HERV-k with 6H5 affects the apoptosis pathway, the cancer pathway, and the p53 signaling pathway (FIGS. 64, 66 and 67). We found that 3 of 84 key genes involved in apoptosis, or programmed cell death were upregulated by 6H5 using a human apoptosis PCR array and the fold changes are shown (FIG. 64). The three upregulated genes are TNFRSF25: tumor necrosis factor receptor superfamily, member 25; TNFSF8: tumor necrosis factor (ligand) superfamily, member 8; and CIDEA: cell death-inducing DFFA-like effector a. CIDEA was further confirmed by Western blot using anti-CIDEA antibody (FIG. 65). The expression of CIDEA was detected only in cancer cells treated with 6E11, but not mIgG. In FIG. 66, TWIST1 (Probable transcription factor) and MMP1 (collagenase-1), genes involved in invasion and metastasis, were downregulated in MCF-7 breast cancer cells, as assessed by the Cancer Finder Pathway Superarray, and the fold changes are shown.

As shown in FIG. 67, changes in expression of 84 genes related to p53-mediated signal transduction, including p53-related genes involved in the processes of apoptosis, the cell cycle, cell growth, proliferation and differentiation, and DNA repair were evaluated using the p53 Signaling Pathway RT Profiler PCR Array. The array includes p53-related genes involved in the processes of apoptosis, the cell cycle, cell growth, proliferation and differentiation and DNA repair. We found that 10 of 84 genes were upregulated in the cells treated with 6H5, in comparison to control cells treated with mIgG. The roles of these genes in relation to cancer are shown below:

WT1 2.31: Negative Regulation of the Cell Cycle:
TP53 2.35: Induction of Apoptosis
TNFRSF10D 2.68: Anti-Apoptosis, TNF-related apoptosis-inducing ligand (TRAIL)
MYOD1 2.95: Cell Growth and Differentiation, myogenic differentiation 1
TNF 2.37: Anti-Apoptosis, TNF initiates programmed cell death (PCD) or apoptosis in transformed cells causing DNA fragmentation and cytolysis
P53AIP1 3.59: Other Apoptosis Genes, p53-regulated Apoptosis-Inducing Protein 1, p53AIP1, which is localized within mitochondria, leads to apoptotic cell death through dissipation of mitochondrial A(psi)m. p53AIP1 Regulates the Mitochondrial Apoptotic Pathway, p53AIP1 gene, a novel p53 target that mediates p53-dependent apoptosis
FASLG 3.86: Induction of Apoptosis
GML 3.67: Other Apoptosis Genes: Glycosyl-phosphatidylinositol-anchored molecule-like protein (GML) may play a role in the apoptotic pathway or cell-cycle regulation induced by p53 after DNA damage
IFNB1 3.36: Negative Regulation of Cell Proliferation, interferon, beta 1, fibroblast, has been shown to be frequently deleted or rearranged in a number of human cancers.
IL6 3.05: Positive Regulation of Cell Proliferation: IL-6 was found to protect against p53-induced apoptosis.

TABLE 9

Expression of HERV-K in a tissue array by IHC using 6H5 mAb

| Tissues | Negative | Positive | N |
|---|---|---|---|
| Brain tumor | 21 (100%) | 0 | 21 |
| Breast AdCa | 3 (7.14%) | 39 (92.86%) | 42 |
| Colonic AdCa | 0 | 12 (100%) | 12 |
| Lung cancer | 4 (9.76%) | 37 (90.24%) | 41 |
| Lymphoma | 33 (82.5%) | 7 (17.5%) | 40 |
| Melanoma | 4 (23.53%) | 13 (76.47%) | 17 |
| Prostate AdCa | 0 | 3 (100%) | 3 |
| Normal tissues | 38 (100%) |  | 38 |
| Total cases |  |  | 214 |

TABLE 10

Expression of HERV-K in a lung tissue array by IHC using 6H5 mAb

|          | 3+    | 2+    | 1+    | Neg   | Age   | f/m     | Total |
|----------|-------|-------|-------|-------|-------|---------|-------|
| Adca     | 4*    | 3     | 6     | 2     | 60.12 | 6 f/9 m | 15    |
| squamous | 3     | 4     | 2     | 2     | 59.09 | 1 f/10 m| 11    |
| others   | 1     | 1     | 0     | 3     | 60.2  | 3 f/2 m | 5     |
| Adca     | 26.67 | 20.00 | 40.00 | 13.33 |       |         | 86.67 |
| squamous | 27.27 | 36.36 | 18.18 | 18.18 |       |         | 81.82 |
| others   | 20    | 20    | 0     | 60    |       |         | 40.00 |

The expression of HERV-K env protein was evaluated in 31 tumor cases and 31 matched normal tissues by immunohistochemistry using 6H5 mAb. Results for matched normal tissues are not shown because only 1 matching normal case (matched to Adca) was weakly positive Neg: Negative

*Values are number of tissues in each category. Positive staining was scored as 3 > 2 > 1

Adca: adenocarcinoma

Squamous: squamous cell carcinoma

Others including carcinoid tumor, large cell carcinoma, large cell necroendocrine carcinoma, and bronchiolcalveolar carcinoma

TABLE 11

Expression of HERV-K in a lung tissue array by IHC using 6H5 mAb

|             | 3+    | 2+    | 1+    | Neg   | Age   | f/m     | Total |
|-------------|-------|-------|-------|-------|-------|---------|-------|
| Adca        | 13*   | 7     | 4     | 3     | 58.59 | 16 m/11 f | 27  |
| squamous    | 3     | 3     | 4     | 1     | 62.67 | 2 f/9 m | 11    |
| others      | 1     | 2     | 3     | N/A   | 58.83 | 3 f/3 m | 6     |
| non-neopla  |       |       |       | 7     | 59    | 2 f/5 m | 7     |
| Adca        | 48.15 | 25.93 | 14.81 | 11.11 |       |         | 88.89 |
| squamous    | 27.27 | 27.27 | 36.36 | 9.09  |       |         | 90.91 |
| others      | 16.67 | 33.33 | 50.00 | 0.00  |       |         | 100.00|

The expression of HERV-K env protein was evaluated in 44 tumor cases and 7 normal lung tissues by immunohistochemistry using 6H5 mAb Neg: Negative

*Values are number of tissues in each category. Positive staining was scored as 3 > 2 > 1

Non-neopla: non-neoplastic

Adca: adenocarcinoma

Squamous: squamous cell carcinoma

Others: including carcinoid tumor, large cell carcinoma, large cell necroendocrine carcinoma, and bronchiolcalveolar carcinoma

TABLE 12

The expression profile of HERV-K env protein in melanoma

| Tissue              | Nevi         | In situ melanoma | Non-nodular MM* | Nodular MM    | Metastases    |
|---------------------|--------------|------------------|-----------------|---------------|---------------|
| # positive/# total  | 3/12         | 8/12             | 17/19           | 14/14         | 4/4           |
| score ± SEM         | 0.42 ± 0.23  | 0.67 ± 0.49      | 1.95 ± 0.91     | 2.29 ± 0.61   | 1.25 ± 0.50   |

*MM: malignant melanoma

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

Therefore, the present disclosure is well adapted to attain the ends and advantages mentioned as well as those that are inherent therein. While numerous changes may be made by those skilled in the art, such changes are encompassed within the spirit of this disclosure as illustrated, in part, by the appended claims.

What is claimed is:

1. A monoclonal antibody specifically binding the HERV-K antigen comprising the following:
   a CDR-H1 comprising SEQ ID NO:56;
   a CDR-H2 comprising SEQ ID NO:58;
   a CDR-H3 comprising SEQ ID NO:60;
   a CDR-L1 comprising SEQ ID NO:62;
   a CDR-L2 comprising SEQ ID NO:64; and
   a CDR-L3 comprising SEQ ID NO:66.

2. The antibody of claim 1, further defined as comprising a heavy chain comprising SEQ ID NO:52 and a light chain comprising SEQ ID NO:54.

3. An ScFv comprising SEQ ID NO:50.

4. A monoclonal antibody specifically binding the HERV-K antigen comprising the following:
   a CDR-H1 comprising SEQ ID NO:74;
   a CDR-H2 comprising SEQ ID NO:76;
   a CDR-H3 comprising SEQ ID NO:78;
   a CDR-L1 comprising SEQ ID NO:80;
   a CDR-L2 comprising SEQ ID NO:82; and
   a CDR-L3 comprising SEQ ID NO:84.

5. The antibody of claim 4, further defined as comprising a heavy chain comprising SEQ ID NO:70 and a light chain comprising SEQ ID NO:72.

6. A humanized ScFv comprising SEQ ID NO:68.

* * * * *

SEQUENCE LISTING

```
<160> NUMBER OF SEQ ID NOS: 84

<210> SEQ ID NO 1
<211> LENGTH: 29
<212> TYPE: DNA
<213> ORGANISM: Homo sapiens

<400> SEQUENCE: 1
atcccgagta catctacagt cagccttac                                           29

<210> SEQ ID NO 2
<211> LENGTH: 29
<212> TYPE: DNA
<213> ORGANISM: Homo sapiens

<400> SEQUENCE: 2
gacatttgaa gttctacaat gaacccatc                                           29

<210> SEQ ID NO 3
<211> LENGTH: 7
<212> TYPE: DNA
<213> ORGANISM: Homo sapiens
```

<400> SEQUENCE: 3 tctctat                                                              7

<210> SEQ ID NO 4
<211> LENGTH: 15
<212> TYPE: DNA
<213> ORGANISM: Homo sapiens

<400> SEQUENCE: 4
tcaaaactga caatg                                                    15

<210> SEQ ID NO 5
<211> LENGTH: 34
<212> TYPE: DNA
<213> ORGANISM: Homo sapiens

<400> SEQUENCE: 5
cttttccaaa tctctcatcc caccttacga gaaa                               34

<210> SEQ ID NO 6
<211> LENGTH: 28
<212> TYPE: DNA
<213> ORGANISM: Homo sapiens

<400> SEQUENCE: 6
atcagcttcc tgtttggata cccactag                                      28

<210> SEQ ID NO 7
<211> LENGTH: 36
<212> TYPE: DNA
<213> ORGANISM: Homo sapiens

<400> SEQUENCE: 7
atttctataa atgtttaaaa aatttaaagt atagag                             36

<210> SEQ ID NO 8
<211> LENGTH: 29
<212> TYPE: DNA
<213> ORGANISM: Homo sapiens

<400> SEQUENCE: 8
aaagaaataa ggggacccgg ggaaccagc                                     29

<210> SEQ ID NO 9
<211> LENGTH: 45
<212> TYPE: DNA
<213> ORGANISM: Homo sapiens

<400> SEQUENCE: 9
ttgacgagag atcccgagta catctacagt cagccttgcg ggaga                   45

<210> SEQ ID NO 10
<211> LENGTH: 25
<212> TYPE: DNA
<213> ORGANISM: Homo sapiens

<400> SEQUENCE: 10
gcaccaggat gtttaatgcc taagc                                         25

<210> SEQ ID NO 11
<211> LENGTH: 763
<212> TYPE: DNA
<213> ORGANISM: Artificial Sequence
<220> FEATURE:
<223> OTHER INFORMATION: Description of Artificial Sequence: Synthetic anti HERV-K scFV 4d1 polynucleotide

<400> SEQUENCE: 11

```
ggcccagccg gccatggccc aggtccagct gcaggagtca ggaggtggcc tggtgcagcc      60
tggaggatcc ctgaaactct cctgtgcagc ctcaggattc gattttagta gatactggat     120
gagttgggtc cggcaggctc agggaaagg gctagaatgg attggagaaa ttaatccaga      180
tagcagtacg ataaactata cgccatctct aaaggataaa ttcatcatct ccagagacaa     240
cgccaaaaat acgctgtacc tgcaaatgag caaagtgaga tctgaggaca cagcccctta     300
ttactgtgca agacgagggt actacggtag tagctactgg tttgcttact ggggccaagg     360
caccacggtc accgtctcct caggtggagg cggttcaggc ggaggtggcg ctggcggtgg     420
cggatcggac atcgagctca ctcagtctcc agcaatcatg tctgcatctc taggagaacg     480
ggtcaccatg acctgcactg ccagctcaag tgtaagttcc agttacttgc actggtacca     540
gcagaagcca ggatcctccc ccaaactctg gatttatagc acatccaacc tggcttctgg     600
agtcccagct cgcttcagtg gcagtgggtc tgggacctct tactctctca caatcagcag     660
catggaggct gaagatgctg ccacttatta ctgccaccag tatcatcgtt ccccacccac     720
gttcggctcg ggcaccaagc tggaaatcaa acgggcggcc gca                       763
```

<210> SEQ ID NO 12
<211> LENGTH: 251
<212> TYPE: PRT
<213> ORGANISM: Artificial Sequence
<220> FEATURE:
<223> OTHER INFORMATION: Description of Artificial Sequence: Synthetic anti HERV-K scFV polypeptide

<400> SEQUENCE: 12

```
Met Ala Gln Val Gln Leu Gln Glu Ser Gly Gly Gly Leu Val Gln Pro
1               5                   10                  15

Gly Gly Ser Leu Lys Leu Ser Cys Ala Ala Ser Gly Phe Asp Phe Ser
            20                  25                  30

Arg Tyr Trp Met Ser Trp Val Arg Gln Ala Pro Gly Lys Gly Leu Glu
        35                  40                  45

Trp Ile Gly Glu Ile Asn Pro Asp Ser Ser Thr Ile Asn Tyr Thr Pro
    50                  55                  60

Ser Leu Lys Asp Lys Phe Ile Ile Ser Arg Asp Asn Ala Lys Asn Thr
65                  70                  75                  80

Leu Tyr Leu Gln Met Ser Lys Val Arg Ser Glu Asp Thr Ala Leu Tyr
                85                  90                  95

Tyr Cys Ala Arg Arg Gly Tyr Tyr Gly Ser Ser Tyr Trp Phe Ala Tyr
            100                 105                 110

Trp Gly Gln Gly Thr Thr Val Thr Val Ser Ser Gly Gly Gly Gly Ser
        115                 120                 125

Gly Gly Gly Gly Ala Gly Gly Gly Ser Asp Ile Glu Leu Thr Gln
    130                 135                 140

Ser Pro Ala Ile Met Ser Ala Ser Leu Gly Glu Arg Val Thr Met Thr
145                 150                 155                 160

Cys Thr Ala Ser Ser Ser Val Ser Ser Ser Tyr Leu His Trp Tyr Gln
                165                 170                 175

Gln Lys Pro Gly Ser Ser Pro Lys Leu Trp Ile Tyr Ser Thr Ser Asn
            180                 185                 190
```

```
Leu Ala Ser Gly Val Pro Ala Arg Phe Ser Gly Ser Gly Ser Gly Thr
        195                 200                 205

Ser Tyr Ser Leu Thr Ile Ser Ser Met Glu Ala Glu Asp Ala Ala Thr
    210                 215                 220

Tyr Tyr Cys His Gln Tyr His Arg Ser Pro Pro Thr Phe Gly Ser Gly
225                 230                 235                 240

Thr Lys Leu Glu Ile Lys Arg Ala Ala Ala Glu
                245                 250
```

<210> SEQ ID NO 13
<211> LENGTH: 750
<212> TYPE: DNA
<213> ORGANISM: Artificial Sequence
<220> FEATURE:
<223> OTHER INFORMATION: Description of Artificial Sequence: Synthetic
      4D1 scFv polynucleotide

<400> SEQUENCE: 13

```
atggcccagg tccagctgca ggagtcagga ggtggcctgg tgcagcctgg aggatccctg      60
aaactctcct gtgcagcctc aggattcgat tttagtagat actggatgag ttgggtccgg     120
caggctccag ggaaagggct agaatggatt ggagaaatta atccagatag cagtacgata     180
aactatacgc catctctaaa ggataaattc atcatctcca gagacaacgc caaaaatacg     240
ctgtacctgc aaatgagcaa agtgagatct gaggacacag cccttttatta ctgtgcaaga     300
cgagggtact acggtagtag ctactggttt gcttactggg gccaaggcac cacggtcacc     360
gtctcctcag gtggaggcgg ttcaggcgga ggtggcgctg gcggtggcgg atcggacatc     420
gagctcactc agtctccagc aatcatgtct gcatctctag agaacgggt caccatgacc     480
tgcactgcca gctcaagtgt aagttccagt tacttgcact ggtaccagca gaagccagga     540
tcctccccca aactctggat ttatagcaca tccaacctgg cttctggagt cccagctcgc     600
ttcagtggca gtgggtctgg gacctcttac tctctcacaa tcagcagcat ggaggctgaa     660
gatgctgcca cttattactg ccaccagtat catcgttccc cacccacgtt cggctcgggc     720
accaagctgg aaatcaaacg ggcggccgca                                      750
```

<210> SEQ ID NO 14
<211> LENGTH: 247
<212> TYPE: PRT
<213> ORGANISM: Artificial Sequence
<220> FEATURE:
<223> OTHER INFORMATION: Description of Artificial Sequence: Synthetic
      4D1 scFv polypeptide

<400> SEQUENCE: 14

```
Met Ala Gln Val Gln Leu Gln Glu Ser Gly Gly Gly Leu Val Gln Pro
1               5                   10                  15

Gly Gly Ser Leu Lys Leu Ser Cys Ala Ala Ser Gly Phe Asp Phe Ser
            20                  25                  30

Arg Tyr Trp Met Ser Trp Val Arg Gln Ala Pro Gly Lys Gly Leu Glu
        35                  40                  45

Trp Ile Gly Glu Ile Asn Pro Asp Ser Ser Thr Ile Asn Tyr Thr Pro
    50                  55                  60

Ser Leu Lys Asp Lys Phe Ile Ile Ser Arg Asp Asn Ala Lys Asn Thr
65                  70                  75                  80

Leu Tyr Leu Gln Met Ser Lys Val Arg Ser Glu Asp Thr Ala Leu Tyr
                85                  90                  95

Tyr Cys Ala Arg Arg Gly Tyr Tyr Gly Ser Ser Tyr Trp Phe Ala Tyr
```

```
                100                 105                 110
Trp Gly Gln Gly Thr Val Thr Val Ser Ser Gly Gly Gly Ser
            115                 120                 125

Gly Gly Gly Gly Ala Gly Gly Gly Ser Asp Ile Glu Leu Thr Gln
            130                 135                 140

Ser Pro Ala Ile Met Ser Ala Ser Leu Gly Glu Arg Val Thr Met Thr
145                 150                 155                 160

Cys Thr Ala Ser Ser Val Ser Ser Ser Tyr Leu His Trp Tyr Gln
                165                 170                 175

Gln Lys Pro Gly Ser Ser Pro Lys Leu Trp Ile Tyr Ser Thr Ser Asn
                180                 185                 190

Leu Ala Ser Gly Val Pro Ala Arg Phe Ser Gly Ser Gly Ser Gly Thr
                195                 200                 205

Ser Tyr Ser Leu Thr Ile Ser Ser Met Glu Ala Glu Asp Ala Ala Thr
                210                 215                 220

Tyr Tyr Cys His Gln Tyr His Arg Ser Pro Pro Thr Phe Gly Ser Gly
225                 230                 235                 240

Thr Lys Leu Glu Ile Lys Arg
                245

<210> SEQ ID NO 15
<211> LENGTH: 337
<212> TYPE: DNA
<213> ORGANISM: Artificial Sequence
<220> FEATURE:
<223> OTHER INFORMATION: Description of Artificial Sequence: Synthetic
      heavy chain variable region of 4D1 scFv polynucleotide

<400> SEQUENCE: 15
atggcccagg tccagctgca ggagtcagga ggtggcctgg tgcagcctgg aggatccctg      60
aaactctcct gtgcagcctc aggattcgat tttagtagat actggatgag ttgggtccgg     120
caggctccag ggaagggct agaatggatt ggagaaatta atccagatag cagtacgata      180
aactatacgc atctctaaa ggataaattc atcatctcca gagacaacgc caaaaatacg      240
ctgtacctgc aaatgagcaa agtgagatct gaggacacag ccctttatta ctgtgcaaga     300
cgagggtact acggtagtag ctactggttt gcttact                              337

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      heavy chain variable region of 4D1 scFv polypeptide

<400> SEQUENCE: 16

Met Ala Gln Val Gln Leu Gln Glu Ser Gly Gly Gly Leu Val Gln Pro
1               5                   10                  15

Gly Gly Ser Leu Lys Leu Ser Cys Ala Ala Ser Gly Phe Asp Phe Ser
            20                  25                  30

Arg Tyr Trp Met Ser Trp Val Arg Gln Ala Pro Gly Lys Gly Leu Glu
        35                  40                  45

Trp Ile Gly Glu Ile Asn Pro Asp Ser Ser Thr Ile Asn Tyr Thr Pro
    50                  55                  60

Ser Leu Lys Asp Lys Phe Ile Ile Ser Arg Asp Asn Ala Lys Asn Thr
65                  70                  75                  80

Leu Tyr Leu Gln Met Ser Lys Val Arg Ser Glu Asp Thr Ala Leu Tyr
```

85                  90                  95
Tyr Cys Ala Arg Arg Gly Tyr Tyr Gly Ser Ser Tyr Trp Phe Ala Tyr
                100                 105                 110

<210> SEQ ID NO 17
<211> LENGTH: 303
<212> TYPE: DNA
<213> ORGANISM: Artificial Sequence
<220> FEATURE:
<223> OTHER INFORMATION: Description of Artificial Sequence: Synthetic
      light chain variable region of 4D1 scFv polynucleotide

<400> SEQUENCE: 17
gcaatcatgt ctgcatctct aggagaacgg gtcaccatga cctgcactgc cagctcaagt      60
gtaagttcca gttacttgca ctggtaccag cagaagccag gatcctcccc caaactctgg     120
atttatagca catccaacct ggcttctgga gtcccagctc gcttcagtgg cagtgggtct     180
gggacctctt actctctcac aatcagcagc atggaggctg aagatgctgc cacttattac     240
tgccaccagt atcatcgttc cccacccacg ttcggctcgg gcaccaagct ggaaatcaaa     300
cgg                                                                   303

<210> SEQ ID NO 18
<211> LENGTH: 101
<212> TYPE: PRT
<213> ORGANISM: Artificial Sequence
<220> FEATURE:
<223> OTHER INFORMATION: Description of Artificial Sequence: Synthetic
      light chain variable region of 4D1 scFv polypeptide

<400> SEQUENCE: 18

Ala Ile Met Ser Ala Ser Leu Gly Glu Arg Val Thr Met Thr Cys Thr
1               5                   10                  15

Ala Ser Ser Ser Val Ser Ser Ser Tyr Leu His Trp Tyr Gln Gln Lys
            20                  25                  30

Pro Gly Ser Ser Pro Lys Leu Trp Ile Tyr Ser Thr Ser Asn Leu Ala
        35                  40                  45

Ser Gly Val Pro Ala Arg Phe Ser Gly Ser Gly Ser Gly Thr Ser Tyr
    50                  55                  60

Ser Leu Thr Ile Ser Ser Met Glu Ala Glu Asp Ala Ala Thr Tyr Tyr
65                  70                  75                  80

Cys His Gln Tyr His Arg Ser Pro Pro Thr Phe Gly Ser Gly Thr Lys
                85                  90                  95

Leu Glu Ile Lys Arg
            100

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      4D1 scFv CDR H1 oligonucleotide

<400> SEQUENCE: 19
ggattcgatt ttagtagata ctggatgagt                                       30

<210> SEQ ID NO 20
<211> LENGTH: 10
<212> TYPE: PRT
<213> ORGANISM: Artificial Sequence
<220> FEATURE:

<223> OTHER INFORMATION: Description of Artificial Sequence: Synthetic
     4D1 scFv CDR H1 peptide

<400> SEQUENCE: 20

Gly Phe Asp Phe Ser Arg Tyr Trp Met Ser
1               5                   10

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
     4D1 scFv CDR H2 oligonucleotide

<400> SEQUENCE: 21
gaaattaatc cagatagcag tacgataaac tatacgccat ctctaaagga t        51

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
     4D1 scFv CDR H2 peptide

<400> SEQUENCE: 22

Glu Ile Asn Pro Asp Ser Ser Thr Ile Asn Tyr Thr Pro Ser Leu Lys
1               5                   10                  15

Asp

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
     4D1 scFv CDR H3 oligonucleotide

<400> SEQUENCE: 23
cgagggtact acggtagtag ctactggttt gcttac                          36

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
     heavy chain CDR-H3 peptide

<400> SEQUENCE: 24

Arg Gly Tyr Tyr Gly Ser Ser Tyr Trp Phe Ala Tyr
1               5                   10

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
     4D1 scFv CDR L1 oligonucleotide

<400> SEQUENCE: 25
actgccagct caagtgtaag ttccagttac ttgcac                          36

<210> SEQ ID NO 26

```
<211> LENGTH: 12
<212> TYPE: PRT
<213> ORGANISM: Artificial Sequence
<220> FEATURE:
<223> OTHER INFORMATION: Description of Artificial Sequence: Synthetic
      4D1 scFv CDR L1 peptide

<400> SEQUENCE: 26

Thr Ala Ser Ser Ser Val Ser Ser Ser Tyr Leu His
1               5                   10

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      4D1 scFv CDR L2 oligonucleotide

<400> SEQUENCE: 27
agcacatcca acctggcttc t                                              21

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      4D1 scFv CDR L2 peptide

<400> SEQUENCE: 28

Ser Thr Ser Asn Leu Ala Ser
1               5

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      4D1 scFv CDR L3 oligonucleotide

<400> SEQUENCE: 29
caccagtatc atcgttcccc acccacg                                        27

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Gln Tyr His Arg Ser Pro Pro Thr
1               5

<210> SEQ ID NO 31
<211> LENGTH: 759
<212> TYPE: DNA
<213> ORGANISM: Artificial Sequence
<220> FEATURE:
<223> OTHER INFORMATION: Description of Artificial Sequence: Synthetic
      humanized 4D1 scFv polynucleotide

<400> SEQUENCE: 31
gaggtgcagc tggtggagtc tgggggaggc ttggtccagc ctggggggtc cctgagactc    60
```

```
tcctgtgcag cctctggatt cgattttagt agatactgga tgagctgggt ccgccaggct    120
ccagggaaag gctggagtg gtggccaac attaatccag atagcagtac gatatactat     180
gtggactctg tgaagggccg attcaccatc tccagagaca acgccaagaa ctcactgtat    240
ctgcaaatga acagcctgag agccgaggac acggctgtgt attactgtgc aagacgaggg    300
tactacggta gtagctactg gtttgcttac tggggccaag caccacggt caccgtctcc     360 tcaggtggag gcggttcagg cggaggtggc gctggcggtg gcggatcgga catcgagctc    420
actcagtctc agaaatagt gatgacgcag tctccagcca ccctgtctgt gtctccaggg    480
gaaagagcca ccctctcctg cagggccagt tcaagtgtaa gttccagtta cttagcctgg    540
taccagcaga aacctggcca ggctcccagg ctcctcatct atagcacatc caccagggcc    600
actggtatcc cagccaggtt cagtggcagt gggtctggga cagagttcac tctcaccatc    660
agcagcctgc agtctgaaga ttttgcagtt tattactgtc accagtatca tcgttcccca    720
cccacgttcg gctcgggcac caagctggaa atcaaacgg                          759
```

<210> SEQ ID NO 32
<211> LENGTH: 254
<212> TYPE: PRT
<213> ORGANISM: Artificial Sequence
<220> FEATURE:
<223> OTHER INFORMATION: Description of Artificial Sequence: Synthetic
      humanized 4D1 scFv polypeptide

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Trp Val Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Lys Gly Asn Tyr Phe Tyr Ala Met Asp Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Gly Ser Asp Ile Glu Leu Thr Gln Ser Pro Asp
    130                 135                 140

Ile Val Leu Thr Gln Ser Pro Ala Ser Leu Ala Val Ser Pro Gly Gln
145                 150                 155                 160

Arg Ala Thr Ile Thr Cys Arg Ala Ser Glu Ser Val Asp Ser His Gly
                165                 170                 175

Thr Ser Phe Ile His Trp Tyr Gln Gln Lys Pro Gly Gln Pro Pro Lys
            180                 185                 190

Leu Leu Ile Tyr Arg Ala Ser Asn Lys Asp Thr Gly Val Pro Ala Arg
        195                 200                 205

Phe Ser Gly Ser Gly Ser Gly Thr Asp Phe Thr Leu Thr Ile Asn Pro
    210                 215                 220

Val Glu Ala Asn Asp Thr Ala Asn Tyr Tyr Cys Gln Gln Ser Asn Glu
225                 230                 235                 240
```

Asp Pro Pro Thr Phe Gly Gly Gly Thr Lys Leu Glu Ile Lys
            245                 250

<210> SEQ ID NO 33
<211> LENGTH: 331
<212> TYPE: DNA
<213> ORGANISM: Artificial Sequence
<220> FEATURE:
<223> OTHER INFORMATION: Description of Artificial Sequence: Synthetic
      heavy chain variable region of humanized Ab 4D1 scFv
      polynucleotide

<400> SEQUENCE: 33
gaggtgcagc tggtggagtc tgggggaggc ttggtccagc ctggggggtc cctgagactc    60
tcctgtgcag cctctggatt cgattttagt agatactgga tgagctgggt ccgccaggct   120
ccagggaaag gctggagtg gtggccaac attaatccag atagcagtac gatatactat     180
gtggactctg tgaagggccg attcaccatc tccagagaca acgccaagaa ctcactgtat   240
ctgcaaatga acagcctgag agccgaggac acggctgtgt attactgtgc aagacgaggg   300
tactacggta gtagctactg gtttgcttac t                                  331

<210> SEQ ID NO 34
<211> LENGTH: 254
<212> TYPE: PRT
<213> ORGANISM: Artificial Sequence
<220> FEATURE:
<223> OTHER INFORMATION: Description of Artificial Sequence: Synthetic
      heavy chain variable region of humanized Ab 4D1 scFv
      polypeptide

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Trp Val Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Lys Gly Asn Tyr Phe Tyr Ala Met Asp Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Gly Ser Asp Ile Glu Leu Thr Gln Ser Pro Asp
    130                 135                 140

Ile Val Leu Thr Gln Ser Pro Ala Ser Leu Ala Val Ser Pro Gly Gln
145                 150                 155                 160

Arg Ala Thr Ile Thr Cys Arg Ala Ser Glu Ser Val Asp Ser His Gly
                165                 170                 175

Thr Ser Phe Ile His Trp Tyr Gln Gln Lys Pro Gly Gln Pro Pro Lys
            180                 185                 190

Leu Leu Ile Tyr Arg Ala Ser Asn Lys Asp Thr Gly Val Pro Ala Arg
        195                 200                 205

```
Phe Ser Gly Ser Gly Ser Gly Thr Asp Phe Thr Leu Thr Ile Asn Pro
    210             215                 220
Val Glu Ala Asn Asp Thr Ala Asn Tyr Tyr Cys Gln Gln Ser Asn Glu
225             230                 235                 240
Asp Pro Pro Thr Phe Gly Gly Gly Thr Lys Leu Glu Ile Lys
                245                 250
```

<210> SEQ ID NO 35
<211> LENGTH: 327
<212> TYPE: DNA
<213> ORGANISM: Artificial Sequence
<220> FEATURE:
<223> OTHER INFORMATION: Description of Artificial Sequence: Synthetic
      light chain variable region for humanized 4D1 scFv
      polynucleotide

<400> SEQUENCE: 35

```
gaaatagtga tgacgcagtc tccagccacc ctgtctgtgt ctccagggga aagagccacc    60
ctctcctgca gggccagttc aagtgtaagt tccagttact tagcctggta ccagcagaaa   120
cctggccagg ctcccaggct cctcatctat agcacatcca ccagggccac tggtatccca   180
gccaggttca gtggcagtgg gtctgggaca gagttcactc tcaccatcag cagcctgcag   240
tctgaagatt ttgcagttta ttactgtcac cagtatcatc gttccccacc cacgttcggc   300
tcgggcacca agctggaaat caaacgg                                       327
```

<210> SEQ ID NO 36
<211> LENGTH: 109
<212> TYPE: PRT
<213> ORGANISM: Artificial Sequence
<220> FEATURE:
<223> OTHER INFORMATION: Description of Artificial Sequence: Synthetic
      light chain variable region for humanized 4D1 scFv
      polypeptide

<400> SEQUENCE: 36

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Ser Thr Ser Thr Arg Ala Thr Gly Ile Pro Ala Arg Phe Ser
    50                  55                  60
Gly Ser Gly Ser Gly Thr Glu Phe Thr Leu Thr Ile Ser Ser Leu Gln
65                  70                  75                  80
Ser Glu Asp Phe Ala Val Tyr Tyr Cys His Gln Tyr His Arg Ser Pro
                85                  90                  95
Pro Thr Phe Gly Ser Gly Thr Lys Leu Glu Ile Lys Arg
                100                 105
```

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      mu-CDR-H1 of heavy chain variable region of humanized
      4D1 Ab oligonucleotide

<400> SEQUENCE: 37

```
ggattcgatt ttagtagata ctgg                                          24
```

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      mu-CDR-H1 of heavy chain humanized 4D1 scFv peptide

<400> SEQUENCE: 38

Gly Phe Asp Phe Ser Arg Tyr Trp
1               5

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      mu-CDR-H2 of heavy chain variable region of humanized
      4D1 Ab oligonucleotide

<400> SEQUENCE: 39
attaatccag atagcagtac gata                                              24

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      mu-CDR-H2 humanized Ab peptide

<400> SEQUENCE: 40

Ile Asn Pro Asp Ser Ser Thr Ile
1               5

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      mu-CDR-H3 of heavy chain variable region of humanized
      4D1 Ab oligonucleotide

<400> SEQUENCE: 41
gcaagacgag ggtactacgg tagtagctac tggtttgctt ac                          42

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      mu-CDR3 of heavy chain variable region of humanized
      4D1 Ab peptide

<400> SEQUENCE: 42

Ala Arg Arg Gly Tyr Tyr Gly Ser Ser Tyr Trp Phe Ala Tyr
1               5                   10

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic muCDR-L1 of the light chain variable region for humanized
4D1 scFv oligonucleotide

<400> SEQUENCE: 43
tcaagtgtaa gttccagtta c                                              21

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      muCDR-L1 of the light chain variable region for humanized
      4D1 scFv peptide

<400> SEQUENCE: 44

Ser Ser Val Ser Ser Ser Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: Description of Artificial Sequence: Synthetic
      muCDR-L2 of the light chain variable region for humanized
      4D1 scFv oligonucleotide

<400> SEQUENCE: 45 agcacatcc                                                             9

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      muCDR-L2 of the light chain variable region for humanized
      4D1 scFv peptide

<400> SEQUENCE: 46

Ser Thr Ser
1

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      muCDR-L3 of the light chain variable region for humanized
      4D1 scFv oligonucleotide

<400> SEQUENCE: 47
caccagtatc atcgttcccc acccacg                                        27

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      muCDR-L3 of the light chain variable region for humanized
      4D1 scFv peptide

<400> SEQUENCE: 48

His Gln Tyr His Arg Ser Pro Pro Thr
1               5

<210> SEQ ID NO 49
<211> LENGTH: 745
<212> TYPE: DNA
<213> ORGANISM: Artificial Sequence
<220> FEATURE:
<223> OTHER INFORMATION: Description of Artificial Sequence: Synthetic
      6H5 scFv polynucleotide

<400> SEQUENCE: 49

```
atggcccagg tgaagctgca gcagtcagga cctgacctgg tgaagcctgg ggcttcagtg      60
aagatatcct gcaaggcgtc tggttactca ttcactggct actacatgca ctgggtgaag     120
cagagccatg gaaagagcct tgagtggatt ggacgtgtta atcctaacag tggtggtaca     180
agctacaacc agaagttcaa ggacaaggcc atattaactg tagacaagtc atccagcaca     240
gcctacatgg agctccgcag cctgacatct gaggactctg cggtctatta ctgtgcaaga     300
tcgaaaggta actacttcta tgctatggac tactggggcc aagggaccac ggtcaccgtc     360
tcctcaagtg gaggcggttc aggcggaggt ggctctggcg gtggcggatc ggacatcgag     420
ctcactcagt ctccagcttc tttggctgtg tctctagggc agagggccac catatcctgc     480
agagccagtg aaagtgttga tagtcatggc actagtttta tgcactggta ccagcagaaa     540
ccaggacagc cacccaaatt cctcatctat cgtgcatcca acctagaatc tgggatccct     600
gccaggttca gtggcagtgg gtctaggaca gacttcaccc tcaccattaa tcctgtggag     660
acagatgatg ttgcaatcta ttactgtcag caaagtaatg aggatcctcc gacgttcggt     720
ggaggcacca agctggaaat caaac                                          745
```

<210> SEQ ID NO 50
<211> LENGTH: 248
<212> TYPE: PRT
<213> ORGANISM: Artificial Sequence
<220> FEATURE:
<223> OTHER INFORMATION: Description of Artificial Sequence: Synthetic
      6H5 scFv polypeptide

<400> SEQUENCE: 50

Met Ala Gln Val Lys Leu Gln Gln Ser Gly Pro Asp Leu Val Lys Pro
1               5                   10                  15

Gly Ala Ser Val Lys Ile Ser Cys Lys Ala Ser Gly Tyr Ser Phe Thr
            20                  25                  30

Gly Tyr Tyr Met His Trp Val Lys Gln Ser His Gly Lys Ser Leu Glu
        35                  40                  45

Trp Ile Gly Arg Val Asn Pro Asn Ser Gly Gly Thr Ser Tyr Asn Gln
    50                  55                  60

Lys Phe Lys Asp Lys Ala Ile Leu Thr Val Asp Lys Ser Ser Ser Thr
65                  70                  75                  80

Ala Tyr Met Glu Leu Arg Ser Leu Thr Ser Glu Asp Ser Ala Val Tyr
                85                  90                  95

Tyr Cys Ala Arg Ser Lys Gly Asn Tyr Phe Tyr Ala Met Asp Tyr Trp
            100                 105                 110

Gly Gln Gly Thr Thr Val Thr Val Ser Ser Ser Gly Gly Gly Ser Gly
        115                 120                 125

Gly Gly Gly Ser Gly Gly Gly Ser Asp Ile Glu Leu Thr Gln Ser
    130                 135                 140

Pro Ala Ser Leu Ala Val Ser Leu Gly Gln Arg Ala Thr Ile Ser Cys
145                 150                 155                 160

```
Arg Ala Ser Glu Ser Val Asp Ser His Gly Thr Ser Phe Met His Trp
            165                 170                 175

Tyr Gln Gln Lys Pro Gly Gln Pro Pro Lys Phe Leu Ile Tyr Arg Ala
        180                 185                 190

Ser Asn Leu Glu Ser Gly Ile Pro Ala Arg Phe Ser Gly Ser Gly Ser
            195                 200                 205

Arg Thr Asp Phe Thr Leu Thr Ile Asn Pro Val Glu Thr Asp Asp Val
        210                 215                 220

Ala Ile Tyr Tyr Cys Gln Gln Ser Asn Glu Asp Pro Pro Thr Phe Gly
225                 230                 235                 240

Gly Gly Thr Lys Leu Glu Ile Lys
                245

<210> SEQ ID NO 51
<211> LENGTH: 334
<212> TYPE: DNA
<213> ORGANISM: Artificial Sequence
<220> FEATURE:
<223> OTHER INFORMATION: Description of Artificial Sequence: Synthetic
      6H5 scFv heavy chain variable region polynucleotide

<400> SEQUENCE: 51
atggcccagg tgaagctgca gcagtcagga cctgacctgg tgaagcctgg ggcttcagtg      60
aagatatcct gcaaggcgtc tggttactca ttcactggct actacatgca ctgggtgaag    120
cagagccatg gaaagagcct tgagtggatt ggacgtgtta atcctaacag tggtggtaca    180
agctacaacc agaagttcaa ggacaaggcc atattaactg tagacaagtc atccagcaca    240
gcctacatgg agctccgcag cctgacatct gaggactctg cggtctatta ctgtgcaaga    300
tcgaaaggta actacttcta tgctatggac tact                                334

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      6H5 scFv heavy chain variable region polypeptide

<400> SEQUENCE: 52

Met Ala Gln Val Lys Leu Gln Gln Ser Gly Pro Asp Leu Val Lys Pro
1               5                   10                  15

Gly Ala Ser Val Lys Ile Ser Cys Lys Ala Ser Gly Tyr Ser Phe Thr
            20                  25                  30

Gly Tyr Tyr Met His Trp Val Lys Gln Ser His Gly Lys Ser Leu Glu
        35                  40                  45

Trp Ile Gly Arg Val Asn Pro Asn Ser Gly Gly Thr Ser Tyr Asn Gln
    50                  55                  60

Lys Phe Lys Asp Lys Ala Ile Leu Thr Val Asp Lys Ser Ser Ser Thr
65                  70                  75                  80

Ala Tyr Met Glu Leu Arg Ser Leu Thr Ser Glu Asp Ser Ala Val Tyr
                85                  90                  95

Tyr Cys Ala Arg Ser Lys Gly Asn Tyr Phe Tyr Ala Met Asp Tyr
            100                 105                 110

<210> SEQ ID NO 53
<211> LENGTH: 310
<212> TYPE: DNA
<213> ORGANISM: Artificial Sequence
<220> FEATURE:
```

<223> OTHER INFORMATION: Description of Artificial Sequence: Synthetic
6H5 scFv light chain variable region polynucleotide

<400> SEQUENCE: 53

```
gcttctttgg ctgtgtctct agggcagagg gccaccatat cctgcagagc cagtgaaagt    60
gttgatagtc atggcactag ttttatgcac tggtaccagc agaaaccagg acagccaccc   120
aaattcctca tctatcgtgc atccaaccta gaatctggga tccctgccag gttcagtggc   180
agtgggtcta ggacagactt caccctcacc attaatcctg tggagacaga tgatgttgca   240
atctattact gtcagcaaag taatgaggat cctccgacgt tcggtggagg caccaagctg   300
gaaatcaaac                                                          310
```

<210> SEQ ID NO 54
<211> LENGTH: 103
<212> TYPE: PRT
<213> ORGANISM: Artificial Sequence
<220> FEATURE:
<223> OTHER INFORMATION: Description of Artificial Sequence: Synthetic
6H5 scFv light chain variable region polypeptide

<400> SEQUENCE: 54

Ala Ser Leu Ala Val Ser Leu Gly Gln Arg Ala Thr Ile Ser Cys Arg
1               5                   10                  15

Ala Ser Glu Ser Val Asp Ser His Gly Thr Ser Phe Met His Trp Tyr
            20                  25                  30

Gln Gln Lys Pro Gly Gln Pro Pro Lys Phe Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Thr Asp Asp Val Ala
65                  70                  75                  80

Ile Tyr Tyr Cys Gln Gln Ser Asn Glu Asp Pro Pro Thr Phe Gly Gly
                85                  90                  95

Gly Thr Lys Leu Glu Ile Lys
            100

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
CDR-H1 of 6H5 scFv heavy chain variable region oligonucleotide

<400> SEQUENCE: 55

```
ggttactcat tcactggcta ctacatgcac                                     30
```

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
CDR-H1 of 6H5 scFv heavy chain variable region peptide

<400> SEQUENCE: 56

Gly Tyr Ser Phe Thr Gly Tyr Tyr Met His
1               5                   10

<210> SEQ ID NO 57
<211> LENGTH: 48

```
<212> TYPE: DNA
<213> ORGANISM: Artificial Sequence
<220> FEATURE:
<223> OTHER INFORMATION: Description of Artificial Sequence: Synthetic
      CDR-H2 of 6H5 scFv heavy chain variable region oligonucleotide

<400> SEQUENCE: 57
cgtgttaatc ctaacagtgg tggtacaagc tacaaccaga agttcaag                     48

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      CDR-H2 H chain peptide

<400> SEQUENCE: 58

Arg Val Asn Pro Asn Ser Gly Gly Thr Ser Tyr Asn Gln Lys Phe Lys
1               5                   10                  15

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      CDR-H3 of 6H5 oligonucleotide

<400> SEQUENCE: 59
tcgaaaggta actacttcta tgctatggac tac                                     33

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      CDR-H3 of 6H5 peptide

<400> SEQUENCE: 60

Ser Lys Gly Asn Tyr Phe Tyr Ala Met Asp Tyr
1               5                   10

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic
      CDR L1 of 6H5 scFv light chain variable region oligonucleotide

<400> SEQUENCE: 61
agagccagtg aaagtgttga tagtcatggc actagtttta tgcac                        45

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR L1 of 6H5 scFv light chain variable region peptide

<400> SEQUENCE: 62

Arg Ala Ser Glu Ser Val Asp Ser His Gly Thr Ser Phe Met His
1               5                   10                  15
```

```
<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      CDR L2 of 6H5 scFv light chain variable region oligonucleotide

<400> SEQUENCE: 63
cgtgcatcca acctagaatc t                                              21

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      CDR L2 of 6H5 scFv light chain variable region peptide

<400> SEQUENCE: 64

Arg Ala Ser Asn Leu Glu Ser
1               5

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      CDR L3 of 6H5 scFv light chain variable region oligonucleotide

<400> SEQUENCE: 65
cagcaaagta atgaggatcc tccgacg                                        27

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR L3 of 6H5 scFv light chain variable region peptide

<400> SEQUENCE: 66

Gln Gln Ser Asn Glu Asp Pro Pro Thr
1               5

<210> SEQ ID NO 67
<211> LENGTH: 763
<212> TYPE: DNA
<213> ORGANISM: Artificial Sequence
<220> FEATURE:
<223> OTHER INFORMATION: Description of Artificial Sequence: Synthetic
      humanized 6H5 scFv polynucleotide

<400> SEQUENCE: 67
caggtgcagc tggtgcagtc tggggctgag gtgaagaagc ctggggcctc agtgaaggtc     60
tcctgcaagg cttctggtta ctcattcact ggctactaca tgcactgggt gcgacaggcc    120
cctggacaag gcttgagtg gatgggatgg gttaatccta cagtggtgg tacaaactat    180 gcacagaagt tcagggcag gtcaccatg accaggaca cgtccatcag cacagcctac    240
atggagctga gcaggctgag atctgacgac acggccgtgt attactgtgc aagatcgaaa    300
ggtaactact ctctatgctat ggactactgg ggccaaggga ccacggtcac cgtctcctca    360
agtggaggcg gttcaggcgg aggtggctct ggcggtggcg gatcggacat cgagctcact    420
cagtctccag acattgtgct gacccagtct ccagcctcct tggccgtgtc tccaggacag    480
```

```
agggccacca tcacctgcag agccagtgaa agtgttgata gtcatggcac tagttttatt      540
cactggtatc agcagaaacc aggacaacct cctaaactcc tgatttaccg tgcatccaat      600
aaagacactg gggtcccagc caggttcagc ggcagtgggt ctgggaccga tttcaccctc      660
acaattaatc ctgtggaagc taatgatact gcaaattatt actgtcagca agtaatgag       720 gatcctccga cgttcggtgg aggcaccaag ctggaaatca aac                         763
```

```
<210> SEQ ID NO 68
<211> LENGTH: 254
<212> TYPE: PRT
<213> ORGANISM: Artificial Sequence
<220> FEATURE:
<223> OTHER INFORMATION: Description of Artificial Sequence: Synthetic
      humanized 6H5 scFv polypeptide

<400> SEQUENCE: 68
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Trp Val Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Lys Gly Asn Tyr Phe Tyr Ala Met Asp Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Gly Ser Asp Ile Glu Leu Thr Gln Ser Pro Asp
    130                 135                 140

Ile Val Leu Thr Gln Ser Pro Ala Ser Leu Ala Val Ser Pro Gly Gln
145                 150                 155                 160

Arg Ala Thr Ile Thr Cys Arg Ala Ser Glu Ser Val Asp Ser His Gly
                165                 170                 175

Thr Ser Phe Ile His Trp Tyr Gln Gln Lys Pro Gly Gln Pro Pro Lys
            180                 185                 190

Leu Leu Ile Tyr Arg Ala Ser Asn Lys Asp Thr Gly Val Pro Ala Arg
        195                 200                 205

Phe Ser Gly Ser Gly Ser Gly Thr Asp Phe Thr Leu Thr Ile Asn Pro
    210                 215                 220

Val Glu Ala Asn Asp Thr Ala Asn Tyr Tyr Cys Gln Gln Ser Asn Glu
225                 230                 235                 240

Asp Pro Pro Thr Phe Gly Gly Gly Thr Lys Leu Glu Ile Lys
                245                 250

```
<210> SEQ ID NO 69
<211> LENGTH: 328
<212> TYPE: DNA
<213> ORGANISM: Artificial Sequence
<220> FEATURE:
<223> OTHER INFORMATION: Description of Artificial Sequence: Synthetic
      humanized 6H5 scFv heavy chain variable polynucleotide
```

<400> SEQUENCE: 69

```
caggtgcagc tggtgcagtc tggggctgag gtgaagaagc ctggggcctc agtgaaggtc    60
tcctgcaagg cttctggtta ctcattcact ggctactaca tgcactgggt gcgacaggcc   120
cctggacaag gcttgagtg gatgggatgg gttaatccta acagtggtgg tacaaactat   180
gcacagaagt tcagggcag ggtcaccatg accaggaca cgtccatcag cacagcctac   240
atggagctga gcaggctgag atctgacgac acggccgtgt attactgtgc aagatcgaaa   300
ggtaactact tctatgctat ggactact                                      328
```

<210> SEQ ID NO 70
<211> LENGTH: 109
<212> TYPE: PRT
<213> ORGANISM: Artificial Sequence
<220> FEATURE:
<223> OTHER INFORMATION: Description of Artificial Sequence: Synthetic humanized 6H5 scFv heavy chain variable region polypeptide

<400> SEQUENCE: 70

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Ser Phe Thr Gly Tyr
            20                  25                  30
Tyr Met His Trp Val Arg Gln Ala Pro Gly Gln Gly Leu Glu Trp Met
        35                  40                  45
Gly Trp Val Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser Lys Gly Asn Tyr Phe Tyr Ala Met Asp Tyr
            100                 105
```

<210> SEQ ID NO 71
<211> LENGTH: 334
<212> TYPE: DNA
<213> ORGANISM: Artificial Sequence
<220> FEATURE:
<223> OTHER INFORMATION: Description of Artificial Sequence: Synthetic humanized 6H5 scFv light chain variable polynucleotide

<400> SEQUENCE: 71

```
gacattgtgc tgacccagtc tccagcctcc ttggccgtgt ctccaggaca gagggccacc    60
atcacctgca gagccagtga aagtgttgat agtcatggca ctagttttat tcactggtat   120
cagcagaaac aggacaaacc tcctaaactc ctgatttacc gtgcatccaa taaagacact   180
ggggtcccag ccaggttcag cggcagtggg tctgggaccg atttcaccct cacaattaat   240
cctgtggaag ctaatgatac tgcaaattat tactgtcagc aaagtaatga ggatcctccg   300
acgttcggtg gaggcaccaa gctggaaatc aaac                                334
```

<210> SEQ ID NO 72
<211> LENGTH: 111
<212> TYPE: PRT
<213> ORGANISM: Artificial Sequence
<220> FEATURE:
<223> OTHER INFORMATION: Description of Artificial Sequence: Synthetic humanized 6H5 scFv Light chain variable region polypeptide

<400> SEQUENCE: 72

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Ser His
            20                  25                  30

Gly Thr Ser Phe Ile His Trp Tyr Gln Gln Lys Pro Gly Gln Pro Pro
        35                  40                  45

Lys Leu Leu Ile Tyr Arg Ala Ser Asn Lys Asp Thr Gly Val Pro Ala
    50                  55                  60

Arg Phe Ser Gly Ser Gly Ser Gly Thr Asp Phe Thr Leu Thr Ile Asn
65              70                  75                  80

Pro Val Glu Ala Asn Asp Thr Ala Asn Tyr Tyr Cys Gln Gln Ser Asn
                85                  90                  95

Glu Asp Pro Pro Thr Phe Gly Gly Gly Thr Lys Leu Glu Ile Lys
            100                 105                 110
```

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      mu-CDR H1 from humanized 6H5 scFv heavy chain oligonucleotide

<400> SEQUENCE: 73
ggttactcat tcactggcta ctac                                          24

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      mu-CDR H1 from Humanized 6H5 scFv heavy chain peptide

<400> SEQUENCE: 74

```
Gly Tyr Ser Phe Thr Gly Tyr Tyr
1               5
```

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      mu-CDR H2 from humanized 6H5 scFv heavy chain oligonucleotide

<400> SEQUENCE: 75
gttaatccta acagtggtgg taca                                          24

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      mu-CDR H2 from humanized 6H5 scFv heavy chain peptide

<400> SEQUENCE: 76

```
Val Asn Pro Asn Ser Gly Gly Thr
1               5
```

<210> SEQ ID NO 77
<211> LENGTH: 39

```
<212> TYPE: DNA
<213> ORGANISM: Artificial Sequence
<220> FEATURE:
<223> OTHER INFORMATION: Description of Artificial Sequence: Synthetic
      mu-CDR H3 from humanized 6H5 scFv heavy chain oligonucleotide

<400> SEQUENCE: 77
gcaagatcga aggtaacta cttctatgct atggactac                              39

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      mu-CDR H3 from humanized 6H5 scFv heavy chain peptide

<400> SEQUENCE: 78

Ala Arg Ser Lys Gly Asn Tyr Phe Tyr Ala Met Asp Tyr
1               5                   10

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      mu-CDR-L1 from humanized 6H5 scFv light chain oligonucleotide

<400> SEQUENCE: 79
gaaagtgttg atagtcatgg cactagtttt                                       30

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      mu-CDR-L1 from humanized 6H5 scFv light chain peptide

<400> SEQUENCE: 80

Glu Ser Val Asp Ser His Gly Thr Ser Phe
1               5                   10

<210> SEQ ID NO 81
<211> LENGTH: 9
<212> TYPE: DNA
<213> ORGANISM: Artificial Sequence
<220> FEATURE:
<223> OTHER INFORMATION: Description of Artificial Sequence: Synthetic
      mu-CDR-L2 from humanized 6H5 scFv light chain oligonucleotide

<400> SEQUENCE: 81 cgtgcatcc                                                               9

<210> SEQ ID NO 82
<211> LENGTH: 3
<212> TYPE: PRT
<213> ORGANISM: Artificial Sequence
<220> FEATURE:
<223> OTHER INFORMATION: Description of Artificial Sequence: Synthetic
      mu-CDR-L2 from humanized 6H5 scFv light chain peptide

<400> SEQUENCE: 82

Arg Ala Ser
1
```

```
<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      mu-CDR-L3 from humanized 6H5 scFv light chain oligonucleotide

<400> SEQUENCE: 83
cagcaaagta atgaggatcc tccgacg                                              27

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      mu-CDR-L3 from humanized 6H5 scFv light chain peptide

<400> SEQUENCE: 84

Gln Gln Ser Asn Glu Asp Pro Pro Thr
1               5
```